US008741810B2

(12) United States Patent
Zauderer et al.

(10) Patent No.: US 8,741,810 B2
(45) Date of Patent: *Jun. 3, 2014

(54) IN VITRO METHODS OF PRODUCING AND IDENTIFYING IMMUNOGLOBULIN MOLECULES IN EUKARYOTIC CELLS

(75) Inventors: Maurice Zauderer, Pittsford, NY (US); Ernest S. Smith, Ontario, NY (US)

(73) Assignee: University of Rochester, Rochester, NY (US)

( * ) Notice: Subject to any disclaimer, the term of this patent is extended or adjusted under 35 U.S.C. 154(b) by 1160 days.

This patent is subject to a terminal disclaimer.

(21) Appl. No.: 11/892,027

(22) Filed: Aug. 17, 2007

(65) Prior Publication Data
US 2008/0167193 A1    Jul. 10, 2008

Related U.S. Application Data

(63) Continuation of application No. 09/987,456, filed on Nov. 14, 2001, now Pat. No. 7,858,559.

(60) Provisional application No. 60/249,268, filed on Nov. 17, 2000, provisional application No. 60/262,067, filed on Jan. 18, 2001, provisional application No. 60/271,424, filed on Feb. 27, 2001, provisional application No. 60/298,087, filed on Jun. 15, 2001.

(51) Int. Cl.
*C40B 10/00* (2006.01)

(52) U.S. Cl.
USPC .............................................. 506/1; 436/500

(58) Field of Classification Search
None
See application file for complete search history.

(56) References Cited

U.S. PATENT DOCUMENTS

| | | | |
|---|---|---|---|
| 4,603,112 A | 7/1986 | Paoletti et al. | |
| 4,642,334 A | 2/1987 | Moore et al. | |
| 4,656,134 A | 4/1987 | Ringold | |
| 4,769,330 A | 9/1988 | Paoletti et al. | |
| 4,800,159 A | 1/1989 | Mullis et al. | |
| 4,816,397 A * | 3/1989 | Boss et al. | 435/69.6 |
| 4,889,818 A | 12/1989 | Gelfand et al. | |
| 4,946,786 A | 8/1990 | Tabor et al. | |
| 4,965,188 A | 10/1990 | Mullis et al. | |
| 5,023,171 A | 6/1991 | Ho et al. | |
| 5,110,587 A | 5/1992 | Paoletti et al. | |
| 5,223,409 A * | 6/1993 | Ladner et al. | 506/1 |
| 5,225,539 A | 7/1993 | Winter | |
| 5,445,953 A | 8/1995 | Dorner et al. | |
| 5,565,332 A | 10/1996 | Hoogenboom et al. | |
| 5,571,698 A | 11/1996 | Ladner et al. | |
| 5,576,195 A | 11/1996 | Robinson et al. | |
| 5,618,920 A | 4/1997 | Robinson et al. | |
| 5,650,150 A | 7/1997 | Gillies | |
| 5,693,493 A | 12/1997 | Robinson et al. | |
| 5,733,743 A | 3/1998 | Johnson et al. | |
| 5,759,808 A | 6/1998 | Casterman et al. | |
| 5,770,212 A | 6/1998 | Falkner et al. | |
| 5,780,225 A | 7/1998 | Wigler et al. | |
| 5,789,208 A | 8/1998 | Sharon | |
| 5,800,988 A | 9/1998 | Casterman et al. | |
| 5,807,715 A | 9/1998 | Morrison et al. | |
| 5,830,663 A | 11/1998 | Embleton et al. | |
| 5,830,721 A | 11/1998 | Stemmer et al. | |
| 5,837,500 A | 11/1998 | Ladner et al. | |
| 5,871,907 A | 2/1999 | Winter et al. | |
| 5,885,793 A | 3/1999 | Griffiths et al. | |
| 5,916,771 A | 6/1999 | Hori et al. | |
| 5,959,177 A | 9/1999 | Hein et al. | |
| 5,962,255 A | 10/1999 | Griffiths et al. | |
| 5,965,405 A | 10/1999 | Winter et al. | |
| 5,972,597 A | 10/1999 | Paoletti et al. | |
| 6,005,079 A | 12/1999 | Casterman et al. | |
| 6,010,861 A | 1/2000 | Blume | |
| 6,057,098 A | 5/2000 | Buechler et al. | |
| 6,130,364 A | 10/2000 | Jakobovits et al. | |
| 6,248,516 B1 | 6/2001 | Winter et al. | |
| 6,291,158 B1 | 9/2001 | Winter et al. | |
| 6,291,159 B1 | 9/2001 | Winter et al. | |
| 6,291,160 B1 | 9/2001 | Lerner et al. | |
| 6,291,161 B1 | 9/2001 | Lerner et al. | |
| 6,297,004 B1 | 10/2001 | Russell et al. | |
| 6,331,415 B1 * | 12/2001 | Cabilly et al. | 435/69.6 |
| 6,335,163 B1 | 1/2002 | Sharon | |
| 6,410,246 B1 | 6/2002 | Zhu et al. | |
| 6,420,113 B1 | 7/2002 | Buechler et al. | |

(Continued)

FOREIGN PATENT DOCUMENTS

| | | |
|---|---|---|
| AU | 606320 | 5/1987 |
| AU | 632462 | 1/1989 |

(Continued)

OTHER PUBLICATIONS

Persic et al., Gene, 187: 9-18, 1997.*

(Continued)

*Primary Examiner* — Heather Calamita
*Assistant Examiner* — Jonah Smith
(74) *Attorney, Agent, or Firm* — Thompson Coburn, LLP; Elizabeth J. Haanes

(57) ABSTRACT

The present invention relates to a high efficiency method of expressing immunoglobulin molecules in eukaryotic cells. The invention is further drawn to a method of producing immunoglobulin heavy and light chain libraries, particularly using the trimolecular recombination method, for expression in eukaryotic cells. The invention further provides methods of selecting and screening for antigen-specific immunoglobulin molecules, and antigen-specific fragments thereof. The invention also provides kits for producing, screening and selecting antigen-specific immunoglobulin molecules. Finally, the invention provides immunoglobulin molecules, and antigen-specific fragments thereof, produced by the methods provided herein.

15 Claims, 18 Drawing Sheets

(56) References Cited

U.S. PATENT DOCUMENTS

| | | |
|---|---|---|
| 6,479,243 B1 | 11/2002 | Wigler et al. |
| 6,599,697 B1 | 7/2003 | Sodoyer et al. |
| 6,635,424 B2 | 10/2003 | Wigler et al. |
| 6,696,245 B2 | 2/2004 | Winter et al. |
| 6,706,477 B2 | 3/2004 | Zauderer |
| 6,800,442 B2 | 10/2004 | Zauderer |
| 6,861,229 B2 | 3/2005 | Carrión et al. |
| 6,872,518 B2 | 3/2005 | Zauderer |
| 6,998,252 B1 | 2/2006 | Moss et al. |
| 7,015,024 B1 | 3/2006 | Moss et al. |
| 7,045,313 B1 | 5/2006 | Moss et al. |
| 7,067,251 B2 | 6/2006 | Zauderer et al. |
| 2002/0123057 A1 | 9/2002 | Zauderer |
| 2002/0192675 A1 | 12/2002 | Zauderer et al. |
| 2003/0104402 A1 | 6/2003 | Zauderer et al. |
| 2003/0186374 A1 | 10/2003 | Hufton et al. |
| 2003/0194696 A1 | 10/2003 | Zauderer et al. |
| 2004/0072740 A1 | 4/2004 | Iverson et al. |
| 2004/0265900 A1 | 12/2004 | Zauderer |
| 2005/0196755 A1 | 9/2005 | Zauderer et al. |
| 2005/0266425 A1 | 12/2005 | Zauderer et al. |
| 2006/0160129 A1 | 7/2006 | Zauderer |

FOREIGN PATENT DOCUMENTS

| | | |
|---|---|---|
| CA | 1341235 | 5/2001 |
| EP | 0 120 694 A2 | 10/1984 |
| EP | 0 120 694 B1 | 10/1984 |
| EP | 0 171 496 A2 | 2/1986 |
| EP | 0 200 362 A2 | 12/1986 |
| EP | 0 201 184 B1 | 12/1986 |
| EP | 0 239 400 A2 | 9/1987 |
| EP | 0 239 400 B1 | 9/1987 |
| EP | 0 274 394 A2 | 7/1988 |
| EP | 0 368 684 A1 | 5/1990 |
| EP | 0 371 998 B2 | 6/1990 |
| GB | 2 137 631 A | 10/1984 |
| GB | 2 188 638 A | 10/1987 |
| WO | WO 86/01533 A1 | 3/1986 |
| WO | WO 87/02671 A1 | 5/1987 |
| WO | WO 88/06630 A1 | 9/1988 |
| WO | WO 89/00999 A1 | 2/1989 |
| WO | WO 89/01526 A1 | 2/1989 |
| WO | WO 90/14424 A1 | 11/1990 |
| WO | WO 90/14430 A1 | 11/1990 |
| WO | WO 90/14443 A1 | 11/1990 |
| WO | WO 92/20791 A1 | 11/1992 |
| WO | WO 93 01296 * | 1/1993 |
| WO | WO 93/01296 A1 | 1/1993 |
| WO | WO 94/25591 A1 | 11/1994 |
| WO | WO 96/34103 A1 | 10/1996 |
| WO | WO 97/08320 A1 | 3/1997 |
| WO | WO 99/30151 A1 | 6/1999 |
| WO | WO 99/37681 A2 | 7/1999 |
| WO | WO 99/46300 A1 | 9/1999 |
| WO | WO 00/28016 A1 | 5/2000 |
| WO | WO 00/43507 A1 | 7/2000 |
| WO | WO 00/69907 A1 | 11/2000 |
| WO | WO 01/18058 A2 | 3/2001 |
| WO | WO 01/72995 A2 | 10/2001 |
| WO | WO 2004/037993 A2 | 5/2004 |

OTHER PUBLICATIONS

Barbas III, C.F., et al., "Assembly of combinatorial antibody libraries on phage surfaces: The gene III site," *Proc. Natl. Acad. Sci. USA* 88:7978 7982, National Academy Press (1991).

Belyaysky, A., et al., "PCR based cDNA library construction: general cDNA libraries at the level of a few cells," *Nucleic Acids Res.* 17:2919 2932, Oxford University Press (1989).

Better, M. et al., "*Escherichia coli* Secretion of an Active Chimeric Antibody Fragment," *Science* 240:957-1112, American Association for the Advancement of Sciences (1988).

Boder, E.T., et al., "Directed evolution of antibody fragments with monovalent femtomolar antigen-binding affinity," *Proc. Natl. Acad. Sci. USA* 97:10701-10705, National Academy of Sciences (Sep. 2000).

Brüggemann, M., et al., "Construction, Function and Immunogenicity of Recombinant Monoclonal Antibodies," *Behring Inst. Mitt.* 87:21-24, Medizinsche Verlagsges Mbh (1990).

Burton, D.R., et al., "A large array of human monoclonal antibodies to type 1 human immunodeficiency virus from combinatorial libraries of asymptomatic seropositive individuals," *Proc. Natl. Acad. Sci. USA* 88:10134-10137, National Academy Press (1991).

Chames, P. and Batey, D., "Antibody engineering and its applications in tumor targeting and intracellular immunization," *FEMS Microbiol. Lett.* 189:1-8, Elsevier Science Publishers B.V. (2000).

Chang, C.N., et al., "Expression of Anitbody Fab Domains on Bacteriophage Surfaces: Potential Use for Antibody Selection," *J. Immunol.* 147:3610-3614, American Association of Immunologists (1991).

Chiang, Y.L., et al., "Direct cDNA Cloning of the Rearranged Immunoglobulin Variable Region," *Biotechniques* 7:360-366, Eaton Publishing Company(1989).

Clackson, T., et al., "Making antibody fragments using phage display libraries," *Nature* 352:624-628, Macmillan Magazines Ltd. (1991).

Cottet, S. and Corthesy, B., "Cellular processing limits the heterologous expression of secretory component in mammalian cells," *Eur. J. Biochem.* 246:23-31, Blackwell Science, Ltd. (1997).

Davies, J. and Riechmann L., "Camelising human antibody fragments: NMR studies on VH domains," *FEBS Letters* 339:285-290, Elsevier Science Publishers B.V. (1994).

Davies, J. and Riechmann, L., "Antibody VH Domains as Small Recognition Units," *Bio/Technology (N Y)* 13:475-479, Nature Publishing Co. (1995).

Davies, J. and Riechmann, L., "Single antibody domains as small recognition units: design and in vitro antigen selection of camelized, human VH domains with improved protein stability," *Protein Eng.* 9:531-537, Oxford University Press (1996).

Eckert, D. and Merchlinsky M., "Vaccinia virus-bacteriophage T7 expression vector for complementation analysis of late gene processes," *J. Gen. Virol.* 80:1463-1469, Society for General Microbiology (1999).

Elroy-Stein O., et al., "Cap-independent translation of mRNA conferred by encephalomyocarditis virus 5' sequence improves the performance of the vaccinia cirus/bacteriophage T7 hybrid expression system," *Proc. Natl. Acad. Sci. USA* 86:6126-6130, National Academy Press (1989).

Elroy-Stein, O. and Moss, B., "Cytoplasmic expression system based on constitutive synthesis of bacteriophage T7 RNA polymerase in mammalian cells," *Proc. Natl. Acad. Sci. USA* 87:6743-6747 (1990).

Fenner, F., "Genetic Studies with Mammalian Poxviruses," *Virology* 8:499-507, Academic Press, Inc. (1959).

Fields, S. and Song, O., "A novel genetic system to detect protein-protein interactions," *Nature* 340:245-246, Macmillan Magazines, Ltd. (1989).

Foot, J., and Winter, G., "Antibody Framework Residues Affecting the Conformation of the Hypervariable Loops," *J. Mol. Biol.* 224:487-499, Academic Press, Ltd. (1992).

Frischauf, A., "Construction and Characterization of a Genomic Library in λ," *Methods Enzymol.* 152:190-199, Academic Press, Inc. (1987).

Fuerst T.R., et al., "Use of a Hybrid Vaccinia Virus-T7 RNA Polymerase System for Expression of Target Genes," *Mol Cell Biol* 7:2538-2544, American Society for Microbiology/DC (1987).

Galfrè, G. and Milstein, C., "Preparation of Monoclonal Antibodies: Strategies and Procedures," *Methods Enzymol* 73:3-47, Academic Press, Inc. (1981).

Glockshuber, R., et al., "The Disulfide Bonds in Antibody Variable Domains: Effects on Stability, Folding in Vitro, and Functional Expression in *Escherichia coli*," *Biochemistry* 31:1270-1279, American Chemical Society (1992).

Gossen, M., et al., "Transcriptional Activation by Tetracyclines in Mammalian Cells," *Science* 268:1766-1769, American Association for the Adcancement of Science (1995).

(56) References Cited

OTHER PUBLICATIONS

Griffiths, A.D., et al., "Isolation of high affinity human antibodies directly from large synthetic repertoires," *Embo J.* 13:3245-3260, Oxford University Press (1994).
Griffiths, G.M. and Milstein C., "The Analysis of Structural Diversity in the Antibody Response," in *Hybridoma Technology in the Biosciences and Medicine*, Springer, T.A., ed., Plenum Press, New York, NY, pp. 103-115, (1985).
Güssow, D., et al., "Generating Binding Acitivities from *Escherichia coli* by Expression of a Repertoire of Immunoglobulin Variable Domains," *Cold Spring Harb. Symp. Quant. Biol.* 6:265-272, Cold Spring Harbor Laboratory Press (1989).
Hammers-Casterman, C., et al., "Naturally occurring antibodies devoid of light chains," *Nature* 363:446-448, Macmillan Magazines, Ltd. (1993).
Higuchi, K., et al., "Cell display library for gene cloning of variable regions of human antibodies to hepatitis B surface antigen," *J. Immunol. Methods* 202:193-204, Elsevier Science B.V. (1997).
Himly, M., et al., "Defective Vaccinia Virus as a Biologically Safe Tool for the Overproduction of Recombinant Human Secretory Proteins," *Protein Expr.Purif.* 14:317-326, Academic Press, Inc. (1998).
Hirata, Y., et al., "Molecular Structure of a Gene, *VMA1*, Encoding the Catalytic Subunit of $H^+$-Translocating Adenosine Triphosphate from Vacuolar Membranes of *Saccharomyces cerevisiae*," *J. Biol. Chem.* 265:6726-6733, American Society for Biochemistry and Molecular Biology, Inc. (1990).
Hogrefe, H.H., et al., "A bacteriophage lambda vector for the cloning and expression of immunoglobulin Fab fragments on the surface of filamentous phage," *Gene* 128:119-126, Elsevier Science Publishers B.V. (1993).
Holzer, G.W., et al., "Construction of a Vaccinia Virus Deficient in the Essential DNA Repair Enzyme Uracil DNA Glycosylase by a Complementing Cell Line," *J. Virol.* 71:4997-5002, American Society for Microbiology/DC (1997).
Hoogenboom, H.R., et al., "Multi-subunit proteins on the surface of filamentous phage: methodologies for displaying antibody (Fab) heavy and light chains," *Nucleic Acids Res.* 19:4133-4137, Oxford University Press (1991).
Huse, W.D., et al., "Generation of a Large Combinatorial Library of the Immunoglobulin Repertoire in Phage Lambda," *Science* 246:1275-1281, American Association for the Advancement of Science (1989).
Huse, W., "Combinatorial Antibody Expression Libraries in Filamentous Phage," in *Antibody Engineering: A Practical Guide*, Borrebaeck, C.A.K., ed., W.H. Freeman and Company, New York, N.Y., (1992).
Huston, J.S., et al., "Protein Enigeering of Single-Chain Fv Analogs and Fusion Proteins," *Methods Enzymol.* 203:46-121, Academic Press, Inc. (1991).
Huston, J.S., et al., "Protein Engineering of antibody binding sites: Recovery of specific activity in an anti-dioxin single-chain Fv analogue produced in *Escherichia coli*," *Proc. Natl. Acad. Sci. USA* 85:5879-5883, National Academy Press (1988).
Iverson, S.A., et al., "A Combinatorial System for Cloning and Expressing Catalytic Antibody Repertoire in *Escherichia coli*," *Cold Spring Harb. Symp. Quant. Biol.* 6:273-281, Cold Spring Harbor Laboratory Press, 1989.
Jespers, L.S., et al., "Guiding the Selection of Human Antibodies from Phage Display Repertoires to a Single Epitope of an Antigen," *Biotechnology (N Y)* 12:899-903, Nature America, Inc. (1994).
Kang, A.S., et al., "Linkage of recognition and replication functions by assembling combinatorial antibody Fab libraries along phage surfaces," *Proc. Natl. Acad. Sci. USA* 88:4363-4366, National Academy Press (1991).
Kang, A.S., et al. "Antibody redesign by chain shuffling from random combinatorial immunoglobulin libraries," *Proc. Natl. Acad. Sci. USA* 88:11120-11123, National Academy Press (1991).
Kearney, J.F., et al., "A new mouse myeloma cell line that has lost immunoglobulin expression but permits the construction of antibody-secreting hybrid cell lines," *J. Immunol.* 123:1548-1550, The Williams & Wilkens Co. (1979).
Kitamura, T., et al., "Efficient screening of retroviral cDNA expression libraries," *Proc. Natl. Acad. Sci. USA* 92:9146-9150, National Academy Press (1995).
Kitamura, T., "New experimental approaches in retrovirus-mediated expression screening," *Int. J. Hematol.* 67:351-359, Elsevier Science Ireland, Ltd. (1998).
Larrick, J.W., et al., "Rapid cloning of rearranged immunoglobulin genes from human hybridoma cells using mixed primers and the polymerase chain reaction," *Biochem. Biophys. Res. Commun.* 160:1250-1256, Academic Press Inc. (1989).
Larrick, J.W., et al., "Generation of specific human monoclonal antibodies by in vitro expansion of human B cells: A novel recombinant DNA approach," in *Progress in Biotechnology*, Borrebaeck, C.A.K., Elsevier, Amsterdam, pp. 231-246 (1988).
Lee, C.C., et al., "Generation of cDNA Probes Directed by Amino Acid Sequence: Cloning of Urate Oxidase," *Science* 239:1288-1291, American Association for the Advancement of Science (1988).
Loh, E.Y., et al., "Polymerase Chain Reaction with Single-Sided Specificity: Analysis of T Cell Receptor ÿChain," *Science* 243:217-220, American Association for the Advancement of Science (1989).
Mack, D.H., et al., "A sensitive method for the identification of uncharacterized viruses related to known virus groups: Hepadnavirus model system," *Proc. Natl. Acad. Sci. USA* 85:6977-6981, National Acadamy Press (1988).
Mahon, G.M. and Whitehead, I.P., "Retrovirus cDNA Expression Library Screening for Oncogenes," *Methods Enzymol.* 332:211-221, Academic Press, Inc. (2001).
Marks, J.D., et al., "By-passing immunization from V-gene libraries displayed on phage," *J. Mol. Biol.* 222:581-597, Academic Press, Inc. (1991).
Marks, J.D., et al., "Oligonucleotide primers for polymerase chain reaction amplification of human immunoglobulin variable genes and design of family-specific oligonucleotide probes," *Eur. J. Immunol.* 21:985-991, VCH Verlagsgesellschaft mbH, (1991).
Marks, J., "Learning How to Bottle the Immune System," *Science* 246:1250-1251, American Association for the Advancement of Science (1989).
Martin, F., et al., "Affinity selection of a camelized VH domain antibody inhibitor of hepatits C virus NS3 protease," *Protein Eng.* 10:607-614, Oxford University Press (1997).
McCafferty, J., et al., "Phage antibodies: filamentous phage displaying antibody variable domains," *Nature* 348:552-554, Macmillan Magazines, Ltd. (1990).
Merchlinsky, M. and Moss, B., "Introduction of Foreign DNA into the Vaccinia Virus Genome by in Vitro Ligation: Recombination-Independent Selectable Cloning Vectors," *Virology* 190:522-526, Academic Press, Inc. (1992).
Merchlinsky, M., et al., "Construction and Characterization of Vaccinia Direct Ligation Vectors," *Virol.* 238:444-451, Academic Press, Inc. (1997).
Misawa, K., et al., "A method to identify cDNAs based on localization of green fluorescent protein fusion products," *Proc. Natl. Acad. Sci. USA* 97:3062-3066, National Academy Press (2000).
Moore, G.P., et al., "Genetically Engineered Antibodies," *Clin. Chem.* 35:1849-1853, American Association of Clinical Chemistry (1989).
Morrison, S.L., et al., "Transfectomas Provide Novel Chimeric Antibodies," *Science* 229:1202-1207, American Association for the Advancement of Science (1985).
Moss, B., "Vaccinia Virus: A Tool for Research and Vaccine Development," *Science* 252:1662-1667, American Association for the Advancement of Science (1991).
Mullinax, R.L., et al., "Identification of human antibody fragment clones specific for tetanus toxoid in a bacteriophage ÿimmunoexpression library," *Proc. Natl. Acad. Sci. USA* 87:8095-8099, National Academy Press (1990).
Muyldermans, S., et al., "Recognition of antigens by single-domain antibody fragments: the superfluous luxury of paired domains," *Trends Biochem. Sci.* 26:230-235, Elsevier Science, Ltd. (Apr. 2001).

(56) References Cited

OTHER PUBLICATIONS

Neuberger, M.S., "Expression and regulation of immunoglobulin heavy chain gene transected into lymphoid cells," *Embo J.* 2:1373-1378, IRL Press, Ltd. (1983).
Neuberger, M.S., "Making novel antibodies by expressing transfected immunoglobulin genes," *Trends Biochem. Sci.* 10:347-349, Elsevier Science Publishers B.V. (1985).
Neuberger, M.S., et al., "Construction of novel antibodies by use of DNA transfection: design of plasmid vectors," *Philos. Trans. R. Soc. Lond. A.* 317:425-432, Royal Society (1986).
Ohara, O., et al., "One-sided polymerase chain reaction: The amplification of cDNA," *Proc. Natl. Acad. Sci. USA* 86:5673-5677, National Academy Press (1989).
Oi, V.T., et al., "Immunoglobulin gene expression in transformed lymphoid cells," *Proc. Natl. Acad. Sci. USA* 80:825-829, National Academy Press (1983).
Onishi, M., et al., "Applications of retrovirus-mediated expression cloning," *Exp. Hematol.* 24:324-329, Elsevier Science, Inc. (1996).
Orlandi, R., et al., "Cloning immunoglobulin variable domains for expression by the polymerase chain reaction," *Proc. Natl. Acad. Sci. USA* 86:3833-3837, National Academy Press (1989).
Pfleiderer, M., et al., "A novel vaccinia virus expression system allowing construction of recombinants without the need for selection markers, plasmids and bacterial hosts," *J. Gen. Virol.* 76:2957-2962, Society for General Microbiology (1995).
Potter, H., et al., "Enhancer-dependent expression of human ÿimmunoglobulin genes introduced into mouse pre-B lymphocytes by electroporation," *Proc. Natl. Acad. Sci. USA* 81:7161-7165, National Academy Press (1984).
Proba, K., et al., "A Natural Antibody Missing a Cysteine in VH: Consequences for Thermodynamic Stability and Folding," *J. Mol. Biol.* 265:161-172, Academic Press, Ltd. (1997).
Proba, K., et al., "Antibody scFv Fragments Without Disulfide Bonds Made by Molecular Evolution," *J. Mol. Biol.* 275:245-253, Academic Press, Ltd. (1998).
Rader, C., et al., "A phage display approach for rapid antibody humanization: Designed combinatorial V gene libraries," *Proc. Natl. Acad. Sci. USA* 95:8910-8915, National Academy Press (1998).
Rathbun, G., et al., "Making antigen-receptor genes," *Nature* 342:863-864, Macmillan Magazines, Ltd. (1989).
Rayner, J.R. and Gonda, T.J., "A simple and efficient procedure for generating stable expression libraries by cDNA cloning in a retroviral vector" *Molec. Cell. Biol.* 14:880-887, American Society for Microbiology (1994).
Riechmann, L., "Rearrangement of the Former VL Interface in the Solution Structure of a Camelised, Single Antibody VH Domain," *J. Mol. Biol.* 259:957-969, Academic Press Ltd. (1996).
Reichmann., L., et al., "Reshaping human antibodies for therapy," *Nature* 332:323-327, Macmillan Magazines, Ltd. (1988).
Riechmann, L. and Muyldermans, S., "Single domain antibodies: comparison of camel VH and camelised human VH domains," *J. Immunol. Methods* 231:25-38, Elsevier Science B.V. (1999).
Roth, M.E., et al., "Selection of Variable-Joining Region Combinations in the α Chain of the T Cell Receptor," *Science* 241:1354-1358, American Association for the Advancement of Science (1988).
Russell, S.J., et al., "Retroviral vectors displaying functional antibody fragments," *Nucl. Acids Res.* 21:1081-1085, Oxford University Press (1993).
Saiki, R.K., et al., "Primer-Directed Enzymatic Amplification of DNA with a Thermostable DNA Polymerase," *Science* 239:487-491, American Association for the Advancement of Science (1998).
Sastry, L., et al., "Cloning of the immunological repertoire in *Escherichia coli* for generation of monoclonal catalytic antibodies: Construction of a heavy chain variable region-specific cDNA library," *Proc. Natl. Acad. Sci. USA* 86:5728-5732, National Academy Press (1989).
Scharf, S.J., et al., "Direct Cloning and Sequence Analysis of Enzymatically Amplified Genomic Sequences," *Science* 233:1076-1078, American Association for the Advancement of Science (1986).
Scheiflinger, F., et al., "Construction of chimeric vaccinia viruses by molecular cloning and packaging," *Proc. Natl. Acad Sci USA* 89:9977-9981, National Academy Press (1992).
Skerra, A. and Plückthun, A., "Assembly of a Functional Immunoglobulin Fv Fragment in *Esherichia coli*," *Science* 240:1038-1041, American Association for the Advancement of Science (1988).
Smith, E.S., et al., "Lethality-based selection of recombinant genes in mammalian cells: Application to identifying tumor antigens," *Nat. Med.* 7:967-972, Nature Publishing Company (Aug. 2001).
Smith, E.S, et al., "Identification and Characterization of a Shared Murine Tumor Antigen," transcript of Ph.D. Thesis Seminar, Sep. 18, 1998.
Smith, E.S., "Identification and Characterization of a Shared Murine Tumor Antigen," Ph.D. Thesis, University of Rochester, Jun. 30, 1999.
Sommer, R. and Tautz, D., "Minimal homology requirements for PCR primers," *Nucleic Acids Res.* 17:6749, IRL Press (1989).
Songsivilai, S., et al., "Cloning and sequencing of human ÿimmunoglobulin genes by the polymerase chain reaction," *Eur. J. Immunol.* 20:2661-2666, VCH Gesellschaft GmbH (1990).
Sorge, J., et al., "Amphotropic Retrovirus Vector System for Human Cell Gene Transfer," *Mol. Cell Biol.* 4:1730-1737, American Society for Microbiology/DC (1984).
Transue, T.R., et al., "Camel Single-Domain Antibody Inhibits Enzyme by Mimicking Carbohydrate Substrate," *Proteins* 32:515-522, John Wiley & Sons, Inc. (1998).
Verhoeyen, M. and Riechmann, L., "Engineering of Antibodies," *Bioessays* 8:74-78, Company of Biologists, Ltd. (1988).
Ward, E.S., et al., "Binding activities of a repertoire of single immunoglobulin variable domains secreted from *Escherichia coli*," *Nature* 341:544-546, Macmillan Magazines, Ltd. (1989).
Waterhouse, P., et al., "Combinatorial infection and in vivo recombination: a strategy for making large phage antibody repertoires," *Nucl. Acids Res.* 21:2265-2266, Oxford University Press (1993).
Whitehead, I., et al., "Expression Cloning of Oncogenes by Retroviral Transfer of cDNA Libraries," *Mol. Cell Bio.* 15:704-710, American Society for Microbiology/DC (1995).
Winter, G., et al., "Making Antibodies by Phage Display Technology," *Annu. Rev. Immunol.* 12:433-55, Annual Reviews, Inc. (1994).
Winter, G. and Milstein, C., "Man-made antibodies," *Nature* 349:293-299, Macmillan Magazines, Ltd. (1991).
Wong, B.Y., et al., "High-Efficiency Identification of Genes by Functional Analysis from a Retroviral cDNA Expression Library," *J. Virol.* 68:5523-5531, American Society for Microbiology/DC (1994).
Zebedee, S.L., et al., "Human combinatorial antibody libraries to hepatitis B surface antigen," *Proc. Natl. Acad. Sci. USA* 89:3175-3179, National Academy Press (1992).
Declaration Under 37 C.F.R. § 1.132 of Dr. Walter J. Storkus, signed on Oct. 26, 2007, along with Exhibits A1-A3 cited therein, as filed in related co-pending U.S. Appl. No. 10/465,808, on Oct. 30, 2007.
International Search report for International Patent Application No. PCT/US01/43076, mailed Apr. 1, 2003, European Patent Office, The Netherlands, only ref listed separately in IDS were considered.
Office Action in related co-pending U.S. Appl. No. 09/987,456, mailed on Sep. 7, 2004.
Office Action in related co-pending U.S. Appl. No. 09/987,456, mailed on Apr. 21, 2005.
Office Action in related co-pending U.S. Appl. No. 09/987,456, mailed on Nov. 2, 2005.
Office Action in related co-pending U.S. Appl. No. 09/987,456, mailed on Apr. 21, 2006.
Office Action in related co-pending U.S. Appl. No. 09/987,456, mailed on Oct. 31, 2006.
Examiner's Answer in related co-pending U.S. Appl. No. 09/987,456, mailed on Aug. 10, 2007.
Office Action in related co-pending U.S. Appl. No. 10/465,808, mailed on May 8, 2007.
Office Action in related co-pending U.S. Appl. No. 10/465,808, mailed on Oct. 16, 2007.

(56) References Cited

OTHER PUBLICATIONS

Office Action in related co-pending U.S. Appl. No. 10/465,808, mailed on Mar. 3, 2008.
BPAI Decision on Appeal in co-pending U.S. Appl. No. 09/987,456, mailed on Mar. 29, 2010.
Record of Oral Hearing in co-pending U.S. Appl. No. 09/987,456, mailed on Apr. 2, 2010.
Notice of Allowance of co-pending U.S. Appl. No. 09/987,456, mailed on Apr. 6, 2010.

* cited by examiner

CONSTRUCTION OF scFV EXPRESSION VECTORS

CONSTRUCTION OF pVHE-X-G1.

1. p7.5tk 7.5K PROMOTER       NOTI       APAI

5'- GGCCAAAAATTGAAAAAACTAGATCTATTTATTGCACGCGGCCGCCATGGGCCCGGCC -3'

2. p7.5/ATG0/tk 7.5K PROMOTER       NOTI      BAMHI SMAI PSTI

5'- GGCCAAAAATTGAAAAAACTAGATCTATTTATTGCACGCGGCCGCGTGGATCCCCCGGGCTGCAGGAA

TRANSLATION    TRANSCRIPTION
         SALI                                STOP CODONS    STOP SIGNAL

TTCGATATCAAGCTTATCGATACCGTCGACCTCGAGGGGGGGCCTAACTAACTAATTTTGTTTTTGT

APAI

GGGCCCGGCC -3'

FIG.12A 3. p7.5/ATG1/TK

START
   7.5K PROMOTER           NOTI        CODON BAMHI SMAI PSTI

5'- GGCCAAAAATTGAAAAACTAGATCTATTTATTGCACGCGGCCGCCATGGTGGATCCCCCGGGCTGCAGGAA

TRANSLATION     TRANSCRIPTION
      SALI                    STOP CODONS     STOP SIGNAL

TTCGATATCAAGCTTATCGATACCGTCGACCTCGAGGGGGGGCCTAACTAACTAATTTGTTTTTGT

APAI
GGGCCCGGCC -3'

FIG.12B

CONSTRUCTION OF IgM-Fas FUSION PRODUCTS

CONSTRUCTS:

(a) VH-CH1-TM-DD (b) VH-CH1-CH2-CH3-CH4-TM-DD (c) VH-CH1-CH2-CH3-CH4(TM)-DD

Expression of Igα and Igβ in the transfected COS7 and HeLaS3 cell lines.

SEQUENCE LISTING

<160> NUMBER OF SEQ ID NOS: 154

<210> SEQ ID NO 1
<211> LENGTH: 57
<212> TYPE: DNA
<213> ORGANISM: Artificial Sequence
<220> FEATURE:
<223> OTHER INFORMATION: p7.5/tk promoter

<400> SEQUENCE: 1
ggccaaaaat tgaaaaacta gatctatttta ttgcacgcgg ccgccatggg cccggcc    57

<210> SEQ ID NO 2
<211> LENGTH: 145
<212> TYPE: DNA
<213> ORGANISM: Artificial Sequence
<220> FEATURE:
<223> OTHER INFORMATION: p 7.5/ATG0/tk promoter

<400> SEQUENCE: 2
ggccaaaaat tgaaaaacta gatctatttta ttgcacgcgg ccgccgtgga tcccccgggc    60
tgcaggaatt cgatatcaag cttatcgata ccgtcgacct cgaggggggg cctaactaac   120
taattttgtt tttgtgggcc cggcc                                         145

<210> SEQ ID NO 3
<211> LENGTH: 148
<212> TYPE: DNA
<213> ORGANISM: Artificial Sequence
<220> FEATURE:
<223> OTHER INFORMATION: p 7.5/ATG1/tk promoter

<400> SEQUENCE: 3
ggccaaaaat tgaaaaacta gatctatttta ttgcacgcgg ccgccatggt ggatccccg    60 ggctgcagga attcgatatc aagcttatcg ataccgtcga cctcgagggg gggcctaact   120
aactaatttt gttttttgtgg gcccggcc                                    148

<210> SEQ ID NO 4
<211> LENGTH: 149
<212> TYPE: DNA
<213> ORGANISM: Artificial Sequence
<220> FEATURE:
<223> OTHER INFORMATION: p7.5/ATG2/tk vector

<400> SEQUENCE: 4
ggccaaaaat tgaaaaacta gatctatttta ttgcacgcgg ccgccatgag tggatccccc    60
gggctgcagg aattcgatat caagcttatc gataccgtcg acctcgaggg ggggcctaac   120
taactaattt tgttttttgtg ggcccggcc                                   149

<210> SEQ ID NO 5
<211> LENGTH: 150
<212> TYPE: DNA
<213> ORGANISM: Artificial Sequence
<220> FEATURE:
<223> OTHER INFORMATION: p7.5/ATG3/tk vector

<400> SEQUENCE: 5
ggccaaaaat tgaaaaacta gatctatttta ttgcacgcgg ccgccatgac gtggatcccc    60
cgggctgcag gaattcgata tcaagcttat cgataccgtc gacctcgagg gggggcctaa   120
ctaactaatt ttgttttttgt gggcccggcc                                  150

```
<210> SEQ ID NO 6
<211> LENGTH: 15
<212> TYPE: PRT
<213> ORGANISM: Artificial Sequence
<220> FEATURE:
<223> OTHER INFORMATION: linker peptide

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: linker peptide

<400> SEQUENCE: 7

Glu Ser Gly Arg Ser Gly Gly Gly Gly Ser Gly Gly Gly Gly Ser
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: linker peptide

<400> SEQUENCE: 8

Glu Gly Lys Ser Ser Gly Ser Gly Ser Glu Ser Lys Ser Thr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: linker peptide

<400> SEQUENCE: 9

Glu Gly Lys Ser Ser Gly Ser Gly Ser Glu Ser Lys Ser Thr Gln
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: linker peptide

<400> SEQUENCE: 10

Glu Gly Lys Ser Ser Gly Ser Gly Ser Glu Ser Lys Val Asp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: linker peptide

<400> SEQUENCE: 11

Gly Ser Thr Ser Gly Ser Gly Lys Ser Ser Glu Gly Lys Gly
1               5                   10

<210> SEQ ID NO 12
```

```
<211> LENGTH: 18
<212> TYPE: PRT
<213> ORGANISM: Artificial Sequence
<220> FEATURE:
<223> OTHER INFORMATION: linker peptide

<400> SEQUENCE: 12

Lys Glu Ser Gly Ser Val Ser Glu Gln Leu Ala Gln Phe Arg Ser
1               5                   10                  15

Leu Asp

<210> SEQ ID NO 13
<211> LENGTH: 16
<212> TYPE: PRT
<213> ORGANISM: Artificial Sequence
<220> FEATURE:
<223> OTHER INFORMATION: linker peptide

<400> SEQUENCE: 13

Glu Ser Gly Ser Val Ser Ser Glu Glu Leu Ala Phe Arg Ser Leu Asp
1               5                   10                  15

<210> SEQ ID NO 14
<211> LENGTH: 1555
<212> TYPE: DNA
<213> ORGANISM: Artificial Sequence
<220> FEATURE:
<223> OTHER INFORMATION: pVHE transfer plasmid

<400> SEQUENCE: 14
ggccaaaaat tgaaaaacta gatctattta ttgcacgcgg ccgcaaacca tgggatggag      60
ctgtatcatc ctcttcttgg tagcaacagc tacaggcgcg catatggtca ccgtctcctc     120
agggagtgca tccgccccaa ccctttttccc cctcgtctcc tgtgagaatt ccccgtcgga    180
tacgagcagc gtggccgttg ctgcctcgc acaggactttc cttcccgact ccatcacttt    240
ctcctggaaa tacaagaaca actctgacat cagcagcacc cggggcttcc catcagtcct    300 gagaggggggc aagtacgcag ccacctcaca ggtgctgctg ccttccaagg acgtcatgca    360
gggcacagac gaacacgtgg tgtgcaaagt ccagcacccc aacggcaaca agaaaagaa     420 cgtgcctctt ccagtgattg ctgagctgcc tcccaaagtg agcgtcttcg tcccacccccg    480 cgacggcttc ttcggcaacc cccgcagcaa gtccaagctc atctgccagg ccacgggttt    540
cagtccccgg cagattcagg tgtcctggct gcgcgagggg aagcaggtgg ggtctggcgt    600
caccacggac caggtgcagg ctgaggccaa agagtctggg cccacgacct acaaggtgac    660
tagcacactg accatcaaag agagcgactg gctcagccag agcatgttca cctgccgcgt    720
ggatcacagg ggcctgacct tccagcagaa tgcgtcctcc atgtgtgtcc ccgatcaaga    780
cacagccatc cgggtcttcg ccatccccccc atccttgcc agcatcttcc tcaccaagtc    840
caccaagttg acctgcctgg tcacagacct gaccacctat gacagcgtga ccatctcctg    900
gacccgccag aatggcgaag ctgtgaaaac ccacaccaac atctccgaga gccaccccaa    960
tgccactttc agcgccgtgg gtgaggccag catctgcgag gatgactgga attccgggga   1020
gaggttcacg tgcaccgtga cccacacaga cctgccctcg ccactgaagc agaccatctc   1080
ccggcccaag ggggtggccc tgcacaggcc cgatgtctac ttgctgccac cagccccggga  1140 gcagctgaac ctgcgggagt cggccaccat cacgtgcctg gtgacgggct ctctccccgc   1200
ggacgtcttc gtgcagtgga tgcagagggg gcagcccttg tccccggaga agtatgtgac   1260 cagcgccccca atgcctgagc cccaggcccc aggccggtac ttcgcccaca gcatcctgac   1320
```

```
cgtgtccgaa gaggaatgga acacggggga gacctacacc tgcgtggtgg cccatgaggc    1380
cctgcccaac agggtcactg agaggaccgt ggacaagtcc accgaggggg aggtgagcgc    1440
cgacgaggag ggctttgaga acctgtgggc caccgcctcc accttcatcg tcctcttcct    1500
cctgagcctc ttctacagta ccaccgtcac cttgttcaag gtgaaatgag tcgac         1555
```

<210> SEQ ID NO 15
<211> LENGTH: 6
<212> TYPE: DNA
<213> ORGANISM: Artificial Sequence
<220> FEATURE:
<223> OTHER INFORMATION: unique BssHII site in pVHE

<400> SEQUENCE: 15

```
gcgcgc                                                                   6
```

<210> SEQ ID NO 16
<211> LENGTH: 7
<212> TYPE: DNA
<213> ORGANISM: Artificial Sequence
<220> FEATURE:
<223> OTHER INFORMATION: Unique BstEII site in pVHE

<400> SEQUENCE: 16

```
ggtcacc                                                                  7
```

<210> SEQ ID NO 17
<211> LENGTH: 446
<212> TYPE: DNA
<213> ORGANISM: Artificial Sequence
<220> FEATURE:
<223> OTHER INFORMATION: pVKE transfer plasmid

<400> SEQUENCE: 17

```
ggccaaaaat tgaaaaacta gatctatttt ttgcacgcgg ccgcccatgg gatggagctg      60
tatcatcctc ttcttggtag caacagctac aggcgtgcac ttgactcgag atcaaacgaa     120
ctgtggctgc accatctgtc ttcatcttcc cgccatctga tgagcagttg aaatctggaa     180
ctgcctctgt tgtgtgcctg ctgaataact tctatcccag agaggccaaa gtacagtgga     240
aggtggataa cgccctccaa tcgggtaact cccaggagag tgtcacagag caggacagca     300
aggacagcac ctacagcctc agcagcaccc tgacgctgag caaagcagac tacgagaaac     360
acaaagtcta cgcctgcgaa gtcacccatc agggcctgag ctcgcccgtc acaaagagct     420
tcaacagggg agagtgttag gtcgac                                          446
```

<210> SEQ ID NO 18
<211> LENGTH: 6
<212> TYPE: DNA
<213> ORGANISM: Artificial Sequence
<220> FEATURE:
<223> OTHER INFORMATION: unique ApaLI site in pVKE plasmid

<400> SEQUENCE: 18

```
gtgcac                                                                   6
```

<210> SEQ ID NO 19
<211> LENGTH: 6
<212> TYPE: DNA
<213> ORGANISM: Artificial Sequence
<220> FEATURE:
<223> OTHER INFORMATION: unique XhoI site in pVKE plasmid

<400> SEQUENCE: 19

-continued ctcgag                                                                    6

<210> SEQ ID NO 20
<211> LENGTH: 455
<212> TYPE: DNA
<213> ORGANISM: Artificial Sequence
<220> FEATURE:
<223> OTHER INFORMATION: pVLE transfer plasmid

<400> SEQUENCE: 20
ggccaaaaat tgaaaaacta gatctattta ttgcacgcgg ccgcccatgg gatggagctg      60
tatcatcctc ttcttggtag caacagctac aggcgtgcac ttgactcgag aagcttaccg     120
tcctacgaac tgtggctgca ccatctgtct tcatcttccc gccatctgat gagcagttga     180
aatctggaac tgcctctgtt gtgtgcctgc tgaataactt ctatcccaga gaggccaaag     240
tacagtggaa ggtggataac gccctccaat cgggtaactc ccaggagagt gtcacagagc     300
aggacagcaa ggacagcacc tacagcctca gcagcaccct gacgctgagc aaagcagact     360
acgagaaaca caaagtctac gcctgcgaag tcacccatca gggcctgagc tcgcccgtca     420
caaagagctt caacagggga gagtgttagg tcgac                                 455

<210> SEQ ID NO 21
<211> LENGTH: 6
<212> TYPE: DNA
<213> ORGANISM: Artificial Sequence
<220> FEATURE:
<223> OTHER INFORMATION: Unique ApaLI site in pVLE plasmid

<400> SEQUENCE: 21 gtgcac                                                                    6

<210> SEQ ID NO 22
<211> LENGTH: 6
<212> TYPE: DNA
<213> ORGANISM: Artificial Sequence
<220> FEATURE:
<223> OTHER INFORMATION: Unique HindIII site in pVLE

<400> SEQUENCE: 22 aagctt                                                                    6

<210> SEQ ID NO 23
<211> LENGTH: 9
<212> TYPE: PRT
<213> ORGANISM: Artificial Sequence
<220> FEATURE:
<223> OTHER INFORMATION: H-2Kd restricted peptide

<400> SEQUENCE: 23

Gly Tyr Lys Ala Gly Met Ile His Ile
1               5

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
attaggatcc ggtcaccgtc tcctcaggg                                          29

<210> SEQ ID NO 25
<211> LENGTH: 34

```
<212> TYPE: DNA
<213> ORGANISM: Artificial Sequence
<220> FEATURE:
<223> OTHER INFORMATION: primer

<400> SEQUENCE: 25
attagtcgac tcatttcacc ttgaacaagg tgac                                34

<210> SEQ ID NO 26
<211> LENGTH: 47
<212> TYPE: DNA
<213> ORGANISM: Artificial Sequence
<220> FEATURE:
<223> OTHER INFORMATION: cassette used to generate p7.5/tk2

<400> SEQUENCE: 26
gcggccgcaa accatggaaa gcgcgcatat ggtcaccaaa agtcgac                  47

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
attaggatcc ggtcaccgtc tcctcaggg                                     29

<210> SEQ ID NO 28
<211> LENGTH: 31
<212> TYPE: DNA
<213> ORGANISM: Artificial Sequence
<220> FEATURE:
<223> OTHER INFORMATION: primer

<400> SEQUENCE: 28
attagtcgac tcagtagcag gtgccagctg t                                  31

<210> SEQ ID NO 29
<211> LENGTH: 50
<212> TYPE: DNA
<213> ORGANISM: Artificial Sequence
<220> FEATURE:
<223> OTHER INFORMATION: cassette used to generate p7.5/tk3

<400> SEQUENCE: 29
gcggccgccc atggatacgt gcacttgact cgagaagctt agtagtcgac               50

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
caggactcga gatcaaacga actgtggctg                                    30

<210> SEQ ID NO 31
<211> LENGTH: 39
<212> TYPE: DNA
<213> ORGANISM: Artificial Sequence
<220> FEATURE:
<223> OTHER INFORMATION: primer

<400> SEQUENCE: 31
aatatgtcga cctaacactc tcccctgttg aagctcttt                          39
```

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32
aatatgtcga cctaacactc tcccctgttg aagctctt                              38

<210> SEQ ID NO 33
<211> LENGTH: 40
<212> TYPE: DNA
<213> ORGANISM: Artificial Sequence
<220> FEATURE:
<223> OTHER INFORMATION: primer

<400> SEQUENCE: 33
atttaagctt accgtcctac gaactgtggc tgcaccatct                            40

<210> SEQ ID NO 34
<211> LENGTH: 38
<212> TYPE: DNA
<213> ORGANISM: Artificial Sequence
<220> FEATURE:
<223> OTHER INFORMATION: primer

<400> SEQUENCE: 34
ttttgcgcgc actcccaggt gcagctggtg cagtctgg                              38

<210> SEQ ID NO 35
<211> LENGTH: 38
<212> TYPE: DNA
<213> ORGANISM: Artificial Sequence
<220> FEATURE:
<223> OTHER INFORMATION: primer

<400> SEQUENCE: 35
ttttgcgcgc actccgaggt gcagctggtg gagtctgg                              38

<210> SEQ ID NO 36
<211> LENGTH: 38
<212> TYPE: DNA
<213> ORGANISM: Artificial Sequence
<220> FEATURE:
<223> OTHER INFORMATION: primer

<400> SEQUENCE: 36
ttttgcgcgc actcccaggt gcagctgcag gagtcggg                              38

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
gacggtgacc agggtgccct ggcccca                                          27

<210> SEQ ID NO 38
<211> LENGTH: 27
<212> TYPE: DNA
<213> ORGANISM: Artificial Sequence
<220> FEATURE:
<223> OTHER INFORMATION: primer

```
<400> SEQUENCE: 38
gacggtgacc agggtgccac ggccca                                    27

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
gacggtgacc attgtccctt ggccca                                    27

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
gacggtgacc agggttccct ggccca                                    27

<210> SEQ ID NO 41
<211> LENGTH: 27
<212> TYPE: DNA
<213> ORGANISM: Artificial Sequence
<220> FEATURE:
<223> OTHER INFORMATION: primer

<400> SEQUENCE: 41
gacggtgacc gtggtccctt ggccca                                    27

<210> SEQ ID NO 42
<211> LENGTH: 35
<212> TYPE: DNA
<213> ORGANISM: Artificial Sequence
<220> FEATURE:
<223> OTHER INFORMATION: primer

<400> SEQUENCE: 42
tttgtgcact ccgacatcca gatgacccag tctcc                          35

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
tttgtgcact ccgatgttgt gatgactcag tctcc                          35

<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
tttgtgcact ccgaaattgt gttgacgcag tctcc                          35

<210> SEQ ID NO 45
<211> LENGTH: 35
```

```
<212> TYPE: DNA
<213> ORGANISM: Artificial Sequence
<220> FEATURE:
<223> OTHER INFORMATION: primer

<400> SEQUENCE: 45
tttgtgcact ccgacatcgt gatgacccag tctcc                           35

<210> SEQ ID NO 46
<211> LENGTH: 35
<212> TYPE: DNA
<213> ORGANISM: Artificial Sequence
<220> FEATURE:
<223> OTHER INFORMATION: primer

<400> SEQUENCE: 46
tttgtgcact ccgaaacgac actcacgcag tctcc                           35

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47
tttgtgcact ccgaaattgt gctgactcag tctcc                           35

<210> SEQ ID NO 48
<211> LENGTH: 27
<212> TYPE: DNA
<213> ORGANISM: Artificial Sequence
<220> FEATURE:
<223> OTHER INFORMATION: primer

<400> SEQUENCE: 48
gatctcgagc ttggtccctt ggccgaa                                    27

<210> SEQ ID NO 49
<211> LENGTH: 27
<212> TYPE: DNA
<213> ORGANISM: Artificial Sequence
<220> FEATURE:
<223> OTHER INFORMATION: primer

<400> SEQUENCE: 49
gatctcgagc ttggtcccct ggccaaa                                    27

<210> SEQ ID NO 50
<211> LENGTH: 27
<212> TYPE: DNA
<213> ORGANISM: Artificial Sequence
<220> FEATURE:
<223> OTHER INFORMATION: primer

<400> SEQUENCE: 50
gatctcgagt ttggtcccag ggccgaa                                    27

<210> SEQ ID NO 51
<211> LENGTH: 27
<212> TYPE: DNA
<213> ORGANISM: Artificial Sequence
<220> FEATURE:
<223> OTHER INFORMATION: primer

<400> SEQUENCE: 51
gatctcgagc ttggtccctc cgccgaa                                    27
```

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
aatctcgagt cgtgtccctt ggccgaa                                          27

<210> SEQ ID NO 53
<211> LENGTH: 35
<212> TYPE: DNA
<213> ORGANISM: Artificial Sequence
<220> FEATURE:
<223> OTHER INFORMATION: primer

<400> SEQUENCE: 53
tttgtgcact cccagtctgt gttgacgcag ccgcc                                 35

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
tttgtgcact cccagtctgc cctgactcag cctgc                                 35

<210> SEQ ID NO 55
<211> LENGTH: 35
<212> TYPE: DNA
<213> ORGANISM: Artificial Sequence
<220> FEATURE:
<223> OTHER INFORMATION: primer

<400> SEQUENCE: 55
tttgtgcact cctcctatgt gctgactcag ccacc                                 35

<210> SEQ ID NO 56
<211> LENGTH: 35
<212> TYPE: DNA
<213> ORGANISM: Artificial Sequence
<220> FEATURE:
<223> OTHER INFORMATION: primer

<400> SEQUENCE: 56
tttgtgcact cctcttctga gctgactcag gaccc                                 35

<210> SEQ ID NO 57
<211> LENGTH: 35
<212> TYPE: DNA
<213> ORGANISM: Artificial Sequence
<220> FEATURE:
<223> OTHER INFORMATION: primer

<400> SEQUENCE: 57
tttgtgcact cccacgttat actgactcaa ccgcc                                 35

<210> SEQ ID NO 58
<211> LENGTH: 35
<212> TYPE: DNA
<213> ORGANISM: Artificial Sequence
<220> FEATURE:
<223> OTHER INFORMATION: primer

<400> SEQUENCE: 58
tttgtgcact cccaggctgt gctcactcag ccgtc                    35

<210> SEQ ID NO 59
<211> LENGTH: 35
<212> TYPE: DNA
<213> ORGANISM: Artificial Sequence
<220> FEATURE:
<223> OTHER INFORMATION: primer

<400> SEQUENCE: 59
tttgtgcact ccaattttat gctgactcag cccca                    35

<210> SEQ ID NO 60
<211> LENGTH: 35
<212> TYPE: DNA
<213> ORGANISM: Artificial Sequence
<220> FEATURE:
<223> OTHER INFORMATION: primer

<400> SEQUENCE: 60
tttgtgcact cccaggctgt ggtgactcag gagcc                    35

<210> SEQ ID NO 61
<211> LENGTH: 27
<212> TYPE: DNA
<213> ORGANISM: Artificial Sequence
<220> FEATURE:
<223> OTHER INFORMATION: primer

<400> SEQUENCE: 61
ggtaagcttg gtcccagttc cgaagac                             27

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
ggtaagcttg gtccctccgc cgaat                               25

<210> SEQ ID NO 63
<211> LENGTH: 39
<212> TYPE: DNA
<213> ORGANISM: Artificial Sequence
<220> FEATURE:
<223> OTHER INFORMATION: primer

<400> SEQUENCE: 63
aatatgcgcg cactcccagg tgcagctggt gcagtctgg                39

<210> SEQ ID NO 64
<211> LENGTH: 39
<212> TYPE: DNA
<213> ORGANISM: Artificial Sequence
<220> FEATURE:
<223> OTHER INFORMATION: primer

<400> SEQUENCE: 64
aatatgcgcg cactcccagg tcaccttgaa ggagtctgg                39

<210> SEQ ID NO 65
<211> LENGTH: 39

```
<212> TYPE: DNA
<213> ORGANISM: Artificial Sequence
<220> FEATURE:
<223> OTHER INFORMATION: primer

<400> SEQUENCE: 65
aatatgcgcg cactccgagg tgcagctggt ggagtctgg                            39

<210> SEQ ID NO 66
<211> LENGTH: 39
<212> TYPE: DNA
<213> ORGANISM: Artificial Sequence
<220> FEATURE:
<223> OTHER INFORMATION: primer

<400> SEQUENCE: 66
aatatgcgcg cactcccagg tgcagctgca ggagtcggg                            39

<210> SEQ ID NO 67
<211> LENGTH: 38
<212> TYPE: DNA
<213> ORGANISM: Artificial Sequence
<220> FEATURE:
<223> OTHER INFORMATION: primer

<400> SEQUENCE: 67
aatatgcgcg cactccgagg tgcagctggt gcagtctg                             38

<210> SEQ ID NO 68
<211> LENGTH: 29
<212> TYPE: DNA
<213> ORGANISM: Artificial Sequence
<220> FEATURE:
<223> OTHER INFORMATION: primer

<400> SEQUENCE: 68
gagacggtga ccagggtgcc ctggcccca                                       29

<210> SEQ ID NO 69
<211> LENGTH: 29
<212> TYPE: DNA
<213> ORGANISM: Artificial Sequence
<220> FEATURE:
<223> OTHER INFORMATION: primer

<400> SEQUENCE: 69
gagacggtga ccagggtgcc acggcccca                                       29

<210> SEQ ID NO 70
<211> LENGTH: 29
<212> TYPE: DNA
<213> ORGANISM: Artificial Sequence
<220> FEATURE:
<223> OTHER INFORMATION: primer

<400> SEQUENCE: 70
gagacggtga ccattgtccc ttggcccca                                       29

<210> SEQ ID NO 71
<211> LENGTH: 29
<212> TYPE: DNA
<213> ORGANISM: Artificial Sequence
<220> FEATURE:
<223> OTHER INFORMATION: primer

<400> SEQUENCE: 71
gagacggtga ccagggttcc ctggcccca                                       29
```

<210> SEQ ID NO 72
<211> LENGTH: 29
<212> TYPE: DNA
<213> ORGANISM: Artificial Sequence
<220> FEATURE:
<223> OTHER INFORMATION: primer

<400> SEQUENCE: 72
gagacggtga ccgtggtccc ttggcccca                              29

<210> SEQ ID NO 73
<211> LENGTH: 37
<212> TYPE: DNA
<213> ORGANISM: Artificial Sequence
<220> FEATURE:
<223> OTHER INFORMATION: primer

<400> SEQUENCE: 73
caggagtgca ctccgacatc cagatgaccc agtctcc                     37

<210> SEQ ID NO 74
<211> LENGTH: 37
<212> TYPE: DNA
<213> ORGANISM: Artificial Sequence
<220> FEATURE:
<223> OTHER INFORMATION: primer

<400> SEQUENCE: 74
caggagtgca ctccgatgtt gtgatgactc agtctcc                     37

<210> SEQ ID NO 75
<211> LENGTH: 37
<212> TYPE: DNA
<213> ORGANISM: Artificial Sequence
<220> FEATURE:
<223> OTHER INFORMATION: primer

<400> SEQUENCE: 75
caggagtgca ctccgaaatt gtgttgacgc agtctcc                     37

<210> SEQ ID NO 76
<211> LENGTH: 37
<212> TYPE: DNA
<213> ORGANISM: Artificial Sequence
<220> FEATURE:
<223> OTHER INFORMATION: primer

<400> SEQUENCE: 76
caggagtgca ctccgacatc gtgatgaccc agtctcc                     37

<210> SEQ ID NO 77
<211> LENGTH: 37
<212> TYPE: DNA
<213> ORGANISM: Artificial Sequence
<220> FEATURE:
<223> OTHER INFORMATION: primer

<400> SEQUENCE: 77
caggagtgca ctccgaaacg acactcacgc agtctcc                     37

<210> SEQ ID NO 78
<211> LENGTH: 37
<212> TYPE: DNA
<213> ORGANISM: Artificial Sequence
<220> FEATURE:
<223> OTHER INFORMATION: primer

```
<400> SEQUENCE: 78
caggagtgca ctccgaaatt gtgctgactc agtctcc                                37

<210> SEQ ID NO 79
<211> LENGTH: 29
<212> TYPE: DNA
<213> ORGANISM: Artificial Sequence
<220> FEATURE:
<223> OTHER INFORMATION: primer

<400> SEQUENCE: 79
ttgatctcga gcttggtccc ttggccgaa                                         29

<210> SEQ ID NO 80
<211> LENGTH: 29
<212> TYPE: DNA
<213> ORGANISM: Artificial Sequence
<220> FEATURE:
<223> OTHER INFORMATION: primer

<400> SEQUENCE: 80
ttgatctcga gcttggtccc ctggccaaa                                         29

<210> SEQ ID NO 81
<211> LENGTH: 29
<212> TYPE: DNA
<213> ORGANISM: Artificial Sequence
<220> FEATURE:
<223> OTHER INFORMATION: primer

<400> SEQUENCE: 81
ttgatctcga gtttggtccc agggccgaa                                         29

<210> SEQ ID NO 82
<211> LENGTH: 29
<212> TYPE: DNA
<213> ORGANISM: Artificial Sequence
<220> FEATURE:
<223> OTHER INFORMATION: primer

<400> SEQUENCE: 82
ttgatctcga gcttggtccc tccgccgaa                                         29

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
ttaatctcga gtcgtgtccc ttggccgaa                                         29

<210> SEQ ID NO 84
<211> LENGTH: 37
<212> TYPE: DNA
<213> ORGANISM: Artificial Sequence
<220> FEATURE:
<223> OTHER INFORMATION: primer

<400> SEQUENCE: 84
cagatgtgca ctcccagtct gtgttgacgc agccgcc                                37

<210> SEQ ID NO 85
<211> LENGTH: 37
```

```
<212> TYPE: DNA
<213> ORGANISM: Artificial Sequence
<220> FEATURE:
<223> OTHER INFORMATION: primer

<400> SEQUENCE: 85
cagatgtgca ctcccagtct gccctgactc agcctgc                             37

<210> SEQ ID NO 86
<211> LENGTH: 37
<212> TYPE: DNA
<213> ORGANISM: Artificial Sequence
<220> FEATURE:
<223> OTHER INFORMATION: primer

<400> SEQUENCE: 86
cagatgtgca ctcctcctat gtgctgactc agccacc                             37

<210> SEQ ID NO 87
<211> LENGTH: 37
<212> TYPE: DNA
<213> ORGANISM: Artificial Sequence
<220> FEATURE:
<223> OTHER INFORMATION: primer

<400> SEQUENCE: 87
cagatgtgca ctcctcttct gagctgactc aggaccc                             37

<210> SEQ ID NO 88
<211> LENGTH: 37
<212> TYPE: DNA
<213> ORGANISM: Artificial Sequence
<220> FEATURE:
<223> OTHER INFORMATION: primer

<400> SEQUENCE: 88
cagatgtgca ctcccacgtt atactgactc aaccgcc                             37

<210> SEQ ID NO 89
<211> LENGTH: 37
<212> TYPE: DNA
<213> ORGANISM: Artificial Sequence
<220> FEATURE:
<223> OTHER INFORMATION: primer

<400> SEQUENCE: 89
cagatgtgca ctcccaggct gtgctcactc agccgtc                             37

<210> SEQ ID NO 90
<211> LENGTH: 37
<212> TYPE: DNA
<213> ORGANISM: Artificial Sequence
<220> FEATURE:
<223> OTHER INFORMATION: primer

<400> SEQUENCE: 90
cagatgtgca ctccaatttt atgctgactc agcccca                             37

<210> SEQ ID NO 91
<211> LENGTH: 37
<212> TYPE: DNA
<213> ORGANISM: Artificial Sequence
<220> FEATURE:
<223> OTHER INFORMATION: primer

<400> SEQUENCE: 91
cagatgtgca ctcccaggct gtggtgactc aggagcc                             37
```

<210> SEQ ID NO 92
<211> LENGTH: 29
<212> TYPE: DNA
<213> ORGANISM: Artificial Sequence
<220> FEATURE:
<223> OTHER INFORMATION: primer

<400> SEQUENCE: 92
acggtaagct tggtcccagt tccgaagac                               29

<210> SEQ ID NO 93
<211> LENGTH: 29
<212> TYPE: DNA
<213> ORGANISM: Artificial Sequence
<220> FEATURE:
<223> OTHER INFORMATION: primer

<400> SEQUENCE: 93
acggtaagct tggtccctcc gccgaatac                               29

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
atgttacgtc ctgtagaaac c                                       21

<210> SEQ ID NO 95
<211> LENGTH: 21
<212> TYPE: DNA
<213> ORGANISM: Artificial Sequence
<220> FEATURE:
<223> OTHER INFORMATION: primer

<400> SEQUENCE: 95
tcattgtttg cctccctgct g                                       21

<210> SEQ ID NO 96
<211> LENGTH: 28
<212> TYPE: DNA
<213> ORGANISM: Artificial Sequence
<220> FEATURE:
<223> OTHER INFORMATION: primer

<400> SEQUENCE: 96
aaagcggccg ccccgggatg ttacgtcc                                28

<210> SEQ ID NO 97
<211> LENGTH: 29
<212> TYPE: DNA
<213> ORGANISM: Artificial Sequence
<220> FEATURE:
<223> OTHER INFORMATION: primer

<400> SEQUENCE: 97
aaagggcccg gcgcgcctca ttgtttgcc                               29

<210> SEQ ID NO 98
<211> LENGTH: 37
<212> TYPE: DNA
<213> ORGANISM: Artificial Sequence
<220> FEATURE:
<223> OTHER INFORMATION: primer -continued

```
<400> SEQUENCE: 98
aaaggatcca taatgaattc agtgactgta tcacacg                               37

<210> SEQ ID NO 99
<211> LENGTH: 34
<212> TYPE: DNA
<213> ORGANISM: Artificial Sequence
<220> FEATURE:
<223> OTHER INFORMATION: primer

<400> SEQUENCE: 99
cttgcggccg cttaataaat aaaccttga gccc                                   34

<210> SEQ ID NO 100
<211> LENGTH: 34
<212> TYPE: DNA
<213> ORGANISM: Artificial Sequence
<220> FEATURE:
<223> OTHER INFORMATION: primer

<400> SEQUENCE: 100
attgagctct taatactttt gtcgggtaac agag                                  34

<210> SEQ ID NO 101
<211> LENGTH: 29
<212> TYPE: DNA
<213> ORGANISM: Artificial Sequence
<220> FEATURE:
<223> OTHER INFORMATION: primer

<400> SEQUENCE: 101
ttactcgaga gtgtcgcaat tggatttt                                         29

<210> SEQ ID NO 102
<211> LENGTH: 29
<212> TYPE: DNA
<213> ORGANISM: Artificial Sequence
<220> FEATURE:
<223> OTHER INFORMATION: primer

<400> SEQUENCE: 102
aaagaattcc tttattgtca tcggccaaa                                        29

<210> SEQ ID NO 103
<211> LENGTH: 30
<212> TYPE: DNA
<213> ORGANISM: Artificial Sequence
<220> FEATURE:
<223> OTHER INFORMATION: primer

<400> SEQUENCE: 103
aatctgcagt cattgtttgc ctccctgctg                                       30

<210> SEQ ID NO 104
<211> LENGTH: 37
<212> TYPE: DNA
<213> ORGANISM: Artificial Sequence
<220> FEATURE:
<223> OTHER INFORMATION: primer

<400> SEQUENCE: 104
aaagaattca taatgaattc agtgactgta tcacacg                               37

<210> SEQ ID NO 105
<211> LENGTH: 32
```

```
<212> TYPE: DNA
<213> ORGANISM: Artificial Sequence
<220> FEATURE:
<223> OTHER INFORMATION: primer

<400> SEQUENCE: 105
cttggatcct taataaataa acccttgagc cc                              32

<210> SEQ ID NO 106
<211> LENGTH: 27
<212> TYPE: DNA
<213> ORGANISM: Artificial Sequence
<220> FEATURE:
<223> OTHER INFORMATION: primer

<400> SEQUENCE: 106
aataagcttt actccagata atatgga                                    27

<210> SEQ ID NO 107
<211> LENGTH: 23
<212> TYPE: DNA
<213> ORGANISM: Artificial Sequence
<220> FEATURE:
<223> OTHER INFORMATION: primer

<400> SEQUENCE: 107
aatctgcagc ccagttccat ttt                                        23

<210> SEQ ID NO 108
<211> LENGTH: 23
<212> TYPE: DNA
<213> ORGANISM: Artificial Sequence
<220> FEATURE:
<223> OTHER INFORMATION: primer

<400> SEQUENCE: 108
aatggatcct catccagcgg cta                                        23

<210> SEQ ID NO 109
<211> LENGTH: 27
<212> TYPE: DNA
<213> ORGANISM: Artificial Sequence
<220> FEATURE:
<223> OTHER INFORMATION: primer

<400> SEQUENCE: 109
aatgagctct agtacctaca acccgaa                                    27

<210> SEQ ID NO 110
<211> LENGTH: 28
<212> TYPE: DNA
<213> ORGANISM: Artificial Sequence
<220> FEATURE:
<223> OTHER INFORMATION: primer

<400> SEQUENCE: 110
aaagtcgacg gccaaaaatt gaaatttt                                   28

<210> SEQ ID NO 111
<211> LENGTH: 25
<212> TYPE: DNA
<213> ORGANISM: Artificial Sequence
<220> FEATURE:
<223> OTHER INFORMATION: primer

<400> SEQUENCE: 111
aatggatcct cattgtttgc ctccc                                      25
```

```
<210> SEQ ID NO 112
<211> LENGTH: 51
<212> TYPE: DNA
<213> ORGANISM: Artificial Sequence
<220> FEATURE:
<223> OTHER INFORMATION: cassette converting Plasmid p7.5/tk3 to p7.5/
      tk3.1

<400> SEQUENCE: 112
gcggccgccc atggatagcg tgcacttgac tcgagaagct tagtagtcga c          51

<210> SEQ ID NO 113
<211> LENGTH: 22
<212> TYPE: DNA
<213> ORGANISM: Artificial Sequence
<220> FEATURE:
<223> OTHER INFORMATION: region substituted to convert plasmid p7.5/
      tk3.1 to p7.5/tk3.2

<400> SEQUENCE: 113
ctcgagaagc ttagtagtcg ac                                          22

<210> SEQ ID NO 114
<211> LENGTH: 78
<212> TYPE: DNA
<213> ORGANISM: Artificial Sequence
<220> FEATURE:
<223> OTHER INFORMATION: cassette for the conversion of plasmid p7.5/
      tk3.1 to p7.5/tk3.2

<400> SEQUENCE: 114
ctcgagatca agagggtaa atcttccgga tctggttccg aaggcgcgca tgcggtcacc   60
gtctcctcat gagtcgac                                               78

<210> SEQ ID NO 115
<211> LENGTH: 42
<212> TYPE: DNA
<213> ORGANISM: Artificial Sequence
<220> FEATURE:
<223> OTHER INFORMATION: p7.5/tk3.2 linker

<400> SEQUENCE: 115
gagggtaaat cttccggatc tggttccgaa ggcgcgcact cc                     42

<210> SEQ ID NO 116
<211> LENGTH: 14
<212> TYPE: PRT
<213> ORGANISM: Artificial Sequence
<220> FEATURE:
<223> OTHER INFORMATION: p7.5/tk3.2 linker

<400> SEQUENCE: 116

Glu Gly Lys Ser Ser Gly Ser Gly Ser Glu Gly Ala His Ser
1               5                   10

<210> SEQ ID NO 117
<211> LENGTH: 16
<212> TYPE: DNA
<213> ORGANISM: Artificial Sequence
<220> FEATURE:
<223> OTHER INFORMATION: region substituted to convert plasmid p7.5/
      tk3.1 to p7.5/tk3.3

<400> SEQUENCE: 117
aagcttagta gtcgac                                                 16
```

<210> SEQ ID NO 118
<211> LENGTH: 81
<212> TYPE: DNA
<213> ORGANISM: Artificial Sequence
<220> FEATURE:
<223> OTHER INFORMATION: cassette for the conversion of plasmid p7.5/
     tk3.1 to p7.5/tk3.3

<400> SEQUENCE: 118
aagcttaccg tcctagaggg taaatcttcc ggatctggtt ccgaaggcgc gcatgcggtc    60
accgtctcct catgagtcga c                                              81

<210> SEQ ID NO 119
<211> LENGTH: 42
<212> TYPE: DNA
<213> ORGANISM: Artificial Sequence
<220> FEATURE:
<223> OTHER INFORMATION: p7.5/tk3.3 linker

<400> SEQUENCE: 119
gagggtaaat cttccggatc tggttccgaa ggcgcgcact cc                       42

<210> SEQ ID NO 120
<211> LENGTH: 14
<212> TYPE: PRT
<213> ORGANISM: Artificial Sequence
<220> FEATURE:
<223> OTHER INFORMATION: p7.5/tk3.3 linker

<400> SEQUENCE: 120

Glu Gly Lys Ser Ser Gly Ser Gly Ser Glu Gly Ala His Ser
1               5                  10

<210> SEQ ID NO 121
<211> LENGTH: 29
<212> TYPE: DNA
<213> ORGANISM: Artificial Sequence
<220> FEATURE:
<223> OTHER INFORMATION: primer

<400> SEQUENCE: 121
attaggatcc ggtcaccgtc tcctcagcc                                      29

<210> SEQ ID NO 122
<211> LENGTH: 34
<212> TYPE: DNA
<213> ORGANISM: Artificial Sequence
<220> FEATURE:
<223> OTHER INFORMATION: primer

<400> SEQUENCE: 122
attagtcgac tcatttaccc ggagacaggg agag                                34

<210> SEQ ID NO 123
<211> LENGTH: 24
<212> TYPE: DNA
<213> ORGANISM: Artificial Sequence
<220> FEATURE:
<223> OTHER INFORMATION: primer

<400> SEQUENCE: 123
aatatggtca ccgtctcctc agcc                                           24

<210> SEQ ID NO 124
<211> LENGTH: 36
<212> TYPE: DNA

```
<213> ORGANISM: Artificial Sequence
<220> FEATURE:
<223> OTHER INFORMATION: primer
<220> FEATURE:
<221> NAME/KEY: misc_feature
<222> LOCATION: (2)..(3)
<223> OTHER INFORMATION: May be any nucleotide
<220> FEATURE:
<221> NAME/KEY: misc_feature
<222> LOCATION: (5)..(6)
<223> OTHER INFORMATION: May be any nucleotide
<220> FEATURE:
<221> NAME/KEY: misc_feature
<222> LOCATION: (8)..(9)
<223> OTHER INFORMATION: May be any nucleotide
<220> FEATURE:
<221> NAME/KEY: misc_feature
<222> LOCATION: (11)..(12)
<223> OTHER INFORMATION: May be any nucleotide
<220> FEATURE:
<221> NAME/KEY: misc_feature
<222> LOCATION: (14)..(15)
<223> OTHER INFORMATION: May be any nucleotide
<220> FEATURE:
<221> NAME/KEY: misc_feature
<222> LOCATION: (17)..(18)
<223> OTHER INFORMATION: May be any nucleotide

<400> SEQUENCE: 124
mnnmnnmnnm nnmnnmnnntt caggtgctgg gcacgg                                36

<210> SEQ ID NO 125
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(2)
<223> OTHER INFORMATION: May be any Nucleotide
<220> FEATURE:
<221> NAME/KEY: misc_feature
<222> LOCATION: (4)..(5)
<223> OTHER INFORMATION: May be any Nucleotide
<220> FEATURE:
<221> NAME/KEY: misc_feature
<222> LOCATION: (7)..(8)
<223> OTHER INFORMATION: May be any Nucleotide
<220> FEATURE:
<221> NAME/KEY: misc_feature
<222> LOCATION: (10)..(11)
<223> OTHER INFORMATION: May be any Nucleotide
<220> FEATURE:
<221> NAME/KEY: misc_feature
<222> LOCATION: (13)..(14)
<223> OTHER INFORMATION: May be any Nucleotide
<220> FEATURE:
<221> NAME/KEY: misc_feature
<222> LOCATION: (16)..(17)
<223> OTHER INFORMATION: May be any Nucleotide

<400> SEQUENCE: 125
nnknnknnkn nknnknnkgt cttcctcttc ccccca                                36

<210> SEQ ID NO 126
<211> LENGTH: 23
<212> TYPE: DNA
<213> ORGANISM: Artificial Sequence
<220> FEATURE:
<223> OTHER INFORMATION: primer

<400> SEQUENCE: 126
aatatgtcga ctcatttacc cgg                                              23
```

```
<210> SEQ ID NO 127
<211> LENGTH: 28
<212> TYPE: DNA
<213> ORGANISM: Artificial Sequence
<220> FEATURE:
<223> OTHER INFORMATION: primer

<400> SEQUENCE: 127
acacggtcac cgtctcctca gggagtgc                                     28

<210> SEQ ID NO 128
<211> LENGTH: 31
<212> TYPE: DNA
<213> ORGANISM: Artificial Sequence
<220> FEATURE:
<223> OTHER INFORMATION: primer

<400> SEQUENCE: 128
agttagatct ggatcctgga agaggcacgt t                                 31

<210> SEQ ID NO 129
<211> LENGTH: 30
<212> TYPE: DNA
<213> ORGANISM: Artificial Sequence
<220> FEATURE:
<223> OTHER INFORMATION: primer

<400> SEQUENCE: 129
aacgtgcctc ttccaggatc cagatctaac                                   30

<210> SEQ ID NO 130
<211> LENGTH: 33
<212> TYPE: DNA
<213> ORGANISM: Artificial Sequence
<220> FEATURE:
<223> OTHER INFORMATION: primer

<400> SEQUENCE: 130
acgcgtcgac ctagaccaag ctttggattt cat                               33

<210> SEQ ID NO 131
<211> LENGTH: 21
<212> TYPE: DNA
<213> ORGANISM: Artificial Sequence
<220> FEATURE:
<223> OTHER INFORMATION: primer

<400> SEQUENCE: 131
ctctcccgcg gacgtcttcg t                                            21

<210> SEQ ID NO 132
<211> LENGTH: 31
<212> TYPE: DNA
<213> ORGANISM: Artificial Sequence
<220> FEATURE:
<223> OTHER INFORMATION: primer

<400> SEQUENCE: 132
agttagatct ggatccctca aagccctcct c                                 31

<210> SEQ ID NO 133
<211> LENGTH: 30
<212> TYPE: DNA
<213> ORGANISM: Artificial Sequence
<220> FEATURE:
<223> OTHER INFORMATION: primer
```

```
<400> SEQUENCE: 133
gaggagggct tgagggatc cagatctaac                                      30

<210> SEQ ID NO 134
<211> LENGTH: 30
<212> TYPE: DNA
<213> ORGANISM: Artificial Sequence
<220> FEATURE:
<223> OTHER INFORMATION: primer

<400> SEQUENCE: 134
aatagtggtg atatatttca ccttgaacaa                                      30

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
ttgttcaagg tgaaagtgaa gagaaaggaa                                      30

<210> SEQ ID NO 136
<211> LENGTH: 28
<212> TYPE: DNA
<213> ORGANISM: Artificial Sequence
<220> FEATURE:
<223> OTHER INFORMATION: primer

<400> SEQUENCE: 136
attagaattc atgcctgggg gtccagga                                        28

<210> SEQ ID NO 137
<211> LENGTH: 28
<212> TYPE: DNA
<213> ORGANISM: Artificial Sequence
<220> FEATURE:
<223> OTHER INFORMATION: primer

<400> SEQUENCE: 137
attaggatcc tcacggcttc tccagctg                                        28

<210> SEQ ID NO 138
<211> LENGTH: 28
<212> TYPE: DNA
<213> ORGANISM: Artificial Sequence
<220> FEATURE:
<223> OTHER INFORMATION: primer

<400> SEQUENCE: 138
attaggatcc atggccaggc tggcgttg                                        28

<210> SEQ ID NO 139
<211> LENGTH: 34
<212> TYPE: DNA
<213> ORGANISM: Artificial Sequence
<220> FEATURE:
<223> OTHER INFORMATION: primer

<400> SEQUENCE: 139
attaccagca cactggtcac tcctggcctg ggtg                                 34

<210> SEQ ID NO 140
<211> LENGTH: 69
<212> TYPE: DNA
```

```
<213> ORGANISM: Artificial Sequence
<220> FEATURE:
<223> OTHER INFORMATION: p7.5/tk promoter
<220> FEATURE:
<221> NAME/KEY: CDS
<222> LOCATION: (46)..(69)

<400> SEQUENCE: 140
ggccaaaaat tgaaaaacta gatctattta ttgcacgcgg ccgcc atg ggc ccg gcc      57
                                                 Met Gly Pro Ala
                                                  1 gcc aac ggc gga                                                       69
Ala Asn Gly Gly
 5

<210> SEQ ID NO 141
<211> LENGTH: 8
<212> TYPE: PRT
<213> ORGANISM: Artificial Sequence
<220> FEATURE:
<223> OTHER INFORMATION: Synthetic Construct

<400> SEQUENCE: 141

Met Gly Pro Ala Ala Asn Gly Gly
 1               5

<210> SEQ ID NO 142
<211> LENGTH: 75
<212> TYPE: DNA
<213> ORGANISM: Artificial Sequence
<220> FEATURE:
<223> OTHER INFORMATION: pE/Ltk promoter
<220> FEATURE:
<221> NAME/KEY: CDS
<222> LOCATION: (52)..(75)

<400> SEQUENCE: 142
ggccaaaaat tgaaatttta tttttttttt ttggaatata aagcggccgc c atg ggc      57
                                                        Met Gly
                                                         1 ccg gcc gcc aac ggc gga                                               75
Pro Ala Ala Asn Gly Gly
         5

<210> SEQ ID NO 143
<211> LENGTH: 8
<212> TYPE: PRT
<213> ORGANISM: Artificial Sequence
<220> FEATURE:
<223> OTHER INFORMATION: Synthetic Construct

<400> SEQUENCE: 143

Met Gly Pro Ala Ala Asn Gly Gly
 1               5

<210> SEQ ID NO 144
<211> LENGTH: 39
<212> TYPE: DNA
<213> ORGANISM: Artificial Sequence
<220> FEATURE:
<223> OTHER INFORMATION: Primer

<400> SEQUENCE: 144
aatatgcgcg cactcccagg tcaccttgaa ggagtctgg                            39

<210> SEQ ID NO 145
<211> LENGTH: 38
<212> TYPE: DNA
```

```
<213> ORGANISM: Artificial Sequence
<220> FEATURE:
<223> OTHER INFORMATION: Primer

<400> SEQUENCE: 145
aatatgcgcg cactccgagg tgcagctggt gcagtctg                              38

<210> SEQ ID NO 146
<211> LENGTH: 19
<212> TYPE: PRT
<213> ORGANISM: Artificial Sequence
<220> FEATURE:
<223> OTHER INFORMATION: Signal Sequence

<400> SEQUENCE: 146

Met Gly Trp Ser Cys Ile Ile Leu Phe Leu Val Ala Thr Ala Thr Gly
1               5                   10                  15

Ala His Ser

<210> SEQ ID NO 147
<211> LENGTH: 26
<212> TYPE: PRT
<213> ORGANISM: Artificial Sequence
<220> FEATURE:
<223> OTHER INFORMATION: Signal Sequence

<400> SEQUENCE: 147

Asn Leu Trp Thr Thr Ala Ser Thr Phe Ile Val Leu Phe Leu Leu Ser
1               5                   10                  15

Leu Phe Tyr Ser Thr Thr Val Thr Leu Phe
            20                  25

<210> SEQ ID NO 148
<211> LENGTH: 11
<212> TYPE: DNA
<213> ORGANISM: Artificial Sequence
<220> FEATURE:
<223> OTHER INFORMATION: start of VH FR1 primer

<400> SEQUENCE: 148
gcgcgcactc c                                                          11

<210> SEQ ID NO 149
<211> LENGTH: 6
<212> TYPE: DNA
<213> ORGANISM: Artificial Sequence
<220> FEATURE:
<223> OTHER INFORMATION: JH primers

<400> SEQUENCE: 149 gtcacc                                                                 6

<210> SEQ ID NO 150
<211> LENGTH: 9
<212> TYPE: DNA
<213> ORGANISM: Artificial Sequence
<220> FEATURE:
<223> OTHER INFORMATION: VK primer

<400> SEQUENCE: 150 gtgcactcc                                                              9

<210> SEQ ID NO 151
<211> LENGTH: 6
<212> TYPE: DNA
<213> ORGANISM: Artificial Sequence
```

```
<220> FEATURE:
<223> OTHER INFORMATION: JK primer

<400> SEQUENCE: 151 ctcgag                                                                    6

<210> SEQ ID NO 152
<211> LENGTH: 9
<212> TYPE: DNA
<213> ORGANISM: Artificial Sequence
<220> FEATURE:
<223> OTHER INFORMATION: VL primer

<400> SEQUENCE: 152 gtgcactcc                                                                 9

<210> SEQ ID NO 153
<211> LENGTH: 6
<212> TYPE: DNA
<213> ORGANISM: Artificial Sequence
<220> FEATURE:
<223> OTHER INFORMATION: JL primer

<400> SEQUENCE: 153 aagctt                                                                    6

<210> SEQ ID NO 154
<211> LENGTH: 8
<212> TYPE: PRT
<213> ORGANISM: Artificial Sequence
<220> FEATURE:
<223> OTHER INFORMATION: ovalbumin epitope

<400> SEQUENCE: 154

Ser Ile Ile Asn Phe Glu Lys Leu
1               5
```

IN VITRO METHODS OF PRODUCING AND IDENTIFYING IMMUNOGLOBULIN MOLECULES IN EUKARYOTIC CELLS

CROSS REFERENCE TO RELATED APPLICATIONS

This application is a continuation of U.S. patent application Ser. No. 09/987,456, filed Nov. 14, 2001, which claims benefit of U.S. Provisional Application No. 60/249,268, filed Nov. 17, 2000, U.S. Provisional Application No. 60/262,067, filed Jan. 18, 2001, U.S. Provisional Application No. 60/271,424, filed Feb. 27, 2001, and U.S. Provisional Application No. 60/298,087, filed Jun. 15, 2001, all of which are incorporated herein by reference in their entireties.

REFERENCE TO SEQUENCE LISTING SUBMITTED ELECTRONICALLY

The content of the electronically submitted substitute sequence listing, file name: 18210070008_sequence_listing_ascii.txt; Size: 35,313 bytes; and Date of Creation: Oct. 22, 2010, filed herewith, is incorporated herein by reference in its entirety.

BACKGROUND OF THE INVENTION

1. Field of the Invention

The present invention relates to a high efficiency method of expressing immunoglobulin molecules in eukaryotic cells, a method of producing immunoglobulin heavy and light chain libraries for expression in eukaryotic cells, methods of isolating immunoglobulins which bind specific antigens, and immunoglobulins produced by any of these methods.

2. Related Art

Immunoglobulin Production

Antibodies of defined specificity are being employed in an increasing number of diverse therapeutic applications.

Defined antibodies directed against self antigens are of particular value for in vivo therapeutic and diagnostic purposes. Many rodent monoclonal antibodies have been isolated using hybridoma technology and utilized for in vivo therapeutic and diagnostic purposes in humans. For example, an early application of these mouse monoclonal antibodies was as targeting agents to kill or image tumors (F. H. Deland and D. M. Goldenberg 1982 in 'Radionuclide Imaging' ed. D. E. Kuhl pp 289-297, Pergamon, Paris; R. Levy and R. A. Miller Ann. Rev. Med. 1983, 34 pp 107-116). However, the use of such antibodies in vivo can lead to problems. The foreign immunoglobulins can elicit an anti-immunoglobulin response which can interfere with therapy (R. A. Miller et al, 1983 Blood 62 988-995) or cause allergic or immune complex hypersensitivity (B. Ratner, 1943, Allergy, Anaphylaxis and Immunotherapy Williams and Wilkins, Baltimore). Accordingly, it is especially important for such applications to develop antibodies that are not themselves immunogenic in host, for example, to develop antibodies against human antigens that are not themselves immunogenic in humans.

It is a demanding task to isolate an antibody fragment with specificity against self antigen. Animals do not normally produce antibodies to self antigens, a phenomenon called tolerance (Nossal, G. J. *Science* 245:147-153 (1989)). In general, vaccination with a self antigen does not result in production of circulating antibodies. It is therefore difficult to raise antibodies to self antigens.

Previously, three general strategies have been employed to produce immunoglobulin molecules which specifically recognize "self" antigens. In one approach, rodent antibody sequences have been converted into human antibody sequences, by grafting the specialized complementarity-determining regions (CDR) that comprise the antigen-binding site of a selected rodent monoclonal antibody onto the framework regions of a human antibody (Winter, et al., United Kingdom Patent No. GB2188638B (1987); Reichmann. L., et al. *Nature* (London) 332:323-327 (1988); Foote, J., and Winter, G. *J. Mol. Biol.* 224:487-499 (1992)). In this approach, which has been termed antibody humanization, the three CDR loops of each rodent immunoglobulin heavy and light chain are grafted into homologous positions of the four framework regions of a corresponding human immunoglobulin chain. Because some of the framework residues also contribute to antibody affinity, the structure must, in general, be further refined by additional framework substitutions to enhance affinity. This can be a laborious and costly process.

More recently, transgenic mice have been generated that express human immunoglobulin sequences (Mendez, M. J., et al., *Nat. Genet.* 15:146-156 (1997)). While this strategy has the potential to accelerate selection of human antibodies, it shares with the antibody humanization approach the limitation that antibodies are selected from the available mouse repertoire which has been shaped by proteins encoded in the mouse genome rather than the human genome. This could bias the epitope specificity of antibodies selected in response to a specific antigen. For example, immunization of mice with a human protein for which a mouse homolog exists might be expected to result predominantly in antibodies specific for those epitopes that are different in humans and mice. These may, however, not be the optimal target epitopes.

An alternative approach, which does not suffer this same limitation, is to screen recombinant human antibody fragments displayed on bacteriophage (Vaughan, T. J., et al., *Nat. Biotechnol.* 14:309-314 (1996); Barbas, C. F., III Nat. Med. 1:837-839 (1995); Kay, B. K., et al. (eds.) "Phage Display of Peptides and Proteins" Academic Press (1996)) In phage display methods, functional immunoglobulin domains are displayed on the surface of a phage particle which carries polynucleotide sequences encoding them. In typical phage display methods, immunoglobulin fragments, e.g., Fab, Fv or disulfide stabilized Fv immunoglobulin domains are displayed as fusion proteins, i.e., fused to a phage surface protein. Examples of phage display methods that can be used to make the antibodies include those disclosed in Brinkman U. et al. (1995) J. Immunol. Methods 182:41-50; Ames, R. S. et al. (1995) J. Immunol. Methods 184:177-186; Kettleborough, C. A. et al. (1994) Eur. J. Immunol. 24:952-958; Persic, L. et al. (1997) Gene 187 9-18; Burton, D. R. et al. (1994) Advances in Immunology 57:191-280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

Since phage display methods normally only result in the expression of an antigen-binding fragment of an immunoglobulin molecule, after phage selection, the immunoglobulin coding regions from the phage must be isolated and re-cloned to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *Bio-*

*Techniques* 12(6):864-869 (1992); and Sawai, H. et al., *AJRI* 34:26-34 (1995); and Better, M. et al., *Science* 240:1041-1043 (1988) (said references incorporated by reference in their entireties).

Immunoglobulin libraries constructed in bacteriophage may derive from antibody producing cells of naïve or specifically immunized individuals and could, in principle, include new and diverse pairings of human immunoglobulin heavy and light chains. Although this strategy does not suffer from an intrinsic repertoire limitation, it requires that complementarity determining regions (CDRs) of the expressed immunoglobulin fragment be synthesized and fold properly in bacterial cells. Many antigen binding regions, however, are difficult to assemble correctly as a fusion protein in bacterial cells. In addition, the protein will not undergo normal eukaryotic post-translational modifications. As a result, this method imposes a different selective filter on the antibody specificities that can be obtained.

There is a need, therefore, for an alternative method to identify immunoglobulin molecules, and antigen-specific fragments thereof, from an unbiased immunoglobulin repertoire that can be synthesized, properly glycosylated and correctly assembled in eukaryotic cells.

Eukaryotic Expression Libraries. A basic tool in the field of molecular biology is the conversion of poly(A)$^+$ mRNA to double-stranded (ds) cDNA, which then can be inserted into a cloning vector and expressed in an appropriate host cell. A method common to many cDNA cloning strategies involves the construction of a "cDNA library" which is a collection of cDNA clones derived from the poly(A)$^+$ mRNA derived from a cell of the organism of interest. For example, in order to isolate cDNAs which express immunoglobulin genes, a cDNA library might be prepared from pre B cells, B cells, or plasma cells. Methods of constructing cDNA libraries in different expression vectors, including filamentous bacteriophage, bacteriophage lambda, cosmids, and plasmid vectors, are known. Some commonly used methods are described, for example, in Sambrook et al., *Molecular Cloning: A Laboratory Manual*, 2d Edition, Cold Spring Harbor Laboratory, publisher, Cold Spring Harbor, N.Y. (1990).

Many different methods of isolating target genes from cDNA libraries have been utilized, with varying success. These include, for example, the use of nucleic acid hybridization probes, which are labeled nucleic acid fragments having sequences complementary to the DNA sequence of the target gene. When this method is applied to cDNA clones in transformed bacterial hosts, colonies or plaques hybridizing strongly to the probe are likely to contain the target DNA sequences. Hybridization methods, however, do not require, and do not measure, whether a particular cDNA clone is expressed. Alternative screening methods rely on expression in the bacterial host, for example, colonies or plaques can be screened by immunoassay for binding to antibodies raised against the protein of interest. Assays for expression in bacterial hosts are often impeded, however, because the protein may not be sufficiently expressed in bacterial hosts, it may be expressed in the wrong conformation, and it may not be processed, and/or transported as it would in a eukaryotic system. Many of these problems have been encountered in attempts to produce immunoglobulin molecules in bacterial hosts, as alluded to above.

Accordingly, use of mammalian expression libraries to isolate cDNAs encoding immunoglobulin molecules would offer several advantages over bacterial libraries. For example, immunoglobulin molecules, and subunits thereof, expressed in eukaryotic hosts should be functional and should undergo any normal posttranslational modification. A protein ordinarily transported through the intracellular membrane system to the cell surface should undergo the complete transport process. Further, use of a eukaryotic system would make it possible to isolate polynucleotides based on functional expression of eukaryotic RNA or protein. For example, immunoglobulin molecules could be isolated based on their specificity for a given antigen.

With the exception of some recent lymphokine cDNAs isolated by expression in COS cells (Wong, G. G., et al., *Science* 228:810-815 (1985); Lee, F. et al., *Proc. Natl. Acad. Sci. USA* 83:2061-2065 (1986); Yokota, T., et al., *Proc. Natl. Acad. Sci. USA* 83:5894-5898 (1986); Yang, Y., et al., *Cell* 47:3-10 (1986)), few cDNAs have been isolated from mammalian expression libraries. There appear to be two principal reasons for this: First, the existing technology (Okayama, H. et al., *Mol. Cell. Biol.* 2:161-170 (1982)) for construction of large plasmid libraries is difficult to master, and library size rarely approaches that accessible by phage cloning techniques. (Huynh, T. et al., In: *DNA Cloning Vol, I, A Practical Approach*, Glover, D. M. (ed.), IRL Press, Oxford (1985), pp. 49-78). Second, the existing vectors are, with one exception (Wong, G. G., et al., *Science* 228:810-815 (1985)), poorly adapted for high level expression. Thus, expression in mammalian hosts previously has been most frequently employed solely as a means of verifying the identity of the protein encoded by a gene isolated by more traditional cloning methods.

Poxvirus Vectors. Poxvirus vectors are used extensively as expression vehicles for protein and antigen expression in eukaryotic cells. The ease of cloning and propagating vaccinia in a variety of host cells has led to the widespread use of poxvirus vectors for expression of foreign protein and as vaccine delivery vehicles (Moss, B., *Science* 252:1662-7 (1991)).

Large DNA viruses are particularly useful expression vectors for the study of cellular processes as they can express many different proteins in their native form in a variety of cell lines. In addition, gene products expressed in recombinant vaccinia virus have been shown to be efficiently processed and presented in association with MHC class I for stimulation of cytotoxic T cells. The gene of interest is normally cloned in a plasmid under the control of a promoter flanked by sequences homologous to a non-essential region in the virus and the cassette is introduced into the genome via homologous recombination. A panoply of vectors for expression, selection and detection have been devised to accommodate a variety of cloning and expression strategies. However, homologous recombination is an ineffective means of making a recombinant virus in situations requiring the generation of complex libraries or when the insert DNA is large. An alternative strategy for the construction of recombinant genomes relying on direct ligation of viral DNA "arms" to an insert and the subsequent rescue of infectious virus has been explored for the genomes of poxvirus (Merchlinsky, et al., 1992, Virology 190:522-526; Pfleiderer, et al., 1995, J. General Virology 76:2957-2962; Scheiflinger, et al., 1992, Proc. Natl. Acad. Sci. USA 89:9977-9981), herpesvirus (Rixon, et al., 1990, J. General Virology 71:2931-2939) and baculovirus (Ernst, et al., 1994, Nucleic Acids Research 22:2855-2856).

Poxviruses are ubiquitous vectors for studies in eukaryotic cells as they are easily constructed and engineered to express foreign proteins at high levels. The wide host range of the virus allows one to faithfully express proteins in a variety of cell types. Direct cloning strategies have been devised to extend the scope of applications for poxvirus viral chimeras in which the recombinant genomes are constructed in vitro by direct ligation of DNA fragments to vaccinia "arms" and transfection of the DNA mixture into cells infected with a helper virus (Merchlinsky, et al., 1992, Virology 190:522-526; Scheiflinger, et al., 1992, Proc. Natl. Acad. Sci. USA 89:9977-9981). This approach has been used for high level expression of foreign proteins (Pfleiderer, et al., 1995, J. Gen. Virology 76:2957-2962) and to efficiently clone fragments as large as 26 kilobases in length (Merchlinsky, et al., 1992, Virology 190:522-526).

Naked vaccinia virus DNA is not infectious because the virus cannot utilize cellular transcriptional machinery and relies on its own proteins for the synthesis of viral RNA. Previously, temperature sensitive conditional lethal (Merchlinsky, et al., 1992, Virology 190:522-526) or non-homologous poxvirus fowlpox (Scheiflinger, et al., 1992, Proc. Natl. Acad. Sci. USA 89:9977-9981) have been utilized as helper virus for packaging. An ideal helper virus will efficiently facilitate the production of infectious virus from input DNA, but will not replicate in the host cell or recombine with the vaccinia DNA products. Powlpox virus is a very useful helper virus for these reasons. It can enter mammalian cells and provide proteins required for the replication of input vaccinia virus DNA. However, it does not recombine with vaccinia DNA, and infectious fowlpox virions are not produced in mammalian cells. Therefore, it can be used at relatively high multiplicity of infection (MOI).

Customarily, a foreign protein coding sequence is introduced into the poxvirus genome by homologous recombination with infectious virus. In this traditional method, a previously isolated foreign DNA is cloned in a transfer plasmid behind a vaccinia promoter flanked by sequences homologous to a region in the poxvirus which is non-essential for viral replication. The transfer plasmid is introduced into poxvirus-infected cells to allow the transfer plasmid and poxvirus genome to recombine in vivo via homologous recombination. As a result of the homologous recombination, the foreign DNA is transferred to the viral genome.

Although traditional homologous recombination in poxviruses is useful for expression of previously isolated foreign DNA in a poxvirus, the method is not conducive to the construction of libraries, since the overwhelming majority of viruses recovered have not acquired a foreign DNA insert. Using traditional homologous recombination, the recombination efficiency is in the range of approximately 0.1% or less. Thus, the use of poxvirus vectors has been limited to subcloning of previously isolated DNA molecules for the purposes of protein expression and vaccine development.

Alternative methods using direct ligation vectors have been developed to efficiently construct chimeric genomes in situations not readily amenable for homologous recombination (Merchlinsky, M. et al., 1992, Virology 190:522-526; Scheiflinger, F. et al., 1992, Proc. Natl. Acad. Sci. USA. 89:9977-9981). In such protocols, the DNA from the genome is digested, ligated to insert DNA in vitro, and transfected into cells infected with a helper virus (Merchlinsky, M. et al., 1992, Virology 190:522-526, Scheiflinger, F. et al., 1992, Proc. Natl. Acad. Sci. USA 89:9977-9981). In one protocol, the genome was digested at a unique NotI site and a DNA insert containing elements for selection or detection of the chimeric genome was ligated to the genomic arms (Scheiflinger, F. et al., 1992, Proc. Natl. Acad. Sci. USA. 89:9977-9981). This direct ligation method was described for the insertion of foreign DNA into the vaccinia virus genome (Pfleiderer et al., 1995, J. General Virology 76:2957-2962).

Alternatively, the vaccinia WR genome was modified to produce vNotI/tk by removing the NotI site in the HindIII F fragment and reintroducing a NotI site proximal to the thymidine kinase gene such that insertion of a sequence at this locus disrupts the thymidine kinase gene, allowing isolation of chimeric genomes via use of drug selection (Merchlinsky, M. et al., 1992, *Virology* 190:522-526). The direct ligation vector vNotI/tk allows one to efficiently clone and propagate previously isolated DNA inserts at least 26 kilobase pairs in length (Merchlinsky, M. et al., 1992, Virology, 190:522-526). Although large DNA fragments are efficiently cloned into the genome, proteins encoded by the DNA insert will only be expressed at the low level corresponding to the thymidine kinase gene, a relatively weakly expressed early class gene in vaccinia. In addition, the DNA will be inserted in both orientations at the NotI site, and therefore might not be expressed at all. Additionally, although the recombination efficiency using direct ligation is higher than that observed with traditional homologous recombination, the resulting titer is relatively low.

Accordingly, poxvirus vectors were previously not used to identify previously unknown genes of interest from a complex population of clones, because a high efficiency, high titer-producing method of cloning did not exist for poxviruses. More recently, however, the present inventor developed a method for generating recombinant poxviruses using tri-molecular recombination. See Zauderer, WO 00/028016, published May 18, 2000, which is incorporated herein by reference in its entirety.

Tri-molecular recombination is a novel, high efficiency, high titer-producing method for producing recombinant poxviruses. Using the tri-molecular recombination method in vaccinia virus, the present inventor has achieved recombination efficiencies of at least 90%, and titers at least 2 orders of magnitude higher, than those obtained by direct ligation. According to the tri-molecular recombination method, a poxvirus genome is cleaved to produce two nonhomologous fragments or "arms." A transfer vector is produced which carries the heterologous insert DNA flanked by regions of homology with the two poxvirus arms. The arms and the transfer vector are delivered into a recipient host cell, allowing the three DNA molecules to recombine in vivo. As a result of the recombination, a single poxvirus genome molecule is produced which comprises each of the two poxvirus arms and the insert DNA.

SUMMARY OF THE INVENTION

In accordance with one aspect of the present invention, there is provided a method of identifying polynucleotides which encode an antigen-specific immunoglobulin molecule, or antigen-specific fragment thereof, from libraries of polynucleotides expressed in eukaryotic cells.

Also provided is a method of identifying polynucleotides which encode immunoglobulin molecules, or fragments thereof, which possess altered effector function.

Also provided is a method of constructing libraries of polynucleotides encoding immunoglobulin subunit polypeptides in eukaryotic cells using virus vectors, where the libraries are constructed by trimolecular recombination.

Further provided are methods of identifying host cells expressing antigen-specific immunoglobulin molecules, or antigen-specific fragments thereof on their surface by selecting and/or screening for antigen-induced cell death, antigen-induced signaling, or antigen-specific binding.

Also provided are methods of screening for soluble immunoglobulin molecules, or antigen-specific fragments thereof, expressed from eukaryotic host cells expressing libraries of polynucleotides encoding soluble secreted immunoglobulin molecules, through antigen binding or through detection of an antigen- or organism-specific function of the immunoglobulin molecule.

BRIEF DESCRIPTION OF THE FIGURES

FIG. 12A A modification in the nucleotide sequence of the p7.5/tk (SEQ ID NO:1) vaccinia transfer plasmid. A new vector, p7.5/ATG0/tk (SEQ ID NO:2), derived as described in the text from the p7.5/tk vaccinia transfer plasmid.

FIG. 12B A new vector, p7.5/ATG1/tk (SEQ ID NO:3) derived as described in the text from the p7.5/tk vaccinia transfer plasmid.

DETAILED DESCRIPTION OF THE PREFERRED EMBODIMENTS

Figure 1:
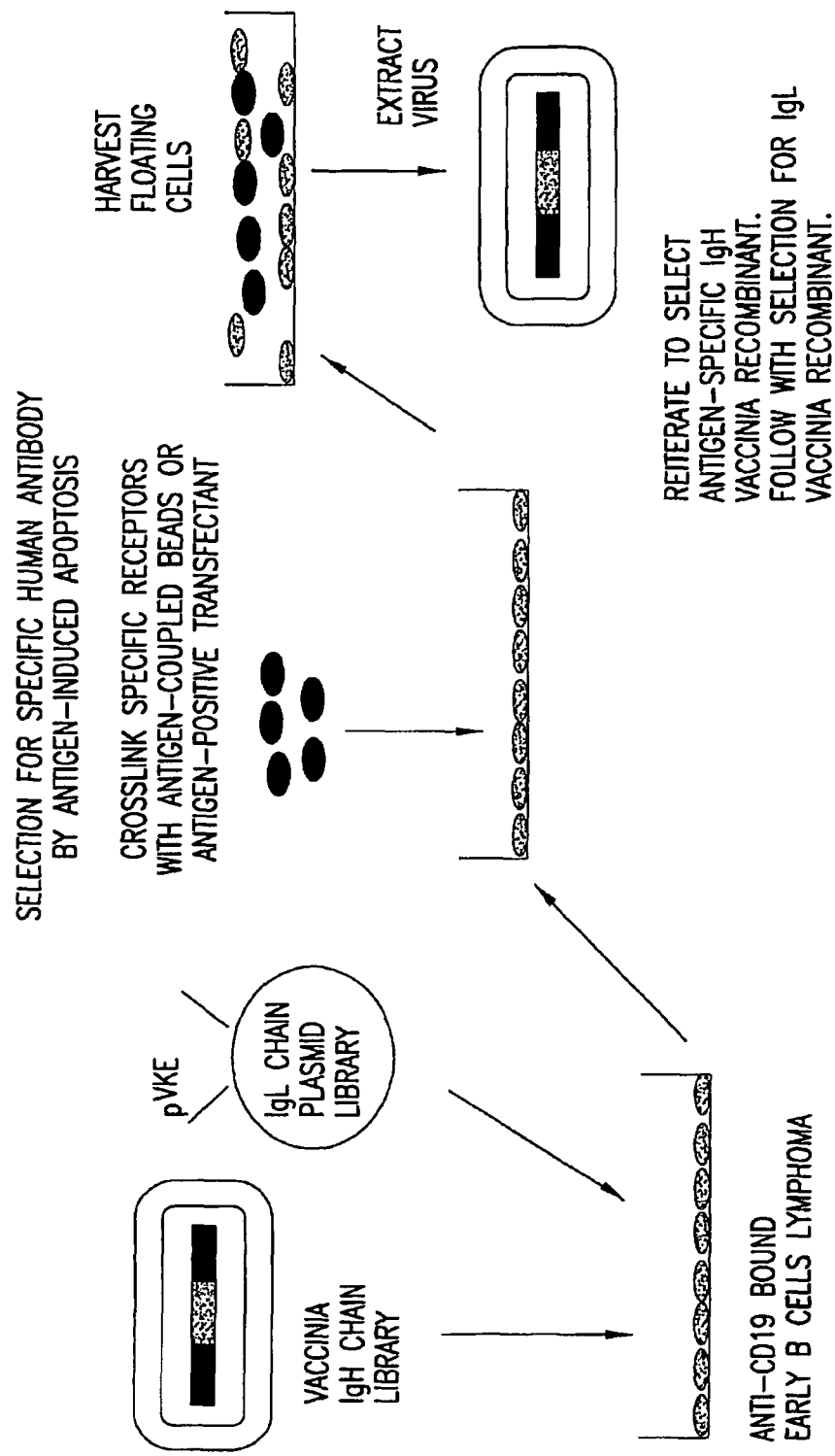
FIG. 1. Selection for specific human antibody by antigen-induced apoptosis.

The present invention is broadly directed to methods of identifying and/or producing functional, antigen-specific immunoglobulin molecules, or antigen-specific fragments (i.e., antigen-binding fragments) thereof, in a eukaryotic system. In addition, the invention is directed to methods of identifying polynucleotides which encode an antigen-specific immunoglobulin molecule, or an antigen-specific fragment thereof, from complex expression libraries of polynucleotides encoding such immunoglobulin molecules or fragments, where the libraries are constructed and screened in eukaryotic host cells. Further embodiments include an isolated antigen-specific immunoglobulin molecule, or antigen-specific fragment thereof, produced by any of the above methods, and a kit allowing production of such isolated immunoglobulins.

A particularly preferred aspect of the present invention is the construction of complex immunoglobulin libraries in eukaryotic host cells using poxvirus vectors constructed by trimolecular recombination. The ability to construct complex cDNA libraries in a pox virus based vector and to select and/or screen for specific recombinants on the basis of either antigen induced cell death, antigen induced signaling, or antigen-specific binding can be the basis for identification of immunoglobulins, particularly human immunoglobulins, with a variety of well-defined specificities in eukaryotic cells. It would overcome the bias imposed by selection of antibody repertoire in rodents or the limitations of synthesis and assembly in phage or bacteria.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

The term "eukaryote" or "eukaryotic organism" is intended to encompass all organisms in the animal, plant, and protist kingdoms, including protozoa, fungi, yeasts, green algae, single celled plants, multi celled plants, and all animals, both vertebrates and invertebrates. The term does not encompass bacteria or viruses. A "eukaryotic cell" is intended to encompass a singular "eukaryotic cell" as well as plural "eukaryotic cells," and comprises cells derived from a eukaryote.

The term "vertebrate" is intended to encompass a singular "vertebrate" as well as plural "vertebrates," and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. Preferably, the mammal is a human subject.

The terms "tissue culture" or "cell culture" or "culture" or "culturing" refer to the maintenance or growth of plant or animal tissue or cells in vitro under conditions that allow preservation of cell architecture, preservation of cell function, further differentiation, or all three. "Primary tissue cells" are those taken directly from tissue, i.e., a population of cells of the same kind performing the same function in an organism. Treating such tissue cells with the proteolytic enzyme trypsin, for example, dissociates them into individual primary tissue cells that grow or maintain cell architecture when seeded onto culture plates. Cell cultures arising from multiplication of primary cells in tissue culture are called "secondary cell cultures." Most secondary cells divide a finite number of times and then die. A few secondary cells, however, may pass through this "crisis period," after which they are able to multiply indefinitely to form a continuous "cell line." The liquid medium in which cells are cultured is referred to herein as "culture medium" or "culture media." Culture medium into which desired molecules, e.g., immunoglobulin molecules, have been secreted during culture of the cells therein is referred to herein as "conditioned medium."

The term "polynucleotide" refers to any one or more nucleic acid segments, or nucleic acid molecules, e.g., DNA or RNA fragments, present in a nucleic acid or construct. A "polynucleotide encoding an immunoglobulin subunit polypeptide" refers to a polynucleotide which comprises the coding region for such a polypeptide. In addition, a polynucleotide may encode a regulatory element such as a promoter or a transcription terminator, or may encode a specific element of a polypeptide or protein, such as a secretory signal peptide or a functional domain.

As used herein, the term "identify" refers to methods in which desired molecules, e.g., polynucleotides encoding immunoglobulin molecules with a desired specificity or function, are differentiated from a plurality or library of such molecules. Identification methods include "selection" and "screening." As used herein, "selection" methods are those in which the desired molecules may be directly separated from the library. For example, in one selection method described herein, host cells comprising the desired polynucleotides are directly separated from the host cells comprising the remainder of the library by undergoing a lytic event and thereby being released from the substrate to which the remainder of the host cells are attached. As used herein, "screening" methods are those in which pools comprising the desired molecules are subjected to an assay in which the desired molecule can be detected. Aliquots of the pools in which the molecule is detected are then divided into successively smaller pools which are likewise assayed, until a pool which is highly enriched from the desired molecule is achieved. For example, in one screening method described herein, pools of host cells comprising library polynucleotides encoding immunoglobulin molecules are assayed for antigen binding through expression of a reporter molecule.

Immunoglobulins. As used herein, an "immunoglobulin molecule" is defined as a complete, bi-molecular immunoglobulin, i.e., generally comprising four "subunit polypeptides," i.e., two identical heavy chains and two identical light chains. In some instances, e.g., immunoglobulin molecules derived from camelid species or engineered based on camelid immunglobulins, a complete immunoglobulin molecule may consist of heavy chains only, with no light chains. See, e.g., Hamers-Casterman et al., Nature 363:446-448 (1993). Thus, by an "immunoglobulin subunit polypeptide" is meant a single heavy chain polypeptide or a single light chain polypeptide. Immunoglobulin molecules are also referred to as "antibodies," and the terms are used interchangeably herein. An "isolated immunoglobulin" refers to an immunoglobulin molecule, or two or more immunoglobulin molecules, which are substantially removed from the milieu of proteins and other substances, and which bind a specific antigen.

The heavy chain, which determines the "class" of the immunoglobulin molecule, is the larger of the two subunit polypeptides, and comprises a variable region and a constant region. By "heavy chain" is meant either a full-length secreted heavy chain form, i.e., one that is released from the cell, or a membrane bound heavy chain form, i.e., comprising a membrane spanning domain and an intracellular domain. The membrane spanning and intracellular domains can be the naturally-occurring domains associated with a certain heavy chain, i.e., the domain found on memory B-cells, or it may be a heterologous membrane spanning and intracellular domain, e.g., from a different immunoglobulin class or from a heterologous polypeptide, i.e., a non-immunoglobulin polypeptide. As will become apparent, certain aspects of the present invention are preferably carried out using cell membrane-bound immunoglobulin molecules, while other aspects are preferably carried out with using secreted immunoglobulin molecules, i.e., those lacking the membrane spanning and intracellular domains. Immunoglobulin "classes" refer to the broad groups of immunoglobulins which serve different functions in the host. For example, human immunoglobulins are divided into five classes, i.e., IgG, comprising a γ heavy chain, IgM, comprising a μ heavy chain, IgA, comprising an α heavy chain, IgE, comprising an ϵ heavy chain, and IgD, comprising a δ heavy chain. Certain classes of immunoglobulins are also further divided into "subclasses." For example, in humans, there are four different IgG subclasses, IgG1, IgG2, IgG3, and IgG4 comprising γ-1, γ-2, γ-3, and γ-4 heavy chains, respectively, and two different IgA subclasses, IgA-1 and IgA-2, comprising α-1 and α-2 heavy chains, respectively. It is to be noted that the class and subclass designations of immunoglobulins vary between animal species, and certain animal species may comprise additional classes of immunoglobulins. For example, birds also produce IgY, which is found in egg yolk.

By "light chain" is meant the smaller immunoglobulin subunit which associates with the amino terminal region of a heavy chain. As with a heavy chain, a light chain comprises a variable region and a constant region. There are two different kinds of light chains, κ and λ, and a pair of these can associate with a pair of any of the various heavy chains to form an immunoglobulin molecule.

Immunoglobulin subunit polypeptides each comprise a constant region and a variable region. In most species, the heavy chain variable region, or $V_H$ domain, and the light chain variable region, or $V_L$ domain, combine to form a "complementarity determining region" or CDR, the portion of an immunoglobulin molecule which specifically recognizes an antigenic epitope. In camelid species, however, the heavy chain variable region, referred to as $V_HH$, forms the entire CDR. The main differences between camelid $V_HH$ variable regions and those derived from conventional antibodies ($V_H$) include (a) more hydrophobic amino acids in the light chain contact surface of $V_H$ as compared to the corresponding region in $V_HH$, (b) a longer CDR3 in $V_HH$, and (c) the frequent occurrence of a disulfide bond between CDR1 and CDR3 in $V_HH$. Each complete immunoglobulin molecule comprises two identical CDRs. A large repertoire of variable regions associated with heavy and light chain constant regions are produced upon differentiation of antibody-producing cells in an animal through rearrangements of a series of germ line DNA segments which results in the formation of a gene which encodes a given variable region. Further variations of heavy and light chain variable regions take place through somatic mutations in differentiated cells. The structure and in vivo formation of immunoglobulin molecules is well understood by those of ordinary skill in the art of immunology. Concise reviews of the generation of immunoglobulin diversity may be found, e.g., in Harlow and Lane, *Antibodies, A Laboratory Manual* Cold Spring Harbor Laboratory, Cold Spring Harbor, N.Y. (1988) (hereinafter, "Harlow"); and Roitt, et al., *Immunology* Gower Medical Publishing, Ltd., London (1985) (hereinafter, "Roitt"). Harlow and Roitt are incorporated herein by reference in their entireties.

Immunoglobulins further have several effector functions mediated by binding of effector molecules. For example, binding of the Cl component of complement to an immunoglobulin activates the complement system. Activation of complement is important in the opsonisation and lysis of cell pathogens. The activation of complement also stimulates the inflammatory response and may also be involved in autoimmune hypersensitivity. Further, immunoglobulins bind to cells via the Fc region, with an Fc receptor site on the antibody Fc region binding to an Fc receptor (FcR) on a cell. There are a number of Fc receptors which are specific for different classes of antibody, including, but not limited to, IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Immunoglobulins of the present invention may be from any animal origin including birds, fish, and mammals. Preferably, the antibodies are of human, mouse, dog, cat, rabbit, goat, guinea pig, camel, llama, horse, or chicken origin. In a preferred aspect of the present invention, immunoglobulins are identified which specifically interact with "self" antigens, e.g., human immunoglobulins which specifically bind human antigens.

As used herein, an "antigen-specific fragment" of an immunoglobulin molecule is any fragment or variant of an immunoglobulin molecule which remains capable of binding an antigen. Antigen-specific fragments include, but are not limited to, Fab, Fab' and F(ab)$_2$, Fd, single-chain Fvs (scFv), single-chain immunoglobulins (e.g., wherein a heavy chain, or portion thereof, and light chain, or portion thereof, are fused), disulfide-linked Fvs (sdFv), diabodies, triabodies, tetrabodies, scFv minibodies, Fab minibodies, and dimeric scFv and any other fragments comprising a $V_L$ and a $V_H$ domain in a conformation such that a specific CDR is formed. Antigen-specific fragments may also comprise a $V_H H$ domain derived from a camelid antibody. The $V_H H$ may be engineered to include CDRs from other species, for example, from human antibodies. Alternatively, a human-derived heavy chain $V_H$ fragment may be engineered to resemble a single-chain camelid CDR, a process referred to as "camelization." See, e.g., Davies J., and Riechmann, L., *FEBS Letters* 339:285-290 (1994), and Riechmann, L., and Muyldermans, S., *J. Immunol. Meth.* 231:25-38 (1999), both of which are incorporated herein by reference in their entireties.

Antigen-specific immunoglobulin fragments, including single-chain immunoglobulins, may comprise the variable region(s) alone or in combination with the entire or partial of the following: a heavy chain constant domain, or portion thereof, e.g., a CH1, CH2, CH3, transmembrane, and/or cytoplasmic domain, on the heavy chain, and a light chain constant domain, e.g., a $C_\kappa$ or $C_\lambda$ domain, or portion thereof on the light chain. Also included in the invention are any combinations of variable region(s) and CH1, CH2, CH3, $C_\kappa$, $C_\lambda$, transmembrane and cytoplasmic domains.

As is known in the art, Fv comprises a VH domain and a VL domain, Fab comprises VH joined to CH1 and an L chain, a Fab minibody comprises a fusion of CH3 domain to Fab, etc.

As is known in the art, scFv comprises VH joined to VL by a peptide linker, usually 15-20 residues in length, diabodies comprise scFv with a peptide linker about 5 residues in length, triabodies comprise scFv with no peptide linker, tetrabodies comprise scFv with peptide linker 1 residue in length, a scFv minibody comprises a fusion of CH3 domain to scFv, and dimeric scFv comprise a fusion of two scFvs in tandem using another peptide linker (reviewed in Chames and Baty, *FEMS Microbiol. Letts.* 189:1-8 (2000)). Preferably, an antigen-specific immunoglobulin fragment includes both antigen binding domains, i.e., $V_H$ and $V_L$. Other immunoglobulin fragments are well known in the art and disclosed in well-known reference materials such as those described herein.

In certain embodiments, the present invention is drawn to methods to identify, i.e., select or alternatively screen for, polynucleotides which singly or collectively encode antigen-specific immunoglobulin molecules, antigen-specific fragments thereof, or immunoglobulin molecules or fragments with specific antigen-related functions. In related embodiments, the present invention is drawn to isolated immunoglobulin molecules encoded by the polynucleotides identified by these methods.

The preferred methods comprise a two-step screening and/or selection process. In the first step, a polynucleotide encoding a first immunoglobulin subunit, i.e., either a heavy chain or a light chain, is identified from a library of polynucleotides encoding that subunit by introducing the library into a population of eukaryotic host cells, and expressing the immunoglobulin subunit in combination with one or more species of a second immunoglobulin subunit, where the second immunoglobulin subunit is not the same as the first immunoglobulin subunit, i.e., if the first immunoglobulin subunit polypeptide is a heavy chain polypeptide, the second immunoglobulin subunit polypeptide will be a light chain polypeptide.

Once one or more polynucleotides encoding one or more first immunoglobulin subunit are isolated from the library in the first step, a second immunoglobulin subunit is identified in the second step. Isolated polynucleotides encoding the isolated first immunoglobulin subunit polypeptide(s) are transferred into and expressed in host cells in which a library of polynucleotides encoding the second immunoglobulin subunit are expressed, thereby allowing identification of a polynucleotide encoding a second immunoglobulin subunit polypeptide which, when combined with the first immunoglobulin subunit identified in the first step, forms a functional immunoglobulin molecule, or fragment thereof, which recognizes a specific antigen and/or performs a specific function.

Where immunoglobulin fragments are composed of one polypeptide, i.e., a single-chain fragment or a fragment comprising a $V_H H$ domain, and therefore encoded by one polynucleotide, preferred methods comprise a one-step screening and/or selection process. Polynucleotides encoding a single-chain fragment, comprising a heavy chain variable region and a light chain variable region, or comprising a $V_H H$ region, are identified from a library by introducing the library into host cells such as eukaryotic cells and recovering polynucleotides of said library from those host cells which encode immunoglobulin fragments.

In certain embodiments, particular immunoglobulin molecules are identified through contacting the host cells expressing immunoglobulin molecules on their surface to antigen, which allows for selection and/or screening of antigen-binding cells in a number of different ways as described below. In other embodiments, desired soluble secreted immunoglobulin molecules are identified by assaying pools of conditioned media for desired functional characteristics of the immunoglobulin molecule, e.g., virus neutralization.

Where the immunoglobulin molecules are bound to the host cell surface, the first step comprises introducing into a population of host cells capable of expressing the immunoglobulin molecule a first library of polynucleotides encoding a plurality of first immunoglobulin subunit polypeptides through operable association with a transcriptional control region, introducing into the same host cells a second library of polynucleotides encoding, through operable association with a transcriptional control region, a plurality of second immunoglobulin subunit polypeptides, permitting expression of immunoglobulin molecules, or antigen-specific fragments thereof, on the membrane surface of the host cells, contacting the host cells with an antigen, and recovering polynucleotides derived from the first library from those host cells which bind the antigen.

Where the immunoglobulin molecules are fully secreted into the cell medium, the first step comprises introducing into a population of host cells capable of expressing the immunoglobulin molecule a first library of polynucleotides encoding a plurality of first immunoglobulin subunit polypeptides through operable association with a transcriptional control region, introducing into the same host cells a second library of polynucleotides encoding, through operable association with a transcriptional control region, a plurality of second immunoglobulin subunit polypeptides, permitting expression and secretion of immunoglobulin molecules, or antigen-specific fragments thereof, into the cell medium, assaying aliquots of conditioned medium for desired antigen-related antibody functions, and recovering polynucleotides derived from the first library from those host cell pools grown in conditioned medium in which the desired function was observed.

As used herein, a "library" is a representative genus of polynucleotides, i.e., a group of polynucleotides related through, for example, their origin from a single animal species, tissue type, organ, or cell type, where the library collectively comprises at least two different species within a given genus of polynucleotides. A library of polynucleotides preferably comprises at least 10, 100, $10^3$, $10^4$, $10^5$, $10^6$, $10^7$, $10^8$, or $10^9$ different species within a given genus of polynucleotides. More specifically, a library of the present invention encodes a plurality of a certain immunoglobulin subunit polypeptide, i.e., either a heavy chain subunit polypeptide or a light chain subunit polypeptide. In this context, a "library" of the present invention comprises polynucleotides of a common genus, the genus being polynucleotides encoding an immunoglobulin subunit polypeptide of a certain type and class e.g., a library might encode a human $\mu$, $\gamma$-1, $\gamma$-2, $\gamma$-3, $\gamma$-4, $\alpha$-1, $\alpha$-2, $\epsilon$, or $\delta$ heavy chain, or a human $\kappa$ or $\lambda$ light chain. Although each member of any one library of the present invention will encode the same heavy or light chain constant region, the library will collectively comprise at least two, preferably at least 10, 100, $10^3$, $10^4$, $10^5$, $10^6$, $10^7$, $10^8$, or $10^9$ different variable regions i.e., a "plurality" of variable regions associated with the common constant region.

In other embodiments, the library encodes a plurality of immunoglobulin single-chain fragments which comprise a variable region, such as a light chain variable region or a heavy chain variable region, and preferably comprises both a light chain variable region and a heavy chain variable region. Optionally, such a library comprises polynucleotides encoding an immunoglobulin subunit polypeptide of a certain type and class, or domains thereof.

In one aspect, the present invention encompasses methods to produce libraries of polynucleotides encoding immunoglobulin subunits. Furthermore, the present invention encompasses libraries of immunoglobulin subunits constructed in eukaryotic expression vectors according to the methods described herein. Such libraries are preferably produced in eukaryotic virus vectors, even more preferably in poxvirus vectors. Such methods and libraries are described herein.

By "recipient cell" or "host cell" or "cell" is meant a cell or population of cells into which polynucleotide libraries of the present invention are introduced. A host cell of the present invention is preferably a eukaryotic cell or cell line, preferably a plant, animal, vertebrate, mammalian, rodent, mouse, primate, or human cell or cell line. By "a population of host cells" is meant a group of cultured cells into which a "library" of the present invention can be introduced and expressed. Any host cells which will support expression from a given library constructed in a given vector is intended. Suitable and preferred host cells are disclosed herein. Furthermore, certain host cells which are preferred for use with specific vectors and with specific selection and/or screening schemes are disclosed herein. Although it is preferred that a population of host cells be a monoculture, i.e., where each cell in the population is of the same cell type, mixed cultures of cells are also contemplated. Host cells of the present invention may be adherent, i.e., host cells which grow attached to a solid substrate, or, alternatively, the host cells may be in suspension. Host cells may be cells derived from primary tumors, cells derived from metastatic tumors, primary cells, cells which have lost contact inhibition, transformed primary cells, immortalized primary cells, cells which may undergo apoptosis, and cell lines derived therefrom.

As noted above, preferred methods to identify immunoglobulin molecules comprise the introduction of a "first" library of polynucleotides into a population of host cells, as well as a "second" library of polynucleotides into the same population of host cells. The first and second libraries are complementary, i.e., if the "first" library encodes immunoglobulin heavy chains, the "second" library will encode immunoglobulin light chains, thereby allowing assembly of immunoglobulin molecules, or antigen-specific fragments thereof, in the population of host cells. Also, as noted above, another method to identify immunoglobulins or immunoglobulin fragments comprises introduction of a single library of polynucleotides encoding single-chain fragments into a population of host cells. The description of polynucleotide libraries, the composition of the polynucleotides in the library, and the polypeptides encoded by the polynucleotides therefore encompass both the polynucleotides which comprise the "first library" and the polynucleotides which comprise the "second library," and the polypeptides encoded thereby. The libraries may be constructed in any suitable vectors, and both libraries may, but need not be, constructed in the same vector. Suitable and preferred vectors for the first and second libraries are disclosed infra.

Polynucleotides contained in libraries of the present invention encode immunoglobulin subunit polypeptides through "operable association with a transcriptional control region." One or more nucleic acid molecules in a given polynucleotide are "operably associated" when they are placed into a functional relationship. This relationship can be between a coding region for a polypeptide and a regulatory sequence(s) which are connected in such a way as to permit expression of the coding region when the appropriate molecules (e.g., transcriptional activator proteins, polymerases, etc.) are bound to the regulatory sequences(s). "Transcriptional control regions" include, but are not limited to promoters, enhancers, operators, and transcription termination signals, and are included with the polynucleotide to direct its transcription. For example, a promoter would be operably associated with a nucleic acid molecule encoding an immunoglobulin subunit polypeptide if the promoter was capable of effecting transcription of that nucleic acid molecule. Generally, "operably associated" means that the DNA sequences are contiguous or closely connected in a polynucleotide. However, some transcription control regions, e.g., enhancers, do not have to be contiguous.

By "control sequences" or "control regions" is meant DNA sequences necessary for the expression of an operably associated coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhances.

A variety of transcriptional control regions are known to those skilled in the art. Preferred transcriptional control regions include those which function in vertebrate cells, such as, but not limited to, promoter and enhancer sequences from poxviruses, adenoviruses, herpesviruses, e.g., human cytomegalovirus (preferably the intermediate early promoter, preferably in conjunction with intron-A), simian virus 40 (preferably the early promoter), retroviruses (such as Rous sarcoma virus), and picornaviruses (particularly an internal ribosome entry site, or IRES, enhancer region, also referred to herein as a CITE sequence). Other preferred transcriptional control regions include those derived from mammalian genes such as actin, heat shock protein, and bovine growth hormone, as well as other sequences capable of controlling gene expression in eukaryotic cells. Additional suitable transcription control regions include tissue-specific promoters and enhancers as well as inducible promoters (e.g., promoters inducible by tetracycline, and temperature sensitive promoters). As will be discussed in more detail below, especially preferred are promoters capable of functioning in the cytoplasm of poxvirus-infected cells.

In certain preferred embodiments, each "immunoglobulin subunit polypeptide," i.e., either a "first immunoglobulin subunit polypeptide" or a "second immunoglobulin subunit polypeptide" comprises (i) a first immunoglobulin constant region selected from the group consisting of a heavy chain constant region, either a membrane bound form of a heavy chain constant region or a fully secreted form of a heavy chain constant region; and a light chain constant region, (ii) an immunoglobulin variable region corresponding to the first constant region, i.e., if the immunoglobulin constant region is a heavy chain constant region, the immunoglobulin variable region preferably comprises a $V_H$ region, and if the immunoglobulin constant region is a light chain constant region, the immunoglobulin variable region preferably comprises a $V_L$ region, and (iii) a signal peptide capable of directing transport of the immunoglobulin subunit polypeptide through the endoplasmic reticulum and through the host cell plasma membrane, either as a membrane-bound or fully secreted heavy chain, or a light chain associated with a heavy chain. Accordingly, through the association of two identical heavy chains and two identical light chains, either a surface immunoglobulin molecule or a fully secreted immunoglobulin molecule is formed.

Also in certain preferred embodiments in the context of an immunoglobulin fragment, a single-chain fragment comprises an immunoglobulin variable region selected from the group consisting of a heavy chain variable region and a light chain variable region, and preferably comprises both variable regions. If the immunoglobulin fragment comprises both a heavy chain variable region and a light chain variable region, they may be directly joined (i.e., they have no peptide or other linker), or they may be joined by another means. If they are joined by other means, they may be joined directly or by a disulfide bond formed during expression or by a peptide linker, as discussed below. Accordingly, through the association of the heavy chain variable region and the light chain variable region, a CDR is formed.

The heavy chain variable region and light chain variable region of one single-chain fragment may associate with one another or the heavy chain variable region of one single-chain fragment may associate with a light chain variable region of another single-chain fragment, and vise versa, depending on the type of linker. In one embodiment, the single-chain fragment also comprises a constant region selected from the group consisting of a heavy chain constant region, or a domain thereof, and a light chain constant region, or a domain thereof. Two single-chain fragments may associate with one another via their constant regions.

As mentioned above, in certain embodiments, the polynucleotide encoding the light chain variable region and heavy chain variable region of the single-chain fragment encode a linker. The single-chain fragment may comprise a single polypeptide with the sequence $V_H$-linker-$V_L$ or $V_L$-linker-$V_H$. In some embodiments, the linker is chosen to permit the heavy chain and light chain of a single polypeptide to bind together in their proper conformational orientation. See for example, Huston, J. S., et al, *Methods in Enzym.* 203:46-121 (1991). Thus, in these embodiments, the linker should be able to span the 3.5 nm distance between its points of fusion to the variable domains without distortion of the native Fv conformation. In these embodiments, the amino acid residues constituting the linker are such that it can span this distance and should be 5 amino acids or longer. Single-chain fragments with a linker of 5 amino acids form are found in monomer and predominantly dimer form. Preferably, the linker should be at least about 10 or at least about 15 residues in length. In other embodiments, the linker length is chosen to promote the formation of scFv tetramers (tetrabodies), and is 1 amino acid in length. In some embodiments, the variable regions are directly linked (i.e., the single-chain fragment contains no peptide linker) to promote the formation of scFv trimers (triabodies). These variations are well known in the art. (See, for example, Chames and Baty, *FEMS Microbiol. Letts.* 189: 1-8 (2000). The linker should not be so long it causes steric interference with the combining site. Thus, it preferably should be about 25 residues or less in length.

The amino acids of the peptide linker are preferably selected so that the linker is hydrophilic so it does not get buried into the antibody. The linker(Gly -Gly-Gly-Gly-Ser)$_3$ (SEQ ID NO:6) is a preferred linker that is widely applicable to many antibodies as it provides sufficient flexibility. Other linkers include Glu Ser Gly Arg Ser Gly Gly Gly Gly Ser Gly Gly Gly Gly Ser (SEQ ID NO:7), Glu Gly Lys Ser Ser Gly Ser Gly Ser Glu Ser Lys Ser Thr (SEQ ID NO:8), Glu Gly Lys Ser Ser Gly Ser Gly Ser Glu Ser Lys Ser Thr Gln (SEQ ID NO:9), Glu Gly Lys Ser Ser Gly Ser Gly Ser Glu Ser Lys Val Asp (SEQ ID NO:10), Gly Ser Thr Ser Gly Ser Gly Lys Ser Ser Glu Gly Lys Gly (SEQ ID NO:11), Lys Glu Ser Gly Ser Val Ser Ser Glu Gln Leu Ala Gln Phe Arg Ser Leu Asp (SEQ ID NO:12), and Glu Ser Gly Ser Val Ser Ser Glu Glu Leu Ala Phe Arg Ser Leu Asp (SEQ ID NO:13). Alternatively, a linker such as the (Gly-Gly-Gly-Gly-Ser)$_3$ (SEQ ID NO:6) linker, although any sequence can be used, is mutagenized or the amino acids in the linker are randomized, and using phage display vectors or the methods of the invention, antibodies with different linkers are screened or selected for the highest affinity or most affect on phenotype. Examples of shorter linkers include fragments of the above linkers, and examples of longer linkers include combinations of the linkers above, combinations of fragments of the linkers above, and combinations of the linkers above with fragments of the linkers above.

Also preferred are immunoglobulin subunit polypeptides which are variants or fragments of the above-described immunoglobulin subunit polypeptides. Any variants or fragments which result in an antigen binding fragment of an immunoglobulin molecule are contemplated. Such variants may be attached to the host cell surface, e.g., through association with a naturally-occurring transmembrane domain, through a receptor-ligand interaction, or as a fusion with a heterologous transmembrane domain, or may be secreted into the cell medium. Examples of antigen binding fragments of immunoglobulin molecules are described herein.

In those embodiments where the immunoglobulin subunit polypeptide comprises a heavy chain polypeptide, any immunoglobulin heavy chain, from any animal species, is intended. Suitable and preferred immunoglobulin heavy chains are described herein. Immunoglobulin heavy chains from vertebrates such as birds, especially chickens, fish, and mammals are included, with mammalian immunoglobulin heavy chains being preferred. Examples of mammalian immunoglobulin heavy chains include human, mouse, dog, cat, horse, goat, rat, sheep, cow, pig, guinea pig, camel, llama, and hamster immunoglobulin heavy chains. Of these, human immunoglobulin heavy chains are particularly preferred. Also contemplated are hybrid immunoglobulin heavy chains comprising portions of heavy chains from one or more species, such as mouse/human hybrid immunoglobulin heavy chains, or "camelized" human immunoglobulin heavy chains. Of the human immunoglobulin heavy chains, preferably, an immunoglobulin heavy chain of the present invention is selected from the group consisting of a μ heavy chain, i.e., the heavy chain of an IgM immunoglobulin, a γ-1 heavy chain, i.e., the heavy chain of an IgG1 immunoglobulin, a γ-2 heavy chain, i.e., the heavy chain of an IgG2 immunoglobulin, a γ-3 heavy chain, i.e., the heavy chain of an IgG3 immunoglobulin, a γ-4 heavy chain, i.e., the heavy chain of an IgG4 immunoglobulin, an α-1 heavy chain, i.e., the heavy chain of an IgA1 immunoglobulin, an α-2 heavy chain, i.e., the heavy chain of an IgA2 immunoglobulin, and ε heavy chain, i.e., the heavy chain of an IgE immunoglobulin, and a δ heavy chain, i.e., the heavy chain of an IgD immunoglobulin. In certain embodiments, the preferred immunoglobulin heavy chains include membrane-bound forms of human μ, γ-1, γ-2, γ-3, γ-4, α-1, α-2, ε, and δ heavy chains. Especially preferred is a membrane bound form of the human μ heavy chain.

Membrane bound forms of immunoglobulins are typically anchored to the surface of cells by a transmembrane domain which is made part of the heavy chain polypeptide through alternative transcription termination and splicing of the heavy chain messenger RNA. See, e.g., Roitt at page 9.10. By "transmembrane domain" "membrane spanning region," or related terms, which are used interchangeably herein, is meant the portion of heavy chain polypeptide which is anchored into a cell membrane. Typical transmembrane domains comprise hydrophobic amino acids as discussed in more detail below. By "intracellular domain," "cytoplasmic domain," "cytosolic region," or related terms, which are used interchangeably herein, is meant the portion of the polypeptide which is inside the cell, as opposed to those portions which are either anchored into the cell membrane or exposed on the surface of the cell. Membrane-bound forms of immunoglobulin heavy chain polypeptides typically comprise very short cytoplasmic domains of about three amino acids. A membrane-bound form of an immunoglobulin heavy chain polypeptide of the present invention preferably comprises the transmembrane and intracellular domains normally associated with that immunoglobulin heavy chain, e.g., the transmembrane and intracellular domains associated with μ and ε heavy chains in pre-B cells, or the transmembrane and intracellular domains associated with any of the immunoglobulin heavy chains in B-memory cells. However, it is also contemplated that heterologous transmembrane and intracellular domains could be associated with a given immunoglobulin heavy chain polypeptide, for example, the transmembrane and intracellular domains of a μ heavy chain could be associated with the extracellular portion of a γ heavy chain. Alternatively, transmembrane and/or cytoplasmic domains of an entirely heterologous polypeptide could be used, for example, the transmembrane and cytoplasmic domains of a major histocompatibility molecule, a cell surface receptor, a virus surface protein, chimeric domains, or synthetic domains.

In those embodiments where the immunoglobulin subunit polypeptide comprises a light chain polypeptide, any immunoglobulin light chain, from any animal species, is intended. Suitable and preferred immunoglobulin light chains are described herein. Immunoglobulin light chains from vertebrates such as birds, especially chickens, fish, and mammals are included, with mammalian immunoglobulin light chains being preferred. Examples of mammalian immunoglobulin light chains include human, mouse, dog, cat, horse, goat, rat, sheep, cow, pig, guinea pig, and hamster immunoglobulin light chains. Of these, human immunoglobulin light chains are particularly preferred. Also contemplated are hybrid immunoglobulin light chains comprising portions of light chains from one or more species, such as mouse/human hybrid immunoglobulin light chains. Preferred immunoglobulin light chains include human κ and λ light chains. A pair of either light chain may associate with an identical pair of any of the heavy chains to produce an immunoglobulin molecule, with the characteristic $H_2L_2$ structure which is well understood by those of ordinary skill in the art.

According to a preferred aspect of the invention, each member of a library of polynucleotides as described herein, e.g., a first library of polynucleotides or a second library of polynucleotides, comprises (a) a first nucleic acid molecule encoding an immunoglobulin constant region common to all members of the library, and (b) a second nucleic acid molecule encoding an immunoglobulin variable region, where the second nucleic acid molecule is directly upstream of and in-frame with the first nucleic acid molecule. Accordingly, an immunoglobulin subunit polypeptide encoded by a member of a library of polynucleotides of the present invention, i.e., an immunoglobulin light chain or an immunoglobulin heavy chain encoded by such a polynucleotide, preferably comprises an immunoglobulin constant region associated with an immunoglobulin variable region.

The constant region of a light chain encoded by the "first nucleic acid molecule," comprises about half of the subunit polypeptide and is situated C-terminal, i.e., in the latter half of the light chain polypeptide. A light chain constant region, referred to herein as a $C_L$ constant region, or, more specifically a Cκ constant region or a Cλ constant region, comprises about 110 amino acids held together in a "loop" by an interchain disulfide bond.

The constant region of a heavy chain encoded by the "first nucleic acid molecule" comprises three quarters or more of the subunit polypeptide, and is situated in the C-terminal, i.e., in the latter portion of the heavy chain polypeptide. The heavy chain constant region, referred herein as a $C_H$ constant region, comprises either three or four peptide loops or "domains" of about 110 amino acid each enclosed by interchain disulfide bonds. More specifically, the heavy chain constant regions in human immunoglobulins include a Cμ constant region, a Cδ constant region, a Cγ constant region, a Cα constant region, and a Cε constant region. Cγ, Cα, and Cδ heavy chains each contain three constant region domains, referred to generally as $C_H1$, $C_H2$, and $C_H3$, while Cμ and Cε heavy chains contain four constant region domains, referred to generally as $C_H1$, $C_H2$, $C_H3$, and $C_H4$. Nucleic acid molecules encoding human immunoglobulin constant regions are readily obtained from cDNA libraries derived from, for example, human B cells or their precursors by methods such as PCR, which are well known to those of ordinary skill in the art and further, are disclosed in the Examples, infra.

Immunoglobulin subunit polypeptides of the present invention each comprise an immunoglobulin variable region, encoded by the "second nucleic acid molecule." Within a library of polynucleotides, each polynucleotide will comprise the same constant region, but the library will contain a plurality, i.e., at least two, preferably at least 10, 100, $10^3$, $10^4$, $10^5$, $10^6$, $10^7$, $10^8$, or $10^9$ different variable regions. As is well known by those of ordinary skill in the art, a light chain variable region is encoded by rearranged nucleic acid molecules, each comprising a light chain $V_L$ region, specifically a Vκ region or a Vλ region, and a light chain J region, specifically a Jκ region or a Jλ region. Similarly, a heavy chain variable region is encoded by rearranged nucleic acid molecules, each comprising a heavy chain $V_H$ region, a D region and J region. These rearrangements take place at the DNA level upon cellular differentiation. Nucleic acid molecules encoding heavy and light chain variable regions may be derived, for example, by PCR from mature B cells and plasma cells which have terminally differentiated to express an antibody with specificity for a particular epitope. Furthermore, if antibodies to a specific antigen are desired, variable regions may be isolated from mature B cells and plasma cells of an animal who has been immunized with that antigen, and has thereby produced an expanded repertoire of antibody variable regions which interact with the antigen. Alternatively, if a more diverse library is desired, variable regions may be isolated from precursor cells, e.g., pre-B cells and immature B cells, which have undergone rearrangement of the immunoglobulin genes, but have not been exposed to antigen, either self or non-self. For example, variable regions might be isolated by PCR from normal human bone marrow pooled from multiple donors. Alternatively, variable regions may be synthetic, for example, made in the laboratory through generation of synthetic oligonucleotides, or may be derived through in vitro manipulations of germ line DNA resulting in rearrangements of the immunoglobulin genes.

In addition to first and second nucleic acid molecules encoding immunoglobulin constant regions and variable regions, respectively, each member of a library of polynucleotides of the present invention as described above may further comprise a third nucleic acid molecule encoding a signal peptide directly upstream of and in frame with the second nucleic acid molecule encoding the variable region.

By "signal peptide" is meant a polypeptide sequence which, for example, directs transport of nascent immunoglobulin polypeptide subunit to the surface of the host cells. Signal peptides are also referred to in the art as "signal sequences," "leader sequences," "secretory signal peptides," or "secretory signal sequences." Signal peptides are normally expressed as part of a complete or "immature" polypeptide, and are normally situated at the N-terminus. The common structure of signal peptides from various proteins is commonly described as a positively charged n-region, followed by a hydrophobic h-region and a neutral but polar c-region. In many instances the amino acids comprising the signal peptide are cleaved off the protein once its final destination has been reached, to produce a "mature" form of the polypeptide. The cleavage is catalyzed by enzymes known as signal peptidases. The (−3, −1)-rule states that the residues at positions −3 and −1 (relative to the cleavage site) must be small and neutral for cleavage to occur correctly. See, e.g., McGeoch, *Virus Res.* 3:271-286 (1985), and von Heinje, *Nucleic Acids Res.* 14:46834690 (1986).

All cells, including host cells of the present invention, possess a constitutive secretory pathway, where proteins, including secreted immunoglobulin subunit polypeptides destined for export, are secreted from the cell. These proteins pass through the ER-Golgi processing pathway where modifications may occur. If no further signals are detected on the protein it is directed to the cells surface for secretion. Alternatively, immunoglobulin subunit polypeptides can end up as integral membrane components expressed on the surface of the host cells. Membrane-bound forms of immunoglobulin subunit polypeptides initially follow the same pathway as the secreted forms, passing through to the ER lumen, except that they are retained in the ER membrane by the presence of stop-transfer signals, or "transmembrane domains." Transmembrane domains are hydrophobic stretches of about 20 amino acid residues that adopt an alpha-helical conformation as they transverse the membrane. Membrane embedded proteins are anchored in the phospholipid bilayer of the plasma membrane. As with secreted proteins, the N-terminal region of transmembrane proteins have a signal peptide that passes through the membrane and is cleaved upon exiting into the lumen of the ER. Transmembrane forms of immunoglobulin heavy chain polypeptides utilize the same signal peptide as the secreted forms.

A signal peptide of the present invention may be either a naturally-occurring immunoglobulin signal peptide, i.e., encoded by a sequence which is part of a naturally occurring heavy or light chain transcript, or a functional derivative of that sequence that retains the ability to direct the secretion of the immunoglobulin subunit polypeptide that is operably associated with it. Alternatively, a heterologous signal peptide, or a functional derivative thereof, may be used. For example, a naturally-occurring immunoglobulin subunit polypeptide signal peptide may be substituted with the signal peptide of human tissue plasminogen activator or mouse β-glucuronidase.

Signal sequences, transmembrane domains, and cytosolic domains are known for a wide variety of membrane bound proteins. These sequences may be used accordingly, either together as pairs (e.g., signal sequence and transmembrane domain, or signal sequence and cytosolic domain, or transmembrane domain and cytosolic domain) or threesomes from a particular protein, or with each component being taken from a different protein, or alternatively, the sequences may be synthetic, and derived entirely from consensus as artificial delivery domains, as mentioned above.

Particularly preferred signal sequences and transmembrane domains include, but are not limited to, those derived from CD8, ICAM-2, IL-8R, CD4 and LFA-1. Additional useful sequences include sequences from: 1) class I integral membrane proteins such as IL-2 receptor beta-chain (residues 1-26 are the signal sequence, 241-265 are the transmembrane residues; see Hatakeyama et al, Science 244:551 (1989) and von Heijne et al, Eur. J. Biochem. 174:671 (1988)) and insulin receptor beta-chain (residues 1-27 are the signal, 957-959, are the transmembrane domain and 960-1382 are the cytoplasmic domain; see Hatakeyama supra, and Ebina et al., Cell 40:747 (1985)); 2) class II integral membrane proteins such as neutral endopeptidase (residues 29-51 are the transmembrane domain, 2-28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). In this alternative, CD8 and ICAM-2 are particularly preferred. For example, the signal sequences from CD8 and ICAM-2 lie at the extreme 5' end of the transcript. These consist of the amino acids 1-32 in the case of CD8 (Nakauchi et al., PNAS USA 82:5126 (1985)) and 1-21 in the case of ICAM-2 (Staunton et al., Nature (London) 339:61 (1989)). These transmembrane domains are encompassed by amino acids 145-195 from CD8 (Nakauchi, supra) and 224-256 from ICAM-2 (Staunton, supra).

Alternatively, membrane anchoring domains include the GPI anchor, which results in a covalent bond between the molecule and the lipid bilayer via a glycosyl-phosphatidylinositol bond for example in DAF (see Homans et al., Nature 333(6170):269-72 (1988), and Moran et al., J. Biol. Chem. 266:1250 (1991)). In order to do this, the GPI sequence from Thy-1 can be cassetted 3' of the immunoglobulin or immunoglobulin fragment in place of a transmembrane sequence.

Similarly, myristylation sequences can serve as membrane anchoring domains. It is known that the myristylation of c-src recruits it to the plasma membrane. This is a simple and effective method of membrane localization, given that the first 14 amino acids of the protein are solely responsible for this function (see Cross et al., Mol. Cell. Biol. 4(9) 1834 (1984); Spencer et al., Science 262:1019 1024 (1993)). This motif has already been shown to be effective in the localization of reporter genes and can be used to anchor the zeta chain of the TCR. This motif is placed 5' of the immunoglobulin or immunoglobulin fragment in order to localize the construct to the plasma membrane. Other modifications such as palmitoylation can be used to anchor constructs in the plasma membrane; for example, palmitoylation sequences from the G protein-coupled receptor kinase GRK6 sequence (Stoffel et al, J. Biol. Chem. 269:27791 (1994)); from rhodopsin (Barnstable et al., J. Mol. Neurosci. 5(3):207 (1994)); and the p21H-ras 1 protein (Capon et al., Nature 302:33 (1983)).

In addition to first and second nucleic acid molecules encoding immunoglobulin constant regions and variable regions, respectively, each member of a library of polynucleotides of the present invention as described above may further comprise additional nucleic acid molecule encoding heterologous polypeptides. Such additional polynucleotides may be in addition to or as an alternative of the third nucleic acid molecule encoding a signal peptide. Such additional nucleic acid molecules encoding heterologous polypeptides may be upstream of or downstream from the nucleic acid molecules encoding the variable chain region or the heavy chain region.

A heterologous polypeptide encoded by an additional nucleic acid molecule may be a rescue sequence. A rescue sequence is a sequence which may be used to purify or isolate either the immunoglobulin or fragment thereof or the polynucleotide encoding it. Thus, for example, peptide rescue sequences include purification sequences such as the 6-His tag for use with Ni affinity columns and epitope tags for detection, immunoprecipitation, or FACS (fluorescence-activated cell sorting). Suitable epitope tags include myc (for use with commercially available 9E10 antibody), the BSP biotinylation target sequence of the bacterial enzyme BirA, flu tags, LacZ, and GST. The additional nucleic acid molecule may also encode a peptide linker.

In a preferred embodiment, combinations of heterologous polypeptides are used. Thus, for example, any number of combinations of signal sequences, rescue sequences, and stability sequences may be used, with or without linker sequences. One can cassette in various fusion polynucleotides encoding heterologous polypeptides 5' and 3 of the immunoglobulin or fragment thereof-encoding polynucleotide. As will be appreciated by those in the art, these modules of sequences can be used in a large number of combinations and variations.

The polynucleotides comprised in the first and second libraries are introduced into suitable host cells. Suitable host cells are characterized by being capable of expressing immunoglobulin molecules attached to their surface. Polynucleotides may be introduced into host cells by methods which are well known to those of ordinary skill in the art. Suitable and preferred introduction methods are disclosed herein.

As is easily appreciated, introduction methods vary depending on the nature of the vector in which the polynucleotide libraries are constructed. For example, DNA plasmid vectors may be introduced into host cells, for example, by lipofection (such as with anionic liposomes (see, e.g., Felgner et al., 1987 Proc. Natl. Acad. Sci. U.S.A. 84:7413 or cationic liposomes (see, e.g., Brigham, K. L. et al. Am. J. Med. Sci. 298(4):278-2821 (1989); U.S. Pat. No. 4,897,355 (Eppstein, et al.)), by electroporation, by calcium phosphate precipitation (see generally, Sambrook et al., Molecular Cloning: A Laboratory Manual, 2nd Ed., Cold Spring Harbor Laboratory, Cold Spring Harbor, N.Y., 1989), by protoplast fusion, by spheroplast fusion, or by the DEAE dextran method (Sussman et al., Cell. Biol. 4:1641-1643 (1984)). The above references are incorporated herein by reference in their entireties.

When the selected method is lipofection, the nucleic acid can be complexed with a cationic liposome, such as DOTMA: DOPE, DOTMA, DOPE, DC-cholesterol, DOTAP, Transfectam® (Promega), Tfx® (Promega), LipoTAXI™ (Stratagene), PerFect Lipid™ (Invitrogen), SuperFect™ (Qiagen). When the nucleic acid is transfected via an anionic liposome, the anionic liposome can encapsulate the nucleic acid. Preferably, DNA is introduced by liposome-mediated transfection using the manufacturer's protocol (such as for Lipofectamine; Life Technologies Incorporated).

Where the plasmid is a virus vector, introduction into host cells is most conveniently carried out by standard infection. However, in many cases viral nucleic acids may be introduced into cells by any of the methods described above, and the viral nucleic acid is "infectious," i.e., introduction of the viral nucleic acid into the cell, without more, is sufficient to allow the cell to produce viable progeny virus particles. It is noted, however, that certain virus nucleic acids, for example, poxvirus nucleic acids, are not infectious, and therefore must be introduced with additional elements provided, for example, by a virus particle enclosing the viral nucleic acid, by a cell which has been engineered to produce required viral elements, or by a helper virus.

The first and second libraries of polynucleotides may be introduced into host cells in any order, or simultaneously. For example, if both the first and second libraries of polynucleotides are constructed in virus vectors, whether infectious or inactivated, the vectors may be introduced by simultaneous infection as a mixture, or may be introduced in consecutive infections. If one library is constructed in a virus vector, and the other is constructed in a plasmid vector, introduction might be carried out most conveniently by introduction of one library before the other.

Following introduction into the host cells of the first and second libraries of polynucleotides, expression of immunoglobulin molecules, or antigen-specific fragments thereof, is permitted to occur either on the membrane surface of said host cells, or through secretion into the cell medium. By "permitting expression" is meant allowing the vectors which have been introduced into the host cells to undergo transcription and translation of the immunoglobulin subunit polypeptides, preferably allowing the host cells to transport fully assembled immunoglobulin molecules, or antigen-specific fragments thereof, to the membrane surface or into the cell medium. Typically, permitting expression requires incubating the host cells into which the polynucleotides have been introduced under suitable conditions to allow expression. Those conditions, and the time required to allow expression will vary based on the choice of host cell and the choice of vectors, as is well known by those of ordinary skill in the art.

In certain embodiments, host cells which have been allowed to express immunoglobulin molecules on their surface, or soluble immunoglobulin molecules secreted into the cell medium are then contacted with an antigen. As used herein, an "antigen" is any molecule that can specifically bind to an antibody, immunoglobulin molecule, or antigen-specific fragment thereof. By "specifically bind" is meant that the antigen binds to the CDR of the antibody. The portion of the antigen which specifically interacts with the CDR is an "epitope," or an "antigenic determinant." An antigen may comprise a single epitope, but typically, an antigen comprises at least two epitopes, and can include any number of epitopes, depending on the size, conformation, and type of antigen.

Antigens are typically peptides or polypeptides, but can be any molecule or compound. For example, an organic compound, e.g., dinitrophenol or DNP, a nucleic acid, a carbohydrate, or a mixture of any of these compounds either with or without a peptide or polypeptide can be a suitable antigen. The minimum size of a peptide or polypeptide epitope is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide antigens preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred peptides or polypeptides comprising, or alternatively consisting of, antigenic epitopes are at least 10, 15, 20, 25, 30, 35, 40, 45, 50, 55, 60, 65, 70, 75, 80, 85, 90, 95, or 100 amino acid residues in length. The antigen may be in any form and may be free, for example dissolved in a solution, or may be attached to any substrate. Suitable and preferred substrates are disclosed herein. In certain embodiments, an antigen may be part of an antigen-expressing presenting cell as described in more detail below.

It is to be understood that immunoglobulin molecules specific for any antigen may be produced according to the methods of the present invention. Preferred antigens are "self" antigens, i.e., antigens derived from the same species as the immunoglobulin molecules produced. As an example, it might be desired to produce human antibodies directed to human tumor antigens such as, but not limited to, a CEA antigen, a GM2 antigen, a Tn antigen, an sTn antigen, a Thompson-Friedenreich antigen (TF), a Globo H antigen, an Le(y) antigen, a MUC1 antigen, a MUC2 antigen, a MUC3 antigen, a MUC4 antigen, a MUC5AC antigen, a MUC5B antigen, a MUC7 antigen, a carcinoembryonic antigen, a beta chain of human chorionic gonadotropin (hCG beta) antigen, a HER2/neu antigen, a PSMA antigen, a EGFRvIII antigen, a KSA antigen, a PSA antigen, a PSCA antigen, a GP100 antigen, a MAGE 1 antigen, a MAGE 2 antigen, a TRP 1 antigen, a TRP 2 antigen, and a tyrosinase antigen. Other desired "self" antigens include, but are not limited to, cytokines, receptors, ligands, glycoproteins, and hormones.

It is also contemplated to produce antibodies directed to antigens on infectious agents. Examples of such antigens include, but are not limited to, bacterial antigens, viral antigens, parasite antigens, and fungal antigens. Examples of viral antigens include, but are not limited to, adenovirus antigens, alphavirus antigens, calicivirus antigens, e.g., a calicivirus capsid antigen, coronavirus antigens, distemper virus antigens, Ebola virus antigens, enterovirus antigens, flavivirus antigens, hepatitis virus (A-E) antigens, e.g., a hepatitis B core or surface antigen, herpesvirus antigens, e.g., a herpes simplex virus or varicella zostervirus glycoprotein antigen, immunodeficiency virus antigens, e.g., a human immunodeficiency virus envelope or protease antigen, infectious peritonitis virus antigens, influenza virus antigens, e.g., an influenza A hemagglutinin or neuraminidase antigen, leukemia virus antigens, Marburg virus antigens, oncogenic virus antigens, orthomyxovirus antigens, papilloma virus antigens, parainfluenza virus antigens, e.g., hemagglutinin/neuraminidase antigens, paramyxovirus antigens, parvovirus antigens, pestivirus antigens, picorna virus antigens, e.g., a poliovirus capsid antigen, rabies virus antigens, e.g., a rabies virus glycoprotein G antigen, reovirus antigens, retrovirus antigens, rotavirus antigens, as well as other cancer causing or cancer-related virus antigens.

Examples of bacterial antigens include, but are not limited to, *Actinomyces*, antigens *Bacillus* antigens, *Bacteroides* antigens, *Bordetella* antigens, *Bartonella antigens, Borrelia* antigens, e.g., a *B. bergdorferi* OspA antigen, *Brucella* antigens, *Campylobacter* antigens, *Capnocytophaga* antigens, *Chlamydia* antigens, *Clostridium* antigens, *Corynebacterium* antigens, *Coxiella* antigens, *Dermatophilus* antigens, *Enterococcus* antigens, *Ehrlichia* antigens, *Escherichia* antigens, *Francisella* antigens, *Fusobacterium* antigens, *Haemobartonella* antigens, *Haemophilus* antigens, e.g., *H. influenzae* type b outer membrane protein antigens, *Helicobacter* antigens, *Klebsiella* antigens, L-form bacteria antigens, *Leptospira* antigens, *Listeria* antigens, *Mycobacteria* antigens, *Mycoplasma* antigens, *Neisseria* antigens, *Neorickettsia* antigens, *Nocardia* antigens, *Pasteurella* antigens, *Peptococcus* antigens, *Peptostreptococcus* antigens, *Pneumococcus* antigens, *Proteus* antigens, *Pseudomonas* antigens, *Rickettsia* antigens, *Rochalimaea* antigens, *Salmonella* antigens, *Shigella* antigens, *Staphylococcus antigens, Streptococcus* antigens, e.g., *S. pyogenes* M protein antigens, *Treponema* antigens, and *Yersinia* antigens, e.g., *Y pestis* F1 and V antigens.

Examples of fungal antigens include, but are not limited to, *Absidia* antigens, *Acremonium* antigens, *Alternaria* antigens, *Aspergillus* antigens, *Basidiobolus* antigens, *Bipolaris* antigens, *Blastomyces* antigens, *Candida* antigens, *Coccidioides* antigens, *Conidiobolus* antigens, *Cryptococcus* antigens, *Curvalaria* antigens, *Epidermophyton* antigens, *Exophiala* antigens, *Geotrichum* antigens, *Histoplasma* antigens, *Madurella* antigens, *Malassezia* antigens, *Microsporum* antigens, *Moniliella* antigens, *Mortierella* antigens, *Mucor* antigens, *Paecilomyces* antigens, *Penicillium* antigens, *Phialemonium* antigens, *Phialophora* antigens, *Prototheca* antigens, *Pseudallescheria* antigens, *Pseudomicrodochium* antigens, *Pythium* antigens, *Rhinosporidium* antigens, *Rhizopus* antigens, *Scolecobasidium* antigens, *Sporothrix* antigens, *Stemphylium* antigens, *Trichophyton* antigens, *Trichosporon* antigens, and *Xylohypha* antigens.

Examples of protozoan parasite antigens include, but are not limited to, *Babesia* antigens, *Balantidium* antigens, *Besnoitia* antigens, *Cryptosporidium* antigens, *Eimeri* antigens a antigens, *Encephalitozoon antigens, Entamoeba* antigens, *Giardia* antigens, *Hammondia* antigens, *Hepatozoon* antigens, *Isospora* antigens, *Leishmania* antigens, *Microsporidia* antigens, *Neospora* antigens, *Nosema* antigens, *Pentatrichomonas* antigens, *Plasmodium* antigens, e.g., *P. falciparum* circumsporozoite (PfCSP), sporozoite surface protein 2 (PfSSP2), carboxyl terminus of liver state antigen 1 (PfLSA-1c-term), and exported protein 1 (PfExp-1) antigens, *Pneu-* mocystis antigens, *Sarcocystis* antigens, *Schistosoma* antigens, *Theileria* antigens, *Toxoplasma* antigens, and *Trypanosoma* antigens. Examples of helminth parasite antigens include, but are not limited to, *Acanthocheilonema* antigens, *Aelurostrongylus* antigens, *Ancylostoma* antigens, *Angiostrongylus* antigens, *Ascaris* antigens, *Brugia* antigens, *Bunostomum* antigens, *Capillaria* antigens, *Chabertia* antigens, *Cooperia* antigens, *Crenosonma* antigens, *Dictyocaulus* antigens, *Dioctophyme* antigens, *Dipetalonema* antigens, *Diphyllobothrium* antigens, *Diplydium* antigens, Dirofilaria antigens, *Dracunculus* antigens, *Enterobius* antigens, *Filaroides* antigens *Haemonchus* antigens, *Lagochilascaris* antigens, *Loa* antigens, *Mansonella* antigens, *Muellerius* antigens, *Nanophyetus* antigens, *Necator* antigens, *Nematodirus* antigens, *Oesophagostomum* antigens, *Onchocerca* antigens, *Opisthorchis* antigens, *Ostertagia* antigens, *Parafilaria* antigens, *Paragonimus* antigens, *Parascaris* antigens, *Physaloptera* antigens, *Protostrongylus* antigens, *Setaria* antigens, *Spirocerca* antigens, *Spirometra* antigens, *Stephanofilaria* antigens, *Strongyloides* antigens, *Strongylus* antigens, *Thelazia* antigens, *Toxascaris* antigens, *Toxocara* antigens, *Trichinella* antigens, *Trichostrongylus* antigens, *Trichuris* antigens. *Uncinaria* antigens, and *Wuchereria* antigens.

In certain selection and screening schemes in which immunoglobulin molecules are expressed on the surface of host cells, the host cells of the present invention are "contacted" with antigen by a method which will allow an antigen, which specifically recognizes a CDR of an immunoglobulin molecule expressed on the surface of the host cell, to bind to the CDR, thereby allowing the host cells which specifically bind the antigen to be distinguished from those host cells which do not bind the antigen. Any method which allows host cells expressing an antigen-specific antibody to interact with the antigen is included. For example, if the host cells are in suspension, and the antigen is attached to a solid substrate, cells which specifically bind to the antigen will be trapped on the solid substrate, allowing those cells which do not bind the antigen to be washed away, and the bound cells to be subsequently recovered. Alternatively, if the host cells are attached to a solid substrate, and by specifically binding antigen cells are caused to be released from the substrate (e.g., by cell death), they can be recovered from the cell supernatant. Preferred methods by which to allow host cells of the invention to contact antigen, especially using libraries constructed in vaccinia virus vectors by trimolecular recombination, are disclosed herein.

In a preferred screening method for the detection of antigen-specific immunoglobulin molecules expressed on the surface of host cells, the host cells of the present invention are incubated with a selecting antigen that has been labeled directly with fluorescein-5-isothiocyanate (IC) or indirectly with biotin then detected with FITC-labeled streptavidin. Other fluorescent probes can be employed which will be familiar to those practiced in the art. During the incubation period, the labeled selecting antigen binds the antigen-specific immunoglobulin molecules. Cells expressing an antibody receptor for a specific fluorescence tagged antigen can be selected by fluorescence activated cell sorting, thereby permitting the host cells which specifically bind the antigen to be distinguished from those host cells which do not bind the antigen. With the advent of cell sorters capable of sorting more than $1 \times 10^8$ cells per hour, it is feasible to screen large numbers of cells infected with recombinant vaccinia libraries of immunoglobulin genes to select the subset of cells that express specific antibody receptors to the selecting antigen.

After recovery of host cells which specifically bind antigen, polynucleotides of the first library are recovered from those host cells. By "recovery" is meant a crude separation of a desired component from those components which are not desired. For example, host cells which bind antigen are "recovered" based on their detachment from a solid substrate, and polynucleotides of the first library are recovered from those cells by crude separation from other cellular components. It is to be noted that the term "recovery" does not imply any sort of purification or isolation away from viral and other components. Recovery of polynucleotides may be accomplished by any standard method known to those of ordinary skill in the art. In a preferred aspect, the polynucleotides are recovered by harvesting infectious virus particles, for example, particles of a vaccinia virus vector into which the first library has been constructed, which were contained in those host cells which bound antigen.

In certain screening schemes in which immunoglobulin molecules are fully secreted from the surface of host cells, the cell medium in which pools of host cells are cultured, i.e., "conditioned medium," may be "contacted" with antigen by a method which will allow an antigen which specifically recognizes a CDR of an immunoglobulin molecule to bind to the CDR, and which further allows detection of the antigen-antibody interaction. Such methods include, but are not limited to, immunoblots, ELISA assays, RIA assays, RAST assays, and immunofluorescence assays. Alternatively, the conditioned medium is subjected to a functional assay for specific antibodies. Examples of such assays include, but are not limited to, virus neutralization assays (for antibodies directed to specific viruses), bacterial opsonization/phagocytosis assays (for antibodies directed to specific bacteria), antibody-dependent cellular cytotoxicity (ADCC) assays, assays to detect inhibition or facilitation of certain cellular functions, assays to detect IgE-mediated histamine release from mast cells, hemagglutination assays, and hemagglutination inhibition assays. Such assays will allow detection of antigen-specific antibodies with desired functional characteristics.

After the identification of conditioned medium pools containing immunoglobulin molecules which specifically bind antigen, or which have desired functional characteristics, further screening steps are carried out until host cells which produce the desired immunoglobulin molecules are recovered, and then polynucleotides of the first library are recovered from those host cells.

As will be readily appreciated by those of ordinary skill in the art, identification of polynucleotides encoding immunoglobulin subunit polypeptides may require two or more rounds of selection as described above, and will necessarily require two or more rounds of screening as described above. A single round of selection may not necessarily result in isolation of a pure set of polynucleotides encoding the desired first immunoglobulin subunit polypeptides; the mixture obtained after a first round may be enriched for the desired polynucleotides but may also be contaminated with non-target insert sequences. Screening assays described herein identify pools containing the reactive host cells, and/or immunoglobulin molecules, but such pools will also contain non-reactive species. Therefore, the reactive pools are further fractionated and subjected to further rounds of screening. Thus, identification of polynucleotides encoding a first immunoglobulin subunit polypeptide which, in association with a second immunoglobulin subunit polypeptide, is capable of forming a desired immunoglobulin molecule, or antigen-specific fragment thereof, may require or benefit from several rounds of selection and/or screening, which thus increases the proportion of cells containing the desired polynucleotides. Accordingly, this embodiment further provides that the polynucleotides recovered after the first round be introduced into a second population of cells and be subjected to a second round of selection.

Accordingly, the first selection step, as described, may, or must be repeated one or more times, thereby enriching for the polynucleotides encoding the desired immunoglobulin subunit polypeptides. In order to repeat the first step of this embodiment, those polynucleotides, or pools of polynucleotides, recovered as described above are introduced into a population of host cells capable of expressing the immunoglobulin molecules encoded by the polynucleotides in the library. The host cells may be of the same type used in the first round of selection, or may be a different host cell, as long as they are capable of expressing the immunoglobulin molecules. The second library of polynucleotides are also introduced into these host cells, and expression of immunoglobulin molecules, or antigen-specific fragments thereof, on the membrane surface of said host cells, or in the cell medium, is permitted. The cells or condition medium are similarly contacted with antigen, or the medium is tested in a functional assay, and polynucleotides of the first library are again recovered from those cells or pools of host cells which express an immunoglobulin molecule that specifically binds antigen, and/or has a desired functional characteristic. These steps may be repeated one or more times, resulting in enrichment for polynucleotides derived from the first library which encode an immunoglobulin subunit polypeptide which, as part of an immunoglobulin molecule, or antigen-specific fragment thereof, specifically binds the antigen and/or has a desired functional characteristic.

Following suitable enrichment for the desired polynucleotides from the first library as described above, those polynucleotides which have been recovered are "isolated," i.e., they are substantially removed from their native environment and are largely separated from polynucleotides in the library which do not encode antigen-specific immunoglobulin subunit polypeptides. For example, cloned polynucleotides contained in a vector are considered isolated for the purposes of the present invention. It is understood that two or more different immunoglobulin subunit polypeptides which specifically bind the same antigen can be recovered by the methods described herein. Accordingly, a mixture of polynucleotides which encode polypeptides binding to the same antigen is also considered to be "isolated." Further examples of isolated polynucleotides include those maintained in heterologous host cells or purified (partially or substantially) DNA molecules in solution. However, a polynucleotide contained in a clone that is a member of a mixed library and that has not been isolated from other clones of the library, e.g., by virtue of encoding an antigen-specific immunoglobulin subunit polypeptide, is not "isolated" for the purposes of this invention. For example, a polynucleotide contained in a virus vector is "isolated" after it has been recovered, and plaque purified, and a polynucleotide contained in a plasmid vector is isolated after it has been expanded from a single bacterial colony.

Given that an antigen may comprise two or more epitopes, and several different immunoglobulin molecules may bind to any given epitope, it is contemplated that several suitable polynucleotides, e.g., two, three, four, five, ten, 100 or more polynucleotides, may be recovered from the first step of this embodiment, all of which may encode an immunoglobulin subunit polypeptide which, when combined with a suitable immunoglobulin subunit polypeptide encoded by a polynucleotide of the second library, will form an immunoglobulin molecule, or antigen binding fragment thereof, capable of specifically binding the antigen of interest. It is contemplated that each different polynucleotide recovered from the first library would be separately isolated. However, these polynucleotides may be isolated as a group of polynucleotides which encode polypeptides with the same antigen specificity, and these polynucleotides may be "isolated" together. Such mixtures of polynucleotides, whether separately isolated or collectively isolated, may be introduced into host cells in the second step, as explained below, either individually, or with two, three, four, five, ten, 100 or more of the polynucleotides pooled together.

Once one or more suitable polynucleotides from the first library are isolated, in the second step of this embodiment, one or more polynucleotides are identified in the second library which encode immunoglobulin subunit polypeptides which are capable of associating with the immunoglobulin subunit polypeptide(s) encoded by the polynucleotides isolated from the first library to form an immunoglobulin molecule, or antigen-binding fragment thereof, which specifically binds an antigen of interest, or has a desired functional characteristic.

Accordingly, the second step comprises introducing into a population of host cells capable of expressing an immunoglobulin molecule the second library of polynucleotides encoding a second immunoglobulin subunit polypeptide, introducing into the same population of host cells at least one of the polynucleotides isolated from the first library as described above, permitting expression of immunoglobulin molecules, or antigen-specific fragments thereof, on the surface of the host cells, or fully secreted into the cell medium, contacting those host cells, or conditioned medium in which the host cells were grown, with the specific antigen of interest, or subjecting the conditioned medium to a functional assay, and recovering polynucleotides of the second library from those host cells which bind the antigen of interest, or those host cells which were grown in the conditioned medium which exhibits a desired reactivity. The second step is thus carried out very similarly to the first step, except that the second immunoglobulin subunit polypeptides encoded by the polynucleotides of the second library are combined in the host cells with just those polynucleotides isolated from the first library. As mentioned above, a single cloned polynucleotide isolated from the first library may be used, or alternatively a pool of several polynucleotides isolated from the first library may be introduced simultaneously. As with the first step described above, one or more rounds of enrichment are carried out, i.e., either selection or screening of successively smaller pools, thereby enriching for polynucleotides of the second library which encode a second immunoglobulin subunit polypeptide which, as part of an immunoglobulin molecule, or antigen-specific fragment thereof, specifically binds the antigen of interest, or exhibits a desired functional characteristic. Also as with the first step, one or more desired polynucleotides from the second library are then isolated. If a pool of isolated polynucleotides is used in the earlier rounds of enrichment during the second step, preferred subsequent enrichment steps may utilize smaller pools of polynucleotides isolated from the first library, or even more preferably individual cloned polynucleotides isolated from the first library. For any individual polynucleotide isolated from the first library which is then used in the selection process for polynucleotides of the second library, it is possible that several, i.e. two, three, four, five, ten, 100, or more polynucleotides may be isolated from the second library which encode a second immunoglobulin subunit polypeptide capable of associating with a first immunoglobulin subunit polypeptide encoded by a polynucleotide isolated from the first library to form an immunoglobulin molecule, or antigen binding fragment thereof, which specifically binds the antigen of interest, or exhibits a desired functional characteristic.

The selection/screening methods for libraries encoding single-chain fragments require only one library rather than first and second libraries, and only one selection/screening step is necessary. Similar to each of the two-steps for the immunoglobulins this one-step selection/screening method may also benefit from two or more rounds of enrichment.

Vectors. In constructing antibody libraries in eukaryotic cells, any standard vector which allows expression in eukaryotic cells may be used. For example, the library could be constructed in a virus, plasmid, phage, or phagemid vector as long as the particular vector chosen comprises transcription and translation regulatory regions capable of functioning in eukaryotic cells. However, antibody libraries as described above are preferably constructed in eukaryotic virus vectors.

Eukaryotic virus vectors may be of any type, e.g., animal virus vectors or plant virus vectors. The naturally-occurring genome of the virus vector may be RNA, either positive strand, negative strand, or double stranded, or DNA, and the naturally-occurring genomes may be either circular or linear. Of the animal virus vectors, those that infect either invertebrates, e.g., insects, protozoans, or a helminth parasites; or vertebrates, e.g., mammals, birds, fish, reptiles, and amphibians are included. The choice of virus vector is limited only by the maximum insert size, and the level of protein expression achieved. Suitable virus vectors are those that infect yeast and other fungal cells, insect cells, protozoan cells, plant cells, bird cells, fish cells, reptilian cells, amphibian cells, or mammalian cells, with mammalian virus vectors being particularly preferred. Any standard virus vector could be used in the present invention, including, but not limited to poxvirus vectors (e.g., vaccinia virus), herpesvirus vectors (e.g., herpes simplex virus), adenovirus vectors, baculovirus vectors, retrovirus vectors, picorna virus vectors (e.g., poliovirus), alphavirus vectors (e.g., sindbis virus), and enterovirus vectors (e.g., mengovirus). DNA virus vectors, e.g., poxvirus, herpes virus, baculovirus, and adenovirus are preferred. As described in more detail below, the poxviruses, particularly orthopoxviruses, and especially vaccinia virus, are particularly preferred. In a preferred embodiment, host cells are utilized which are permissive for the production of infectious viral particles of whichever virus vector is chosen. Many standard virus vectors, such as vaccinia virus, have a very broad host range, thereby allowing the use of a large variety of host cells.

As mentioned supra, the first and second libraries of the invention may be constructed in the same vector, or may be constructed in different vectors. However, in preferred embodiments, the first and second libraries are prepared such that polynucleotides of the first library can be conveniently recovered, e.g., separated, from the polynucleotides of the second library in the first step, and the polynucleotides of the second library can be conveniently recovered from the polynucleotides of the first library in the second step. For example, in the first step, if the first library is constructed in a virus vector, and the second library is constructed in a plasmid vector, the polynucleotides of the first library are easily recovered as infectious virus particles, while the polynucleotides of the second library are left behind with cellular debris. Similarly, in the second step, if the second library is constructed in a virus vector, while the polynucleotides of the first library isolated in the first step are introduced in a plasmid vector, infectious virus particles containing polynucleotides of the second library are easily recovered.

When the second library of polynucleotides, or the polynucleotides isolated from the first library are introduced into host cells in a plasmid vector, it is preferred that the immunoglobulin subunit polypeptides encoded by polynucleotides comprised in such plasmid vectors be operably associated with transcriptional regulatory regions which are driven by proteins encoded by virus vector which contains the other library. For example, if the first library is constructed in a poxvirus vector, and the second library is constructed in a plasmid vector, it is preferred that the polynucleotides encoding the second immunoglobulin subunit polypeptides constructed in the plasmid library be operably associated with a transcriptional control region, preferably a promoter, which functions in the cytoplasm of poxvirus-infected cells. Similarly in the second step, if it is desired to insert the polynucleotides isolated from the first library into a plasmid vector, and the second library is constructed in a poxvirus vector, it is preferred that polynucleotides isolated from the first library and inserted into plasmids be operably associated with a transcriptional regulatory region, preferably a promoter, which functions in the cytoplasm of poxvirus-infected cells. Suitable and preferred examples of such transcriptional control regions are disclosed herein. In this way, the polynucleotides of the second library are only expressed in those cells which have also been infected by a poxvirus.

However, it is convenient to be able to maintain both the first and second libraries, as well as those polynucleotides isolated from the first library, in just a virus vector rather than having to maintain one or both of the libraries in two different vector systems. Accordingly, the present invention provides that samples of the first or second libraries, maintained in a virus vector, are inactivated such that the virus vector infects cells and the genome of virus vector is transcribed, but the vector is not replicated, i.e., when the virus vector is introduced into cells, gene products carried on the virus genome, e.g., immunoglobulin subunit polypeptides, are expressed, but infectious virus particles are not produced.

In a preferred aspect, inactivation of either the first or second library constructed in a eukaryotic virus vector is carried out by treating a sample of the library constructed in a virus vector with 4'-aminomethyl-trioxsalen (psoralen) and then exposing the virus vector to ultraviolet (UV) light. Psoralen and UV inactivation of viruses is well known to those of ordinary skill in the art. See, e.g., Tsung, K., et al., *J. Virol.* 70:165-171 (1996), which is incorporated herein by reference in its entirety.

Psoralen treatment typically comprises incubating a cell-free sample of the virus vector with a concentration of psoralen ranging from about 0.1 µg/ml to about 20 µg/1 ml, preferably about 1 µg/ml to about 17.5 µg/ml, about 2.5 µg/ml to about 15 µg/ml, about 5 µg/ml to about 12.5 µg/ml, about 7.5 µg/ml to about 12.5 µg/ml, or about 9 µg/ml to about 1 µg/ml. Accordingly, the concentration of psoralen may be about 0.1 µg/ml, 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, or 20 µg/ml. Preferably, the concentration of psoralen is about 10 µg/ml. As used herein, the term "about" takes into account that measurements of time, chemical concentration, temperature, pH, and other factors typically measured in a laboratory or production facility are never exact, and may vary by a given amount based on the type of measurement and the instrumentation used to make the measurement.

The incubation with psoralen is typically carried out for a period of time prior to UV exposure. This time period preferably ranges from about one minute to about 20 minutes prior to the UV exposure. Preferably, the time period ranges from about 2 minutes to about 19 minutes, from about 3 minutes to about 18 minutes, from about 4 minutes to about 17 minutes, from about 5 minutes to about 16 minutes, from about 6 minutes to about 15 minutes, from about 7 minutes to about 14 minutes, from about 8 minutes to about 13 minutes, or from about 9 minutes to about 12 minutes. Accordingly, the incubation time may be about 1 minute, about 2 minutes, about three minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes. More preferably, the incubation is carried out for 10 minutes prior to the UV exposure.

The psoralen-treated viruses are then exposed to UV light. The UV may be of any wavelength, but is preferably long-wave UV light, e.g., about 365 nm. Exposure to V is carried out for a time period ranging from about 0.1 minute to about 20 minutes. Preferably, the time period ranges from about 0.2 minute to about 19 minutes, from about 0.3 minute to about 18 minutes, from about 0.4 minute to about 17 minutes, from about 0.5 minute to about 16 minutes, from about 0.6 minute to about 15 minutes, from about 0.7 minute to about 14 minutes, from about 0.8 minute to about 13 minutes, from about 0.9 minute to about 12 minutes from about 1 minute to about 11 minutes, from about 2 minutes to about 10 minutes, from about 2.5 minutes to about 9 minutes, from about 3 minutes to about 8 minutes, from about 4 minutes to about 7 minutes, or from about 4.5 minutes to about 6 minutes. Accordingly, the incubation time may be about 0.1 minute, about 0.5 minute, about 1 minute, about 2 minutes, about three minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes. More preferably, the virus vector is exposed to UV light for a period of about 5 minutes.

The ability to assemble and express immunoglobulin molecules or antigen-specific fragments thereof in eukaryotic cells from two libraries of polynucleotides encoding immunoglobulin subunit polypeptides provides a significant improvement over the methods of producing single-chain antibodies in bacterial systems, in that the two-step selection process can be the basis for selection of immunoglobulin molecules or antigen-specific fragments thereof with a variety of specificities.

Examples of specific embodiments which further illustrate, but do not limit this embodiment, are provided in the Examples below. As described in detail, supra, selection of specific immunoglobulin subunit polypeptides, e.g., immunoglobulin heavy and light chains, is accomplished in two phases. First, a library of diverse heavy chains from immunoglobulin producing cells of either naïve or immunized donors is constructed in a eukaryotic virus vector, for example, a poxvirus vector, and a similarly diverse library of immunoglobulin light chains is constructed either in a plasmid vector, in which expression of the recombinant gene is regulated by a virus promoter, or in a eukaryotic virus vector which has been inactivated, e.g., through psoralen and UV treatment. Host cells capable of expressing immunoglobulin molecules, or antigen-specific fragments thereof, are infected with virus vector encoding the heavy chain library at a multiplicity of infection of about 1 (MOI=1). "Multiplicity of infection" refers to the average number of virus particles available to infect each host cell. For example, if an MOI of 1, i.e., an infection where, on average, each cell is infected by one virus particle, is desired, the number of infectious virus particles to be used in the infection is adjusted to be equal to the number of cells to be infected.

According to this strategy, host cells are either transfected with the light chain plasmid library, or infected with the inactivated light chain virus library under conditions which allow, on average, 10 or more separate polynucleotides encoding light chain polypeptides to be taken up and expressed in each cell. Under these conditions, a single host cell can express multiple immunoglobulin molecules, or fragments thereof, with different light chains associated with the same heavy chains in characteristic $H_2L_2$ structures in each host cell.

It will be appreciated by those of ordinary skill in the art that controlling the number of plasmids taken up by a cell is difficult, because successful transfection depends on inducing a competent state in cells which may not be uniform and could lead to taking up variable amounts of DNA. Accordingly, in those embodiments where it is desired to carefully control the number of polynucleotides from the second library which are introduced into each infected host cell, the use of an inactivated virus vector is preferred, because the multiplicity of infection of viruses is more easily controlled.

The expression of multiple light chains in a single host cell, associated with a single heavy chain, has the effect of reducing the avidity of specific antigen immunoglobulin, but may be beneficial for selection of relatively high affinity binding sites. As used herein, the term "affinity" refers to a measure of the strength of the binding of an individual epitope with the CDR of an immunoglobulin molecule. See, e.g., Harlow at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. As will be appreciated by those of ordinary skill in the art, if a host cell expresses immunoglobulin molecules on its surface, each comprising a given heavy chain, but where different immunoglobulin molecules on the surface comprise different light chains, the "avidity" of that host cell for a given antigen will be reduced. However, the possibility of recovering a group of immunoglobulin molecules which are related in that they comprise a common heavy chain, but which, through association with different light chains, react with a particular antigen with a spectrum of affinities, is increased. Accordingly, by adjusting the number of different light chains, or fragments thereof, which are allowed to associate with a certain number of heavy chains, or fragments thereof in a given host cell, the present invention provides a method to select for and enrich for immunoglobulin molecules, or antigen-specific fragments thereof, with varied affinity levels.

In utilizing this strategy in the first step of the method for selecting immunoglobulin molecules, or antigen-specific fragments thereof as described above, the first library is preferably constructed in a eukaryotic virus vector, and the host cells are infected with the first library at an MOI ranging from about 1 to about 10, preferably about 1, while the second library is introduced under conditions which allow up to 20 polynucleotides of said second library to be taken up by each infected host cell. For example, if the second library is constructed in an inactivated virus vector, the host cells are infected with the second library at an MOI ranging from about 1 to about 20, although MOIs higher or lower than this range may be desirable depending on the virus vector used and the characteristics of the immunoglobulin molecules desired. If the second library is constructed in a plasmid vector, transfection conditions are adjusted to allow anywhere from 0 plasmids to about 20 plasmids to enter each host cell. Selection for lower or higher affinity responses to antigen is controlled by increasing or decreasing the average number of polynucleotides of the second library allowed to enter each infected cell.

More preferably, where the first library is constructed in a virus vector, host cells are infected with the first library at an MOI ranging from about 1-9, about 1-8, about 1-7, about 1-6, about 1-5, about 1-4, or about 1-2. In other words, host cells are infected with the first library at an MOI of about 10, about 9, about 8, about 7, about 6, about 5, about 4, about 3, about 2, or about 1. Most preferably, host cells are infected with the first library at an MOI of about 1.

Where the second library is constructed in a plasmid vector, the plasmid vector is more preferably introduced into host cells under conditions which allow up to about 19, about 18, about 17, about 16, about 15, about 14, about 13, about 12, about 10, about 9, about 8, about 7, about 6, about 5, about 4, about 3 about 2, or about 1 polynucleotide(s) of the second library to be taken up by each infected host cell. Most preferably, where the second library is constructed in a plasmid vector, the plasmid vector is introduced into host cells under conditions which allow up to about 10 polynucleotides of the second library to be taken up by each infected host cell.

Similarly, where the second library is constructed in an inactivated virus vector, it is more preferred to introduce the second library into host cells at an MOI ranging from about 1-19, about 2-18, about 3-17, about 4-16, about 5-15, about 6-14, about 7-13, about 8-12, or about 9-11. In other words, host cells are infected with the second library at an MOI of about 20, about 19, about 18, about 17, about 16, about 15, about 14, about 13, about 12, about 11, about 10, about 9, about 8, about 7, about 6, about 5, about 4, about 3, about 2, or about 1. In a most preferred aspect, host cells are infected with the second library at an MOI of about 10. As will be understood by those of ordinary skill in the art, the titer, and thus the "MOI" of an inactivated virus cannot be directly measured, however, the titer may be inferred from the titer of the starting infectious virus stock which was subsequently inactivated.

In a most preferred aspect, the first library is constructed in a virus vector and the second library is constructed in a virus vector which has been inactivated, the host cells are infected with said first library at an MOI of about 1, and the host cells are infected with the second library at an MOI of about 10.

In the present invention, a preferred virus vector is derived from a poxvirus, e.g., vaccinia virus. If the first library encoding the first immunoglobulin subunit polypeptide is constructed in a poxvirus vector and the expression of second immunoglobulin subunit polypeptides, encoded by the second library constructed either in a plasmid vector or an inactivated virus vector, are regulated by a poxvirus promoter, high levels of the second immunoglobulin subunit polypeptide are expressed in the cytoplasm of the poxvirus infected cells without a requirement for nuclear integration.

In the second step of the immunoglobulin selection as described above, the second library is preferably constructed in an infectious eukaryotic virus vector, and the host cells are infected with the second library at an MOI ranging from about 1 to about 10. More preferably, where the second library is constructed in a virus vector, host cells are infected with the second library at an MOI ranging from about 1-9, about 1-8, about 1-7, about 1-6, about 1-5, about 14, or about 1-2. In other words, host cells are infected with the second library at an MOI of about 10, about 9, about 8, about 7, about 6, about 5, about 4, about 3, about 2, or about 1. Most preferably, host cells are infected with the second library at an MOI of about 1.

In the second step of the immunoglobulin selection, polynucleotides from the first library have been isolated. In certain embodiments, a single first library polynucleotide, i.e., a clone, is introduced into the host cells used to isolate polynucleotides from the second library. In this situation, the polynucleotides isolated from the first library are introduced into host cells under conditions which allow at least about 1 polynucleotide per host cell. However, since all the polynucleotides being introduced from the first library will be the same, i.e., copies of a cloned polynucleotide, the number of polynucleotides introduced into any given host cell is less important. For example, if a cloned polynucleotide isolated from the first library is contained in an inactivated virus vector, that vector would be introduced at an MOI of about 1, but an MOI greater than 1 would be acceptable. Similarly, if a cloned polynucleotide isolated from the first library is introduced in a plasmid vector, the number of plasmids which are introduced into any given host cell is of little importance, rather, transfection conditions should be adjusted to insure that at least one polynucleotide is introduced into each host cell. An alternative embodiment may be utilized if, for example, several different polynucleotides were isolated from the first library. In this embodiment, pools of two or more different polynucleotides isolated from the first library may be advantageously introduced into host cells infected with the second library of polynucleotides. In this situation, if the polynucleotides isolated from the first library are contained in an inactivated virus vector, an MOI of inactivated virus particles of greater than about 1, e.g., about 2, about 3, about 4, about 5, or more may be preferred, of if the polynucleotides isolated from the first library are contained in a plasmid vector, conditions which allow at least about 2, 3, 4, 5, or more polynucleotides to enter each cell, may be preferred.

Poxvirus Vectors. As noted above, a preferred virus vector for use in the present invention is a poxvirus vector. "Poxvirus" includes any member of the family Poxyiridae, including the subfamilies Chordopoxyiridae (vertebrate poxviruses) and Entomopoxyiridae (insect poxviruses). See, for example, B. Moss in: *Virology, 2d Edition*, B. N. Fields, D. M. Knipe et al., Eds., Raven Press, p. 2080 (1990). The chordopoxviruses comprise, inter alia, the following genera: Orthopoxvirus (e.g., vaccinia, variola virus, raccoon poxvirus); A vipoxvirus (e.g., fowlpox); Capripoxvirus (e.g., sheeppox) Leporipoxvirus (e.g., rabbit (Shope) fibroma, and myxoma); and Suipoxvirus (e.g., swinepox). The entomopoxviruses comprise three genera: A, B and C. In the present invention, orthopoxviruses are preferred. Vaccinia virus is the prototype orthopoxvirus, and has been developed and is well-characterized as a vector for the expression of heterologous proteins. In the present invention, vaccinia virus vectors, particularly those that have been developed to perform trimolecular recombination, are preferred. However, other orthopoxviruses, in particular, raccoon poxvirus have also been developed as vectors and in some applications, have superior qualities.

Poxviruses are distinguished by their large size and complexity, and contain similarly large and complex genomes. Notably, poxviruses replication takes place entirely within the cytoplasm of a host cell. The central portions of poxvirus genomes are similar, while the terminal portions of the virus genomes are characterized by more variability. Accordingly, it is thought that the central portion of poxvirus genomes carry genes responsible for essential functions common to all poxviruses, such as replication. By contrast, the terminal portions of poxvirus genomes appear responsible for characteristics such as pathogenicity and host range, which vary among the different poxviruses, and may be more likely to be non-essential for virus replication in tissue culture. It follows that if a poxvirus genome is to be modified by the rearrangement or removal of DNA fragments or the introduction of exogenous DNA fragments, the portion of the naturally-occurring DNA which is rearranged, removed, or disrupted by the introduction of exogenous DNA is preferably in the more distal regions thought to be non-essential for replication of the virus and production if infectious virions in tissue culture.

The naturally-occurring vaccinia virus genome is a cross-linked, double stranded linear DNA molecule, of about 186,000 base pairs (bp), which is characterized by inverted terminal repeats. The genome of vaccinia virus has been completely sequenced, but the functions of most gene products remain unknown. Goebel, S. J., et al., *Virology* 179:247-266, 517-563 (1990); Johnson, G. P., et al., *Virology* 196:381-401. A variety of non-essential regions have been identified in the vaccinia virus genome. See, e.g., Perkus, M. E., et al, *Virology* 152:285-97 (1986); and Kotwal, G. J. and Moss B., *Virology* 167:524-37.

In those embodiments where poxvirus vectors, in particular vaccinia virus vectors, are used to express immunoglobulin subunit polypeptides, any suitable poxvirus vector may be used. It is preferred that the libraries of immunoglobulin subunit polypeptides be carried in a region of the vector which is non-essential for growth and replication of the vector so that infectious viruses are produced. Although a variety of non-essential regions of the vaccinia virus genome have been characterized, the most widely used locus for insertion of foreign genes is the thymidine kinase locus, located in the HindIII J fragment in the genome. In certain preferred vaccinia virus vectors, the tk locus has been engineered to contain one or two unique restriction enzyme sites, allowing for convenient use of the trimolecular recombination method of library generation. See infra, and also Zauderer, PCT Publication No. WO 00/028016.

Libraries of polynucleotides encoding immunoglobulin subunit polypeptides are inserted into poxvirus vectors, particularly vaccinia virus vectors, under operable association with a transcriptional control region which functions in the cytoplasm of a poxvirus-infected cell.

Poxvirus transcriptional control regions comprise a promoter and a transcription termination signal. Gene expression in poxviruses is temporally regulated, and promoters for early, intermediate, and late genes possess varying structures. Certain poxvirus genes are expressed constitutively, and promoters for these "early-late" genes bear hybrid structures. Synthetic early-late promoters have also been developed. See Hammond J. M., et al., *J. Virol. Methods* 66:135-8 (1997); Chakrabarti S., et al., *Biotechniques* 23:1094-7 (1997). In the present invention, any poxvirus promoter may be used, but use of early, late, or constitutive promoters may be desirable based on the host cell and/or selection scheme chosen. Typically, the use of constitutive promoters is preferred.

Examples of early promoters include the 7.5-kD promoter (also a late promoter), the DNA pol promoter, the tk promoter, the RNA pol promoter, the 19-kD promoter, the 22-kD promoter, the 42-kD promoter, the 37-kD promoter, the 87-kD promoter, the H3' promoter, the H6 promoter, the D1 promoter, the D4 promoter, the D5 promoter, the D9 promoter, the D12 promoter, the 13 promoter, the M1 promoter, and the N2 promoter. See, e.g., Moss, B., "Poxyiridae and their Replication" IN *Virology, 2d Edition*, B. N. Fields, D. M. Knipe et al., Eds., Raven Press, p. 2088 (1990). Early genes transcribed in vaccinia virus and other poxviruses recognize the transcription termination signal TTTTTNT, where N can be any nucleotide. Transcription normally terminates approximately 50 bp upstream of this signal. Accordingly, if heterologous genes are to be expressed from poxvirus early promoters, care must be taken to eliminate occurrences of this signal in the coding regions for those genes. See, e.g., Earl, P. L., et al., *J. Virol.* 64:2448-51 (1990).

Example of late promoters include the 7.5-kD promoter, the MIL promoter, the 37-kD promoter, the 11-kD promoter, the 11L promoter, the 12L promoter, the 13L promoter, the 15L promoter, the 17L promoter, the 28-kD promoter, the H1L promoter, the H3L promoter, the H5L promoter, the H6L promoter, the H8L promoter, the D11L promoter, the D12L promoter, the D13L promoter, the A1L promoter, the A2L promoter, the A3L promoter, and the P4b promoter. See, e.g., Moss, B., "Poxyiridae and their Replication" IN *Virology, 2d Edition*, B. N. Fields, D. M. Knipe et al., Eds., Raven Press, p. 2090 (1990). The late promoters apparently do not recognize the transcription termination signal recognized by early promoters.

Preferred constitutive promoters for use in the present invention include the synthetic early-late promoters described by Hammond and Chakrabarti, the MH-5 early-late promoter, and the 7.5-kD or "p7.5" promoter. Examples utilizing these promoters are disclosed herein.

As will be discussed in more detail below, certain selection and screening methods based on host cell death require that the mechanisms leading to cell death occur prior to any cytopathic effect (CPE) caused by virus infection. The kinetics of the onset of CPE in virus-infected cells is dependent on the virus used, the multiplicity of infection, and the type of host cell. For example, in many tissue culture lines infected with vaccinia virus at an MOI of about 1, CPE is not significant until well after 48 to 72 hours post-infection. This allows a 2 to 3 day time frame for high level expression of immunoglobulin molecules, and antigen-based selection independent of CPE caused by the vector. However, this time frame may not be sufficient for certain selection methods, especially where higher MOIs are used, and further, the time before the onset of CPE may be shorter in a desired cell line. There is, therefore, a need for virus vectors, particularly poxvirus vectors such as vaccinia virus, with attenuated cytopathic effects so that, wherever necessary, the time frame of selection can be extended.

For example, certain attenuations are achieved through genetic mutation. These may be fully defective mutants, i.e., the production of infectious virus particles requires helper virus, or they may be conditional mutants, e.g., temperature sensitive mutants. Conditional mutants are particularly preferred, in that the virus-infected host cells can be maintained in a non-permissive environment, e.g., at a non-permissive temperature, during the period where host gene expression is required, and then shifted to a permissive environment, e.g., a permissive temperature, to allow virus particles to be produced. Alternatively, a fully infectious virus may be "attenuated" by chemical inhibitors which reversibly block virus replication at defined points in the infection cycle. Chemical inhibitors include, but are not limited to hydroxyurea and 5-fluorodeoxyuridine. Virus-infected host cells are maintained in the chemical inhibitor during the period where host gene expression is required, and then the chemical inhibitor is removed to allow virus particles to be produced.

A number of attenuated poxviruses, in particular vaccinia viruses, have been developed. For example, modified vaccinia Ankara (MVA) is a highly attenuated strain of vaccinia virus that was derived during over 570 passages in primary chick embryo fibroblasts (Mayr, A. et al., *Infection* 3:6-14 (1975)). The recovered virus deleted approximately 15% of the wild type vaccinia DNA which profoundly affects the host range restriction of the virus. MVA cannot replicate or replicates very inefficiently in most mammalian cell lines. A unique feature of the host range restriction is that the block in non-permissive cells occurs at a relatively late stage of the replication cycle. Expression of viral late genes is relatively unimpaired but virion morphogenesis is interrupted (Suter, G. and Moss, B., *Proc Natl Acad Sci USA* 89:10847-51 (1992); Carroll, M. W. and Moss, B., Virology 238:198-211 (1997)). The high levels of viral protein synthesis even in non-permissive host cells make MVA an especially safe and efficient expression vector. However, because MVA cannot complete the infectious cycle in most mammalian cells, in order to recover infectious virus for multiple cycles of selection it will be necessary to complement the MVA deficiency by coinfection or superinfection with a helper virus that is itself deficient and that can be subsequently separated from infectious MVA recombinants by differential expansion at low MOI in MVA permissive host cells.

Poxvirus infection can have a dramatic inhibitory effect on host cell protein and RNA synthesis. These effects on host gene expression could, under some conditions, interfere with the selection of specific poxvirus recombinants that have a defined physiological effect on the host cell. Some strains of vaccinia virus that are deficient in an essential early gene have been shown to have greatly reduced inhibitory effects on host cell protein synthesis. Attenuated poxviruses which lack defined essential early genes have also been described. See, e.g., U.S. Pat. Nos. 5,766,882, and 5,770,212, by Falkner, et al. Examples of essential early genes which may be rendered defective include, but are not limited to the vaccinia virus 17L, F18R, D13L, D6R, A8L, J1R, E7L, F11L, E4L, I1L, J3R, J4R, H7R, and A6R genes. A preferred essential early gene to render defective is the D4R gene, which encodes a uracil DNA glycosylase enzyme. Vaccinia viruses defective in defined essential genes are easily propagated in complementing cell lines which provides the essential gene product.

As used herein, the term "complementation" refers to a restoration of a lost function in trans by another source, such as a host cell, transgenic animal or helper virus. The loss of function is caused by loss by the defective virus of the gene product responsible for the function. Thus, a defective poxvirus is a non-viable form of a parental poxvirus, and is a form that can become viable in the presence of complementation. The host cell, transgenic animal or helper virus contains the sequence encoding the lost gene product, or "complementation element." The complementation element should be expressible and stably integrated in the host cell, transgenic animal or helper virus, and preferably would be subject to little or no risk for recombination with the genome of the defective poxvirus.

Viruses produced in the complementing cell line are capable of infecting non-complementing cells, and further are capable of high-level expression of early gene products. However, in the absence of the essential gene product, host shut-off, DNA replication, packaging, and production of infectious virus particles does not take place.

In particularly preferred embodiments described herein, selection of desired target gene products expressed in a complex library constructed in vaccinia virus is accomplished through coupling induction of expression of the complementation element to expression of the desired target gene product. Since the complementation element is only expressed in those host cells expressing the desired gene product, only those host cells will produce infectious virus which is easily recovered.

The preferred embodiments relating to vaccinia virus may be modified in ways apparent to one of ordinary skill in the art for use with any poxvirus vector. In the direct selection method, vectors other than poxvirus or vaccinia virus may be used.

The Tri-Molecular Recombination Method. Traditionally, poxvirus vectors such as vaccinia virus have not been used to identify previously unknown genes of interest from a complex libraries because a high efficiency, high titer-producing method of constructing and screening libraries did not exist for vaccinia. The standard methods of heterologous protein expression in vaccinia virus involve in vivo homologous recombination and in vitro direct ligation. Using homologous recombination, the efficiency of recombinant virus production is in the range of approximately 0.1% or less. Although efficiency of recombinant virus production using direct ligation is higher, the resulting titer is relatively low. Thus, the use of vaccinia virus vector has been limited to the cloning of previously isolated DNA for the purposes of protein expression and vaccine development.

Tri-molecular recombination, as disclosed in Zauderer, PCT Publication No. WO 00/028016, is a novel, high efficiency, high titer-producing method for cloning in vaccinia virus. Using the tri-molecular recombination method, the present inventor has achieved generation of recombinant viruses at efficiencies of at least 90%, and titers at least at least 2 orders of magnitude higher than those obtained by direct ligation.

Thus, in a preferred embodiment, libraries of polynucleotides capable of expressing immunoglobulin subunit polypeptides are constructed in poxvirus vectors, preferably vaccinia virus vectors, by tri-molecular recombination.

By "tri-molecular recombination" or a "tri-molecular recombination method" is meant a method of producing a virus genome, preferably a poxvirus genome, and even more preferably a vaccinia virus genome comprising a heterologous insert DNA, by introducing two nonhomologous fragments of a virus genome and a transfer vector or transfer DNA containing insert DNA into a recipient cell, and allowing the three DNA molecules to recombine in vivo. As a result of the recombination, a viable virus genome molecule is produced which comprises each of the two genome fragments and the insert DNA. Thus, the tri-molecular recombination method as applied to the present invention comprises: (a) cleaving an isolated virus genome, preferably a DNA virus genome, more preferably a linear DNA virus genome, and even more preferably a poxvirus or vaccinia virus genome, to produce a first viral fragment and a second viral fragment, where the first viral fragment is nonhomologous with the second viral fragment; (b) providing a population of transfer plasmids comprising polynucleotides which encode immunoglobulin subunit polypeptides, e.g., immunoglobulin light chains, immunoglobulin heavy chains, or antigen-specific fragments of either, through operable association with a transcription control region, flanked by a 5' flanking region and a 3' flanking region, wherein the 5' flanking region is homologous to said the viral fragment described in (a), and the 3' flanking region is homologous to said second viral fragment described in (a); and where the transfer plasmids are capable of homologous recombination with the first and second viral fragments such that a viable virus genome is formed; (c) introducing the transfer plasmids described in (b) and the first and second viral fragments described in (a) into a host cell under conditions where a transfer plasmid and the two viral fragments undergo in vivo homologous recombination, i.e., trimolecular recombination, thereby producing a viable modified virus genome comprising a polynucleotide which encodes an immunoglobulin subunit polypeptide; and (d) recovering modified virus genomes produced by this technique. Preferably, the recovered modified virus genome is packaged in an infectious viral particle.

By "recombination efficiency" or "efficiency of recombinant virus production" is meant the ratio of recombinant virus to total virus produced during the generation of virus libraries of the present invention. As shown in Example 5, the efficiency may be calculated by dividing the titer of recombinant virus by the titer of total virus and multiplying by 100%. For example, the titer is determined by plaque assay of crude virus stock on appropriate cells either with selection (e.g., for recombinant virus) or without selection (e.g., for recombinant virus plus wild type virus). Methods of selection, particularly if heterologous polynucleotides are inserted into the viral thymidine kinase (tk) locus, are well-known in the art and include resistance to bromdeoxyuridine (BDUR) or other nucleotide analogs due to disruption of the tk gene. Examples of selection methods are described herein.

By "high efficiency recombination" is meant a recombination efficiency of at least 1%, and more preferably a recombination efficiency of at least about 2%, 2.5%, 3%, 3.5%, 4%, 5%, 10%, 20%, 30%, 40%, 50%, 60%, 70%, 75%, 80%, 85%, 90%, 95%, or 99%.

A number of selection systems may be used, including but not limited to the thymidine kinase such as herpes simplex virus thyridine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes which can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Together, the first and second viral fragments or "arms" of the virus genome, as described above, preferably contain all the genes necessary for viral replication and for production of infectious viral particles. Examples of suitable arms and methods for their production using vaccinia virus vectors are disclosed herein. See also Falkner et al., U.S. Pat. No. 5,770, 212 for guidance concerning essential regions for vaccinia replication.

However, naked poxvirus genomic DNAs such as vaccinia virus genomes cannot produce infectious progeny without virus-encoded protein protein(s)/function(s) associated with the incoming viral particle. The required virus-encoded functions, include an RNA polymerase that recognizes the transfected vaccinia DNA as a template, initiates transcription and, ultimately, replication of the transfected DNA. See Dorner, et al. U.S. Pat. No. 5,445,953.

Thus, to produce infectious progeny virus by trimolecular recombination using a poxvirus such as vaccinia virus, the recipient cell preferably contains packaging function. The packaging function may be provided by helper virus, i.e., a virus that, together with the transfected naked genomic DNA, provides appropriate proteins and factors necessary for replication and assembly of progeny virus.

The helper virus may be a closely related virus, for instance, a poxvirus of the same poxvirus subfamily as vaccinia, whether from the same or a different genus. In such a case it is advantageous to select a helper virus which provides an RNA polymerase that recognizes the transfected DNA as a template and thereby serves to initiate transcription and, ultimately, replication of the transfected DNA. If a closely related virus is used as a helper virus, it is advantageous that it be attenuated such that formation of infectious virus will be impaired. For example, a temperature sensitive helper virus may be used at the non-permissive temperature. Preferably, a heterologous helper virus is used. Examples include, but are not limited to an avipox virus such as fowlpox virus, or an ectromelia virus (mouse pox) virus. In particular, avipoxviruses are preferred, in that they provide the necessary helper functions, but do not replicate, or produce infectious virions in mammalian cells (Scheiflinger, et al., Proc. Natl. Acad. Sci. USA 89:9977-9981 (1992)). Use of heterologous viruses minimizes recombination events between the helper virus genome and the transfected genome which take place when homologous sequences of closely related viruses are present in one cell. See Fenner & Comben, Virology 5:530 (1958); Fenner, Virology 8:499 (1959).

Alternatively, the necessary helper functions in the recipient cell is supplied by a genetic element other than a helper virus. For example, a host cell can be transformed to produce the helper functions constitutively, or the host cell can be transiently transfected with a plasmid expressing the helper functions, infected with a retrovirus expressing the helper functions, or provided with any other expression vector suitable for expressing the required helper virus function. See Dorner, et al. U.S. Pat. No. 5,445,953.

According to the trimolecular recombination method, the first and second viral genomic fragments are unable to ligate or recombine with each other, i.e., they do not contain compatible cohesive ends or homologous regions, or alternatively, cohesive ends have been treated with a dephosphorylating enzyme. In a preferred embodiment, a virus genome comprises a first recognition site for a first restriction endonuclease and a second recognition site for a second restriction endonuclease, and the first and second viral fragments are produced by digesting the viral genome with the appropriate restriction endonucleases to produce the viral "arms," and the first and second viral fragments are isolated by standard methods. Ideally, the first and second restriction endonuclease recognition sites are unique in the viral genome, or alternatively, cleavage with the two restriction endonucleases results in viral "arms" which include the genes for all essential functions, i.e., where the first and second recognition sites are physically arranged in the viral genome such that the region extending between the first and second viral fragments is not essential for virus infectivity.

In a preferred embodiment where a vaccinia virus vector is used in the trimolecular recombination method, a vaccinia virus vector comprising a virus genome with two unique restriction sites within the tk gene is used. In certain preferred vaccinia virus genomes, the first restriction enzyme is NotI, having the recognition site GCGGCCGC in the tk gene, and the second restriction enzyme is ApaI, having the recognition site GGGCCC in the tk gene. Even more preferred are vaccinia virus vectors comprising a v7.5/tk virus genome or a vEL/tk virus genome.

According to this embodiment, a transfer plasmid with flanking regions capable of homologous recombination with the region of the vaccinia virus genome containing the thymidine kinase gene is used. A fragment of the vaccinia virus genome comprising the HindIII-J fragment, which contains the tk gene, is conveniently used.

Where the virus vector is a poxvirus, the insert polynucleotides are preferably operably associated with poxvirus expression control sequences, more preferably, strong constitutive poxvirus promoters such as p7.5 or a synthetic early/late promoter.

Accordingly, a transfer plasmid of the present invention comprises a polynucleotide encoding an immunoglobulin subunit polypeptide, e.g., an heavy chain, and immunoglobulin light chain, or an antigen-specific fragment of a heavy chain or a light chain, through operable association with a vaccinia virus p7.5 promoter, or a synthetic early/late promoter.

A preferred transfer plasmid of the present invention which comprises a polynucleotide encoding an immunoglobulin heavy chain polypeptide through operable association with a vaccinia virus p7.5 promoter is pVHE, which comprises the sequence:

GGCCAAAAATTGAAAAACTAGATCTATTTATTGCACGCGGCCGCAAACCA

TGGGATGGAGCTGTATCATCCTCTTCTTGGTAGCAACAGCTACAGGCGCG

CATATGGTCACCGTCTCCTCAGGGAGTGCATCCGCCCCAACCCTTTTCCC

CCTCGTCTCCTGTGAGAATTCCCCGTCGGATACGAGCAGCGTGGCCGTTG

GCTGCCTCGCACAGGACTTCCTTCCCGACTCCATCACTTTCTCCTGGAAA

TACAAGAACAACTCTGACATCAGCAGCACCCGGGGCTTCCCATCAGTCCT

GAGAGGGGGCAAGTACGCAGCCACCTCACAGGTCCTGCTGCCTTCCAAGG

ACGTCATGCAGGGCACAGACGAACACGTGGTGTGCAAAGTCCAGCACCCC

AACGGCAACAAAGAAAGAACGTGCCTCTTCCAGTGATTGCTGAGCTGCC

TCCCAAAGTGAGCGTCTTCGTCCCACCCCGCGACGGCTTCTTCGGCAACC

CCCGCAGCAAGTCCAAGCTCATCTGCCAGGCCACGGGTTTCAGTCCCCGG

CAGATTCAGGTGTCCTGGCTGCGCGAGGGGAAGCAGGTGGGGTCTGGCGT

CACCACGGACCAGGTGCAGGCTGAGGCCAAAGAGTCTGGGCCCACGACCT

ACAAGGTGACTAGCACACTGACCATCAAAGAGAGCGACTGGCTCAGCCAG

AGCATGTTCACCTGCCGCGTGGATCACAGGGGCCTGACCTTCCAGCAGAA

TGCGTCCTCCATGTGTGTCCCCGATCAAGACACAGCCATCCGGGTCTTCG

CCATCCCCCCATCCTTTGCCAGCATCTTCCTCACCAAGTCCACCAAGTTG

ACCTGCCTGGTCACAGACCTGACCACCTATGACAGCGTGACCATCTCCTG

GACCCGCCAGAATGGCGAAGCTGTGAAAACCCACACCAACATCTCCGAGA

GCCACCCCAATGCCACTTTCAGCGCCGTGGGTGAGGCCAGCATCTGCGAG

GATGACTGGAATTCCGGGGAGAGGTTCACGTGCACCGTGACCCACACAGA

CCTGCCCTCGCCACTGAAGCAGACCATCTCCCGGCCCAAGGGGGTGGCCC

TGCACAGGCCCGATGTCTACTTGCTGCCACCAGCCCGGGAGCAGCTGAAC

CTGCGGGAGTCGGCCACCATCACGTGCCTGGTGACGGGCTTCTCTCCCGC

GGACGTCTTCGTGCAGTGGATGCAGAGGGGGCAGCCCTTGTCCCCGGAGA

AGTATGTGACCAGCGCCCCAATGCCTGAGCCCCAGGCCCCAGGCCGGTAC

TTCGCCCACAGCATCCTGACCGTGTCCGAAGAGGAATGGAACACGGGGGA

GACCTACACCTGCGTGGTGGCCCATGAGGCCCTGCCCAACAGGGTCACTG

AGAGGACCGTGGACAAGTCCACCGAGGGGGAGGTGAGCGCCGACGAGGAG

GGCTTTGAGAACCTGTGGGCCACCGCCTCCACCTTCATCGTCCTCTTCCT

CCTGAGCCTCTTCTACAGTACCACCGTCACCTTGTTCAAGGTGAAATGAG

TCGAC designated herein as SEQ ID NO:14. PCR-amplified heavy chain variable regions may be inserted in-frame into unique BssHII (at nucleotides 96-100 of SEQ ID NO:15), and BstEII (nucleotides 106-112 of SEQ ID NO:16) sites, which are indicated above in bold.

Furthermore, pVHE may be used in those embodiments where it is desired to transfer polynucleotides isolated from the first library into a plasmid vector for subsequent selection of polynucleotides of the second library as described above.

Another preferred transfer plasmid of the present invention which comprises a polynucleotide encoding an immunoglobulin kappa light chain polypeptide through operable association with a vaccinia virus p7.5 promoter is pVKE, which comprises the sequence:

GGCCAAAAATTGAAAAACTAGATCTATTTATTGCACGCGGCCGCCCATGG

GATGGAGCTGTATCATCCTCTTCTTGGTAGCAACAGCTACAGGCGTGCAC

TTGACTCGAGATCAAACGAACTGTGGCTGCACCATCTGTCTTCATCTTCC

CGCCATCTGATGAGCAGTTGAAATCTGGAACTGCCTCTGTTGTGTGCCTG

CTGAATAACTTCTATCCCAGAGAGGCCAAAGTACAGTGGAAGGTGGATAA

CGCCCTCCAATCGGGTAACTCCCAGGAGAGTGTCACAGAGCAGGACAGCA

AGGACAGCACCTACAGCCTCAGCAGCACCCTGACGCTGAGCAAAGCAGAC

TACGAGAAACACAAAGTCTACGCCTGCGAAGTCACCCATCAGGGCCTGAG

CTCGCCCGTCACAAAGAGCTTCAACAGGGGAGAGTGTTAGGTCGAC designated herein as SEQ ID NO:17. PCR-amplified kappa light chain variable regions may be inserted in-frame into unique ApaLI (nucleotides 95-100 of SEQ ID NO:18), and XhoI (nucleotides 105-110 of SEQ ID NO:19) sites, which are indicated above in bold.

Furthermore, pVKE may be used in those embodiments where it is desired to have polynucleotides of the second library in a a plasmid vector during the selection of polynucleotides of the first library as described above.

Another preferred transfer plasmid of the present invention which comprises a polynucleotide encoding an immunoglobulin lambda light chain polypeptide through operable association with a vaccinia virus p7.5 promoter is pVLE, which comprises the sequence:

GGCCAAAAATTGAAAAACTAGATCTATTTATTGCACGCGGCCGCCCATGG

GATGGAGCTGTATCATCCTCTTCTTGGTAGCAACAGCTACAGGCGTGCAC

TTGACTCGAGAAGCTTACCGTCCTACGAACTGTGGCTGCACCATCTGTCT

TCATCTTCCCGCCATCTGATGAGCAGTTGAAATCTGGAACTGCCTCTGTT

GTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGC

```
-continued
AGGACAGCAAGGACAGCACCTACAGCCTCAGCAGCACCCTGACGCTGAGC

AAAGCAGACTACGAGAAACACAAAGTCTACGCCTGCGAAGTCACCCATCA

GGGCCTGAGCTCGCCCGTCACAAAGAGCTTCAACAGGGGAGAGTGTTAGG

TCGAC
``` designated herein as SEQ ID NO:20. PCR-amplified lambda light chain variable regions may be inserted in-frame into unique ApaLI (nucleotides 95-100 of SEQ ID NO:21) and HindIII (nucleotides 111-116 of SEQ ID NO:22) sites, which are indicated above in bold.

Furthermore, pVLE may be used in those embodiments where it is desired to have polynucleotides of the second library in a a plasmid vector during the selection of polynucleotides of the first library as described above.

By "insert DNA" is meant one or more heterologous DNA segments to be expressed in the recombinant virus vector. According to the present invention, "insert DNAs" are polynucleotides which encode immunoglobulin subunit polypeptides. A DNA segment may be naturally occurring, non naturally occurring, synthetic, or a combination thereof. Methods of producing insert DNAs of the present invention are disclosed herein.

By "transfer plasmid" is meant a plasmid vector containing an insert DNA positioned between a 5' flanking region and a 3' flanking region as described above. The 5' flanking region shares homology with the first viral fragment, and the 3' flanking region shares homology with the second viral fragment. Preferably, the transfer plasmid contains a suitable promoter, such as a strong, constitutive vaccinia promoter where the virus vector is a poxvirus, upstream of the insert DNA. The term "vector" means a polynucleotide construct containing a heterologous polynucleotide segment, which is capable of effecting transfer of that polynucleotide segment into a suitable host cell. Preferably the polynucleotide contained in the vector is operably linked to a suitable control sequence capable of effecting the expression of the polynucleotide in a suitable host. Such control sequences include a promoter to effect transcription, an optional operator sequence to control such transcription, a sequence encoding suitable mRNA ribosome binding sites, and sequences which control the termination of transcription and translation. As used herein, a vector may be a plasmid, a phage particle, a virus, a messenger RNA, or simply a potential genomic insert. Once transformed into a suitable host, the vector may replicate and function independently of the host genome, or may in some instances, integrate into the genome itself. Typical plasmid expression vectors for mammalian cell culture expression, for example, are based on pRK5 (EP 307,247), pSV16B (WO 91/08291) and pVL1392 (Pharmingen).

However, "a transfer plasmid," as used herein, is not limited to a specific plasmid or vector. Any DNA segment in circular or linear or other suitable form may act as a vehicle for transferring the DNA insert into a host cell along with the first and second viral "arms" in the tri-molecular recombination method. Other suitable vectors include lambda phage, mRNA, DNA fragments, etc., as described herein or otherwise known in the art. A plurality of plasmids may be a "primary library" such as those described herein for lambda.

Modifications of Trimolecular Recombination. Trimolecular recombination can be used to construct cDNA libraries in vaccinia virus with titers of the order of about $10^7$ pfu. There are several factors that limit the complexity of these cDNA libraries or other libraries. These include: the size of the primary cDNA library or other library, such as a library of polynucleotides encoding immunoglobulin subunit polypeptides, that can be constructed in a plasmid vector, and the labor involved in the purification of large quantities (hundreds of micrograms) of virus "arms," preferably vaccinia virus "arms" or other poxvirus "arms." Modifications of trimolecular recombination that would allow for vaccinia or other virus DNA recombination with primary cDNA libraries or other libraries, such as polynucleotides encoding immunoglobulin subunit polypeptides, constructed in bacteriophage lambda or DNA or phagemids derived therefrom, or that would allow separate virus DNA arms to be generated in vivo following infection with a modified viral vector could greatly increase the quality and titer of the eukaryotic virus cDNA libraries or other libraries that are constructed using these methods.

Transfer of cDNA inserts from a Bacteriophage Lambda Library to Vaccinia Virus. Lambda phage vectors have several advantages over plasmid vectors for construction of cDNA libraries or other libraries, such as polynucleotides encoding immunoglobulin subunit polypeptides. Plasmid cDNA (or other DNA insert) libraries or linear DNA libraries are introduced into bacteria cells by chemical/heat shock transformation, or by electroporation. Bacteria cells are preferentially transformed by smaller plasmids, resulting in a potential loss of representation of longer cDNAs or other insert DNA, such as polynucleotides encoding immunoglobulin subunit polypeptides, in a library. In addition, transformation is a relatively inefficient process for introducing foreign DNA or other DNA into a cell requiring the use of expensive commercially prepared competent bacteria in order to construct a cDNA library or other library, such as polynucleotides encoding immunoglobulin subunit polypeptides. In contrast, lambda phage vectors can tolerate cDNA inserts of 12 kilobases or more without any size bias. Lambda vectors are packaged into virions in vitro using high efficiency commercially available packaging extracts so that the recombinant lambda genomes can be introduced into bacterial cells by infection. This results in primary libraries with higher titers and better representation of large cDNAs or other insert DNA, such as polynucleotides encoding immunoglobulin subunit polypeptides, than is commonly obtained in plasmid libraries.

To enable transfer of cDNA inserts or other insert DNA, such as polynucleotides encoding immunoglobulin subunit polypeptides, from a library constructed in a lambda vector to a eukaryotic virus vector such as vaccinia virus, the lambda vector must be modified to include vaccinia virus DNA sequences that allow for homologous recombination with the vaccinia virus DNA. The following example uses vaccinia virus homologous sequences, but other viruses may be similarly used. For example, the vaccinia virus HindIII J fragment (comprising the vaccinia tk gene) contained in plasmid p7.5/ ATG0/tk (as described in Example 5, infra) can be excised using HindIII and SnaBI (3 kb of vaccinia DNA sequence), and subcloned into the HindIII/SnaBI sites of pT7Blue3 (Novagen cat no. 70025-3) creating pT7B3.Vtk. The vaccinia tk gene can be excised from this vector with SacI and SnaBI and inserted into the SacI/SmaI sites of Lambda Zap Express (Stratagene) to create lambda.Vtk. The lambda.Vtk vector will contain unique NotI, BamHI, SmaI, and SalI sites for insertion of cDNA downstream of the vaccinia 7.5 k promoter. cDNA libraries can be constructed in lambda.Vtk employing methods that are well known in the art.

DNA from a cDNA library or other library, such as polynucleotides encoding immunoglobulin subunit polypeptides, constructed in lambda.Vtk, or any similar bacteriophage that includes cDNA inserts or other insert DNA with flanking vaccinia DNA sequences to promote homologous recombination, can be employed to generate cDNA or other insert DNA recombinant vaccinia virus. Methods are well known in the art for excising a plasmid from the lambda genome by coinfection with a helper phage (ExAssist phage, Stratagene cat no. 211203). Mass excision from a lambda based library creates an equivalent cDNA library or other library in a plasmid vector. Plasmids excised from, for example, the lambda.Vtk cDNA library will contain the vaccinia tk sequences flanking the cDNA inserts or other insert DNAs, such as polynucleotides encoding immunoglobulin subunit polypeptides. This plasmid DNA can then be used to construct vaccinia recombinants by trimolecular recombination. Another embodiment of this method is to purify the lambda DNA directly from the initial lambda.Vtk library, and to transfect this recombinant viral (lambda) DNA or fragments thereof together with the two large vaccinia virus DNA fragments for trimolecular recombination.

Generation of vaccinia arms in vivo. Purification and transfection of vaccinia DNA or other virus DNA "arms" or fragments is a limiting factor in the construction of polynucleotide libraries by trimolecular recombination. Modifications to the method to allow for the requisite generation of virus arms, in particular vaccinia virus arms, in vivo would allow for more efficient construction of libraries in eukaryotic viruses.

Host cells can be modified to express a restriction endonuclease that recognizes a unique site introduced into a virus vector genome. For example, when a vaccinia virus infects these host cells, the restriction endonuclease will digest the vaccinia DNA, generating "arms" that can only be repaired, i.e., rejoined, by trimolecular recombination. Examples of restriction endonucleases include the bacterial enzymes NotI and ApaI, the Yeast endonuclease VDE (R. Hirata, Y. Ohsumi, A. Nakano, H. Kawasaki, K. Suzuki, Y. Anraku. 1990 *J. Biological Chemistry* 265: 6726-6733), the *Chlamydomonas eugametos* endonuclease I-CeuI and others well-known in the art. For example, a vaccinia strain containing unique NotI and ApaI sites in the tk gene has already been constructed, and a strain containing unique VDE and/or I-CeuI sites in the tk gene could be readily constructed by methods known in the art.

Constitutive expression of a restriction endonuclease would be lethal to a cell, due to the fragmentation of the chromosomal DNA by that enzyme. To avoid this complication, in one embodiment host cells are modified to express the gene(s) for the restriction endonuclease(s) under the control of an inducible promoter.

A preferred method for inducible expression utilizes the Tet-On Gene Expression System (Clontech). In this system expression of the gene encoding the endonuclease is silent in the absence of an inducer (tetracycline). This makes it possible to isolate a stably transfected cell line that can be induced to express a toxic gene, i.e., the endonuclease (Gossen, M. et al., *Science* 268: 1766-1769 (1995)). The addition of the tetracycline derivative doxycycline induces expression of the endonuclease. In a preferred embodiment, BSC1 host cells will be stably transfected with the Tet-On vector controlling expression of the NotI gene. Confluent monolayers of these cells will be induced with doxycycline and then infected with v7.5/tk (unique NotI site in tk gene), and transfected with cDNA or insert DNA recombinant transfer plasmids or transfer DNA or lambda phage or phagemid DNA. Digestion of exposed vaccinia DNA at the unique NotI site, for example, in the tk gene or other sequence by the NotI endonuclease encoded in the host cells produces two large vaccinia DNA fragments which can give rise to full-length viral DNA only by undergoing trimolecular recombination with the transfer plasmid or phage DNA. Digestion of host cell chromosomal DNA by NotI is not expected to prevent production of modified infectious viruses because the host cells are not required to proliferate during viral replication and virion assembly.

In another embodiment of this method to generate virus arms such as vaccinia arms in vivo, a modified vaccinia strain is constructed that contains a unique endonuclease site in the tk gene or other non-essential gene, and also contains a heterologous polynucleotide encoding the endonuclease under the control of the T7 bacteriophage promoter at another non-essential site in the vaccinia genome. Infection of cells that express the T7 RNA polymerase would result in expression of the endonuclease, and subsequent digestion of the vaccinia DNA by this enzyme. In a preferred embodiment, the v7.5/tk strain of vaccinia is modified by insertion of a cassette containing the cDNA encoding NotI with expression controlled by the T7 promoter into the HindIII C or F region (Coupar, E. H. B. et al., *Gene* 68: 1-10 (1988); Flexner, C. et al., *Nature* 330: 259-262 (1987)), generating v7.5/tk/T7NotI. A cell line is stably transfected with the cDNA encoding the 17 RNA polymerase under the control of a mammalian promoter as described (O. Elroy-Stein, B. Moss. 1990 *Proc. Natl. Acad. Sci. USA* 87: 6743-6747). Infection of this packaging cell line with v7.5/tk/T7NotI will result in T7 RNA polymerase dependent expression of NotI, and subsequent digestion of the vaccinia DNA into arms. Infectious full-length viral DNA can only be reconstituted and packaged from the digested vaccinia DNA arms following trimolecular recombination with a transfer plasmid or phage DNA. In yet another embodiment of this method, the T7 RNA polymerase can be provided by co-infection with a T7 RNA polymerase recombinant helper virus, such as fowlpox virus (P. Britton, P. Green, S. Kottier, K. L. Mawditt, Z. Penzes, D. Cavanagh, M. A. Skinner. 1996 *J. General Virology* 77: 963-967).

A unique feature of trimolecular recombination employing these various strategies for generation of large virus DNA fragments, preferably vaccinia DNA fragments in vivo is that digestion of the vaccinia DNA may, but does not need to precede recombination. It suffices that only recombinant virus escapes destruction by digestion. This contrasts with trimolecular recombination employing transfection of vaccinia DNA digested in vitro where, of necessity, vaccinia DNA fragments are created prior to recombination. It is possible that the opportunity for bimolecular recombination prior to digestion will yield a greater frequency of recombinants than can be obtained through trimolecular recombination following digestion.

Selection and Screening Strategies for Isolation of Recombinant Immunoglobulin Molecules Using Virus Vectors, Especially Poxviruses. In certain embodiments of the present invention, the trimolecular recombination method is used in the production of libraries of polynucleotides expressing immunoglobulin subunit polypeptides. In this embodiment, libraries comprising full-length immunoglobulin subunit polypeptides, or fragments thereof, are prepared by first inserting cassettes encoding immunoglobulin constant regions and signal peptides into a transfer plasmid which contains 5' and 3' regions homologous to vaccinia virus. Rearranged immunoglobulin variable regions are isolated by PCR from pre-B cells from unimmunized animals of from B cells or plasma cells from immunized animals. These PCR fragments are cloned between, and in frame with the immunoglobulin signal peptide and constant region, to produce a coding region for an immunoglobulin subunit polypeptide. These transfer plasmids are introduced into host cells with poxvirus "arms," and the tri-molecular recombination method is used to produce the libraries.

The present invention provides a variety of methods for identifying, i.e., selecting or screening for immunoglobulin molecules with a desired specificity, where the immunoglobulin molecules are produced in vitro in eukaryotic cells. These include selecting for host cell effects such as antigen-induced cell death and antigen-induced signaling, screening pools of host cells for antigen-specific binding, and screening the medium in which pools of host cells are grown for the presence of soluble immunoglobulin molecules with a desired antigenic specificity or a desired functional characteristic.

As disclosed in detail herein, methods are provided to identify immunoglobulin molecules, or antigen-specific fragments thereof expressed in eukaryotic cells on the basis of either antigen-induced cell death, antigen-induced signaling, antigen-specific binding, or other antigen-specific functions. The selection and screening techniques of the present invention eliminate the bias imposed by selection of antibodies in rodents or the limitations of synthesis and assembly in bacteria.

Many of the identification methods described herein depend on expression of host cell genes or host cell transcriptional regulatory regions, which directly or indirectly induce cell death or produce a detectable signal in response to antigen binding to immunoglobulin molecules, or antigen-specific fragments thereof, expressed on the surface of the host cells. It is important to note that most preferred embodiments of the present invention require that host cells be infected with a eukaryotic virus vector, preferably a poxvirus vector, and even more preferably a vaccinia virus vector. It is well understood by those of ordinary skill in the art that some host cell protein synthesis is rapidly shut down upon poxvirus infection in some cell lines, even in the absence of viral gene expression. This is problematic if upregulation of host cell genes or host cell transcriptional regulatory regions is required in order to induce antigen-induced cell death or cell signaling. This problem is not intractable, however, because in certain cell lines, inhibition of host protein synthesis remains incomplete until after viral DNA replication. See Moss, B., "Poxyiridae and their Replication" IN *Virology*, 2d Edition, B. N. Fields, D. M. Knipe et al., Eds., Raven Press, p. 2096 (1990). There is a need, however, to rapidly screen a variety of host cells for their ability to express gene products which are upregulated upon cross linking of surface-expressed immunoglobulin molecules upon infection by a eukaryotic virus vector, preferably a poxvirus vector, and even more preferably a vaccinia virus vector; and to screen desired host cells for differential expression of cellular genes upon virus infection with various mutant and attenuated viruses.

Accordingly, a method is provided for screening a variety of host cells for the expression of host cell genes and/or the operability of host cell transcriptional regulatory regions effecting antigen-induced cell death or cell signaling, upon infection by a virus vector, through expression profiling of particular host cells in microarrays of ordered cDNA libraries. Expression profiling in microarrays is described in Duggan, D. J., et al., *Nature Genet.* 21(1 Suppl):10-14 (1999), which is incorporated herein by reference in its entirety.

According to this method, expression profiling is used to compare host cell gene expression patterns in uninfected host cells and host cells infected with a eukaryotic virus expression vector, preferably a poxvirus vector, even more preferably a vaccinia virus vector, where the particular eukaryotic virus vector is the vector used to construct said first and said second libraries of polynucleotides of the present invention. In this way, suitable host cells capable of expressing immunoglobulin molecules, or antigen-specific fragments thereof on their surface, and which further continue to undergo expression of the necessary inducible proteins upon infection with a given virus, can be identified.

Expression profiling is also used to compare host cell gene expression patterns in a given host cell, for example, comparing expression patterns when the host cell is infected with a fully infectious virus vector, and when the host cell is infected with a corresponding attenuated virus vector. Expression profiling in microarrays allows large-scale screening of host cells infected with a variety of attenuated viruses, where the attenuation is achieved in a variety of different ways. For example, certain attenuations are achieved through genetic mutation. Many vaccinia virus mutants have been characterized. These may be fully defective mutants, i.e., the production of infectious virus particles requires helper virus, or they may be conditional mutants, e.g., temperature sensitive mutants. Conditional mutants are particularly preferred, in that the virus-infected host cells can be maintained in a non-permissive environment, e.g., at a non-permissive temperature, during the period where host gene expression is required, and then shifted to a permissive environment, e.g., a permissive temperature, to allow virus particles to be produced. Alternatively, a fully infectious virus may be "attenuated" by chemical inhibitors which reversibly block virus replication at defined points in the infection cycle. Chemical inhibitors include, but are not limited to hydroxyurea and 5-fluorodeoxyuridine. Virus-infected host cells are maintained in the chemical inhibitor during the period where host gene expression is required, and then the chemical inhibitor is removed to allow virus particles to be produced.

Using this method, expression profiling in microarrays may be used to identify suitable host cells, suitable transcription regulatory regions, and/or suitable attenuated viruses in any of the selection methods described herein.

In one embodiment, a selection method is provided to select polynucleotides encoding immunoglobulin molecules, or antigen-specific fragments thereof, based on direct antigen-induced apoptosis. According to this method, a host cell is selected for infection and/or transfection that is an early B cell lymphoma. Suitable early B cell lymphoma cell lines include, but are not limited to CH33 cells, CH31 cells (Pennell, C. A., et al., *Proc. Natl. Acad. Sci. USA* 82:3799-3803 (1985)), or WEHI-231 cells (Boyd, A. W. and Schrader, J. W. *J. Immunol.* 126:2466-2469 (1981)). Early B cell lymphoma cell lines respond to crosslinking of antigen-specific immunoglobulin by induction of spontaneous growth inhibition and apoptotic cell death (Pennell, C. A., and Scott, D. W. *Eur. J. Immunol.* 16:1577-1581 (1986); Tisch, R., et al., *Proc. Natl. Acad. Sci. USA* 85:69114-6918 (1988); Ales-Martinez, J. E., et al., *Proc. Natl. Acad. Sci. USA* 85:69119-6923 (1988); Warner, G. L., and Scott, D. W. *Cell. Immunol.* 115:195-203 (1988)). Following infection and/or transfection with the first and second polynucleotide libraries as described above, synthesis and assembly of antibody molecules is allowed to proceed for a time period ranging from about 5 hours to about 48 hours, preferably for about 6 hours, about 10 hours, about 12 hours, about 16 hours about 20 hours, about 24 hours about 30 hours, about 36 hours, about 40 hours, or about 48 hours, even more preferably for about 12 hours or for about 24 hours; at which time the host cells are contacted with specific antigen, in order to cross-link any specific immunoglobulin receptors (i.e., membrane-bound immunoglobulin molecules, or antigen-specific fragments thereof) and induce apoptosis in those immunoglobulin expressing host cells which directly respond to cross-linking of antigen-specific immunoglobulin by induction of growth inhibition and apoptotic cell death. Host cells which have undergone apoptosis, or their contents, including the polynucleotides encoding an immunoglobulin subunit polypeptide which are contained therein, are recovered, thereby enriching for polynucleotides of the first library which encode a first immunoglobulin subunit polypeptide which, as part of an immunoglobulin molecule, or antigen-specific fragment thereof, specifically binds the antigen of interest.

Upon further selection and enrichment steps for polynucleotides of the first library, and isolation of those polynucleotides, a similar process is carried out to recover polynucleotides of the second library which, as part of an immunoglobulin molecule, or antigen-specific fragment thereof, bind the desired specific antigen.

An example of this method is shown in FIG. 1. A "first library" of polynucleotides encoding diverse heavy chains from antibody producing cells of either naïve or immunized donors is constructed in a poxvirus vector, preferably a vaccinia virus vector, and a similarly diverse "second library" of polynucleotides encoding immunoglobulin light chains is constructed in a plasmid vector in which expression of the polynucleotides is regulated by a vaccinia promoter, preferably a synthetic early/late promoter, for example the p11 promoter, or the p7.5 promoter. Preferably for this embodiment, the immunoglobulin heavy chain constant region encoded by the poxvirus constructs is designed to retain the transmembrane region that results in expression of immunoglobulin receptor on the surface membrane. Eukaryotic cells, preferably early B cell lymphoma cells, are infected with the pox virus heavy chain library at a multiplicity of infection of about 1 (MOI=1). Two hours later the infected cells are transfected with the light chain plasmid library under conditions which allow, on average, 10 or more separate light chain recombinant plasmids to be taken up and expressed in each cell. Because expression of the recombinant gene in this plasmid is regulated by a vaccinia virus promoter, high levels of the recombinant gene product are expressed in the cytoplasm of vaccinia virus infected cells without a requirement for nuclear integration. In addition, a sequence independent mechanism for amplification of circular DNA in the cytoplasm of vaccinia virus infected cell results in even higher concentrations of the transfected light chain recombinant plasmids (Merchlinsky, M., and Moss, B. *Cancer Cells* 6:87-93 (1988). These two factors contribute to the high levels of expression that result in excess light chain synthesis.

Another preferred embodiment utilizes a T7 phage promoter, which is active in cells in which T7 RNA polymerase is expressed, for the regulation of the expression of polynucleotides encoding a "first library" of polynucleotides encoding diverse heavy chains from antibody producing cells of either naïve or immunized donors constructed in a poxvirus vector, preferably a vaccinia virus vector, and a similarly diverse "second library" of polynucleotides encoding immunoglobulin light chains is constructed in a plasmid vector (Eckert D. and Merchlinsky M. *J Gen Virol.* 80 (Pt 6):1463-9 (1999); Elroy-Stein O., Fuerst T. R. and Moss B. *Proc Natl Acad Sci USA.* 86(16):6126-30 (1989); Fuerst T. R., Earl P. L. and Moss B. *Mol Cell Biol.* 7(7):2538-44 (1987); Elroy-Stein O. and Moss B. *Proc Natl Acad Sci USA.* 87(17):6743-7 (1990); Cottet S, and Corthesy B. *Eur J Biochem* 246(1):23-31).

As will be readily appreciated by those of ordinary skill in the art, kinetic considerations are very important in the design of this experiment as the pox virus derived expression vector is itself cytopathic in a time frame of about 1 to 10 days, more usually about 2 to 8 days, 2 to 6 days, or 2 to 4 days, depending on the virus vector used, the particular host cell, and the multiplicity of infection. In a preferred embodiment, a B cell lymphoma is selected for which the apoptotic response to surface immunoglobulin crosslinking is rapid relative to the natural cytopathic effects of pox virus infection in that cell. Accordingly, it is preferred that apoptosis in response to antigen-induced cross-linking of immunoglobulin molecules on the surface of the host cells occurs within a period between about 1 hour to about 4 days after contacting the host cells with antigen, so as to precede induction of CPE. More preferably, apoptosis occurs within about 1 hour about 2 hours, about 3 hours about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 24 hours, about 28 hours, about 32 hours, about 36 hours, about 40 hours, about 44 hours, or about 48 hours after contacting the host cells with antigen. Even more preferably apoptosis is induced within about 12 hours of contacting the host cells with antigen. Alternatively, an attenuated poxvirus vector is employed with a much slower kinetics of induction of cytopathic effects. Attenuated poxvirus vectors are disclosed herein.

According to this method, host cells which express antigen-specific immunoglobulins on their surface are selected upon undergoing apoptosis. For example, if the host cells are attached to a solid substrate, those cells which undergo apoptosis are released from the substrate and are recovered by harvesting the liquid medium in which the host cells are cultured. Alternatively, the host cells are attached to a solid substrate, and those cells which undergo apoptosis undergo a lytic event, thereby releasing their cytoplasmic contents into the liquid medium in which the host cells are cultured. Virus particles released from these cells can then be harvested in the liquid medium.

A host cell containing a polynucleotide encoding an immunoglobulin subunit polypeptide may become "nonadherent" or "nonviable" by any mechanism, which may include lysis, inability to adhere, loss of viability, loss of membrane integrity, loss of structural stability, disruption of cytoskeletal elements, inability to maintain membrane potential, arrest of cell cycle, inability to generate energy, etc. Thus, host cells containing target polynucleotides may be recovered, i.e., separated from remaining cells, by any physical means such as aspiration, washing, filtration, centrifugation, cell sorting, fluorescence activated cell sorting (FACS), etc.

For example, host cells containing polynucleotides encoding immunoglobulin subunit polypeptides may lyse and thereby release recombinant virus particles, preferably poxvirus particles even more preferably vaccinia virus particles into the culture media or may become nonadherent and therefore lift away from the solid support. Thus, in a preferred embodiment, released recombinant viruses and/or nonadherent cells are separated from adherent cells by aspiration or washing.

Where the host cells are an early B cell lymphoma cell line, the cells may be attached to a solid substrate through interaction with a B cell-specific antibody which has been bound to the substrate. Suitable B cell-specific antibodies include, but are not limited to an anti-CD 19 antibody and an anti-CD 20 antibody.

In other preferred embodiments, antigen-induced cell death is effected directly or indirectly by employing a host cell transfected with a construct in which a foreign polynucleotide, the expression of which indirectly results in cell death, is operably associated with a transcriptional regulatory region which is induced upon cross-linking of surface immunoglobulin molecules.

By a "transcriptional regulatory region induced upon cross-linking of surface immunoglobulin molecules" is meant a region, for example, a host cell promoter, which normally regulates a gene that is upregulated in the host cell upon cross linking of surface-expressed immunoglobulin molecules. A preferred example of such a transcriptional regulatory region is the BAX promoter, which is upregulated in early B cell lymphoma cells upon cross linking of surface immunoglobulin molecules.

Figure 2A:
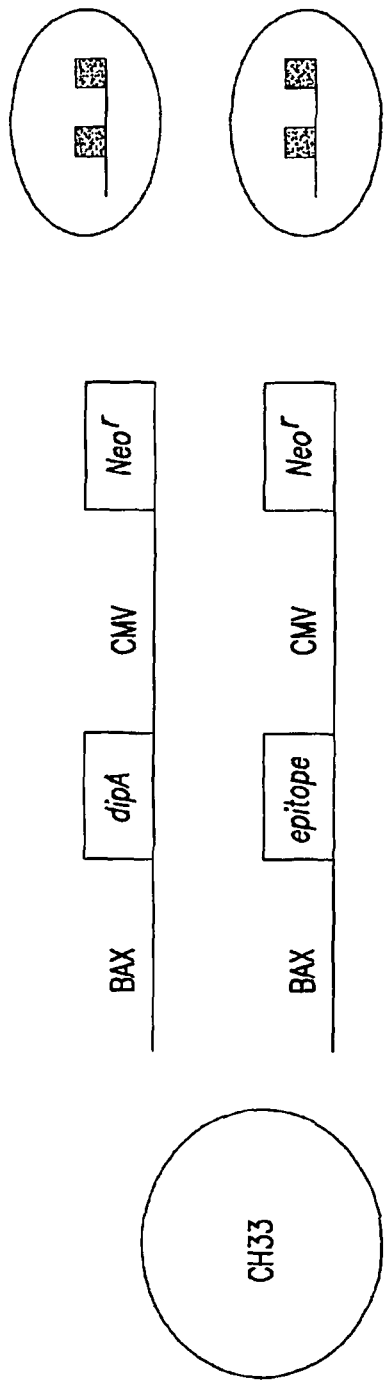
FIG. 2A. Preparation of host cells which directly or indirectly undergo cell death in response to antigen cross linking of surface immunoglobulins.
Figure 2B:
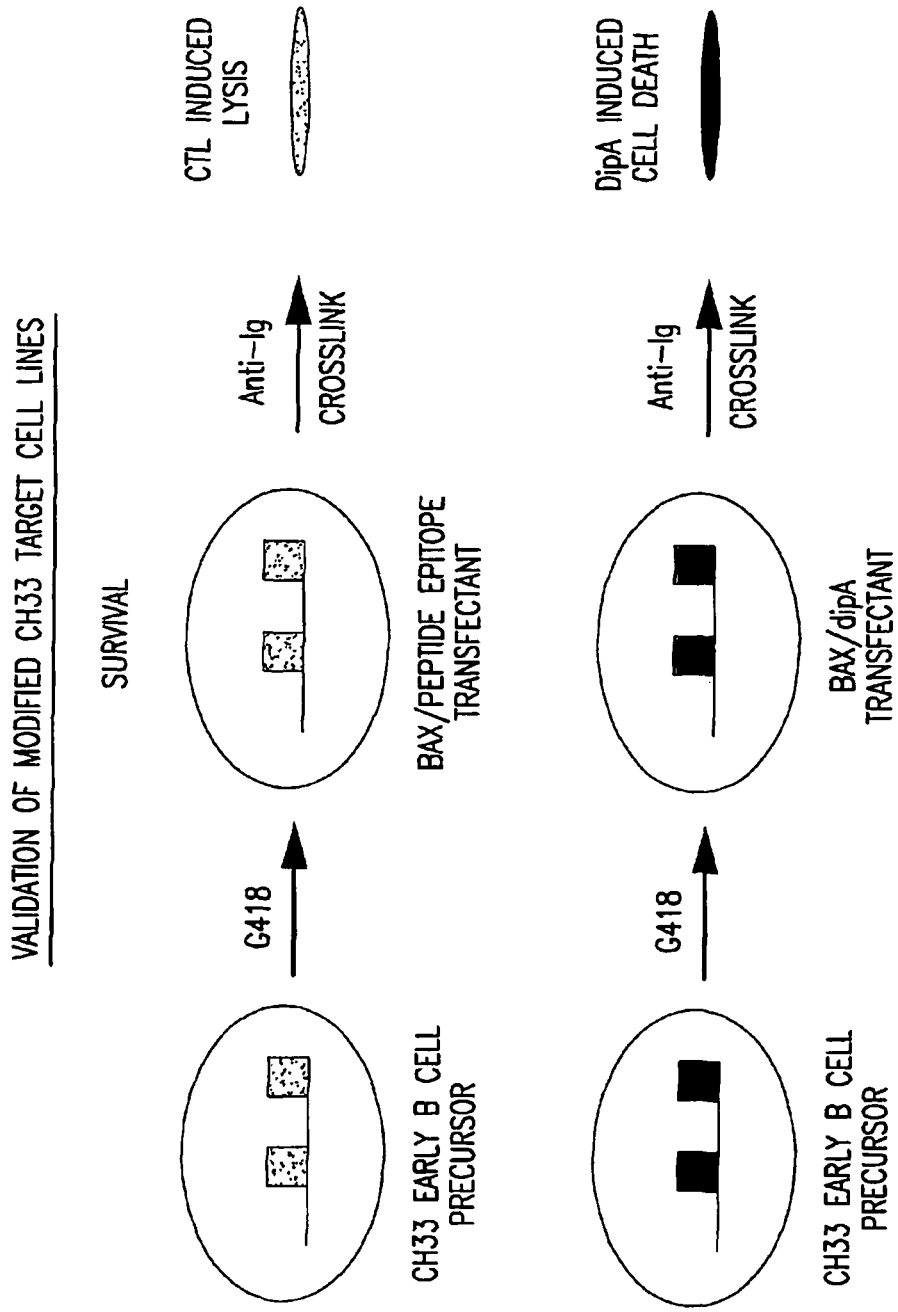
FIG. 2B. Validation of modified CH33 host cells designed to undergo CTL-induced lysis or cell death in response to antigen cross linking of surface immunoglobulins.

In one embodiment, illustrated in FIG. 2A and FIG. 2B, a method is provided to induce cell death upon expression of a foreign polynucleotide encoding a cytotoxic T cell (CTL) epitope. The foreign polynucleotide encoding the CTL epitope is placed in operable association with a transcriptional regulatory region which is induced upon cross-linking of surface immunoglobulin molecules. Upon antigen-induced cross-linking of immunoglobulin molecules of the surface of host cells, the CTL epitope is expressed on the surface of the host cell in the context of a defined MHC molecule, also expressed on the surface of the host cell. The cells are contacted with epitope-specific CTLs which recognize the CTL epitope in the context of the defined MHC molecule, and the cells expressing the CTL epitope rapidly undergo a lytic event. Methods of selecting and recovering host cells expressing specific CTL epitopes are further disclosed in Zauderer, PCT Publication No. WO 00/028016.

Selection of the host cells is accomplished through recovering those cells, or the contents thereof, which have succumbed to cell death and/or have undergone a lytic event. For example, if host cells are chosen which grow attached to a solid support, those host cells which succumb to cell death and/or undergo a lytic event will be released from the support and can be recovered in the cell supernatant. Alternatively virus particles released from host cells which have succumbed to cell death and/or undergone a lytic event may be recovered from the cell supernatant.

According to this embodiment, the MHC molecule expressed on the surface of the host cells may be either a class I MHC molecule or a class II MHC molecule. In a particularly preferred embodiment, the MHC molecule expressed on the host cells is an H-2 $K^d$ molecule, and the CTL epitope which is expressed upon antigen-induced cross linking is the peptide GYKAGMIHI, designated herein as SEQ ID NO:23.

In utilizing this method, any host cell which is capable of expressing immunoglobulin molecules, or antigen-specific fragments thereof, on its surface may be used. Suitable host cells include immunoglobulin-negative plasmacytoma cell lines. Examples of such cell lines include, but are not limited to, an NS1 cell line, an Sp2/0 cell line, and a P3 cell line. Other suitable cell lines will be apparent to those of ordinary skill in the art.

In another preferred embodiment, also illustrated in FIG. 2A and FIG. 2B, a method is provided wherein cell death is induced indirectly by employing a host cell transfected with a construct in which the a heterologous polynucleotide comprising a "suicide" gene is operably associated with a transcriptional regulatory region which is induced upon cross-linking of surface immunoglobulin molecules. By "suicide gene" is meant a nucleic acid molecule which causes cell death when expressed. Polynucleotides useful as suicide genes include many cell death-inducing sequences which are known in the art. Preferred suicide genes are those which encode toxins such as *Pseudomonas* exotoxin A chain, diphtheria A chain, ricin A chain, abrin A chain, modeccin A chain, and alpha-sarcin. A preferred suicide gene encodes the diphtheria A toxin subunit. Upon antigen-induced cross-linking of immunoglobulin molecules of the surface of host cells, the promoter of the apoptosis induced gene is induced, thereby allowing expression of the suicide gene, and thereby promoting cell death.

In utilizing this method, any host cell may be used which is capable of expressing immunoglobulin molecules, or antigen-specific fragments thereof, on its surface, and in which a transcriptional regulatory region can be identified by expression profiling, which is induced upon cross-linking of surface immunoglobulin molecules. Suitable host cells include early B cell lymphoma cell lines and immunoglobulin-negative plasmacytoma cell lines. Examples of such cell lines include, but are not limited to, a CH33 cell line, a CH 31 cell line, a WEHI-231 cell line, an NS1 cell line, an Sp2/0 cell line, and a P3 cell line. Other suitable cell lines will be apparent to those of ordinary skill in the art.

Where the host cells are an Ig-negative plasmacytoma cell line, the cells may be attached to a solid substrate through interaction with a plasmacytoma-specific antibody which has been bound to the substrate. Suitable plasmacytoma-specific antibodies include, but are not limited to an anti-CD38 antibody (Yi, Q., et al., *Blood* 90:1960-1967 (1997)), an anti-CD31 antibody (Medina, F., et al., *Cytometry* 39:231-234 (2000)), an anti-CD20 antibody (Haghighi, B., et al., *Am. J. Hematol.* 59:302-308 (1998)), and an anti-CD10 antibody (Dunphy, C. H., *Acta. Cytol.* 40:358-362 (1996)).

Direct and indirect antigen-induced cell death methods as described herein may also be combined. For example, in those embodiments where the host cell is an early B cell lymphoma, and antigen cross-linking directly induces apoptosis, antigen-induced cell death may be accelerated by transfecting the early B cell lymphoma host cell with a construct in which the a polynucleotide encoding a foreign cytotoxic T cell epitope is operably associated with a transcriptional regulatory region which is induced upon cross-linking of surface immunoglobulin molecules. Upon contacting antigen cross-linked cells with specific cytotoxic T cells as described, cell death is accelerated. Similarly, in those embodiments where the host cell is an early B cell lymphoma, and antigen cross-linking directly effects apoptosis as described above, antigen-induced cell death may be accelerated by transfecting the early B cell lymphoma host cell with a construct in which a suicide gene is operably associated with a transcriptional regulatory region which is induced upon cross-linking of surface immunoglobulin molecules.

Immunoglobulin heavy chains can be modified so that a specific antigen will induce a readily detectable signal in cells in which the receptor is crosslinked by specific antigen. A preferred embodiment is to use an apoptosis induction system to select for cell killing as a consequence of expression of an antigen-specific receptor. An example of an apoptosis induction system involves the human FAS (CD95, APO-1) receptor, which is a member of the tumor necrosis-nerve growth factor receptor superfamily recognized for its role in regulating apoptosis through recruitment and assembly of a death-inducing signaling complex that activates a cascade of proteolytic caspases. Several reports have described a FAS-based inducible cell death system whereby apoptosis could be induced through chimeric proteins containing the cytoplasmic "death domain" of FAS coupled to various receptors allowing for induction of apoptosis through a variety of cell modulators. Ishiwatari-Hayasaka et al. have successfully used the extracellular domain of mouse CD44 with human FAS to induce apoptosis upon cross-linking with polyvalent anti-CD44 antibodies (Ishiwatari-Hayasaka H. et al. *J Immunol* 163:1258-64 (1999)). In addition, Takahashi et al. have demonstrated that a chimeric human G-CSFR/FAS (extracellular/cytoplasmic) protein is capable of inducing apoptosis upon cross-linking with anti-G-CSFR antibodies (Takahashi T. et al. *J Biol Chem* 271:17555-60 (1996)). These authors also demonstrate that the chimeric protein is incapable of inducing apoptosis as a dimer. The complex must be in at least a trimeric form.

Figure 13:
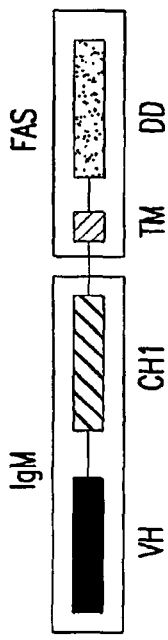
FIG. 13 Construction of IgM-Fas fusion products.
Figure 13:
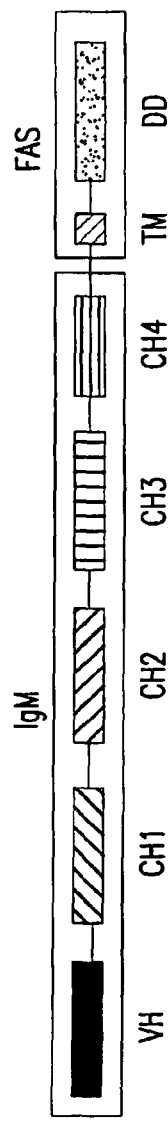
Figure 13:
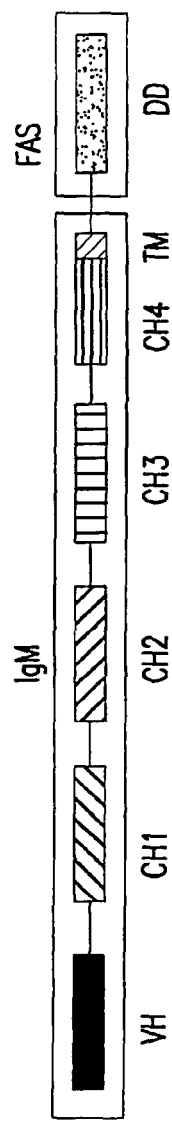

In a preferred embodiment, a chimeric gene is constructed in which the transmembrane domain and cytoplasmic death domain of FAS is fused to the carboxyl terminus of the CH1 domain of the human IgM heavy chain (CH1-Fas, FIG. 13 (*a*)). Diverse VH genes are inserted into this construct as described herein to create a library of VH-CH1-Fas recombinant vaccinia virus. Membrane receptors with VH-CH1-Fas are assembled in host cells which are infected with the VH-CH1-Fas constructs and which are transfected with DNA encoding diverse immunoglobulin light chains or which are infected with psoralin treated recombinant vaccinia virus encoding diverse immunoglobulin light chains. Those cells that express a combination of heavy and light chain variable region genes with a desired specificity will have some of their membrane receptors crosslinked in the presence of the specific immobilized antigen of interest. Apoptosis will be induced as a result of formation of functional complexes of VHCH1/FAS oligomers. Trimer formation can occur through crosslinking with polyvalent antigens or through immobilization of more than one antigen to tissue culture plates or beads.

In an alternative embodiment, the VH library is expressed in fusion proteins in which a polypeptide comprising the transmembrane domain and cytoplasmic death domain of FAS is fused to the carboxyl terminus of the IgM heavy chain CH4 domain (FIG. 13 (*b*)). In yet another embodiment, the cytoplasmic death domain of FAS is fused to the carboxyl terminus of the IgM heavy chain transmembrane domain following the CH4 domain (FIG. 13 (*c*)).

The latter two embodiments (FIG. 13 (b and c)) result in synthesis of an already dimeric Fas death domain which facilitates formation of trimeric complexes required for induction of the apoptotic signal and thereby increases the number of antigen-specific receptors selected. Use of the monomeric construct (FIG. 13(*a*)), however, results in selection of fewer but higher affinity antigen receptors, and also reduces the background of non-antigen specific cell death. The two receptors with dimeric Fas domains differ in terms of whether the transmembrane region encoded in the fusion protein is Fas-derived or IgM-derived. An IgM-derived transmembrane region may function more efficiently for membrane receptor expression in cells of the B lymphocyte lineage. An advantage of this embodiment, however, is that it is not limited to B cells. In particular, the monomeric Fas construct is synthesized and expressed as a membrane receptor in a wide variety of cell types including epithelial cell lines, Hela cells and BSC-1 cells in which high titers of vaccinia virus can be generated.

In another embodiment, a screening method is provided to recover polynucleotides encoding immunoglobulin molecules, or antigen-specific fragments thereof, based on antigen-induced cell signaling. According to this method, host cells are transfected with an easily detected reporter construct, for example luciferase, operably associated with a transcriptional regulatory region which is upregulated as a result of surface immunoglobulin crosslinking. Pools of host cells expressing immunoglobulins or fragments thereof on their surface are contacted with antigen, and upon cross linking, the signal is detected in that pool. Referring to the first step in the immunoglobulin identification method as described above, the signaling method may be carried out as follows. The first library of polynucleotides encoding immunoglobulin subunit polypeptides is divided into a plurality of pools, e.g., about 2, 5, 10, 25, 15, 75, 100, or more pools, each pool containing about 10, 100, $10^3$, $10^4$, $10^5$, $10^6$, $10^7$, $10^8$, or $10^9$ different polynucleotides encoding immunoglobulin subunit polypeptides with different variable regions. Preferred pools initially contain about $10^3$ polynucleotides each. Each pool is expanded and a replicate aliquot is set aside for later recovery. Where the pools of polynucleotides are constructed in virus vectors, preferably poxvirus vectors, and even more preferably vaccinia virus vectors, the pools are prepared, e.g., by diluting a high-titer stock of the virus library and using the portions to infect microcultures of tissue culture cells at a low MOI, e.g., MOI<0.1. Typically a greater than 1,000 fold expansion in the viral titer is obtained after 48 hrs infection. Expanding viral titers in multiple individual pools mitigates the risk that a subset of recombinants will be lost due to relatively rapid growth of a competing subset.

The virus pools are then used to infect pools of host cells equal to the number of virus pools prepared. These host cells have been engineered to express a reporter molecule as a result of surface immunoglobulin crosslinking. The number of host cells infected with each pool depends on the number of polynucleotides contained in the pool, and the MOI desired. The second library of polynucleotides is also introduced into the host cell pools, and expression of immunoglobulin molecules or fragments thereof on the surface of the host cells is permitted.

The host cell pools are then contacted with a desired antigen under conditions wherein host cells expressing antigen-specific immunoglobulin molecules on their surface express the detectable reporter molecule upon cross-linking of said immunoglobulin molecules, and the various pools of host cells are screened for expression of the reporter molecule. Those pools of host cells in which reporter expression is detected are harvested, and the polynucleotides of the first library contained therein are recovered from the aliquot previously set aside following initial expansion of that pool of polynucleotides.

To further enrich for polynucleotides of the first library which encode antigen-specific immunoglobulin subunit polypeptides, the polynucleotides recovered above are divided into a plurality of sub-pools. The sub-pools are set to contain fewer different members than the pools utilized above. For example, if each of the first pools contained $10^3$ different polynucleotides, the sub-pools are set up so as to contain, on average, about 10 or 100 different polynucleotides each. The sub-pools are introduced into host cells with the second library as above, and expression of immunoglobulin molecules, or fragments thereof, on the membrane surface of the host cells is permitted. The host cells are then contacted with antigen as above, and those sub-pools of host cells in which expression of the reporter molecule is detected are identified, and the polynucleotides of the first library contained therein are recovered from the replicate pools previously set aside as described above. It will be appreciated by those of ordinary skill in the art that this process may be repeated one or more additional times in order to adequately enrich for polynucleotides encoding antigen-specific immunoglobulin subunit polypeptides.

Upon further selection and enrichment steps for polynucleotides of the first library, and isolation or those polynucleotides, a similar process is carried out to recover polynucleotides of the second library which, as part of an immunoglobulin molecule, or antigen-specific fragment thereof, bind the desired specific antigen.

Any suitable reporter molecule may be used in this method, the choice depending upon the host cells used, the detection instruments available, and the ease of detection desired. Suitable reporter molecules include, but are not limited to luciferase, green fluorescent protein, and beta-galactosidase.

Any host cell capable of expressing immunoglobulin molecules on its surface may be used in this method. Preferred host cells include immunoglobulin-negative plasmacytoma cells, e.g., NS1 cells, Sp2/0 cells, or P3 cells, and early B-cell lymphoma cells.

Similar to the cell death methods described above, kinetic considerations dictate that expression of the reporter construct take place prior to the induction of CPE. Nonetheless, it is preferred that expression of a detectable reporter molecule in response to antigen-induced cross-linking of immunoglobulin molecules on the surface of the host cells occurs within a period between about 1 hour to about 4 days after contacting the host cells with antigen, so as to precede induction of CPE. More preferably, reporter molecule expression occurs within about 1 hour about 2 hours, about 3 hours about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, about 24 hours, about 28 hours, about 32 hours, about 36 hours, about 40 hours, about 44 hours, or about 48 hours after contacting the host cells with antigen. Even more preferably reporter molecule expression occurs within about 12 hours of contacting the host cells with antigen.

By a "transcriptional regulatory region induced upon cross-linking of surface immunoglobulin molecules" is meant a region, for example, a host cell promoter, which normally regulates a gene that is upregulated in the host cell upon cross linking of surface-expressed immunoglobulin molecules. A preferred example of such a transcriptional regulatory region is the BAX promoter, which is upregulated in early B cell lymphoma cells upon cross linking of surface immunoglobulin molecules.

Figure 5:
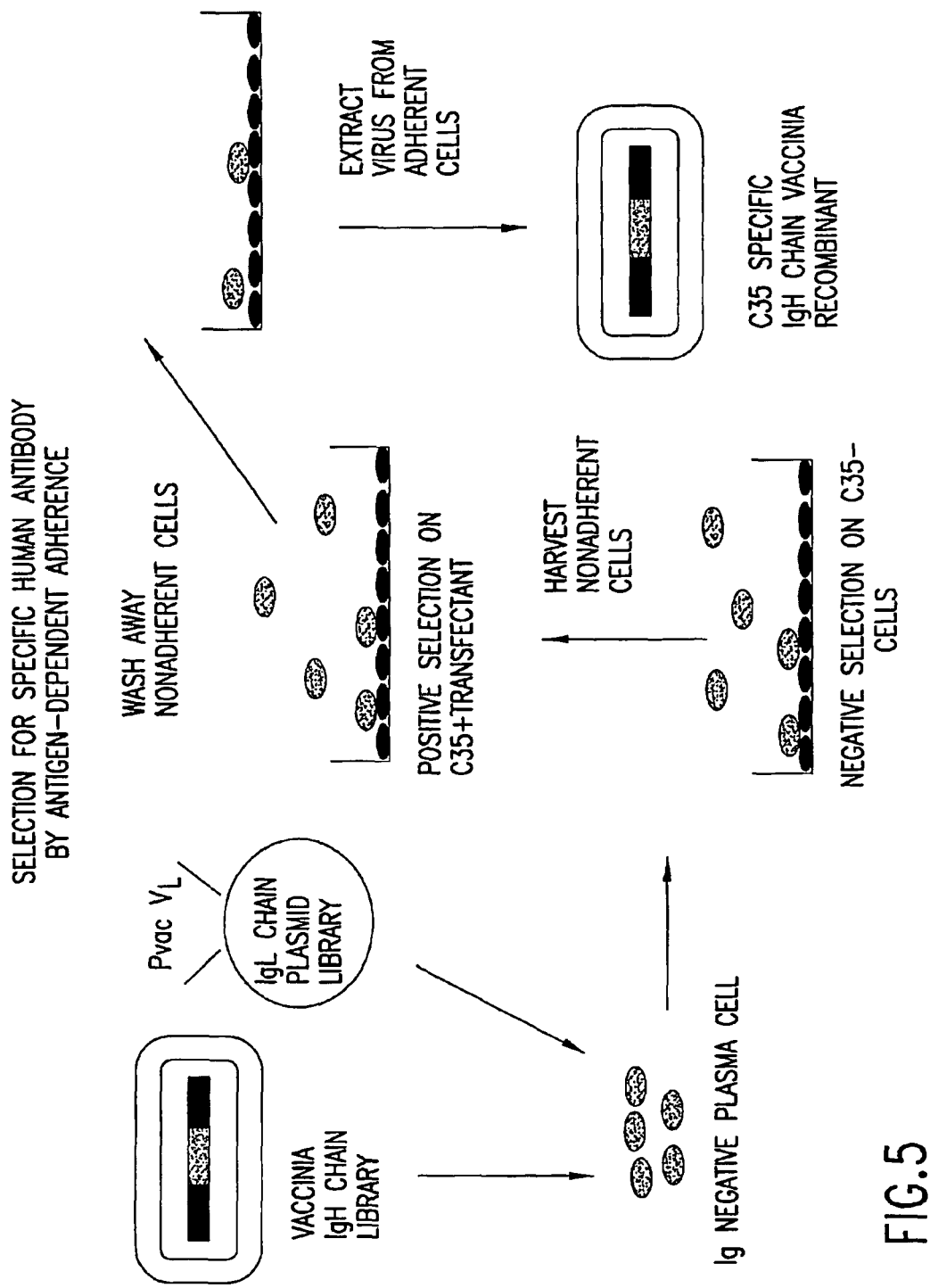
FIG. 5. Selection for Specific Human Antibody by Antigen-dependent Adherence

In yet another embodiment, a selection or screening method is provided to select polynucleotides encoding immunoglobulin molecules, or antigen-specific fragments thereof, based on antigen-specific binding. This embodiment is illustrated in FIG. 5. According to this method, host cells which express antigen-specific immunoglobulin molecules, or fragments thereof on their surface are recovered based solely on the detection of antigen binding. Antigen binding may be utilized as a selection method, i.e., where host cells expressing antigen-specific immunoglobulin molecules are directly selected by virtue of binding antigen, by methods similar to those described for selection based on cell death as described above. For example, if an antigen is bound to a solid substrate, host cells in suspension which bind the antigen may be recovered by binding, through the antigen, to the solid substrate. Alternatively, antigen binding may be used as a screening process, i.e., where pools of host cells are screened for detectable antigen binding by methods similar to that described above for antigen-induced cell signaling. For example, pools of host cells expressing immunoglobulins or fragments thereof on their surface are contacted with antigen, and antigen binding in a given pool is detected through an immunoassay, for example, through detection of an enzyme-antibody conjugate which binds to the antigen.

Referring to the first step in the immunoglobulin identification methods as described above, selection via the antigen-specific binding method may be carried out as follows. A host cell is selected for infection and/or transfection that is capable of high level expression of immunoglobulin molecules on its surface. Preferably, the host cell grows in suspension. Following infection with the first and second polynucleotide libraries as described above, synthesis and assembly of antibody molecules is allowed to proceed. The host cells are then transferred into microtiter wells which have antigen bound to their surface. Host cells which bind antigen thereby become attached to the surface of the well, and those cells that remain unbound are removed by gentle washing. Alternatively, host cells which bind antigen may be recovered, for example, by fluorescence-activated cell sorting (FACS). FACS, also called flow cytometry, is used to sort individual cells on the basis of optical properties, including fluorescence. It is useful for screening large populations of cells in a relatively short period of time. Finally the host cells which bound to the antigen are recovered, thereby enriching for polynucleotides of the first library which encode a first immunoglobulin subunit polypeptide which, as part of an immunoglobulin molecule, or antigen-specific fragment thereof, specifically binds the antigen of interest.

Upon further selection and enrichment steps for polynucleotides of the first library, and isolation or those polynucleotides, a similar process is carried out to recover polynucleotides of the second library which, as part of an immunoglobulin molecule, or antigen-specific fragment thereof, bind the desired specific antigen.

Any host cell capable of expressing immunoglobulin molecules on its surface may be used in this selection method. Preferred host cells include immunoglobulin-negative plasmacytoma cells, e.g., NS1 cells, Sp210 cells, or P3 cells, and early B-cell lymphoma cells. It is preferred that the cells are capable of growth in suspension.

Referring to the first step in the immunoglobulin identification methods as described above, screening via the antigen-specific binding method may be carried out as follows. The first library of polynucleotides, constructed in a virus vector encoding immunoglobulin subunit polypeptides, is divided into a plurality of pools by the method described above. The virus pools are then used to infect pools of host cells equal to the number of virus pools prepared. In this screening method, it is preferred that the host cells are adherent to a solid substrate. The second library of polynucleotides is also introduced into the host cell pools, and expression of immunoglobulin molecules or fragments thereof on the surface of the host cells is permitted.

The host cell pools are then contacted with a desired antigen. Following incubation with the antigen, excess unbound antigen is washed away. Finally the pools of cells are screened for antigen binding. Antigen binding may be detected by a variety of methods. For example, an antigen may be conjugated to an enzyme. Following the removal of unbound antigen, substrate is added, and enzyme reaction products are detected. This method may be enhanced by use of a secondary antibody conjugate, or a streptavidin/biotin system. Such screening methods are well known to those of ordinary skill in the art, and are readily available in kit form from standard vendors. Also, if the antigen is bound to microscopic particles, for example, gold beads, binding of the antigen to the host cells may be detected microscopically. As with the cell signaling methods described above, those pools of host cells in which antigen binding is detected are harvested, and the polynucleotides of the first library contained therein are recovered. Alternatively, pools of host cells in which antigen-binding is detected are identified, and polynucleotides of the first library contained therein are recovered from a replicate aliquot of that pool of polynucleotides set aside following initial expansion of the library.

To further enrich for polynucleotides of the first library which encode antigen-specific immunoglobulin subunit polypeptides, the polynucleotides recovered above are divided into a plurality of sub-pools. The sub-pools are set to contain fewer different members than the pools utilized in the first round. For example, if each of the first pools contained $10^3$ different polynucleotides, the sub-pools are set up so as to contain, on average, about 10 or 100 different polynucleotides each. The sub-pools are introduced into host cells with the second library as above, and expression of immunoglobulin molecules, or fragments thereof, on the membrane surface of the host cells is permitted. The host cells are then contacted with antigen as above, and those sub-pools of host cells in which antigen binding is detected are harvested or simply identified, and the polynucleotides of the first library contained therein, or in a replicate aliquot, are recovered. It will be appreciated by those of ordinary skill in the art that this process may be repeated one or more additional times in order to adequately enrich for polynucleotides encoding antigen-specific immunoglobulin subunit polypeptide.

Upon further selection and enrichment steps for polynucleotides of the first library, and isolation or those polynucleotides, a similar process is carried out to recover polynucleotides of the second library which, as part of an immunoglobulin molecule, or antigen-specific fragment thereof, bind the desired specific antigen.

Any host cell capable of expressing immunoglobulin molecules on its surface may be used in this method. Preferred host cells include immunoglobulin-negative plasmacytoma cells, e.g., NS1 cells, Sp2/0 cells, or P3 cells, and early B-cell lymphoma cells.

An antigen of interest may be contacted with host cells by any convenient method when practicing the direct and indirect antigen-induced cell death methods as described herein. For example, in certain embodiments, antigen, for example a peptide or a polypeptide, is attached to a solid substrate. As used herein, a "solid support" or a "solid substrate" is any support capable of binding a cell or antigen, which may be in any of various forms, as is known in the art. Well-known supports include tissue culture plastic, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration as long as the coupled molecule is capable of binding to a cell. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. The support configuration may include a tube, bead, microbead, well, plate, tissue culture plate, petri plate, microplate, microtiter plate, flask, stick, strip, vial, paddle, etc., etc. A solid support may be magnetic or non-magnetic. Those skilled in the art will know many other suitable carriers for binding cells or antigens, or will be able to readily ascertain the same.

Alternatively, an antigen is expressed on the surface of an antigen-expressing presenting cell. As used herein an "antigen-expressing presenting cell" refers to a cell which expresses an antigen of interest on its surface in a manner such that the antigen may interact with immunoglobulin molecules attached to the surface of host cells of the present invention. An preferred antigen-expressing presenting cell is engineered such that it expresses the antigen of interest as a recombinant protein, but the antigen may be a native antigen of that cell. Recombinant antigen-expressing presenting cells may be constructed by any suitable method using molecular biology and protein expression techniques well-known to those of ordinary skill in the art. Typically, a plasmid vector which encodes the antigen of interest is transfected into a suitable cell, and the cell is screened for expression of the desired polypeptide antigen. Preferred recombinant antigen-expressing presenting cells stably express the antigen of interest. A cell of the same type as the antigen-expressing presenting cell except that it has not been engineered to express the antigen of interest is referred to herein as an "antigen-free presenting cell." Any suitable cell line may be used to prepare antigen-expressing presenting cells. Examples of cell lines include, but are not limited to: monkey kidney CV1 line transformed by SV40 (COS-7, ATCC CRL 165 1); human embryonic kidney line (293, Graham et al. *J. Gen Virol.* 36:59 (1977)); baby hamster kidney cells (BHK, ATCC CCL 10); chinese hamster ovary-cells-DBFR(CHO, Urlaub and Chasin, *Proc. Natl. Acad. Sci.* (USA) 77:4216, (1980); mouse sertoli cells (TM4, Mather, *Biol. Reprod.* 23:243-251 (1980)); monkey kidney cells (CV1 ATCC CCL 70); african green monkey kidney cells (VERO-76, ATCC CRL-1587); human cervical carcinoma cells (BELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TR1 cells (Mather et al., Annals N.Y. Acad. Sci. 383:44-68 (1982)); NIH13T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

As will be appreciated by those of ordinary skill in the art, antigen-expressing presenting cells will comprise many naturally-occurring antigenic determinants on their surface in addition to the antigen of interest. Certain of the host cells of the present invention which express a broad spectrum of different immunoglobulin molecules, or antigen-specific fragments thereof on their surface would be expected to bind to these additional antigenic determinants. Accordingly, when an antigen-expressing presenting cell is used to contact host cells of the invention with the antigen of interest, it is necessary to first deplete the host cell population of those host cells which express immunoglobulins reactive for these additional antigenic determinants. The present invention provides methods to deplete the host cell population of host cells expressing immunoglobulin molecules specific for naturally-occurring surface antigens of the antigen-free presenting cell. This is illustrated in FIG. 5. Essentially, these methods comprise contacting the host cell population with antigen-free presenting cells prior to contacting the population of host cells with antigen-expressing presenting cells.

In one embodiment, this method comprises adsorbing the population of host cells to antigen-free presenting cells which are bound to a solid substrate. The unbound cells and/or the polynucleotides contained therein are recovered, and the recovered host cells, or new host cells into which the recovered polynucleotides have been introduced, are then contacted with antigen-expressing presenting cells. In those selection methods where pools of host cells are contacted with antigen, the pools of host cells are adsorbed to antigen-free presenting cells bound to a solid substrate. The unbound cells in the pool and/or the polynucleotides contained therein, are recovered, and the recovered host cells, or host cells into which the recovered polynucleotides have been introduced, are then contacted with antigen-expressing presenting cells.

In another embodiment, the method comprises contacting the population of host cells with antigen-free presenting cells under conditions wherein host cells expressing surface immunoglobulin molecules which react with surface antigens of antigenic determinants on the antigen-free presenting cells undergo either programmed cell death, e.g., apoptosis, direct or indirect cell death, or cell signaling, i.e., expression of a reporter molecule, all as described above, upon cross-linking of immunoglobulin molecules on the surface of the host cells. Those host cells, and more specifically, polynucleotides from either the first library or second library, from those host cells which have not succumbed to cell death or do not express a reporter molecule, are then recovered. For example, if the host cell population expressing immunoglobulin molecules is maintained attached to a solid substrate, and those cells which undergo cell death are released from the substrate, the contents of the culture fluid are removed and discarded, and the cells which remain attached, and the polynucleotides contained therein, are recovered.

As will be appreciated by those of ordinary skill in the art, depleting the host cell population of those host cells which express immunoglobulins reactive with determinants carried on the antigen-free presenting cells may require more than one round of depletion. It is further contemplated that successive rounds of depletion may be alternated with successive rounds of enrichment for host cells expressing immunoglobulin molecules which specifically bind to the antigen of interest expressed on the antigen-expressing presenting cells.

In yet another embodiment, a screening method is provided to recover polynucleotides encoding immunoglobulin molecules, or antigen-specific functional fragments thereof, based on a desired antigen-specific function of the immunoglobulin molecule. According to this method, pools of host cells are prepared which express fully-soluble immunoglobulin molecules. Expression is permitted, and the resulting cell medium is tested in various functional assays which require certain desired antigenic specificities. According to this method, the "function" being tested may be a standard effector function carried out by an immunoglobulin molecule, e.g., virus neutralization, opsonization, ADCC, antagonist/agonist activity, histamine release, hemagglutination, or hemagglutination inhibition. Alternatively, the "function" may simply refer to binding an antigen.

In a related embodiment, a screening method is provided to select immunoglobulin molecules of a known antigenic specificity, but with altered effector functions. According to these embodiments, libraries of immunoglobulin subunit polypeptides with a known antigenic specificity, but with alterations in constant domain regions known to be involved in a given effector function, are constructed. According to this method, pools of host cells are prepared which express fully-soluble immunoglobulin molecules. Expression is permitted, and the resulting cell medium is tested in various functional assays for improved or suppressed activity. According to this method, the "function" being tested may be a standard effector function carried out by an immunoglobulin molecule, e.g., virus neutralization, opsonization, complement binding, ADCC, antagonist/agonist activity, histamine release, hemagglutination, or hemagglutination inhibition.

Referring to the first step in the immunoglobulin identification method as described above, the screening for effector function may be carried out as follows. The first library of polynucleotides encoding fully secreted immunoglobulin subunit polypeptides is divided into a plurality of pools, as described above, each pool containing about 10, 100, $10^3$, $10^4$, $10^5$, $10^6$, $10^7$, $10^8$, or $10^9$ different polynucleotides encoding fully-secreted immunoglobulin subunit polypeptides with different variable regions. Preferred pools initially contain about $10^3$ polynucleotides each. Each pool is expanded and a replicate aliquot is set aside for later recovery. Where the pools of polynucleotides are constructed in virus vectors, preferably poxvirus vectors, and even more preferably vaccinia virus vectors, the pools are prepared, e.g., by diluting a high-titer stock of the virus library and using the portions to infect microcultures of tissue culture cells at a low MOI, e.g., MOI<0.1. Typically a greater than 1,000 fold expansion in the viral titer is obtained after 48 hrs infection. Expanding viral titers in multiple individual pools mitigates the risk that a subset of recombinants will be lost due to relatively rapid growth of a competing subset.

The virus pools are then used to infect pools of host cells equal to the number of virus pools prepared. The number of host cells infected with each pool depends on the number of polynucleotides contained in the pool, and the MOI desired. Virtually any host cell which is permissive for infection with the virus vector used, and which is capable of expressing fully-secreted immunoglobulin molecules may be used in this method. Preferred host cells include immunoglobulin-negative plasmacytoma cells, e.g., NS1 cells, Sp2/0 cells, or P3 cells, and early B-cell lymphoma cells. The cells may be cultured in suspension or attached to a solid surface. The second library of polynucleotides is also introduced into the host cell pools, and expression of fully secreted immunoglobulin molecules or fragments thereof is permitted.

The conditioned medium in which the host cell pools were cultured is then recovered and tested in a standardized functional assay for effector function in response to a specific target antigen.

Any suitable functional assay may be used in this method. For example, the harvested cell supernatants may be tested in a virus neutralization assay to detect immunoglobulin molecules with the ability to neutralize a target virus, for example, HIV. Alternatively, the harvested cell supernatants may be tested for the ability to block or facilitate, i.e., act as an antagonist or an agonist of, a target cellular function, for example, apoptosis. Exemplary suitable functional assays are described in the Examples, infra. As used herein, a "functional assay" also included simple detection of antigen binding, for example, through use of a standard ELISA assay, which is well known to those of ordinary skill in the art.

Where the conditioned medium in which a given host cell pool was grown exerts the desired function, the polynucleotides of the first library contained in host cells of that pool are recovered from the aliquot previously set aside following initial expansion of that pool of polynucleotide.

To further enrich for polynucleotides of the first library which encode antigen-specific immunoglobulin subunit polypeptides, the polynucleotides recovered above are divided into a plurality of sub-pools. The sub-pools are set to contain fewer different members than the pools utilized above. For example, if each of the first pools contained $10^3$ different polynucleotides, the sub-pools are set up so as to contain, on average, about 10 or 100 different polynucleotides each. The sub-pools are introduced into host cells with the second library as above, and expression of fully secreted immunoglobulin molecules, or fragments thereof, is permitted. The conditioned medium in which the host cell pools are cultured is recovered and tested in a standardized functional assay for effector function in response to a specific target antigen as described above, conditioned media samples which possess the desired functional characteristic are identified, and the polynucleotides of the first library contained in host cells of that sub-pool are recovered from the aliquot previously set aside as described above. It will be appreciated by those of ordinary skill in the art that this process may be repeated one or more additional times in order to adequately enrich for polynucleotides encoding antigen-specific immunoglobulin subunit polypeptides.

Upon further selection and enrichment steps for polynucleotides of the first library, and isolation of those polynucleotides, a similar process is carried out to recover polynucleotides of the second library which, as part of an fully secreted immunoglobulin molecule, or fragment thereof, exhibits the desired antigen-specific function.

Kits. The present invention further provides a kit for the selection of antigen-specific recombinant immunoglobulins expressed in a eukaryotic host cell. The kit comprises one or more containers filled with one or more of the ingredients required to carry out the methods described herein. In one embodiment, the kit comprises: (a) a first library of polynucleotides encoding, through operable association with a transcriptional control region, a plurality of first immunoglobulin subunit polypeptides, where each first immunoglobulin subunit polypeptide comprises (i) a first immunoglobulin constant region selected from the group consisting of a heavy chain constant region and a light chain constant region, (ii) an immunoglobulin variable region corresponding to said first constant region, and (iii) a signal peptide capable of directing cell surface expression or secretion of said first immunoglobulin subunit polypeptide, wherein said first library is constructed in a eukaryotic virus vector; (b) a second library of polynucleotides encoding, through operable association with a transcriptional control region, a plurality of second immunoglobulin subunit polypeptides, where each comprises: (i) a second immunoglobulin constant region selected from the group consisting of a heavy chain constant region and a light chain constant region, wherein said second immunoglobulin constant region is not the same as the first immunoglobulin constant region, (ii) an immunoglobulin variable region corresponding to said second constant region, and (iii) a signal peptide capable of directing cell surface expression or secretion of said second immunoglobulin subunit polypeptide, where the second immunoglobulin subunit polypeptide is capable of combining with the first immunoglobulin subunit polypeptide to form a surface immunoglobulin molecule, or antigen-specific fragment thereof, attached to the membrane of a host cell, and where the second library is constructed in a eukaryotic virus vector; and (c) a population of host cells capable of expressing said immunoglobulin molecules. In this kit, the first and second libraries are provided both as infectious virus particles and as inactivated virus particles, where the inactivated virus particles are capable of infecting the host cells and allowing expression of the polynucleotides contained therein, but the inactivated viruses do not undergo virus replication. In addition, the host cells provided with the kit are capable of expressing an antigen-specific immunoglobulin molecule which can be selected through interaction with an antigen. Use of the kit is in accordance to the methods described herein. In certain embodiments the kit will include control antigens and reagents to standardize the validate the selection of particular antigens of interest.

Isolated immunoglobulins. The present invention further provides an isolated antigen-specific immunoglobulin, or fragment thereof, produced by any of the methods disclosed herein. Such isolated immunoglobulins may be useful as diagnostic or therapeutic reagents. Further provided is a composition comprising an isolated immunoglobulin of the present invention, and a pharmaceutically acceptable carrier.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W. H. Freeman and Co., New York (1980).

Standard reference works setting forth general principles of immunology include *Current Protocols in Immunology*, John Wiley & Sons, New York; Klein, J., *Immunology: The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, a Elsevere, Amsterdam (1984).

EXAMPLES

Example 1

Construction of Human Immunoglobulin Libraries of Diverse Specificity

Libraries of polynucleotides encoding diverse immunoglobulin subunit polypeptides are produced as follows. Genes for human VH (variable region of heavy chain), VK (variable region of kappa light chain) and VL (variable region of lambda light chains) are amplified by PCR. For each of the three variable gene families, both a recombinant plasmid library and a vaccinia virus library is constructed. The variable region genes are inserted into a p7.5/tk-based transfer/expression plasmid between immunoglobulin leader and constant region sequences of the corresponding heavy chain or light chain. This plasmid is employed to generate the corresponding vaccinia virus recombinants by trimolecular recombination and can also be used directly for high level expression of immunoglobulin chains following transfection into vaccinia virus infected cells. Lymphoma cells are first infected with the vaccinia heavy chain library, followed by transient transfection with a plasmid light chain library. The co-expression of IgM and light chain results in the assembly and surface expression of antibody molecules.

Figure 3:
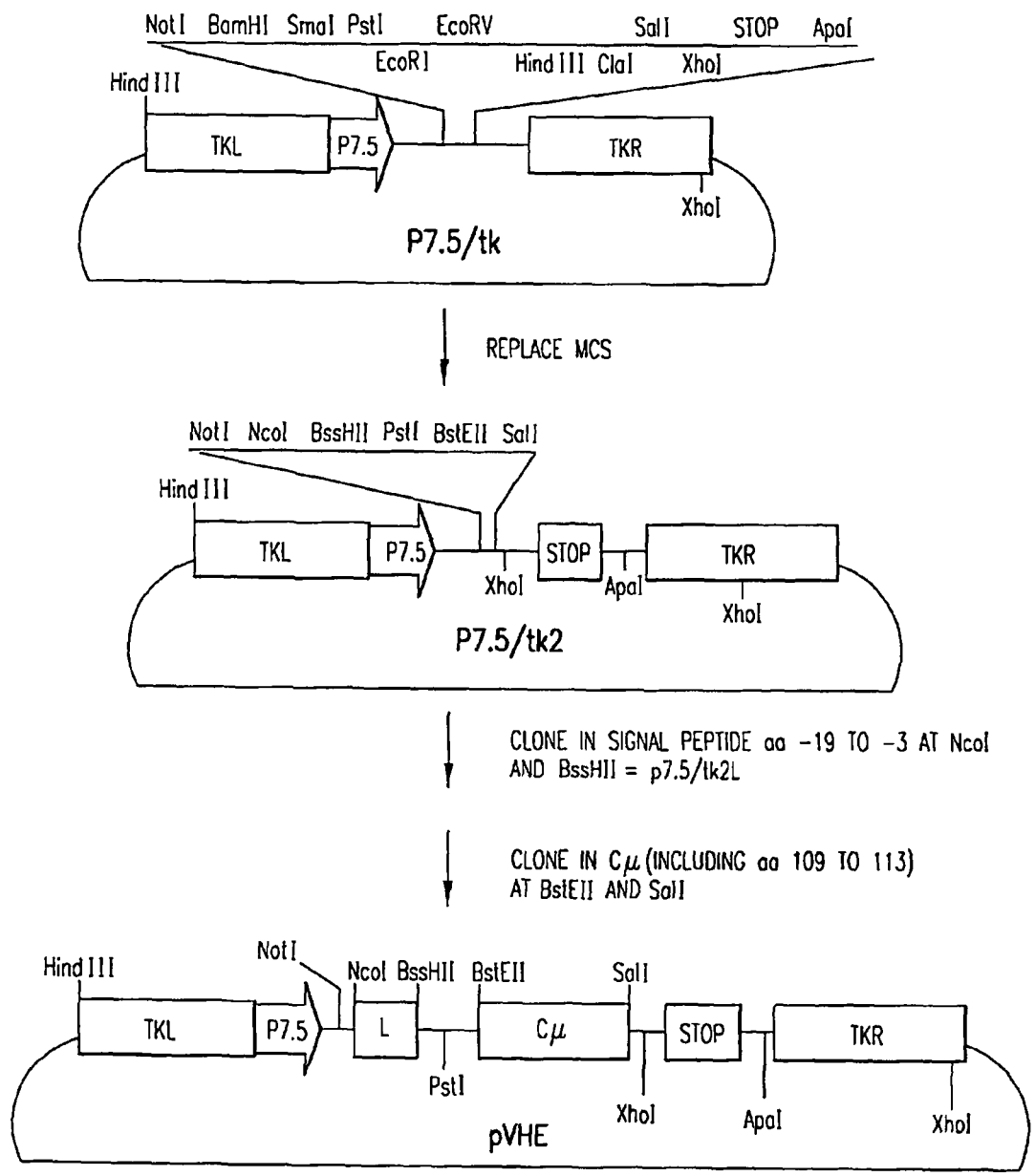
FIG. 3. Construction of pVHE

1.1 pVHE. An expression vector comprising the human g membrane immunoglobulin constant region, designated herein as pVHE is constructed as follows. The strategy is depicted in FIG. 3. A cDNA coding for the membrane-bound human IgM heavy chain is isolated from bone marrow RNA using SMART™ RACE cDNA Amplification Kit available from Clontech, Palo Alto, Calif. The PCR is carried out using the 5' primer (huCμ5B) 5'-ATTAGGATCC GGTCACCGTC TCCTCAGGG-3' (SEQ ID NO:24), and 3' primer (huCμ3S) 5'-ATTAGTCGACTCATITCACCTTGAACAAGGTGAC-3' (SEQ ID NO:25). The PCR product then is inserted into the pBluescript II/KS at BamHI and SalI sites for site-directed mutagenesis to eliminate two BstEII sites located in the CH2 and CH4 domains. Nucleotide substitutions are selected that do not alter the amino acids encoded at these sites.

Plasmid p7.5/tk, produced as described in Zauderer, PCT Publication No. WO 00/028016, and in Example 5, infra, is converted into pVHE by the following method. The multiple cloning site (MCS) of p7.5/tk is replaced with a cassette containing the following restriction sites: NotI-NcoI-BssHII-BstEII-SalI to generate p7.5/tk2. This cassette, having the sequence 5'-GCGGCCGCAA ACCATGGAAA GCGCG-CATAT GGTCACCAAA AGTCGAC-3', is referred to herein as SEQ ID NO:26. A cassette encoding the signal peptide sequence corresponding to amino acids −19 to −3 of the IgM heavy chain is cloned into p7.5/tk2 between the NcoI and BssHII sites to produce p7.5/tk2L. The BstEII-mutagenized IgM heavy chain, produced as described above, is then cloned into p7.5/tk2L between the BstEII and SalI sites to generate pVHE. Heavy chain variable region (VH) cassettes comprising nucleotides encoding amino acids 4 to 110, produced by PCR as described below, are then cloned between the BssHII and BstEII sites of pVHE to generate a library of polynucleotides encoding membrane-bound heavy chains. Because of the overlap between the μ heavy chain sequence and the restriction enzyme sites selected, this results in expression of contiguous membrane-bound heavy chain immunoglobulin subunit polypeptides in the correct translational reading frame.

Figure 8:
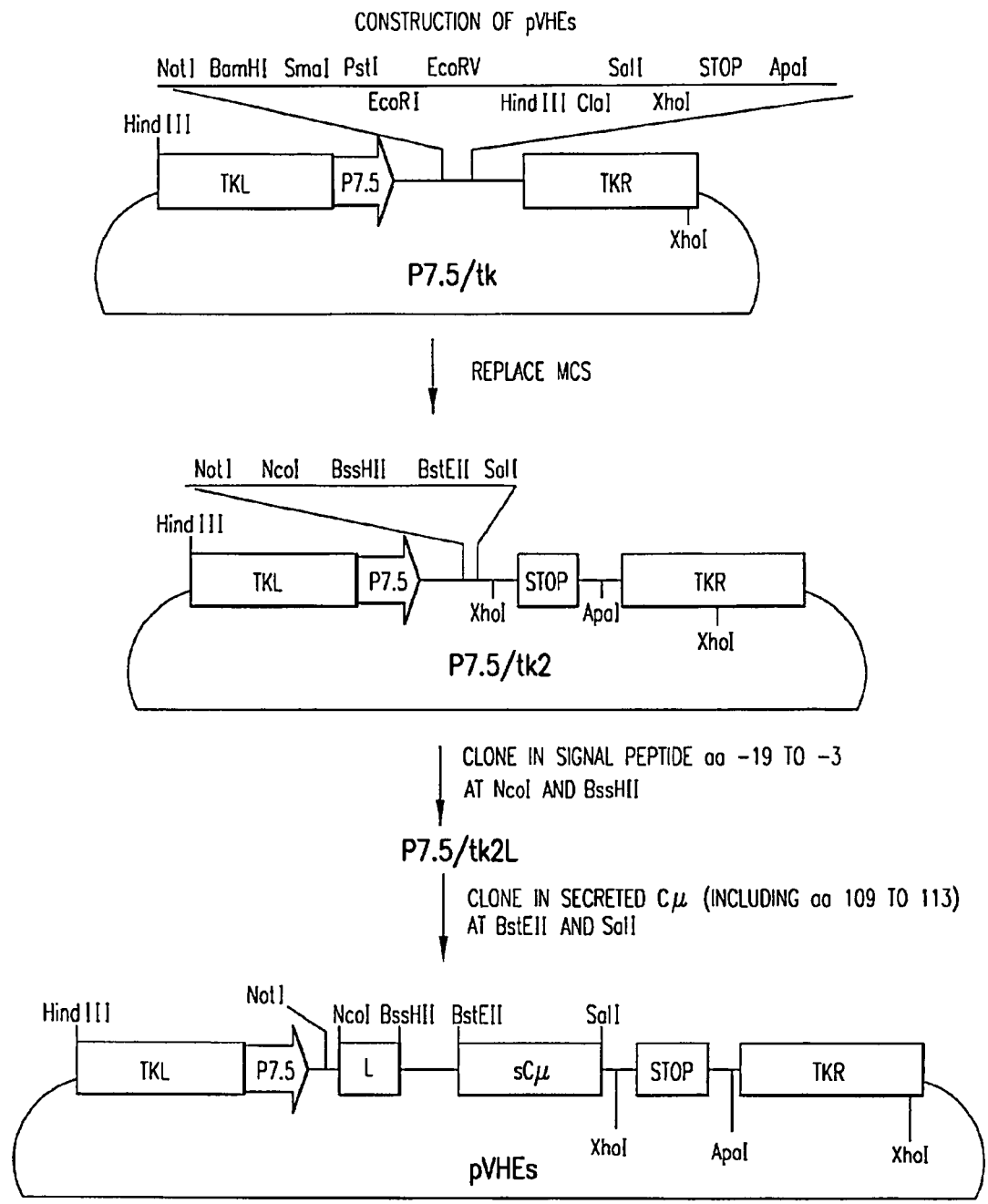
FIG. 8. Construction of pVHEs.
Figure 9:
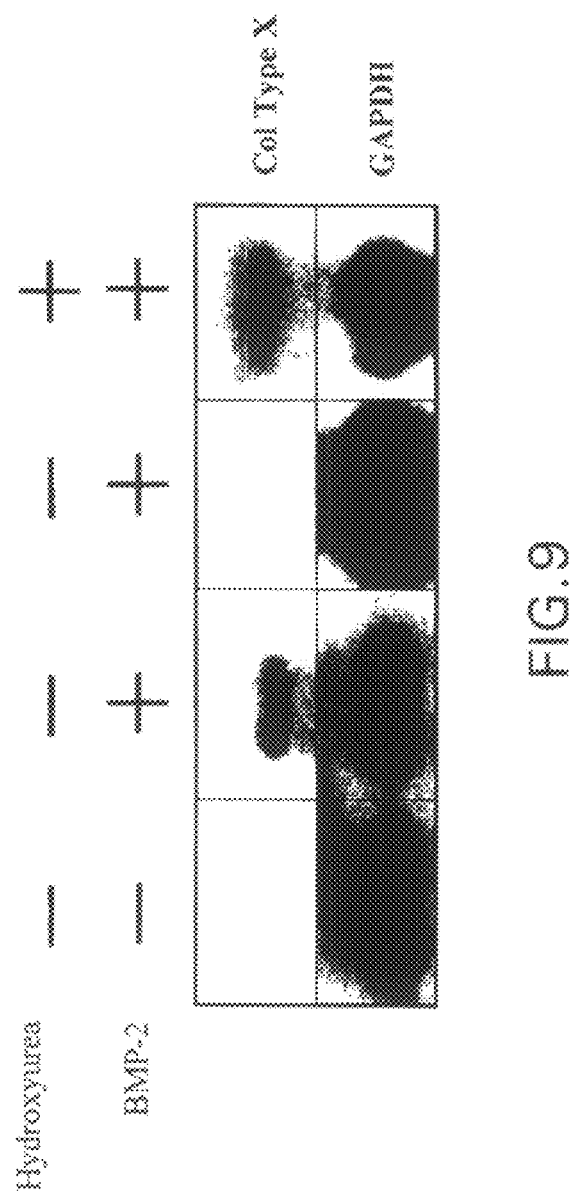
FIG. 9. Attenuation of poxvirus-mediated cytopathic effects.

1.2 pVHEs. An expression vector comprising the human μ secretory immunoglobulin constant region, designated herein as pVHEs is constructed as follows. The strategy is depicted in FIG. 8. A cDNA coding for the secretory human IgM heavy chain is isolated from bone marrow RNA using SMART™ RACE cDNA Amplification Kit. The upstream primer huCμ5B contains an appended BamHI and a BstEII site at the 5' end, followed by amino acids 111-113 of VH and the first amino acid of CμH1. The downstream primer shuCμ3S contains the last 6 amino acids of the secreted Cμ, followed by a stop codon and a SalI site. These primers have the following sequences:

```
                                       (SEQ ID NO: 27)
huCμ5B:  5'-ATTAGGATCC GGTCACCGTC TCCTCAGGG-3';
and
                                       (SEQ ID NO: 28)
shuCμ3S: 5'-ATTAGTCGAC TCAGTAGCAG GTGCCAGCTG T-3'.
```

The PCR product then is inserted into the pBluescript II/KS at BamHI and SalI sites for site-directed mutagenesis to eliminate two BstEII sites located in the CH2 and CH4 domains. Nucleotide substitutions are selected that do not alter the amino acids encoded at these sites.

Plasmid p7.5/tk2L, produced as in section 1.1, is converted into pVHEs by the following method. The BstEII-mutagenized secretory IgM heavy chain, produced as described above, is then cloned into p7.5/tk2L between the BstEII and SalI sites to generate pVHEs. Heavy chain variable region (VH) cassettes comprising nucleotides encoding amino acids −4 to 110, produced by PCR as described below, are then cloned between the BssHII and BstEII sites of pVHEs to generate a library of polynucleotides encoding secreted heavy chains. Because of the overlap between the μ heavy chain sequence and the restriction enzyme sites selected, this results in expression of contiguous secretory heavy chain immunoglobulin subunit polypeptides in the correct translational reading frame.

Figure 4:
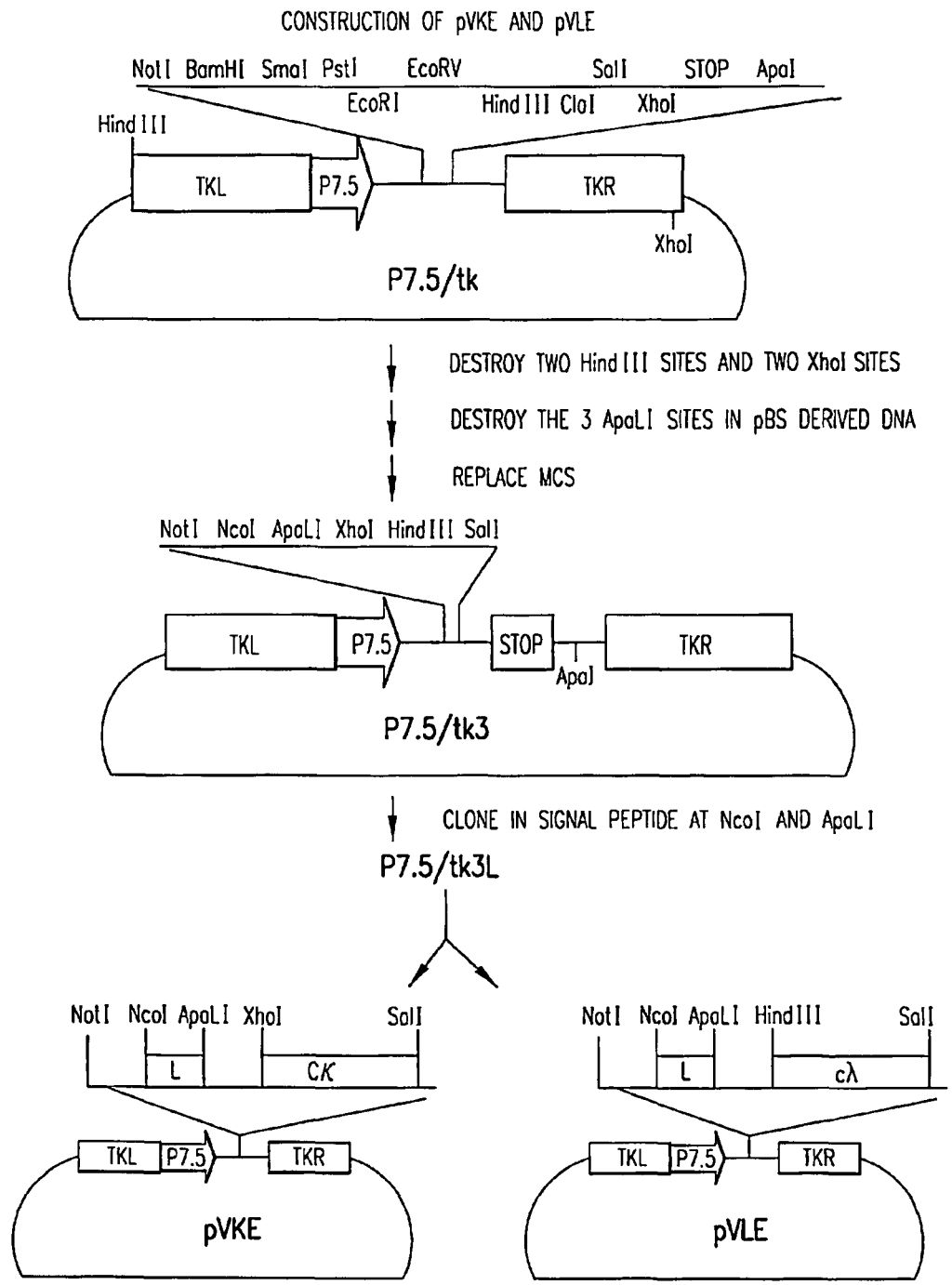
FIG. 4. Construction of pVKE and pVLE

1.3 pVKE and pVLE. Expression vectors comprising the human κ and λ immunoglobulin light chain constant regions, designated herein as pVKE and pVLE, are constructed as follows. The strategy is depicted in FIG. 4.

(a) Plasmid p7.5/tk is converted into pVKE by the following method. The two XhoI sites and two HindII sites of p7.5/tk are removed by fill-in ligation, the 3 ApaL$_1$ sites (one at the backbone, one at ColE1 ori, and the other at Amp) are removed by standard methods, and the multiple cloning site (MCS) of p7.5/tk is replaced with a cassette containing the following restriction sites: NotI-NcoI-ApaLI-XhoI-HindIII-SalI to generate p7.5/tk3. This cassette, having the sequence 5'-GCGGCCGCCC ATGGATACGT GCACTTGACT CGAGAAGCTT AGTAGTCGAC-3', is referred to herein as SEQ ID NO:29. A cassette encoding the signal peptide sequence corresponding to amino acids −19 to −2 of the kappa light chain is cloned into p7.5/tk3 between the NcoI and ApaLI sites to generate p7.5/tk3L. A cDNA coding for the Cκ region is isolated from bone marrow RNA using SMART™ RACE cDNA Amplification Kit as described above, with primers to include an XhoI site at the 5' end of the region encoding amino acids 104-107+Ck, a stop codon, and a SalI site at its 3' end. These primers have the following sequences: huCκ5: 5'-CAGGACTCGA GATCAAACGA ACTGTGGCTG-3' (SEQ ID NO:30); huCκ3: 5'-AATAT-GTCGA CCTAACACTC TCCCCTGTTG AAGCTCTTT-3' (SEQ ID NO:31); and huCκ3: 5'-AATATGTCGA CCTAA-CACTC TCCCCTGTTG AAGCTCTT-3' (SEQ ID NO:32). The Cκ cassette is then cloned into p7.5/tk3L between the XhoI and SalI sites to generate pVKE. Kappa light chain variable region cassettes (VK) comprising nucleotides encoding amino acids −3 to 105, produced by PCR as described below, are then cloned into pVKE between the ApaLI and XhoI sites. Because of the overlap between the κ light chain sequence and the restriction enzyme sites selected, this results in expression of contiguous κ light chain immunoglobulin subunit polypeptides in the correct translational reading frame.

(b) Plasmid p7.5/tk3L is converted into pVLE by the following method. A cDNA coding for the Cκ region is isolated from bone marrow RNA using SMART™ RACE cDNA Amplification Kit as described above, with primers to include a HindIII site and the region encoding amino acids 105 to 107 of V$_λ$ at its 5' end and a stop codon and a SalI site at its 3' end. These primers have the following sequences: huCλ5: 5'-ATT-TAAGCTT ACCGTCCTAC GAACTGTGGC TGCAC-CATCT-3' (SEQ ID NO:33); and huCλ3 (SEQ ID NO:31). The Cκ cassette is then cloned into p7.5/tk3L between the HindIII and SalI sites to generate pVLE. Lambda light chain variable region cassettes (VL) comprising nucleotides encoding amino acids −3 to 104, produced by PCR as described below, are then cloned into pVLE between the ApaLI and HindIII sites. Because of the overlap between the λ light chain sequence and the restriction enzyme sites selected, this results in expression of contiguous λ light chain immunoglobulin subunit polypeptides in the correct translational reading frame.

1.4 Variable Regions. Heavy chain, kappa light chain, and lambda light chain variable regions are isolated by PCR for cloning in the expression vectors produced as described above, by the following method. RNA isolated from normal human bone marrow pooled from multiple donors (available from Clontech) is used for cDNA synthesis. Aliquots of the cDNA preparations are used in PCR amplifications with primer pairs selected from the following sets of primers: VH/JH, VK/JK or VL/JL. The primers used to amplify variable regions are listed in Tables 1 and 2.

(a) Heavy chain variable regions. Due to the way the plasmid expression vectors were designed, VH primers, i.e., the forward primer in the pairs used to amplify heavy chain V regions, have the following generic configuration, with the BssHII restriction site in bold:

(SEQ ID NO: 148)
VH primers: GCGCGCACTCC-start of VH FR1 primer.

The primers are designed to include codons encoding the last 4 amino acids in the leader, with the BssHII site coding for amino acids −4 and −3, followed by the VH family-specific FR1 sequence. Tables 1 and 2 lists the sequences of the different family-specific VH primers. Since the last 5 amino acids of the heavy chain variable region, i.e., amino acids 109-113, which are identical among the six human heavy chain J regions, are embedded in plasmid pVHE, JH primers, i.e., the reverse primers used to amplify the heavy chain variable regions, exhibit the following configuration to include a BstEII site, which codes for amino acids 109 and 110 (shown in bold):

JH primers:
(SEQ ID NO: 149)
- nucleotide sequence for amino acids 103-108 of VH (ending with a G)-GTCACC.

Using these sets of primers, the VH PCR products start with the codons coding for amino acids −4 to 110 with BssHII being amino acids −4 and −3, and end at the BstEII site at the codons for amino acids 109 and 110. Upon digestion with the appropriate restriction enzymes, these PCR products are cloned into pVHE digested with BssHII and BstEII.

In order to achieve amplification of most of the possible rearranged heavy chain variable regions, families of VH and JH primers, as shown in Tables 1 and 2, are used. The VH1, 3, and 4 families account for 44 out of the 51 V regions present in the human genome. The embedding of codons coding for amino acids 109-113 in the expression vector precludes the use of a single common JH primer. However, the 5 JH primers shown in Tables 1 and 2 can be pooled for each VH primer used to reduce the number of PCR reactions required.

(b) Kappa light chain variable regions. The VK primers, i.e., the forward primer in the pairs used to amplify kappa light chain variable regions, have the following generic configuration, with the ApaLI restriction site in bold:

(SEQ ID NO: 150)
VK primer: GTGCACTCC-start of VK FR1 primer

The VK primers contain codons coding for the last 3 amino acids of the kappa light chain leader with the ApaLI site coding for amino acids −3 and−2, followed by the VK family-specific FR1 sequences. Since the codons encoding the last 4 amino acids of the kappa chain variable region (amino acids 104-107) are embedded in the expression vector pVKE, the JK primers, i.e., the reverse primer in the pairs used to amplify kappa light chain variable regions, exhibit the following configuration:

JK primer:
(SEQ ID NO: 151)
nucleotide sequence coding for amino acids 98-103 of VK-CTCGAG

The XhoI site (shown in bold) comprises the codons coding for amino acids 104-105 of the kappa light chain variable region. The PCR products encoding kappa light chain variable regions start at the codon for amino acid −3 and end at the codon for amino acid 105, with the ApaLI site comprising the codons for amino acids −3 and −2 and the XhoI site comprising the codons for amino acids 104 and 105. VK1/4 and VK3/6 primers each have two degenerate nucleotide positions. Employing these JK primers (see Tables 1 and 2), JK1, 3 and 4 will have a Val to Leu mutation at amino acid 104, and JK3 will have an Asp to Glu mutation at amino acid 105.

(c) Lambda light chain variable regions. The VL primers, i.e., the forward primer in the pairs used to amplify lambda light chain variable regions, have the following generic configuration, with the ApaLI restriction site in bold:

(SEQ ID NO: 152)
VL primer: GTGCACTCC-start of VL

The ApaLI site comprises the codons for amino acids −3 and−2, followed by the VL family-specific FR1 sequences. Since the codons encoding the last 5 amino acids of VL (amino acids 103-107) are embedded in the expression vector pVLE, the JL primers exhibit the following configuration to include a HindIII site (shown in bold) comprising the codons encoding amino acids 103-104:

JL primer:
(SEQ ID NO: 153)
-nucleotide sequence for amino acids 97-102 of VL-AAGCTT

The PCR products encoding lambda light chain variable regions start at the codon for amino acid −3 and end at the codon for amino acid 104 with the ApaLI site comprising the codons for amino acids −3 and −2, and HindIII site comprising the codons for amino acids 103 and 104.

TABLE 1

Oligonucleotide primers for PCR amplification of human immunoglobulin variable regions. Recognition sites forrestriction enzymes used in cloning are indicated in bold type. Primer sequences are from 5' to 3'.

| | | |
|---|---|---|
| VH1 | (SEQ ID NO: 34) | TTT TGC GCG CAC TCC CAG GTG CAG CTG GTG CAG TCT GG |
| VH2 | (SEQ ID NO: 144) | AATA TGC GCG CAC TCC CAG GTC ACC TTG AAG GAG TCT GG |
| VH3 | (SEQ ID NO: 35) | TTT TGC GCG CAC TCC GAG GTG CAG CTG GTG GAG TCT GG |

TABLE 1-continued

Oligonucleotide primers for PCR amplification of human immunoglobulin variable regions. Recognition sites forrestriction enzymes used in cloning are indicated in bold type. Primer sequences are from 5' to 3'.

| Name | Sequence |
|---|---|
| VH4 (SEQ ID NO: 36) | TTT TGC GCG CAC TCC CAG GTG CAG CTG CAG GAG TCG GG |
| VH5 (SEQ ID NO: 145) | AATA TGC GCG CAC TCC GAG GTG CAG CTG GTG CAG TCT G |
| JH1 (SEQ ID NO: 37) | GAC GGT GAC CAG GGT GCC CTG GCC CCA |
| JH2 (SEQ ID NO: 38) | GAC GGT GAC CAG GGT GCC ACG GCC CCA |
| JH3 (SEQ ID NO: 39) | GAC GGT GAC CAT TGT CCC TTG GCC CCA |
| JH4/5 (SEQ ID NO: 40) | GAC GGT GAC CAG GGT TCC CTG GCC CCA |
| JH6 (SEQ ID NO: 41) | GAC GGT GAC CGT GGT CCC TTG GCC CCA |
| VK1 (SEQ ID NO: 42) | TTT GTG CAC TCC GAC ATC CAG ATG ACC CAG TCT CC |
| VK2 (SEQ ID NO: 43) | TTT GTG CAC TCC GAT GTT GTG ATG ACT CAG TCT CC |
| VK3 (SEQ ID NO: 44) | TTT GTG CAC TCC GAA ATT GTG TTG ACG CAG TCT CC |
| VK4 (SEQ ID NO: 45) | TTT GTG CAC TCC GAC ATC GTG ATG ACC CAG TCT CC |
| VK5 (SEQ ID NO: 46) | TTT GTG CAC TCC GAA ACG ACA CTC ACG CAG TCT CC |
| VK6 (SEQ ID NO: 47) | TTT GTG CAC TCC GAA ATT GTG CTG ACT CAG TCT CC |
| JK1 (SEQ ID NO: G48) | GAT CTC GAG CTT GGT CCC TTG GCC GAA |
| JK2 (SEQ ID NO: 49) | GAT CTC GAG CTT GGT CCC CTG GCC AAA |
| JK3 (SEQ ID NO: 50) | GAT CTC GAG TTT GGT CCC AGG GCC GAA |
| JK4 (SEQ ID NO: 51) | GAT CTC GAG CTT GGT CCC TCC GCC GAA |
| JK5 (SEQ ID NO: 52) | AAT CTC GAG TCG TGT CCC TTG GCC GAA |
| VL1 (SEQ ID NO: 53) | TTT GTG CAC TCC CAG TCT GTG TTG ACG CAG CCG CC |
| VL2 (SEQ ID NO: 54) | TTT GTG CAC TCC CAG TCT GCC CTG ACT CAG CCT GC |
| VL3A (SEQ ID NO: 55) | TTT GTG CAC TCC TCC TAT GTG CTG ACT CAG CCA CC |
| VL3B (SEQ ID NO: 56) | TTT GTG CAC TCC TCT TCT GAG CTG ACT CAG GAC CC |
| VL4 (SEQ ID NO: 57) | TTT GTG CAC TCC CAC GTT ATA CTG ACT CAA CCG CC |
| VL5 (SEQ ID NO: 58) | TTT GTG CAC TCC CAG GCT GTG CTC ACT CAG CCG TC |

TABLE 1-continued

Oligonucleotide primers for PCR amplification of human immunoglobulin variable regions. Recognition sites forrestriction enzymes used in cloning are indicated in bold type. Primer sequences are from 5' to 3'.

| Name | Sequence |
|---|---|
| VL6 (SEQ ID NO: 59) | TTT GTG CAC TCC AAT TTT ATG CTG ACT CAG CCC CA |
| VL7 (SEQ ID NO: 60) | TTT GTG CAC TCC CAG GCT GTG GTG ACT CAG GAG CC |
| JL1 (SEQ ID NO: 61) | GGT AAG CTT GGT CCC AGT TCC GAA GAC |
| JL2/3 (SEQ ID NO: 62) | GGT AAG CTT GGT CCC TCC GCC GAA T |

TABLE 2

Oligonucleotide primers for PCR amplification of human immunoglobulin variable regions. Recognition sites for restriction enzymes used in cloning are indicated in bold type. Primer sequences are from 5' to 3'.

| Name | Sequence |
|---|---|
| VH1a (SEQ ID NO: 63) | AATA TGC GCG CAC TCC CAG GTG CAG CTG GTG CAG TCT GG |
| VH2a (SEQ ID NO: 64) | AATA TGC GCG CAC TCC CAG GTC ACC TTG AAG GAG TCT GG |
| VH3a (SEQ ID NO: 65) | AATA TGC GCG CAC TCC GAG GTG CAG CTG GTG GAG TCT GG |
| VH4a (SEQ ID NO: 66) | AATA TGC GCG CAC TCC CAG GTG CAG CTG CAG GAG TCG GG |
| VH5a (SEQ ID NO: 67) | AATA TGC GCG CAC TCC GAG GTG CAG CTG GTG CAG TCT G |
| JH1a (SEQ ID NO: 68) | GA GAC GGT GAC CAG GGT GCC CTG GCC CCA |
| JH2a (SEQ ID NO: 69) | GA GAC GGT GAC CAG GGT GCC ACG GCC CCA |
| JH3a (SEQ ID NO: 70) | GA GAC GGT GAC CAT TGT CCC TTG GCC CCA |
| JH4/5a (SEQ ID NO: 71) | GA GAC GGT GAC CAG GGT TCC CTG GCC CCA |
| JH6a (SEQ ID NO: 72) | GA GAC GGT GAC CGT GGT CCC TTG GCC CCA |
| VK1a (SEQ ID NO: 73) | CAGGA GTG CAC TCC GAC ATC CAG ATG ACC CAG TCT CC |
| VK2a (SEQ ID NO: 74) | CAGGA GTG CAC TCC GAT GTT GTG ATG ACT CAG TCT CC |
| VK3a (SEQ ID NO: 75) | CAGGA GTG CAC TCC GAA ATT GTG TTG ACG CAG TCT CC |
| VK4a (SEQ ID NO: 76) | CAGGA GTG CAC TCC GAC ATC GTG ATG ACC CAG TCT CC |
| VK5a (SEQ ID NO: 77) | CAGGA GTG CAC TCC GAA ACG ACA CTC ACG CAG TCT CC |
| VK6a (SEQ ID NO: 78) | CAGGA GTG CAC TCC GAA ATT GTG CTG ACT CAG TCT CC |
| JK1a (SEQ ID NO: 79) | TT GAT CTC GAG CTT GGT CCC TTG GCC GAA |

TABLE 2-continued

Oligonucleotide primers for PCR amplification of human immunoglobulin variable regions. Recognition sites for restriction enzymes used in cloning are indicated in bold type. Primer sequences are from 5' to 3'.

| | |
|---|---|
| JK2a (SEQ ID NO: 80) | TT GAT CTC GAG CTT GGT CCC CTG GCC AAA |
| JK3a (SEQ ID NO: 81) | TT GAT CTC GAG TTT GGT CCC AGG GCC GAA |
| JK4a (SEQ ID NO: 82) | TT GAT CTC GAG CTT GGT CCC TCC GCC GAA |
| JK5a (SEQ ID NO: 83) | TT AAT CTC GAG TCG TGT CCC TTG GCC GAA |
| VL1a (SEQ ID NO: 84) | CAGAT GTG CAC TCC CAG TCT GTG TTG ACG CAG CCG CC |
| VL2a (SEQ ID NO: 85) | CAGAT GTG CAC TCC CAG TCT GCC CTG ACT CAG CCT GC |
| VL3Aa (SEQ ID NO: 86) | CAGAT GTG CAC TCC TCC TAT GTG CTG ACT CAG CCA CC |
| VL3Ba (SEQ ID NO: 87) | CAGAT GTG CAC TCC TCT TCT GAG CTG ACT CAG GAC CC |
| VL4a (SEQ ID NO: 88) | CAGAT GTG CAC TCC CAC GTT ATA CTG ACT CAA CCG CC |
| VL5a (SEQ ID NO: 89) | CAGAT GTG CAC TCC CAG GCT GTG CTC ACT CAG CCG TC |
| VL6a (SEQ ID NO: 90) | CAGAT GTG CAC TCC AAT TTT ATG CTG ACT CAG CCC CA |
| VL7a (SEQ ID NO: 91) | CAGAT GTG CAC TCC CAG GCT GTG GTG ACT CAG GAG CC |
| JL1a (SEQ ID NO: 92) | AC GGT AAG CTT GGT CCC AGT TCC GAA GAC |
| JL2/3a (SEQ ID NO: 93) | AC GGT AAG CTT GGT CCC TCC GCC GAA TAC |

Example 2

Strategies for Selection of Human Immunoglobulins which Bind a Specific Antigen

Vaccinia virus expression vectors comprising polynucleotides encoding recombinant heavy chain immunoglobulin subunit polypeptides which, in combination with some unidentified light chain, confer specificity for a defined antigen, are selected as follows, and as shown in FIG. 1. Selection of specific immunoglobulin heavy and light chains is accomplished in two phases. First, a library of diverse heavy chains from antibody producing cells of either naïve or immunized donors is constructed in a pox virus based vector by trimolecular recombination (see Example 5) using as a transfer plasmid pVHE, constructed as described in Example 1, and a similarly diverse library of immunoglobulin light chains is constructed in a plasmid vector such as pVKE and pVLE, constructed as described in Example 1, in which expression of the recombinant gene is regulated by the p7.5 vaccinia promoter. The immunoglobulin heavy chain constant region in the pox virus constructs is designed to retain the transmembrane region that results in expression of immunoglobulin receptor on the surface membrane. Host cells, e.g., early B cell lymphoma cells, are infected with the pox virus heavy chain library at a multiplicity of infection of 1 (MOI=1). Two hours later the infected cells are transfected with the light chain plasmid library under conditions which allow, on average, 10 or more separate light chain plasmids to be taken up and expressed in each cell. Because expression of the recombinant gene in this plasmid is regulated by a vaccinia virus promoter, high levels of the recombinant gene product are expressed in the cytoplasm of vaccinia virus infected cells without a requirement for nuclear integration. Under these conditions a single cell can express multiple antibodies with different light chains associated with the same heavy chains in characteristic $H_2L_2$ structures in each infected cell.

2.1 Direct antigen-induced apoptosis. An early B cell lymphoma host cell is infected with recombinant vaccinia viruses encoding recombinant heavy chain immunoglobulin subunit polypeptides and transfected with plasmids encoding recombinant light chain immunoglobulin subunit polypeptides as described. The host cells respond to crosslinking of antigen-specific immunoglobulin receptors by induction of spontaneous growth inhibition and apoptotic cell death. As outlined in FIG. 1, synthesis and assembly of antibody molecules is allowed to proceed for 12 hours or more at which time specific antigen is presented on a synthetic particle or polymer, or on the surface of an antigen expressing cell, in order to crosslink any specific immunoglobulin receptors and induce apoptosis of selected antibody expressing indicator cells. The genomes of recombinant vaccinia viruses extracted from cells in which apoptosis has been induced are enriched for polynucleotides encoding immunoglobulin heavy chain genes that confer the desired specificity.

2.2 Indirect antigen-induced cell death. As shown in FIG. 2A (bottom) and FIG. 2B (top), an early B cell lymphoma host cell is transfected with a construct in which the promoter of an apoptosis induced gene, here, a BAX promoter, drives expression of a foreign cytotoxic T cell epitope. The host cells express the CTL epitope in response to crosslinking of antigen-specific immunoglobulin receptors, and these cross-linked cells will undergo a lytic event upon the addition of specific CTL. The stably transfected host cells are then infected with recombinant vaccinia viruses encoding recombinant heavy chain immunoglobulin subunit polypeptides and transfected with plasmids encoding recombinant light chain immunoglobulin subunit polypeptides as described. As outlined in FIG. 1, synthesis and assembly of antibody molecules is allowed to proceed for 12 hours or more at which time specific antigen is presented on a synthetic particle or polymer, or on the surface of an antigen expressing cell, in order to cross-link any specific immunoglobulin receptors. Upon addition of epitope-specific CTL, those cells in which surface immunoglobulin molecules are cross linked undergo a lytic event, thereby indirectly inducing cell death.

2.3 Direct antigen-induced cell death. As shown in FIG. 2A (top) and FIG. 2B (bottom), an early B cell lymphoma host cell is transfected with a construct in which the promoter of an apoptosis induced gene, here, a BAX promoter, drives expression of the cytotoxic A subunit of diphtheria toxin. The host cells express the toxin subunit in response to cross linking of antigen-specific immunoglobulin receptors, and these cross-linked cells will succumb to cell death. The stably transfected host cells are then infected with recombinant vaccinia viruses encoding recombinant heavy chain immunoglobulin subunit polypeptides and transfected with plasmids encoding recombinant light chain immunoglobulin subunit polypeptides as described. As outlined in FIG. 1, synthesis and assembly of antibody molecules is allowed to proceed for 12 hours or more at which time specific antigen is presented on a synthetic particle or polymer, or on the surface of an antigen expressing cell, in order to cross-link any specific immunoglobulin receptors. Those cells in which surface immunoglobulin molecules are cross linked rapidly and directly succumb to cell death.

2.4 Discussion. The reason expression of these recombinant genes is upregulated by crosslinking surface Ig receptors is that expression of each of the two constructs is regulated by the promoter for a gene whose expression is naturally upregulated in early B cell lymphoma cells following Ig crosslinking. This is illustrated by use of the BAX promoter. BAX being an example of a proapoptotic gene that is normally upregulated in early B cell lymphoma cells under these conditions. Regulatory regions (the "promoter") for other genes may serve equally well or better. Such genes are identified, for example, by comparing the gene expression profile of early B cell lymphoma cells on microarrays before and after crosslinking of membrane Ig.

Cells are transfected with a construct leading to expression of the diphtheria A chain (dipA), undergo more rapid apoptosis than is induced by Ig crosslinking alone. An even more rapid cell death is induced by addition of cytotoxic T cells specific for some target peptide that associates with a native MHC molecule expressed in that cell and that is encoded by a minigene whose expression is regulated by a BAX or BAX-like promoter. In addition, host cells other than early B cell lymphoma cells are likewise engineered to express genes which either directly or indirectly induce cell death upon antigen cross linking of surface immunoglobulin molecules, independent of the programmed apoptosis which occurs in early B cell lymphoma cell lines upon antigen cross linking.

A variety of substrates are employed to present antigen and cross-link specific membrane immunoglobulin receptors in the above selection process. These include, but are not limited to, magnetic beads, protein coated tissue culture plates, and cells transfected with a gene encoding the target antigen. Examples of cells that may be transfected for efficient expression of the target antigen include, but are not limited to, L cells and NIH 3T3 cells. However, if a transfected cell is employed to express and present a recombinant antigen, then is necessary to first deplete the immunoglobulin-expressing host cell population of any host cells that express antibodies reactive with membrane antigens of the non-transfected cell. Such depletion could be accomplished in one or more rounds of absorption to non-transfected cells bound to a solid substrate. It would then be possible to employ the antigen expressing transfectant for positive selection of cells expressing specific recombinant antibodies. In a preferred embodiment, alternating cycles of negative and positive selection are repeated as often as necessary to achieve a desired enrichment.

In one example of a positive selection step, antibody expressing B lymphoma cells are allowed to adhere to a solid substrate to which B cell specific anti-CD19 and/or anti-CD20 antibody has been bound. Adherent indicator cells that undergo a lytic event are induced to release their cytoplasmic contents including any viral immunoglobulin heavy chain recombinants into the culture fluid. Recombinant viruses harvested from cells and cell fragments recovered in the culture fluid are enriched for those recombinant viruses that encode an immunoglobulin heavy chain which confers specificity for the selecting antigen when associated with some as yet unidentified light chains. Additional cycles of antigen driven selection in cells freshly infected with this enriched population of recombinant viruses and subsequently transfected with the same initial population of unselected plasmids encoding diverse light chains leads to further enrichment of the desired heavy chains. Following multiple reiterations of this selection process, a small number of heavy chains are isolated which possess optimal specificity for a defined antigen when associated with some unidentified light chains.

In order to select light chains that confer the desired specificity in association with the previously selected heavy chains, the entire selection process as described above is repeated by infecting host cells at MOI=1 with a library of diverse light chain recombinants in the vaccinia based vector followed by transfection with a plasmid recombinant for one of the previously selected heavy chains. The optimal light chain partners for that heavy chain are isolated following multiple cycles of antigen driven selection as described above.

In another preferred embodiment, a similar strategy is implemented by exploiting the binding properties conferred on a cell that expresses specific antibody on its surface membrane. Instead of employing early B cell lymphomas that undergo apoptosis in response to receptor crosslinking as indicator cells, this strategy, depicted in FIG. 5, allows host cells expressing a desired immunoglobulin specificity to be selected by binding to synthetic particles or polymers to which antigen is coupled or to the surface of a specific antigen expressing transfected cell. In this case the indicator cells are chosen for the ability to express high levels of membrane immunoglobulin receptors rather than for an apoptotic response to crosslinking of membrane immunoglobulin receptors. Preferred cell lines include immunoglobulin negative plasmacytomas. Other issues related to the specificity, background and efficiency of the selection process are treated as described above.

Example 3

Selection of an Antibody with Defined Specificity from a Library of $10^9$ Combinations of Immunoglobulin Heavy and Light Chains The affinity of specific antibodies that can be selected from a library is a function of the size of that library. In general, the larger the number of heavy and light chain combinations represented in the library, the greater the likelihood that a high affinity antibody is present and can be selected. Previous work employing phage display methods has suggested that for many antigens a library that includes $10^9$ immunoglobulin heavy and light chain combinations is of a sufficient size to select a relatively high affinity specific antibody. In principle, it is possible to construct a library with $10^9$ recombinants each of which expresses a unique heavy chain and a unique light chain or a single chain construct with a combining site comprising variable regions of heavy and light chains. The most preferred method, however, is to generate this number of antibody combinations by constructing two libraries of $10^5$ immunoglobulin heavy chains and $10^4$ immunoglobulin light chains that can be co-expressed in all $10^9$ possible combinations. In this example greater diversity is represented in the heavy chain pool because heavy chains have often been found to make a greater contribution than the associated light chain to a specific antigen combining site.

3.1 Heavy Chain Genes. A library of vaccinia recombinants at a titer of approximately $10^6$ is constructed from a minimum of $10^5$ immunoglobulin heavy chain cDNA transfer plasmid recombinants synthesized by the methods previously described (Example 1) from RNA derived from a pool of 100 bone marrow donors. As described below, this library must be further expanded to a titer of at least $10^9$ heavy chain recombinants. A preferred method to expand the library is to infect microcultures of approximately $5 \times 10^4$ BSC1 cells with individual pools of $10^3$ vaccinia heavy chain recombinants. Typically a greater than 1,000 fold expansion in the viral titer is obtained after 48 hrs infection. Expanding viral titers in multiple individual pools mitigates the risk that a subset of recombinants will be lost due to relatively rapid growth of a competing subset.

3.2 Light Chain Genes. A library of vaccinia recombinants at a titer of approximately $10^5$ is constructed from a minimum of $10^4$ immunoglobulin light chain cDNA transfer plasmid recombinants synthesized from RNA derived from a pool of bone marrow donors as described in Example 1. For use in multiple cycles of heavy chain selection as described below, this library must be further expanded to a titer of $10^{10}$ to $10^{11}$ light chain recombinants. A preferred method to expand the library is to infect 100 microcultures of approximately $5 \times 10^4$ BSC1 cells with individual pools of $10^3$ vaccinia light chain recombinants. Viral recombinants recovered from each of the 100 infected cultures are further expanded as a separate pool to a titer of between $10^8$ and $10^9$ viral recombinants. It is convenient to label these light chain pools L1 to L100.

3.3 Selection of Immunoglobulin Heavy Chain Recombinants. 100 cultures of $10^7$ cells of a non-producing myeloma, preferably Sp2/0, or early B cell lymphoma, preferably CH33, are infected with viable vaccinia heavy chain recombinants at MOI=1 and simultaneously with psoralen (4'-aminomethyl-Trioxsalen) inactivated vaccinia light chain recombinants at MOI=1 to 10 (see below). For psoralen inactivation, cell-free virus at $10^8$ to $10^9$ pfu/ml is treated with 10 µg/ml psoralen for 10 minutes at 25° C. and then exposed to long-wave (365-nm) UV light for 2 minutes (Tsung, K., J. H. Yim, W. Marti, R. M. L. Buller, and J. A. Norton. *J. Virol.* 70:165-171 (1996)) The psoralen treated virus is unable to replicate but allows expression of early viral genes including recombinant genes under the control of early but not late viral promoters. Under these conditions, lightchains synthesized from psoralen treated recombinants will be assembled into immunoglobulin molecules in association with the single heavy chain that is, on average, expressed in each infected cell.

The choice of infection with psoralen inactivated light chain recombinants at MOI=1 or at MOI=10 will influence the relative concentration in a single positive cell of a particular H+L chain combination which will be high at MOI=1 and low (because of dilution by multiple light chains) at MOI=10. A low concentration and correspondingly reduced density of specific immunoglobulin at the cell surface is expected to select for antibodies with higher affinity for the ligand of interest. On the other hand, a high concentration of specific receptor is expected to facilitate binding or signaling through the immunoglobulin receptor.

Following a first cycle of antigen-specific selection by binding or signaling as described in Example 2, an enriched population of recombinant virus is recovered from each culture with a titer which, during this initial selection and depending on background levels of non-specific binding or spontaneous release of virus, may be between 1% and 10% of the titer of input virus. It is convenient to label as H1a to H100a the heavy chain recombinant pools recovered from cultures in the first cycle of selection that received psoralen treated virus from the original light chain recombinant pools L1 to L100 respectively.

To carry out a second cycle of selection under the same conditions as the first cycle, it is again necessary to expand the titer of recovered heavy chain recombinants by 10 to 100 fold. For the second cycle of selection non-producing myeloma or early B cell lymphoma are again infected with viable viral heavy chain recombinants and psoralen treated light chain recombinants such that, for example, the same culture of $10^7$ cells is infected with heavy chain recombinants recovered in pool H37a and psoralen treated light chain recombinants from the original 137 pool employed to select H37a. Heavy chain recombinants recovered from the H37a pool in the second cycle of selection are conveniently labeled H37b and so on.

Following the second cycle of selection, specific viral recombinants are likely, in general, to be enriched by a factor of 10 or more relative to the initial virus population. In this case, it is not necessary for the third cycle of selection to be carried out under the same conditions as the first or second cycle since specific clones are likely to be well-represented even at a 10 fold lower titer. For the third cycle of selection, therefore, 100 cultures of only $10^6$ non-producing myeloma or early B cell lymphoma are again infected with viable viral heavy chain recombinants and psoralen treated light chain recombinants from cognate Apools. Another reduction by a factor of 10 in the number of infected cells is effected after the 5th cycle of selection.

3.4 Identification of Antigen-Specific Heavy Chain Recombinants.

(a) Following any given cycle of selection it is possible to determine whether antigen-specific heavy chains have been enriched to a level of 10% or more in a particular pool, for example H37f, by picking 10 individual viral pfu from that heavy chain pool to test for antigen-specificity in association with light chains of the original L37 pool. Since the light chain population comprises $10^4$ diverse cDNA distributed among 100 individual pools, the average pool has approximately $10^2$ different light chains. Even if a selected heavy chain confers a desired antigenic specificity only in association with a single type of light chain in the available light chain pool, 1% of cells infected with the selected heavy chain recombinant and the random light chain pool at MOI=1 will express the desired specificity. This frequency can be increased to 10% on average if cells are infected with light chains at MOI=10. A preferred method to confirm specificity is to infect with immunoglobulin heavy chain and a pool of light chains a line of CH33 early B cell lymphoma transfected with an easily detected reporter construct, for example luciferase, driven by the promoter for BAX or another CH33 gene that is activated as a result of membrane receptor crosslinking. Infection of this transfectant with the plaque purified heavy chain recombinant and the relevant light chain pool will result in an easily detected signal if the selected heavy chain confers the desired antigenic specificity in association with any of the 100 or more light chains represented in that pool. Note that this same method is applicable to analysis of heavy chains whether they are selected by specific-binding or by specific-signaling through immunoglobulin receptors of infected cells.

(b) An alternative method to identify the most promising antigen-specific heavy chains is to screen for those that are most highly represented in the selected population. Inserts can be isolated by PCR amplification with vector specific primers flanking the insertion site and these inserts can be sequenced to determine the frequency of any observed sequence. In this case, however, it remains necessary to identify a relevant light chain as described below.

3.5 Selection of Immunoglobulin Light Chain Recombinants. Once an antigen-specific heavy chain has been isolated, a light chain that confers antigen-specificity in association with that heavy chain can be isolated from the pool that was employed to select that heavy chain as described in 3.4(a). Alternatively, it may be possible to select yet another light chain from a larger library that, in association with the same heavy chain, could further enhance affinity. For this purpose a library of vaccinia recombinants at a titer of approximately $10^6$ is constructed from a minimum of $10^5$ immunoglobulin light chain cDNA transfer plasmid recombinants synthesized by the methods previously described (Example 1). The procedure described in 3.3 is reversed such that non-producing myeloma or early B cell lymphoma are now infected with viable viral light chain recombinants at MOI=1 and a single selected psoralen treated specific heavy chain recombinant. To promote selection of higher affinity immunoglobulin, it may be preferable to dilute the concentration of each specific H+L chain pair by infection with light chains at MOI=10.

3.6 Selection of Immunoglobulin Heavy Chain Recombinants in the Presence of a Single Immunoglobulin Light Chain. The selection of an immunoglobulin heavy chain that can contribute to a particular antibody specificity is simplified if a candidate light chain has already been identified. This may be the case if, for example a murine monoclonal antibody has been previously selected. The murine light chain variable region can be grafted to a human light chain constant region to optimize pairing with human heavy chains, a process previously described by others employing phage display methods as "Guided Selection" (Jespers, L. S., A. Roberts, S. M. Mahler, G. Winter, H. R. and Hoogenboom. Bio/Technology 12:899-903, 1994; Figini, M., L. Obici, D. Mezzanzanica, A. Griffiths, M. I. Colnaghi, G. Winters, and S. Canevari. Cancer Res. 58:991-996, 1998). This molecular matching can, in principle, be taken even further if human variable gene framework regions are also grafted into the murine light chain variable region sequence (Rader, C., D. A. Cheresh, and C. F. Barbas III. Proc. Natl. Acad. Sci. USA 95:8910-8915). Any human heavy chains selected to pair with this modified antigen-specific light chain can themselves become the basis for selection of an optimal human light chain from a more diverse pool as described in 3.5.

Example 4

Selection of Specific Human Antibodies from a cDNA Library Constructed in Adenovirus, Herpesvirus, or Retrovirus Vectors 4.1 Herpesvirus. A method has been described for the generation of helper virus free stocks of recombinant, infectious Herpes Simplex Virus Amplicons (T. A. Stavropoulos, C. A. Strathdee. 1998 J. Virology 72:7137-7143). It is possible that a cDNA Library of human Immunoglobulin Heavy and/or Light chain genes or fragments thereof, including single chain fragments, constructed in the plasmid Amplicon vector could be packaged into a library of infectious amplicon particles using this method. An Amplicon library constructed using immunoglobulin heavy chain genes, and another Amplicon library constructed using immunoglobulin light chain genes could be used to coinfect a non-producing myeloma cell line. The myeloma cells expressing an immunoglobulin gene combination with the desired specificity can be enriched by selection for binding to the antigen of interest. The Herpes Amplicons are capable of stable transgene expression in infected cells. Cells selected for binding in a first cycle will retain their immunoglobulin gene combination, and will stably express antibody with this specificity. This allows for the reiteration of selection cycles until immunoglobulin genes with the desired specificity can be isolated. Selection strategies that result in cell death could also be attempted. The amplicon vector recovered from these dead selected cells cannot be used to infect fresh target cells, because in the absence of helper virus the amplicons are replication defective and will not be packaged into infectious form. The amplicon vectors contain a plasmid origin of replication and an antibiotic resistance gene. This makes it possible to recover the selected amplicon vector by transforming DNA purified from the selected cells into bacteria. Selection with the appropriate antibiotic would allow for the isolation of bacterial cells that had been transformed by the amplicon vector. The use of different antibiotic resistance genes on the heavy and light chain Amplicon vectors, for example ampicillin and kanamycin, would allow for the separate selection of heavy and light chain genes from the same population of selected cells. Amplicon plasmid DNA can be extracted from the bacteria and packaged into infectious viral particles by cotransfection of the amplicon DNA and packaging defective HSV genomic DNA into packaging cells. Infectious amplicon particles can then be harvested and used to infect a fresh population of target cells for another round of selection 4.2 Adenovirus. Methods have been described for the production of recombinant Adenovirus (S. Miyake, M. Makimura, Y. Kanegae, S. Harada, Y. Sato, K. Takamori, C. Tokuda, I. Saito. 1996 Proc. Natl. Acad. Sci. USA 93: 1320-1324; T. C. He, S. Zhou, L. T. Da Costa, J. Yu, K. W. Kinzler, B. Volgelstein. 1998 Proc. Natl. Acad. Sci. USA 95: 2509-2514) It is possible that a cDNA library could be constructed in an Adenovirus vector using either of these methods. Insertion of cDNA into the E3 or E4 region of Adenovirus results in a replication competent recombinant virus. This library could be used for similar applications as the vaccinia cDNA libraries constructed by trimolecular recombination. For example a heavy chain cDNA library can be inserted into the E3 or E4 region of Adenovirus. This results in a replication competent heavy chain library. A light chain cDNA library could be inserted into the E1 gene of Adenovirus, generating a replication defective library. This replication defective light chain library can be amplified by infection of cells that provide Adenovirus E1 in trans, such as 293 cells. These two libraries can be used in similar selection strategies as those described using replication competent vaccinia heavy chain library and Psoralen inactivated vaccinia light chain library.

4.3 Advantages of vaccinia virus. Vaccinia virus possesses several advantages over Herpes or Adenovirus for construction of cDNA Libraries. First, vaccinia virus replicates in the cytoplasm of the host cell, while HSV and Adenovirus replicate in the nucleus. A higher frequency of cDNA recombinant transfer plasmid may be available for recombination in the cytoplasm with vaccinia than is able to translocate into the nucleus for packaging/recombination in HSV or Adenovirus. Second, vaccinia virus, but not Adenovirus or Herpes virus, is able to replicate plasmids in a sequence independent manner (M. Merchlinsky, B. Moss. 1988 Cancer Cells 6: 87-93). Vaccinia replication of cDNA recombinant transfer plasmids may result in a higher frequency of recombinant virus being produced. Although we have described the potential construction of cDNA Libraries in Herpes or Adenovirus vectors, it should be emphasized that there has been no reported use of these methods to construct a cDNA Library in either of these viral vectors.

4.4 Retrovirus. Construction of cDNA Libraries in replication defective retroviral vectors have been described (T. Kitamura, M. Onishi, S. Kinoshita, A. Shibuya, A. Miyajima, and G. P. Nolan. 1995 PNAS 92:9146-9150; I. Whitehead, H. Kirk, and R. Kay. 1995 Molecular and Cellular Biology 15:704-710). Retroviral vectors integrate upon infection of target cells, and have gained widespread use for their ability to efficiently transduce target cells, and for their ability to induce stable transgene expression. A Retroviral cDNA library constructed using immunoglobulin heavy chain genes, and another Retroviral library constructed using immunoglobulin light chain genes could be used to coinfect a non-producing myeloma cell line. The myeloma cells expressing an immunoglobulin gene combination with the desired specificity can be enriched for by selection for binding to the antigen of interest. Cells selected for binding in a first cycle will retain their immunoglobulin gene combination, and will stably express immunoglobulins with this specificity. This allows for the reiteration of selection cycles until immunoglobulin genes with the desired specificity can be isolated.

Example 5

Figure 6:
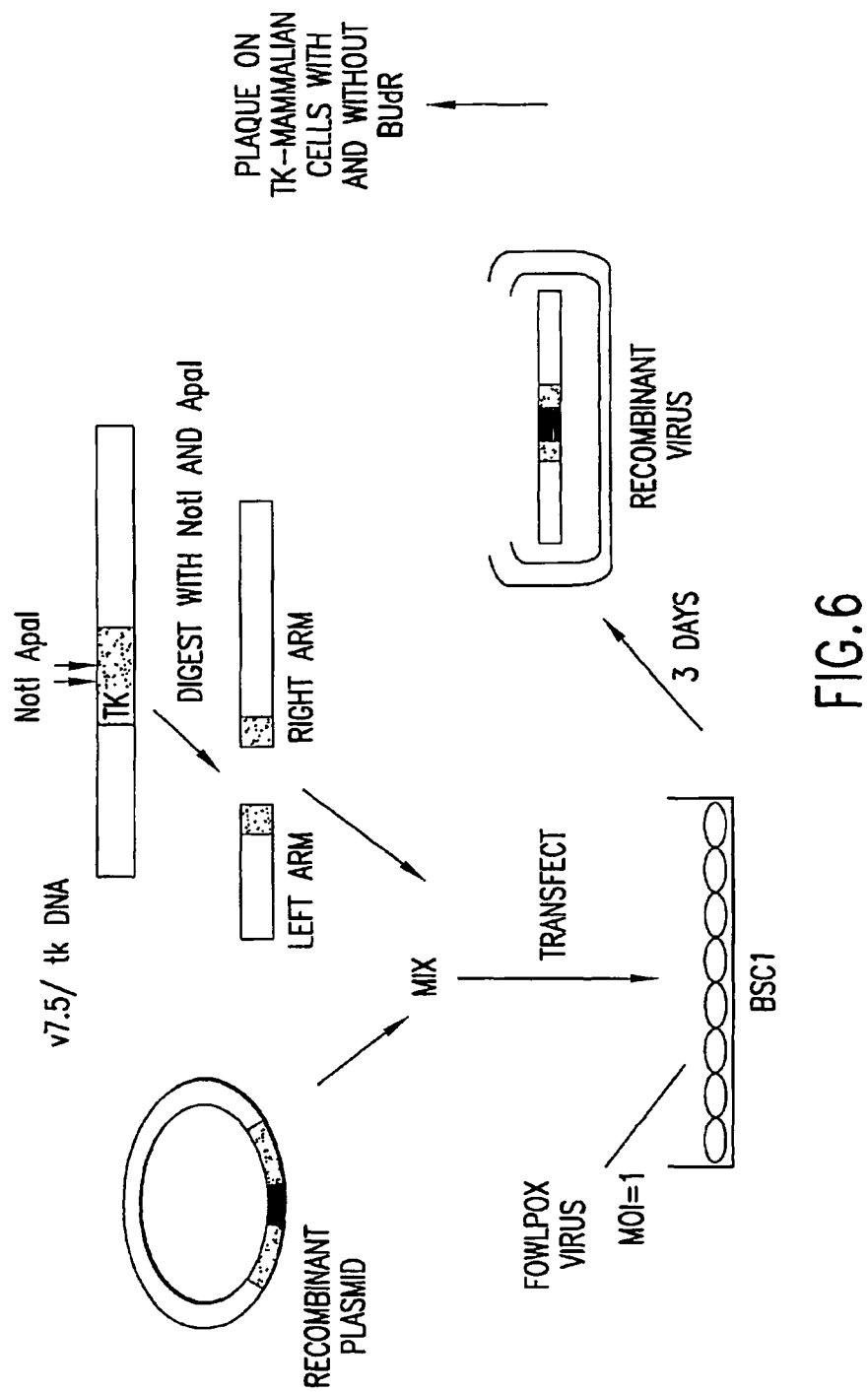
FIG. 6. Schematic of the Tri-Molecular Recombination Method.

Trimolecular Recombination 5.1 Production of an Expression Library. This example describes a tri-molecular recombination method employing modified vaccinia virus vectors and related transfer plasmids that generates close to 100% recombinant vaccinia virus and, for the first time, allows efficient construction of a representative DNA library in vaccinia virus. The trimolecular recombination method is illustrated in FIG. 6.

Figure 7:
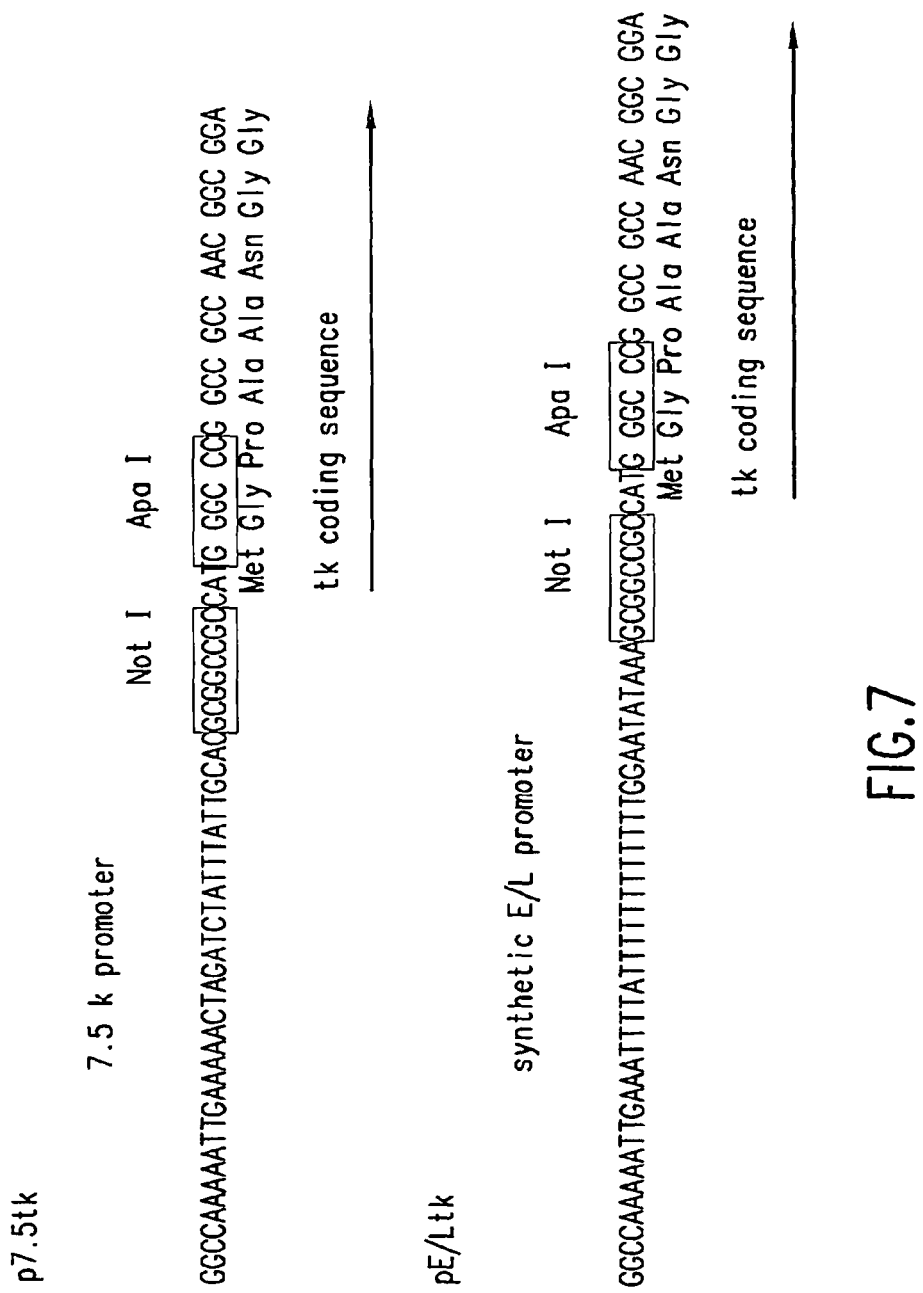
FIG. 7. Nucleotide Sequence of p7.5/tk and pEL/tk promoters. The nucleotide sequence of the promoter and beginning of the thymidine kinase gene for v7.5/tk (SEQ ID NO: 140) and vEL/tk is shown (SEQ ID NO: 142), and the corresponding amino acid sequence including the initiator codon and a portion of the open reading frame, designated wherein as SEQ ID NO: 141 and SEQ ID NO: 143, respectively.

5.2 Construction of the Vectors. The previously described vaccinia virus transfer plasmid pJ/K, a pUC 13 derived plasmid with a vaccinia virus thymidine kinase gene containing an in-frame Not I site (Merchlinsky, M. et al., Virology 190: 522-526), was further modified to incorporate a strong vaccinia virus promoter followed by Not I and Apa I restriction sites. Two different vectors, p7.5/tk and pEL/tk, included, respectively, either the 7.5K vaccinia virus promoter or a strong synthetic early/late (E/L) promoter (FIG. 7). The Apa I site was preceded by a strong translational initiation sequence including the ATG codon. This modification was introduced within the vaccinia virus thymidine kinase (tk) gene so that it was flanked by regulatory and coding sequences of the viral tk gene. The modifications within the tk gene of these two new plasmid vectors were transferred by homologous recombination in the flanking tk sequences into the genome of the Vaccinia Virus WR strain derived vNotI-vector to generate new viral vectors v7.5/tk and vEL/tk. Importantly, following Not I and Apa I restriction endonuclease digestion of these viral vectors, two large viral DNA fragments were isolated each including a separate non-homologous segment of the vaccinia tk gene and together comprising all the genes required for assembly of infectious viral particles. Further details regarding the construction and characterization of these vectors and their alternative use for direct ligation of DNA fragments in vaccinia virus are described in Example 1.

5.3 Generation of an Increased Frequency of Vaccinia Virus Recombinants. Standard methods for generation of recombinants in vaccinia virus exploit homologous recombination between a recombinant vaccinia transfer plasmid and the viral genome. Table 3 shows the results of a model experiment in which the frequency of homologous recombination following transfection of a recombinant transfer plasmid into vaccinia virus infected cells was assayed under standard conditions. To facilitate functional assays, a minigene encoding the immunodominant 257-264 peptide epitope of ovalbumin in association with H-2K$^b$ was inserted at the Not 1 site in the transfer plasmid tk gene. As a result of homologous recombination, the disrupted tk gene is substituted for the wild type viral tk+ gene in any recombinant virus. This serves as a marker for recombination since tk− human 143B cells infected with tk− virus are, in contrast to cells infected with wild type tk+ virus, resistant to the toxic effect of BrdU. Recombinant virus can be scored by the viral pfu on 143B cells cultured in the presence of 125 mM BrdU.

The frequency of recombinants derived in this fashion is of the order of 0.1% (Table 3).

TABLE 3

Generation of Recombinant Vaccinia Virus by Standard Homologous Recombination

| Virus* | DNA | Titer w/o BrdU | Titer w/ BrdU | % Recombinant** |
|---|---|---|---|---|
| vaccinia | — | $4.6 \times 10^7$ | $3.0 \times 10^3$ | 0.006 |
| vaccinia | 30 ng pE/Lova | $3.7 \times 10^7$ | $3.2 \times 10^4$ | 0.086 |
| vaccinia | 300 ng pE/Lova | $2.7 \times 10^7$ | $1.5 \times 10^4$ | 0.056 |

*vaccinia virus strain vNotI
**% Recombinant = (Titer with BrdU/Titer without BrdU) × 100

This recombination frequency is too low to permit efficient construction of a cDNA library in a vaccinia vector. The following two procedures were used to generate an increased frequency of vaccinia virus recombinants.

(1) One factor limiting the frequency of viral recombinants generated by homologous recombination following transfection of a plasmid transfer vector into vaccinia virus infected cells is that viral infection is highly efficient whereas plasmid DNA transfection is relatively inefficient. As a result many infected cells do not take up recombinant plasmids and are, therefore, capable of producing only wild type virus. In order to reduce this dilution of recombinant efficiency, a mixture of naked viral DNA and recombinant plasmid DNA was transfected into Fowl Pox Virus (FPV) infected mammalian cells. As previously described by others (Scheiflinger, F., et al., 1992, Proc. Natl. Acad. Sci. USA 89:9977-9981), FPV does not replicate in mammalian cells but provides necessary helper functions required for packaging mature vaccinia virus particles in cells transfected with non-infectious naked vaccinia DNA. This modification of the homologous recombination technique alone increased the frequency of viral recombinants approximately 35 fold to 3.5% (Table 4).

TABLE 4

Generation of Recombinant Vaccinia Virus by Modified Homologous Recombination

| Virus | DNA | Titer w/o BrdU | Titer w/ BrdU | % Recombinant* |
|---|---|---|---|---|
| PFV | None | 0 | 0 | 0 |
| None | vaccinia WR | 0 | 0 | 0 |
| PFV | vaccinia WR | $8.9 \times 10^6$ | $2.0 \times 10^2$ | 0.002 |
| PFV | vaccinia WR + pE/Lova (1:1) | $5.3 \times 10^6$ | $1.2 \times 10^5$ | 2.264 |
| PFV | vaccinia WR + pE/Lova (1:10) | $8.4 \times 10^5$ | $3.0 \times 10^4$ | 3.571 |

*% Recombinant = (Titer with BrdU/Titer without BrdU) × 100

Table 4. Confluent monolayers of BSC1 cells ($5 \times 10^5$ cells/well) were infected with moi=1.0 of fowlpox virus strain HP1. Two hours later supernatant was removed, cells were washed 2× with Opti-Mem I media, and transfected using lipofectamine with 600ng vaccinia strain WR genomic DNA either alone, or with 1:1 or 1:10 (vaccinia:plasmid) molar ratios of plasmid pE/Lova. This plasmid contains a fragment of the ovalbumin cDNA, which encodes the SIINFEKL epitope (SEQ ID NO:154), known to bind with high affinity to the mouse class I MHC molecule K$^b$. Expression of this minigene is controlled by a strong, synthetic Early/Late vaccinia promoter. This insert is flanked by vaccinia tk DNA. Three days later cells were harvested, and virus extracted by three cycles of freeze/thaw in dry ice isopropanol 37° C. water bath. Crude virus stocks were titered by plaque assay on human TK- 143B cells with and without BrdU.

(2) A further significant increase in the frequency of viral recombinants was obtained by transfection of FPV infected cells with a mixture of recombinant plasmids and the two large approximately 80 kilobases and 100 kilobases fragments of vaccinia virus v7.5/tk DNA produced by digestion with Not I and Apa I restriction endonucleases. Because the Not I and Apa I sites have been introduced into the tk gene, each of these large vaccinia DNA arms includes a fragment of the tk gene. Since there is no homology between the two tk gene fragments, the only way the two vaccinia arms can be linked is by bridging through the homologous tk sequences that flank the inserts in the recombinant transfer plasmid. The results in Table 5 show that >99% of infectious vaccinia virus produced in triply transfected cells is recombinant for a DNA insert as determined by BrdU resistance of infected tk–cells.

TABLE 5

Generation of 100% Recombinant Vaccinia Virus Using Tri-Molecular Recombination

| Virus | DNA | Titer w/o BrdU | Titer w/ BrdU | % Recombinant* |
|---|---|---|---|---|
| PFV | Uncut v7.5/tk | $2.5 \times 10^6$ | $6.0 \times 10^3$ | 0.24 |
| PFV | NotI/ApaI v7.5/tk arms | $2.0 \times 10^2$ | 0 | 0 |
| PFV | NotI/ApaI v7.5/tk arms + pE/Lova (1:1) | $6.8 \times 10^4$ | $7.4 \times 10^4$ | 100 |

*% Recombinant = (Titer with BrdU/Titer without BrdU) x 100

Table 5. Genomic DNA from vaccinia strain V7.5/tk (1.2 micrograms) was digested with ApaI and NotI restriction endonucleases. The digested DNA was divided in half. One of the pools was mixed with a 1:1 (vaccinia:plasmid) molar ratio of pE/Lova. This plasmid contains a fragment of the ovalbumin cDNA, which encodes the SIINFEKL epitope (SEQ ID NO:154), known to bind with high affinity to the mouse class I MHC molecule $K^b$, Expression of this minigene is controlled by a strong, synthetic Early/Late vaccinia promoter. This insert is flanked by vaccinia tk DNA.

DNA was transfected using lipofectamine into confluent monolayers ($5 \times 10^5$ cells/well) of BSC1 cells, which had been infected 2 hours previously with moi=1.0 FFV. One sample was transfected with 600ng untreated genomic V7.5/tk DNA. Three days later cells were harvested, and the virus was extracted by three cycles of freeze/thaw in dry ice isopropanol 37° C water bath. Crude viral stocks were plagued on TK- 143 B cells with and without BrdU selection.

5.4 Construction of a Representative cDNA Library in Vaccinia Virus. A cDNA library is constructed in the vaccinia vector to demonstrate representative expression of known cellular mRNA sequences. Additional modifications have been introduced into the p7.5/tk transfer plasmid and v7.5/tk viral vector to enhance the efficiency of recombinant expression in infected cells. These include introduction of translation initiation sites in three different reading frames and of both translational and transcriptional stop signals as well as additional restriction sites for DNA insertion.

First, the HindIII J fragment (vaccinia tk gene) of p7.5/tk was subcloned from this plasmid into the HindIII site of pBS phagemid (Stratagene) creating pBS.Vtk.

Second, a portion of the original multiple cloning site of pBS.Vtk was removed by digesting the plasmid with SmaI and PstI, treating with Mung Bean Nuclease, and ligating back to itself, generating pBS.Vtk.MCS-. This treatment removed the unique SmaI, BamI, SalI, and PstI sites from pBS.Vtk.

Figure 12C:
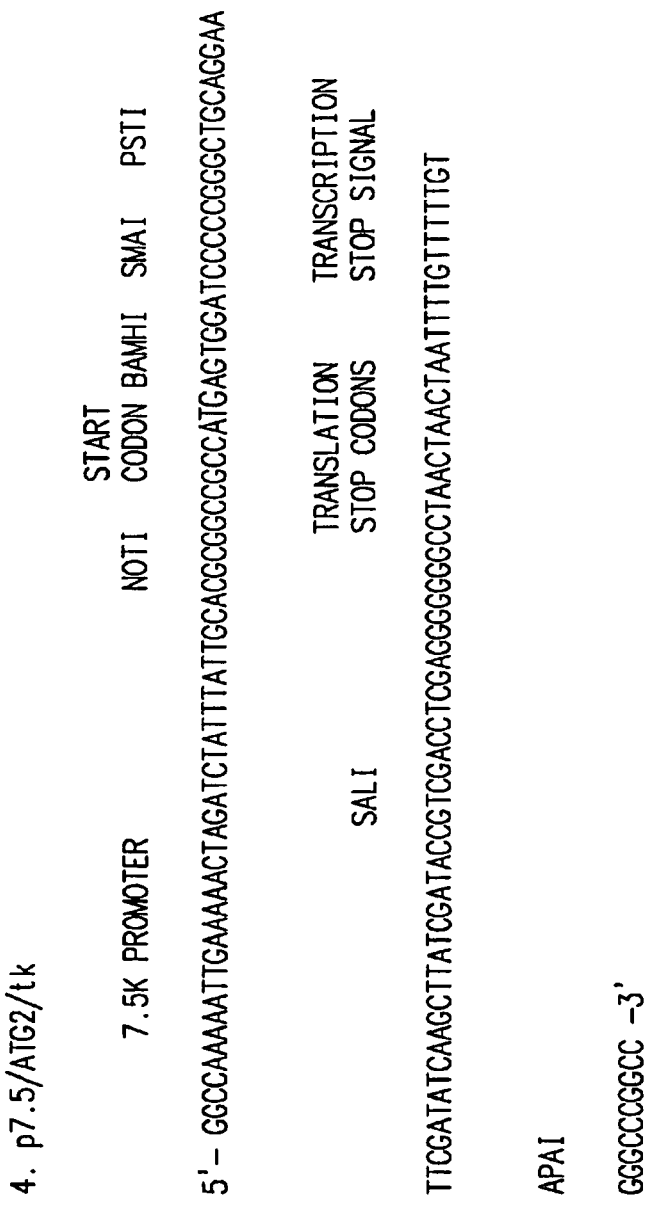
FIG. 12C A new vector, p7.5/ATG2/tk (SEQ ID NO:4) derived as described in the text from the p7.5/tk vaccinia transfer plasmid.
Figure 12D:
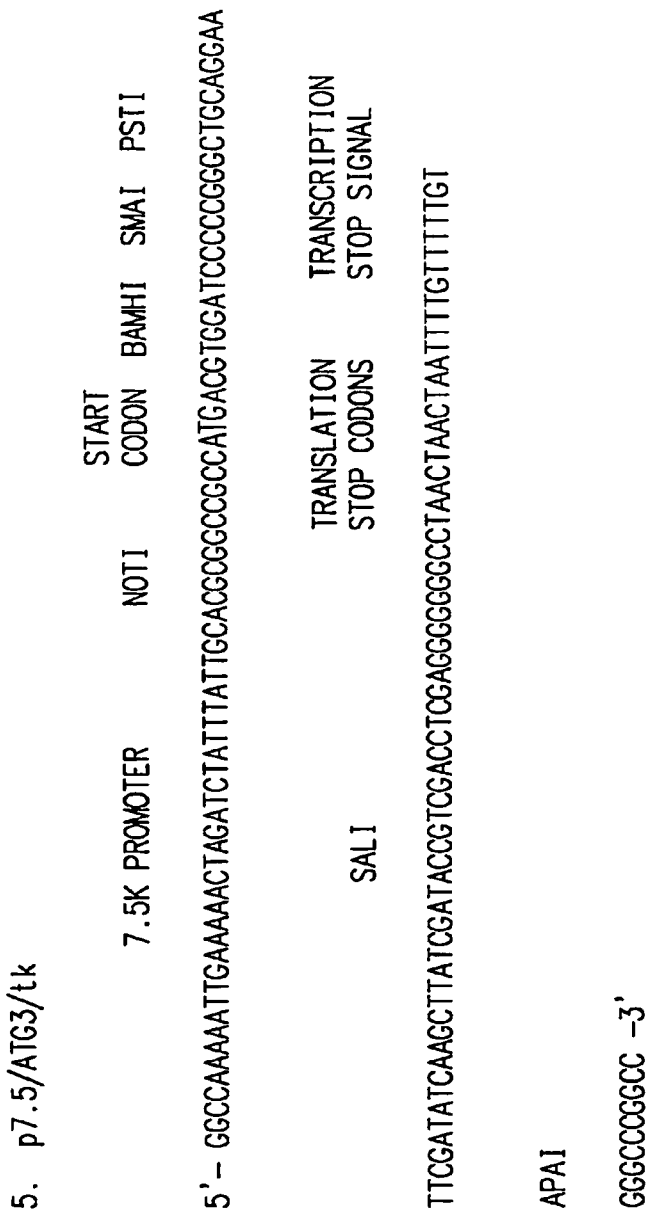
FIG. 12D A new vector, p7.5/ATG3/tk (SEQ ID NO:5) derived as described in the text from the p7.5/tk vaccinia transfer plasmid.

Third, the object at this point was to introduce a new multiple cloning site downstream of the 7.5 k promoter in pBS.Vtk.MCS-. The new multiple cloning site was generated by PCR using 4 different upstream primers, and a common downstream primer. Together, these 4 PCR products would contain either no ATG start codon, or an ATG start codon in each of the three possible reading frames. In addition, each PCR product contains at its 3 prime end, translation stop codons in all three reading frames, and a vaccinia virus transcription double stop signal. These 4 PCR products were ligated separately into the NotI/ApaI sites of pBS.Vtk.MCS-, generating the 4 vectors, p7.5/ATG0/tk, p7.5/ATG1/tk, p7.5/ATG2/tk, and p7.5/ATG3/tk whose sequence modifications relative to the p7.5/tk vector are shown in FIG. 12. Each vector includes unique BamHI, SmaI, PstI, and SalI sites for cloning DNA inserts that employ either their own endogenous translation initiation site (in vector p7.5/ATG0/tk) or make use of a vector translation initiation site in any one of the three possible reading frames (p7.5/ATG1/tk, p7.5/ATG3/tk, and p7.5/ATG4/tk).

In a model experiment cDNA was synthesized from poly-A+ mRNA of a murine tumor cell line (BCA39) and ligated into each of the four modified p7.5/tk transfer plasmids. The transfer plasmid is amplified by passage through procaryotic host cells such as E. coli as described herein or as otherwise known in the art. Twenty micrograms of Not I and Apa I digested v/tk vaccinia virus DNA arms and an equimolar mixture of the four recombinant plasmid cDNA libraries was transfected into FPV helper virus infected BSC-1 cells for tri-molecular recombination. The virus harvested had a total titer of $6 \times 10^6$ pfu of which greater than 90% were BrdU resistant.

In order to characterize the size distribution of cDNA inserts in the recombinant vaccinia library, individual isolated plaques were picked using a sterile pasteur pipette and transferred to 1.5 ml tubes containing 100 µl Phosphate Buffered Saline (PBS). Virus was released from the cells by three cycles of freeze/thaw in dry ice/isopropanol and in a 37° C. water bath. Approximately one third of each virus plaque was used to infect one well of a 12 well plate containing tk–human 143B cells in 250 µl final volume. At the end of the two hour infection period each well was overlayed with 1 ml DMEM with 2.5% fetal bovine serum (DMEM-2.5) and with BUdR sufficient to bring the final concentration to 125 µg/ml. Cells were incubated in a $CO_2$ incubator at 37° C. for three days. On the third day the cells were harvested, pelleted by centrifugation, and resuspended in 500 µl PBS. Virus was released from the cells by three cycles of freeze/thaw as described above. Twenty percent of each virus stock was used to infect a confluent monolayer of BSC-1 cells in a 50 mm tissue culture dish in a final volume of 3 ml DMEM-2.5. At the end of the two hour infection period the cells were overlayed with 3 ml of DMEM-2.5. Cells were incubated in a $CO_2$ incubator at 37° C. for three days. On the third day the cells were harvested, pelleted by centrifugation, and resuspended in 300 µl PBS. Virus was released from the cells by three cycles of freeze/thaw as described above. One hundred microliters of crude virus stock was transferred to a 1.5 ml tube, an equal volume of melted 2% low melting point agarose was added, and the virus/agarose mixture was transferred into a pulsed field gel sample block. When the agar worms were solidified they were removed from the sample block and cut into three equal sections. All three sections were transferred to the same 1.5 ml tube, and 250 µl of 0.5M EDTA, 1% Sarkosyl, 0.5 mg/ml Proteinase K was added. The worms were incubated in this solution at 37° C. for 24 hours. The worms were washed several times in 500 µl 0.5×TBE buffer, and one section of each worm was transferred to a well of a 1% low melting point agarose gel. After the worms were added the wells were sealed by adding additional melted 1% low melting point agarose. This gel was then electorphoresed in a Bio-Rad pulsed field gel electrophoresis apparatus at 200 volts, 8 second pulse times, in 0.5×TBE for 16 hours. The gel was stained in ethidium bromide, and portions of agarose containing vaccinia genomic DNA were excised from the gel and transferred to a 1.5 ml tube. Vaccinia DNA was purified from the agarose using β-Agarase (Gibco) following the recommendations of the manufacturer. Purified vaccinia DNA was resuspended in 50 µl ddH$_2$O. One microliter of each DNA stock was used as the template for a Polymerase Chain Reaction (PCR) using vaccinia TK specific primers MM428 and MM430 (which flank the site of insertion) and Klentaq Polymerase (Clontech) following the recommendations of the manufacturer in a 20 µl final volume. Reaction conditions included an initial denaturation step at 95° C. for 5 minutes, followed by 30 cycles of: 94° C. 30 seconds, 55° C. 30 seconds, 68° C. 3 minutes. Two and a half microliters of each PCR reaction was resolved on a 1% agarose gel, and stained with ethidium bromide. Amplified fragments of diverse sizes were observed. When corrected for flanking vector sequences amplified in PCR the inserts range in size between 300 and 2500 bp.

Representative expression of gene products in this library was established by demonstrating that the frequency of specific cDNA recombinants in the vaccinia library was indistinguishable from the frequency with which recombinants of the same cDNA occur in a standard plasmid library. This is illustrated in Table 6 for an IAP sequence that was previously shown to be upregulated in murine tumors. Twenty separate pools with an average of either 800 or 200 viral pfu from the vaccinia library were amplified by infecting microcultures of 143B tk–cells in the presence of BDUR. DNA was extracted from each infected culture after three days and assayed by PCR with sequence specific primers for the presence of a previously characterized endogenous retrovirus (IAP, intracisternal A particle) sequence. Poisson analysis of the frequency of positive pools indicates a frequency of one IAP recombinant for approximately every 500 viral pfu (Table 6). Similarly, twenty separate pools with an average of either 1,400 or 275 bacterial cfu from the plasmid library were amplified by transformation of DH5 a bacteria. Plasmid DNA from each pool was assayed for the presence of the same IAP sequence. Poisson analysis of the frequency of positive pools indicates a frequency of one IAP recombinant for every 450 plasmids (Table 6).

TABLE 6

Limiting dilution analysis of IAP sequences in a recombinant accinia library and a conventional plasmid cDNA library

| | # Wells Positive by PCR | F$_0$ | µ | Frequency |
|---|---|---|---|---|
| #PFU/well | | Vaccinia Library | | |
| 800 | 18/20 | 0.05 | 2.3 | 1/350 |
| 200 | 6/20 | 0.7 | 0.36 | 1/560 |
| #CFU/well | | Plasmid Library | | |
| 1400 | 20/20 | 0 | — | — |
| 275 | 9/20 | 0.55 | 0.6 | 1/450 |

F$_0$ = fraction negative wells; µ = DNA precursors/well = –lnF$_0$

Similar analysis was carried out with similar results for representation of an alpha tubulin sequence in the vaccinia library. The comparable frequency of arbitrarily chosen sequences in the two libraries constructed from the same tumor cDNA suggests that although construction of the Vaccinia library is somewhat more complex and is certainly less conventional than construction of a plasmid library, it is equally representative of tumor cDNA sequences.

Discussion

The above-described tri-molecular recombination strategy yields close to 100% viral recombinants. This is a highly significant improvement over current methods for generating viral recombinants by transfection of a plasmid transfer vector into vaccinia virus infected cells. This latter procedure yields viral recombinants at a frequency of the order of only 0.1%. The high yield of viral recombinants in tri-molecular recombination makes it possible, for the first time, to efficiently construct genomic or cDNA libraries in a vaccinia virus derived vector. In the first series of experiments a titer of $6 \times 10^6$ recombinant virus was obtained following transfection with a mix of 20 micrograms of Not I and Apa I digested vaccinia vector arms together with an equimolar concentration of tumor cell cDNA. This technological advance creates the possibility of new and efficient screening and selection strategies for isolation of specific genomic and cDNA clones.

The tri-molecular recombination method as herein disclosed may be used with other viruses such as mammalian viruses including vaccinia and herpes viruses. Typically, two viral arms which have no homology are produced. The only way that the viral arms can be linked is by bridging through homologous sequences that flank the insert in a transfer vector such as a plasmid. When the two viral arms and the transfer vector are present in the same cell the only infectious virus produced is recombinant for a DNA insert in the transfer vector.

Libraries constructed in vaccinia and other mammalian viruses by the tri-molecular recombination method of the present invention may have similar advantages to those described here for vaccinia virus and its use in identifying target antigens in the CTL screening system of the invention. Similar advantages are expected for DNA libraries constructed in vaccinia or other mammalian viruses when carrying out more complex assays in eukaryotic cells. Such assays include but are not limited to screening for DNA encoding receptors and ligands of eukaryotic cells.

Example 6

Preparation of Transfer Plasmids

The transfer vectors may be prepared for cloning by known means. A preferred method involves cutting 1-5 micrograms of vector with the appropriate restriction endonucleases (for example SmaI and SalI or BamHI and SalI) in the appropriate buffers, at the appropriate temperatures for at least 2 hours. Linear digested vector is isolated by electrophoresis of the digested vector through a 0.8% agarose gel. The linear plasmid is excised from the gel and purified from agarose using methods that are well known.

Ligation. The cDNA and digested transfer vector are ligated together using well known methods. In a preferred method 50-100 ng of transfer vector is ligated with varying concentrations of cDNA using T4 DNA Ligase, using the appropriate buffer, at 14° C. for 18 to 24 hours.

Transformation. Aliquots of the ligation reactions are transformed by electroporation into E. Coli bacteria such as DH10B or DH5 alpha using methods that are well known. The transformation reactions are plated onto LB agar plates containing a selective antibiotic (ampicillin) and grown for 14-18 hours at 37° C. All of the transformed bacteria are pooled together, and plasmid DNA is isolated using well known methods.

Preparation of buffers mentioned in the above description of preferred methods according to the present invention will be evident to those of skill.

Example 7

Introduction of Vaccinia Virus DNA Fragments and Transfer Plasmids into Tissue Culture Cells for Trimolecular Recombination A cDNA or other library is constructed in the 4 transfer plasmids as described in Example 5, or by other art-known techniques. Trimolecular recombination is employed to transfer this cDNA library into vaccinia virus. Confluent monolayers of BSC1 cells are infected with fowlpox virus HP1 at a moi of 1-1.5. Infection is done in serum free media supplemented with 0.1% Bovine Serum Albumin. The BSC 1 cells may be in 12 well or 6 well plates, 60 mm or 100 mm tissue culture plates, or 25 cm$^2$, 75 cm$^2$, or 150 cm$^2$ flasks. Purified DNA from v7.5/tk or vEL/tk is digested with restriction endonucleases ApaI and NotI. Following these digestions the enzymes are heat inactivated, and the digested vaccinia arms are purified using a centricon 100 column. Transfection complexes are then formed between the digested vaccinia DNA and the transfer plasmid cDNA library. A preferred method uses Lipofectamine or Lipofectamine Plus (Life Technologies, Inc.) to form these transfection complexes. Transfections in 12 well plates usually require 0.5 micrograms of digested vaccinia DNA and long to 200 ng of plasmid DNA from the library. Transfection in cells in larger culture vessels requires a proportional increase in the amounts of vaccinia DNA and transfer plasmid. Following a two hour infection at 37° C. the fowlpox is removed, and the vaccinia DNA, transfer plasmid transfection complexes are added. The cells are incubated with the transfection complexes for 3 to 5 hours, after which the transfection complexes are removed and replaced with 1 ml DMEM supplemented with 2.5% Fetal Bovine Serum. Cells are incubated in a $CO_2$ incubated at 37° C. for 3 days. After 3 days the cells are harvested, and virus is released by three cycles of freeze/thaw in dry ice/isopropanol/37° C. water bath.

Example 8

Transfection of Mammalian Cells

This example describes alternative methods to transfect cells with vaccinia DNA and transfer plasmid. Trimolecular recombination can be performed by transfection of digested vaccinia DNA and transfer plasmid into host cells using for example, calcium-phosphate precipitation (F. L. Graham, A. J. Van derEb (1973) *Virology* 52:456-467, C. Chen, H. Okayama (1987) *Mol. Cell. Biol.* 7: 2745-2752), DEAE-Dextran (D. J. Sussman, G. Milman (1984) *Mol. Cell. Biol.* 4: 1641-1643), or electroporation (T. K. Wong, E. Neumann (1982) *Biochem. Biophys. Res. Commun.* 107: 584-587, E. Neumann, M. Schafer-Ridder, Y. Wang, P. H. Hofschneider (1982) *EMBO J.* 1: 841-845).

Example 9

Construction of MVA Trimolecular Recombination Vectors

In order to construct a Modified Vaccinia Ankara (MVA) vector suitable for trimolecular recombination, two unique restriction endonuclease sites must be inserted into the MVA tk gene. The complete MVA genome sequence is known (GenBank U94848). A search of this sequence revealed that restriction endonucleases AscI, RsrII, SfiI, and XmaI do not cut the MVA genome. Restriction endonucleases AscI and XmaI have been selected due to the commercial availability of the enzymes, and the size of the recognition sequences, 8 bp and 6 bp for AscI and XmaI respectively. In order to introduce these sites into the MVA tk gene a construct will be made that contains a reporter gene (*E. coli* gusA) flanked by XmaI and AscI sites. The Gus gene is available in pCRII.Gus (M. Merchlinsky, D. Eckert, E. Smith, M. Zauderer. 1997 *Virology* 238:444-451). This reporter gene construct will be cloned into a transfer plasmid containing vaccinia tk DNA flanks and the early/late 7.5 k promoter to control expression of the reporter gene. The Gus gene will be PCR amplified from this construct using Gus specific primers. Gus sense 5' ATGTTACGTCCTGTAGAAACC 3' (SEQ ID NO:94), and Gus Antisense 5'TCATTGTTTGCCTCCCTGCTG 3' (SEQ ID NO:95). The Gus PCR product will then be PCR amplified with Gus specific primers that have been modified to include NotI and XmaI sites on the sense primer, and AscI and ApaI sites on the antisense primer. The sequence of these primers is:

```
NX-Gus Sense                        (SEQ ID NO: 96)
5' AAAGCGGCCGCCCCGGGATGTTACGTCC 3';
and AA-Gus antisense                    (SEQ ID NO: 97)
5' AAAGGGCCCGGCGCGCCTCATTGTTTGCC 3'.
```

This PCR product will be digested with NotI and ApaI and cloned into the NotI and ApaI sites of p7.5/tk (M. Merchlinsky, D. Eckert, E. Smith, M. Zauderer. 1997 *Virology* 238: 444-451). The 7.5 k-XmaI-gusA-AscI construct will be introduced into MVA by conventional homologous recombination in permissive QT35 or BHK cells. Recombinant plaques will be selectedby staining with the Gus substrate X-Glu (5-bromo-3 indoyl-β-D-glucuronic acid; Clontech) (M. W. Carroll, B. Moss. 1995 *Biotechniques* 19:352-355). MVA-Gus clones, which will also contain the unique XmaI and AscI sites, will be plaque purified to homogeneity. Large scale cultures of MVA-Gus will be amplified on BHK cells, and naked DNA will be isolated from purified virus. After digestion with XmaI and AscI the MVA-Gus DNA can be used for trimolecular recombination in order to construct cDNA expression libraries in MVA.

MVA is unable to complete its life cycle in most mammalian cells. This attenuation can result in a prolonged period of high levels of expression of recombinant cDNAs, but viable MVA cannot be recovered from infected cells. The inability to recover viable MVA from selected cells would prevent the repeated cycles of selection required to isolate functional cDNA recombinants of interest. A solution to this problem is to infect MVA infected cells with a helper virus that can complement the host range defects of MVA. This helper virus can provide the gene product(s) which MVA lacks that are essential for completion of its life cycle. It is unlikely that another host range restricted helper virus, such as fowlpox, would be able to complement the MVA defect(s), as these viruses are also restricted in mammalian cells. Wild type strains of vaccinia virus would be able to complement MVA. In this case however, production of replication competent vaccinia virus would complicate additional cycles of selection and isolation of recombinant MVA clones. A conditionally defective vaccinia virus could be used which could provide the helper function needed to recover viable MVA from mammalian cells under nonpermissive conditions, without the generation of replication competent virus. The vaccinia D4R open reading frame (orf) encodes a uracil DNA glycosylase enzyme. This enzyme is essential for vaccinia virus replication, is expressed early after infection (before DNA replication), and disruption of this gene is lethal to vaccinia. It has been demonstrated that a stably transfected mammalian cell line expressing the vaccinia D4R gene was able to complement a D4R deficient vaccinia virus (G. W. Holzer, F. G. Falkner. 1997 *J. Virology* 71:4997-5002). A D4R deficient vaccinia virus would be an excellent candidate as a helper virus to complement MVA in mammalian cells.

In order to construct a D4R complementing cell line the D4R orf will be cloned from vaccinia strain v7.5/tk by PCR amplification using primers D4R-Sense 5' AAAGGATCCA TAATGAATTC AGTGACTGTA TCACACG 3' (SEQ ID NO:98), and D4R Antisense 5'CTTGCGGCCG CTTAATAAAT AAACCCTTGA GCCC 3'(SEQ ID NO:99). The sense primer has been modified to include a BamHI site, and the anti-sense primer has been modified to include a NotI site. Following PCR amplification and digestion with BamHI and NotI the D4R orf will be cloned into the BamHI and NotI sites of pIRESHyg (Clontech). This mammalian expression vector contains the strong CMV Immediate Early promoter/Enhancer and the ECMV internal ribosome entry site (IRES). The D4RIRESHyg construct will be transfected into BSC1 cells and transfected clones will be selected with hygromycin. The IRES allows for efficient translation of a polycistronic mRNA that contains the D4Rorf at the 5' end, and the Hygromycin phosphotransferase gene at the 3' end. This results in a high frequency of Hygromycin resistant clones being functional (the clones express D4R). BSC1 cells that express D4R (BSC1.D4R) will be able to complement D4R deficient vaccinia, allowing for generation and propagation of this defective strain.

To construct D4R deficient vaccinia, the D4R orf (position 100732 to 101388 in vaccinia genome) and 983 bp (5' end) and 610 bp (3' end) of flanking sequence will be PCR amplified from the vaccinia genome. Primers D4R Flank sense 5' ATTGAGCTCT TAATACTTTT GTCGGGTAAC AGAG 3' (SEQ ID NO:100), and D4R Flank antisense 5' TTACTCGAGA GTGTCGCAAT TTGGATTTT 3' (SEQ ID NO:101) contain a Sac (Sense) and XhoI (Antisense) site for cloning and will amplify position 99749 to 101998 of the vaccinia genome. This PCR product will be cloned into the SacI and XhoI sites of pBluescript II KS (Stratagene), generating pBS.D4R.Flank. The D4R gene contains a unique EcoRI site beginning at nucleotide position 3 of the 657 bp orf, and a unique PstI site beginning at nucleotide position 433 of the orf. Insertion of a Gus expression cassette into the EcoRI and PstI sites of D4R will remove most of the D4R coding sequence. A 7.5 k promoter—Gus expression vector has been constructed (M. Merchlinsky, D. Eckert, E. Smith, M. Zauderer. 1997 *Virology* 238:444-451). The 7.5-Gus expression cassette will be isolated from this vector by PCR using primers 7.5 Gus Sense 5' AAAGAATTCC TTTATTGTCA TCGGCCAAA 3' (SEQ ID NO:102) and 7.5Gus antisense 5' AATCTGCAGT CATTGTTTGC CTCCCTGCTG 3' (SEQ ID NO:103). The 7.5Gus sense primer contains an EcoRI site and the 7.5Gus antisense primer contains a PstI site. Following PCR amplification the 7.5Gus molecule will be digested with EcoRI and PstI and inserted into the EcoRI and PstI sites in pBS.D4R.Flank, generating pBS.D4R$^-$/7.5Gus$^+$. D4R$^-$/Gus$^+$ vaccinia can be generated by conventional homologous recombination by transfecting the pBS.D4R$^-$/7.5Gus$^+$ construct into v7.5/tk infected BSC1.D4R cells. D4R$^-$/Gus$^+$ virus can be isolated by plaque purification on BSC1.D4R cells and staining with X-Glu. The D4R− virus can be used to complement and rescue the MVA genome in mammalian cells.

In a related embodiment, the MVA genome may be rescued in mammalian cells with other defective poxviruses, and also by a psoralen/UV-inactivated wild-type poxviruses. Psoralen/UV inactivation is discussed herein.

Example 10

Construction and Use of D4R Trimolecular Recombination Vectors

Poxvirus infection can have a dramatic inhibitory effect on host cell protein and RNA synthesis. These effects on host gene expression could, under some conditions, interfere with the selection of specific poxvirus recombinants that have a defined physiological effect on the host cell. Some strains of vaccinia virus that are deficient in an essential early gene have been shown to have greatly reduced inhibitory effects on host cell protein synthesis. Production of recombinant cDNA libraries in a poxvirus vector that is deficient in an early gene function could, therefore, be advantageous for selection of certain recombinants that depend on continued active expression of some host genes for their physiological effect. Disruption of essential viral genes prevents propagation of the mutant strain. Replication defective strains of vaccinia could, however, be rescued by providing the missing function through transcomplementation in host cells or by helper virus that can be induced to express this gene.

Infection of a cell population with a poxvirus library constructed in a replication deficient strain should greatly attenuate the effects of infection on host cell signal transduction mechanisms, differentiation pathways, and transcriptional regulation. An additional and important benefit of this strategy is that expression of the essential gene under the control of a targeted transcriptional regulatory region can itself be the means of selecting recombinant virus that directly or indirectly lead to activation of that transcriptional regulatory region. Examples include the promoter of a gene activated as a result of crosslinking surface immunoglobulin receptors on early B cell precursors or the promoter of a gene that encodes a marker induced following stem cell differentiation. If such a promoter drives expression of an essential viral gene, then only those viral recombinants that directly or indirectly activate expression of that transcriptional regulator will replicate and be packaged as infectious particles. This method has the potential to give rise to much lower background then selection methods based on expression of dipA or a CTL target epitope because uninduced cells will contain no replication competent vaccinia virus that might be released through non-specific bystander effects. The selected recombinants can be further expanded in a complementing cell line or in the presence of a complementing helper virus or transfected plasmid.

A number of essential early vaccinia genes have been described. Preferably, a vaccinia strain deficient for the D4R gene could be employed. The vaccinia D4R open reading frame (orf) encodes a uracil DNA glycosylase enzyme. This enzyme is required for viral DNA replication and disruption of this gene is lethal to vaccinia (A. K. Millns, M. S. Carpenter, and A. M. Delange. 1994 *Virology* 198:504-513). It has been demonstrated that a stably transfected mammalian cell line expressing the vaccinia D4R gene is able to complement a D4R deficient vaccinia virus (G. W. Holzer, F. G. Falkner. 1997 *J. Virology* 71: 4997-5002). In the absence of D4R complementation, infection with the D4R deficient vaccinia results in greatly reduced inhibition of host cell protein synthesis (Holzer and Falkner). It has also been shown that a foreign gene inserted into the tk gene of D4R deficient vaccinia continues to be expressed at high levels, even in the absence of D4R complementation (M. Himly, M. Pfleiderer, G. Holzer, U. Fischer, E. Hannak, F. G. Falkner, and F. Dorner. 1998 *Protein Expression and Purification* 14: 317-326). The replication deficient D4R strain is, therefore, well-suited for selection of viral recombinants that depend on continued active expression of some host genes for their physiological effect.

To implement this strategy for selection of specific recombinants from representative cDNA libraries constructed in a D4R deficient vaccinia strain the following cell lines and vectors are required:

1. D4R expressing complementing cell line is required for expansion of D4R deficient viral stocks.
2. The D4R gene must be deleted or inactivated in a viral strain suitable for trimolecular recombination.
3. Plasmid or viral constructs must be generated that express D4R under the control of different inducible promoters such as that which regulates expression of BAX or other genes induced following crosslinking of membrane immunoglobulin receptors on CH33 B lymphoma cells or the promoter for expression of type X collagen following induction of chondrocyte differentiation from C3H10T½ progenitor cells. Stable transfectants of these constructs in the relevant cell line are required to rescue specific recombinants. Alternatively, a helper virus expressing the relevant construct can be employed for inducible expression in either cell lines or primary cultures.

10.1 Construction of a D4R Complementing Cell Line A D4R complementing cell line is constructed as follows. First, the D4R orf (position 100732 to 101388 in vaccinia genome) is cloned from vaccinia strain v7.5/tk by PCR amplification using the following primers:

```
D4R-sense, 5' AAAGAATTCA TAATGAATTC AGTGACTGTA

TCACACG 3', designated herein as SEQ ID NO: 104;
and

D4R-antisense: 5' CTTGGATCCT TAATAAATAA

ACCCTTGAGC CC 3', designated herein as

SEQ ID NO:  105.
```

The sense primer is modified to include an EcoRI site, and the anti-sense primer is modified to include a BamHI site (both underlined). Following standard PCR amplification and digestion with EcoRI and BamHI, the resulting D4R orf is cloned into the EcoRI and BamHI sites of pIRESneo (available from Clontech, Palo Alto, Calif.). This mammalian expression vector contains the strong CMV immediate early promoter/enhancer and the ECMV internal ribosome entry site (IRES). The D4R/IRESneo construct is transfected into BSC1 cells and transfected clones are selected with G418. The IRES allows for efficient translation of a polycistronic mRNA that contains the D4Rorf at the 5' end, and the neomycin phosphotransferase gene at the 3' end. This results in a high frequency of G418 resistant clones being functional (the clones express D4R). Transfected clones are tested by northern blot analysis using the D4R gene as probe in order to identify clones that express high levels of D4R mRNA. BSC1 cells that express D4R (BSC1.D4R) are able to complement D4R deficient vaccinia, allowing for generation and propagation of D4R defective viruses.

10.2. Construction of D4R Deficient vaccinia vector A D4R-deficient vaccinia virus, suitable for trimolecular recombination as described in Example 5, supra, is constructed by disruption of the D4R orf (position 100732 to 101388 in vaccinia genome) through the insertion of an *E. Coli* GusA expression cassette into a 300-bp deletion, by the following method.

In order to insert the GusA gene, regions flanking the insertion site are amplified from vaccinia virus as follows. The left flanking region is amplified with the following primers:

```
D4R left flank sense: 5' AATAAGCTTT ACTCCAGATA

ATATGGA 3', designated herein as SEQ ID NO:  106;
and

D4R left flank antisense: 5' AATCTGCAGC CCAGTTCCAT

TTT 3', designated herein as SEQ ID NO:  107.
```

These primers amplify a region extending from position 100167 to position 100960 of the vaccinia genome, and have been modified to include a HindIII (Sense) and PstI (Antisense) site for cloning (both underlined). The resulting PCR product is digested with HindIII and PstI, and cloned into the HindIII and PstI sites of pBS (available from Stratagene), generating pBS.D4R.LF. The right flanking region is amplified with the following primers: D4R right flank sense: 5' AATGGATCCT CATCCAGCGG CTA 3', designated herein as SEQ ID NO:108; and

```
D4R right flank antisense: 5' AATGAGCTCT

AGTACCTACA ACCCGAA 3', designated herein as SEQ

ID NO:  109.
```

These primers amplify a region extending from position 101271 to position 101975 of the vaccinia genome, and have been modified to include a BamHI (Sense) and SacI (Antisense) site for cloning (both underlined). The resulting PCR product is digested with BamHI and SacI, and cloned into the BamHI and SacI sites of pBS.D4R.LF, creating pBS.D4R.LF/RF.

An expression cassette comprising the GusA coding region operably associated with a poxvirus synthetic early/late (E/L) promoter, is inserted into pBS.D4R.LF/RF by the following method. The E/L promoter—Gus cassette is derived from the pEL/tk-Gus construct described in Merchlinsky, M., et al., *Virology* 238: 444-451 (1997). The NotI site immediately upstream of the Gus ATG start codon is removed by digestion of pEL/tk-Gus with NotI, followed by a fill in reaction with Klenow fragment and religation to itself, creating pEL/tk-Gus(NotI-). The E/L-Gus expression cassette is isolated from pEL/tk-Gus(NotI-) by standard PCR using the following primers:

```
EL-Gus sense: 5' AAAGTCGACG GCCAAAAATT GAAATTTT

3', designated herein as SEQ ID NO: 110;
and

EL-Gus antisense: 5' AATGGATCCT CATTGTTTGC CTCCC

3', designated herein as SEQ ID NO: 111.
```

The EL-Gus sense primer contains a SalI site and the EL-Gus antisense primer contains a BamHI site (both underlined). Following PCR amplification the EL. Gus cassette is digested with SalI and BamHI and inserted into the SalI and BamHI sites in pBS.D4R.LF/RF generating pBS.D4R-/ELGus. This transfer plasmid contains an EL-Gus expression cassette flanked on both sides by D4R sequence. There is also a 300 bp deletion engineered into the D4R orf.

$D4R^-/Gus^+$ vaccinia viruses suitable for trimolecular recombination are generated by conventional homologous recombination following transfection of the $pBS.D4R^-/EL$-Gus construct into v7.5/tk-infected BSC1.D4R cells. $D4R^-/Gus^+$ virus are isolated by plaque purification on BSC1.D4R cells and staining with X-Glu (M. W. Carroll, B. Moss. 1995. *Biotechniques* 19: 352-355). This new strain is designated v7.5/tk/Gus/D4R.

DNA purified from v7.5/tk/Gus/D4R is used to construct representative vaccinia cDNA libraries by trimolecular recombination according to the method described in Example 5, except that the reactions are carried out in the BSC1.D4R complementing cell line.

10.3. Preparation of host cells expressing D4R under the control of inducible promoters Host cells which express the D4R gene upon induction of an inducible promoter are prepared as follows. Plasmid constructs are generated that express the vaccinia D4R gene under the control of an inducible promoter. Examples of inducible promoters include, but are not limited to, promoters which are upregulated following crosslinking of membrane immunoglobulin on CH33 cells (for antibody selection), e.g., the BAX promoter as described in Examples 2 and 3. The vaccinia D4R orf is amplified by PCR using primers D4R sense and D4R antisense described above in section 10.1. These PCR primers are modified as needed to include desirable restriction endonuclease sites. The D4R orf is then cloned in a suitable eukaryotic expression vector (which allows for the selection of stably transformed cells) in operable association of any desired promoter employing methods known to those skilled in the art.

The construct is then transfected into a suitable host cell, for example, the for selection of antibodies as described in Examples 2 and 3, the D4R gene, in operable association with the BAX promoter, is stably transfected into a suitable cell line, for example, a CH33 cell line, a CH 31 cell line, or a WEHI-231 cell line. The resulting host cells are utilized in the production of antibodies, essentially as described in Example 3, using libraries prepared in v7.5/tk/Gus/D4R. Antigen-induced cross-linking of membrane-expressed immunoglobulin molecules on the surface of host cells results in the induction of expression of the D4R gene product in the cross-linked cells. Expression of D4R complements the defect in the v7.5/tk/Gus/D4R genomes in which the libraries are produced, allowing the production of infectious virus particles.

Example 11

Attenuation of Poxvirus Mediated Host Shut-Off by Reversible Inhibitor of DNA Synthesis As discussed infra, attenuated or defective virus is sometimes desired to reduce cytopathic effects. Cytopathic effects during viral infection might interfere with selection and identification of immunoglobulin molecules using methods which take advantage of host cell death (e.g. apoptosis induced by cross-linking). Such effects can be attenuated with a reversible inhibitor of DNA synthesis such as hydroxyurea (HU) (Pogo, B. G. and S. Dales Virology, 1971. 43(1):144-51). HU inhibits both cell and viral DNA synthesis by depriving replication complexes of deoxyribonucleotide precursors (Hendricks, S. P. and C. K. Mathews J Biol Chem, 1998. 273(45): 29519-23). Inhibition of viral DNA replication blocks late viral RNA transcription while allowing transcription and translation of genes under the control of early vaccinia promoters (Nagaya, A., B. G. Pogo, and S. Dales Virology, 1970. 40(4):1039-51). Thus, treatment with reversible inhibitor of DNA synthesis such as HU allows the detection of effects of cross-linking. Following appropriate incubation, HU inhibition can be reversed by washing the host cells so that the viral replication cycle continues and infectious recombinants can be recovered (Pogo, B. G. and S. Dales Virology, 1971. 43(1): 144-51).

The results in FIG. 9 demonstrate that induction of type X collagen synthesis, a marker of chondrocyte differentiation, in $C_3H_{10}T$ ½ progenitor cells treated with BMP-2 (Bone Morphogenetic Protein-2) is blocked by vaccinia infection but that its synthesis can be rescued by HU mediated inhibition of viral DNA synthesis. When HU is removed from cultures by washing with fresh medium, viral DNA synthesis and assembly of infectious particles proceeds rapidly so that infectious viral particles can be isolated as soon as 2 hrs post-wash.

$C_3H_{10}T$ ½ cells were infected with WR vaccinia virus at MOI=1 and 1 hour later either medium or 400 ng/ml of BMP-2 in the presence or absence of 2 mM HU was added. After a further 21 hour incubation at 37° C., HU was removed by washing with fresh medium. The infectious cycle was allowed to continue for another 2 hours to allow for initiation of viral DNA replication and assembly of infectious particles. At 24 hours RNA was extracted from cells maintained under the 4 different culture conditions. Northern analysis was carried out using a type X collagen specific probe. The uninduced C3H10T ½ cells have a mesenchymal progenitor cell phenotype and as such do not express type X collagen (first lane from left). Addition of BMP-2 to normal, uninfected C3H10T ½ cells induces differentiation into mature chondrocytes and expression of type X collagen (compare first and second lanes from left), whereas addition of BMP-2 to vaccinia infected C3H10T ½ cells fails to induce synthesis of type X collagen (third lane from left). In the presence of 2 mM HU, BMP-2 induces type X collagen synthesis even in vaccinia virus infected $C_3H_{10}T$ ½ cells (fourth lane from left).

This strategy for attenuating viral cytopathic effects is applicable to other viruses, other cell types and to selection of immunoglobulin molecules that, for example, induce apoptosis upon cross-linking.

Example 12

Construction of Human Fab Fragment Libraries of Diverse Specificity

Libraries of polynucleotides encoding fully human, diverse immunoglobulin Fab fragments are produced as follows. These Fab fragments comprise a heavy chain variable region linked to a first constant region domain (VH-CH1) paired with an immunoglobulin light chain. Genes for human VH (variable region of heavy chain), VK (variable region of kappa light chain) and VL (variable region of lambda light chains) are amplified by PCR. For each of the three variable gene families, both a recombinant plasmid library and a vaccinia virus library is constructed. The variable region genes are inserted into a p7.5/tk-based transfer/expression plasmid immediately upstream of a constant region sequence corresponding to the CH1 domain of heavy chains or the kappa light chain constant region, CK. These plasmids are employed to generate the corresponding vaccinia virus recombinants by trimolecular recombination and can also be used directly for high level expression of Fab fragments following transfection of one immunoglobulin chain or fragment thereof into cells infected with vaccinia virus recombinants of a second immunoglobulin chain or fragment thereof. The two chains are synthesized and assembled to form an Fab fragment. These Fab fragments may be membrane bound or secreted by attaching coding sequences for signal sequences, transmembrane domains, and/or intracellular domains, as is understood by one of ordinary skill in the art.

12.1 pVHEc. An expression vector which encodes a human heavy chain fragment comprising VH and the CH1 domain of Cµ, designated pVHEc, is constructed as follows. Plasmid p7.5/tk2 is produced as described in Example 1.1, supra. A DNA construct encoding amino acids 109-113 of VH and the CH1 domain, i.e., amino acids 109-223B of Cµ, is amplified from the IgM heavy chain gene isolated as described in Example 1, and is modified by PCR to include a BstEII site at the 5' end of the region encoding amino acids 109-113+ the Cµ CH1 domain, and a stop codon and a SalI site at its 3' end. This DNA is inserted into p7.5/tk2 between the BstEII and SalI sites to generate pVHEc. Heavy chain variable region (VH) PCR products (amino acids (–4) to (110)), produced as described in Example 1.4(a), using the primers listed in Tables 1 and 2, are cloned into BssHII and BstEII sites. Because of the overlap between the CH1 domain sequence and the restriction enzyme sites selected, this results in construction of a contiguous heavy chain fragment which lacks a functional signal peptide but remains in the correct translational reading frame.

12.2 pVKEc and pVLEc. Expression vectors encoding the human κ and λ immunoglobulin light chain constant regions, designated herein as pVKEc and pVLEc, are constructed as follows. Plasmid p7.5/tk3.1, is produced as described in Example 1.3, supra.

(a) Plasmid p7.5/tk3.1 is converted into pVKEc by the following method. A cDNA coding for the $C_\kappa$ region is isolated as described in Example 1, with primers to include an XhoI site at the 5' end of the region encoding amino acids 104-107+$C_\kappa$, and a stop codon and a SalI site at its 3' end, which is then cloned into p7.5/tk3.1 at XhoI and SalI sites to generate pVKEc. Kappa light chain variable region (VK) PCR products (amino acids (–3) to (105)), produced as described in Example 1.4(b), using the primers listed in Tables 1 and 2, are then cloned into pVKEc at the ApaLI and XhoI sites. Because of the overlap between the κ light chain sequence and the restriction enzyme sites selected, this results in construction of contiguous κ light chains which lacks a functional signal peptide but remains in the correct translational reading frame.

(b) Plasmid p7.5/tk3.1 is converted into pVLEc by the following method. A cDNA coding for the $C_\kappa$ region is isolated as described in Example 1, with primers to include a HindIII site and amino acids 105 to 107 of $V_\lambda$ at its 5' end and a stop codon and a SalI site at its 3' end, which is then cloned into p7.5/tk3 at HindIII and SalI sites to generate pVLEc. Lambda light chain variable region (VL) PCR products (amino acids (–3) to (104)), produced as described in Example 1.4(c), using the primers listed in Tables 1 and 2, are then cloned into pVLEc at ApaLI and HindIII sites. Because of the overlap between the λ light chain sequence and the restriction enzyme sites selected, this results in construction of contiguous λ light chains which lacks a functional signal peptide but remains in the correct translational reading frame.

12.3 Secreted or Membrane Bound Forms of Fab. The expression vectors (pVHEc, pVKEc and pVLEc) serve as prototype vectors into which secretion signals, transmembrane domains, cytoplasmic domains, or combinations thereof can be cloned to target Fab to the cell surface or the extracellular space. These signals and domains, examples of which are shown in Table 7, may be inserted either in the N-terminus of Fab between NcoI and BssHII of pVHEc (or NcoI and ApaLI of pVKEc and pVLEc) and/or in the C-terminus at SalI site. To target an Fab for secretion into the extracellular compartment, a signal peptide is inserted at the N-terminus of either or both Fab chains, VH-CH1 or light chain. To anchor an Fab in the plasma membrane for extracellular presentation, a transmembrane domain is added to the carboxyl-terminus of VH-CH1 chain and/or to the light chain. A cytoplasmic domain may also be added.

TABLE 7

Localization signals

| Signal sequence | Terminus | Location | Protein |
|---|---|---|---|
| MGWSCIILFLVATATGAHS (SEQ ID NO: 146) | N | ES | IgG1 |
| NLWTTASTFIVLFLLSLFYSTTVT LF (SEQ ID NO: 147) | C/N | PM | IgM |

Abbreviations for items under Location: ES, extracellular space; PM, plasma membrane.

Example 13

Figure 10:
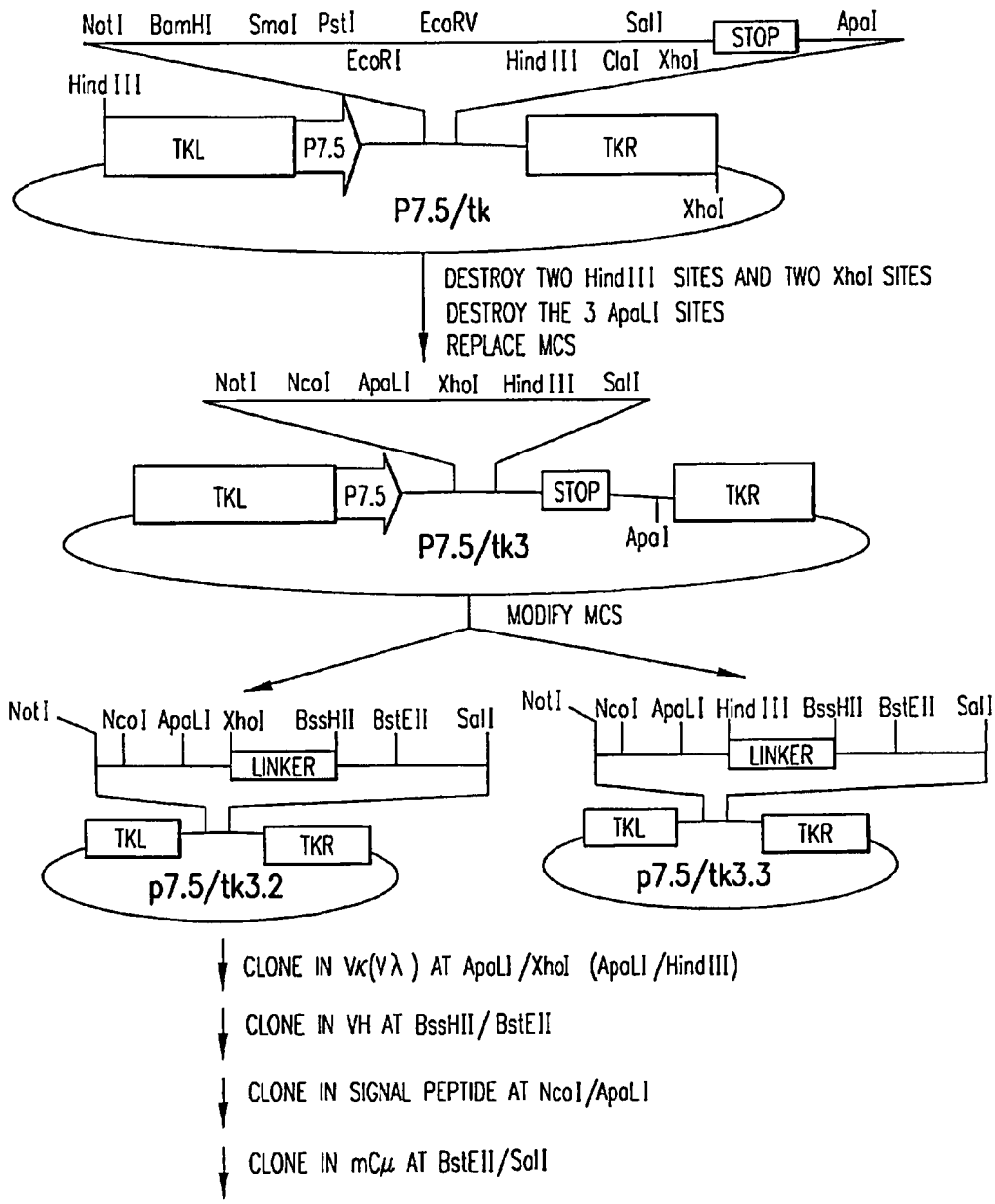
FIG. 10 Construction of scFv expression vectors.

Construction of Human Single-Chain-Fv (ScFv) Antibody Libraries 13.1 Human scFv expression vectors p7.5/tk3.2 and p7.5/tk3.3 are constructed by the following method, as illustrated in FIG. 10. Plasmid p7.5/tk3 is produced as described in Example 1.3, supra. Plasmid p7.5/tk3 is converted to p7.5/tk3.1 by changing the four nucleotides ATAC between NcoI and ApaLI sites into ATAGC, so that the ATG start codon in NcoI is in-frame with ApaLI without the inserted signal peptide. This is conveniently accomplished by replacing the NotI-to-SalI cassette described in Example 1.3 (SEQ ID NO:29) with a cassette having the sequence 5'-GCGGC-CGCCC ATGGATAGCG TGCACTTGAC TCGAGAAGCT TAGTAGTCGA C-3', referred to herein as SEQ ID NO:112.

Plasmid p7.5/tk3.1 is converted to p7.5/tk3.2 by substituting the region between XhoI and SalI (i.e., nucleotides 30 to 51 of SEQ ID NO:112), referred to herein as SEQ ID NO:113, with the following cassette: XhoI-(nucleotides encoding amino acids 106-107 of Vκ)-(nucleotides encoding a 10 amino acid linker)-G-BssHII-ATGC-BstEII-(nucleotides encoding amino acids 111-113 of VH)-stop codon-SalI. This is accomplished by digesting p7.5/tk3.1 with XhoI and SalI, and inserting a cassette having the sequence 5'CTCGAGAT CAAAGAGGGT AAATCTTCCG GATCTGGTTC CGAAGGCGCG CATGCGGTCA CCGTCTCCTC ATGAGTCGAC 3', referred to herein as SEQ ID NO:114. The linker between Vκ and VH will have a final size of 14 amino acids, with the last 4 amino acids contributed by the VH PCR products, inserted as described below. The sequence of the linker is 5'GAG GGT AAA TCT TCC GGA TCT GGT TCC GAA GGC GCG CAC TCC 3' (SEQ ID NO:115), which encodes amino acids EGKSSGSGSEGAHS (SEQ ID NO: 116).

Plasmid p7.5/tk3.1 is converted to p7.5/tk3.3 by substituting the region between HindIII and SalI (i.e., nucleotide 36 to 51 of SEQ ID NO: 112), referred to herein as SEQ ID NO:117, with the following cassette: HindIII-(nucleotides encoding amino acid residues 105-107 of Vλ)-(nucleotides encoding a 10 amino acid linker)-G-BssHII-ATGC-BstEII-(nucleotides encoding amino acids 111-113 of VH)-stop codon-SalI. This is accomplished by digesting p7.5/tk3.1 with HindIII and SalI, and inserting a cassette having the sequence 5'AAGCTTACCG TCCTAGAGGG TAAATCT-TCC GGATCTGGTTC CGAAGGCGCG CATGCGGTCA CCGTCTCCTC ATGAGTCGAC 3' (SEQ ID NO:118). The linker between Vλ and VH will have a final size of 14 amino acids, with the last 4 amino acids contributed by the VH PCR products, inserted as described below. The sequence of the linker is 5'GAG GGT AAA TCT TCC GGA TCT GGT TCC GAA GGC GCG CAC TCC 3' (SEQ ID NO:119), which encodes amino acids EGKSSGSGSEGAHS (SEQ ID NO:120).

13.2 Cytosolic Forms of scFv. Expression vectors encoding scFv polypeptides comprising human κ or λ immunoglobulin light chain variable regions, fused in frame with human heavy chain variable regions, are constructed as follows.

(a) Cytosolic VκVH scFv expression products are prepared as follows. Kappa light chain variable region (Vκ) PCR products (amino acids (−3) to (105)), produced as described in Example 1.4(b), using the primers listed in Tables 1 and 2, are cloned into p7.5/tk3.2 between the ApaLI and XhoI sites. Because of the overlap between the κ light chain sequence and the restriction enzyme sites selected, this results in construction of a contiguous κ light chain in the same translational reading frame as the downstream linker. Heavy chain variable region (VH) PCR products (amino acids (−4) to (110)), produced as described in Example 1.4(a), using the primers listed in Tables 1 and 2, are cloned between the BssHII and BstEII sites of p7.5/tk3.2 to form complete scFv open reading frames. The resulting products are cytosolic forms of Vκ-VH fusion proteins connected by a linker of 14 amino acids. The scFv is also preceded by 6 extra amino acids at the amino terminus encoded by the restriction sites and part of the Vκ signal peptide.

(b) Cytosolic VλVHscFv expression products are prepared as follows. Lambda light chain variable region (VL) PCR products (amino acids (−3) to (104)), produced as described in Example 1.4(c), using the primers listed in Tables 1 and 2, are cloned into p7.5/tk3.3 between the ApaLI and HindIII sites. Because of the overlap between the λ light chain sequence and the restriction enzyme sites selected, this results in construction of a contiguous λ light chain in the same translational reading frame as the downstream linker. Heavy chain variable region (VH) PCR products (amino acids (−4) to (110)), produced as described in Example 1.4(a), using the primers listed in Tables 1 and 2, are cloned between BssHII and BstEII sites of p7.5/tk3.3 to form complete scFv open reading frames. The resulting products are cytosolic forms of Vλ-VH fusion proteins connected by a linker of 14 amino acids. The scFv is also preceded by 6 extra amino acids at the amino terminus encoded by the restriction sites and part of the Vλ signal peptide.

13.3 Secreted or Membrane Bound Forms of scFv. The cytosolic scFv expression vectors described in section 13.2 serve as the prototype vectors into which secretion signals, transmembrane domains, cytoplasmic domains, or combinations thereof can be cloned to target scFv polypeptides to the cell surface or the extracellular space. Examples of signal peptides and membrane anchoring domains are shown in Table 7, supra. To generate scFv polypeptides to be secreted into the extracellular space, a cassette encoding an in-frame secretory signal peptide is inserted so as to be expressed in the N-terminus of scFv polypeptides between the NcoI and ApaLI sites of p7.5/tk3.2 or p7.5/tk3.3. To generate membrane-bound scFv for Ig-crosslinking or Ig-binding based selection, in addition to the signal peptide, a cassette encoding the membrane-bound form of Cμ is cloned into the C-terminus of scFv between the BstEII and SalI sites, downstream of and in-frame with the nucleotides encoding amino acids 111-113 of VH. A cytoplasmic domain may also be added.

Example 14

Construction of Camelized Human Single-Domain Antibody Libraries

Camelid species use only heavy chains to generate antibodies, which are termed heavy chain antibodies. The poxvirus expression system is amendable to generate both secreted and membrane-bound human single-domain libraries, wherein the human $V_H$ domain is "camelized," i.e., is altered to resemble the $V_H$H domain of a camelid antibody, which can then be selected based on either functional assays or Ig-crosslinking/binding. Human $V_H$ genes are camelized by standard mutagenesis methods to more closely resemble camelid $V_H$H genes. For example, human $V_H$3 genes, produced using the methods described in Example 1.4 using appropriate primer pairs selected from Tables 1 and 2, is camelized by substituting G44 with E, L45 with R, and W47 with G or I. See, e.g., Riechmann, L., and Muyldermans, S. *J. Immunol. Meth.* 231:25-38. To generate a secreted single-domain antibody library, cassettes encoding camelized human $V_H$ genes are cloned into pVHEs, produced as described in Example 1.2, to be expressed in-frame between the BssHII and BstEII sites. To generate a membrane-bound single-domain antibody library, cassettes encoding camelized human $V_H$ genes are cloned into pVHE, produced as described in Example 1.1, to be expressed in-frame between the BssHII and BstEII sites. Vectors pVHE and pVHEs already have the signal peptide cloned in between the NcoI and BssHII sites. Amino acid residues in the three CDR regions of the camelized human $V_H$ genes are subjected to extensive randomization, and the resulting libraries can be selected in poxviruses as described herein.

Example 15

Selection of Fc-Modified Antibodies for Enhanced Immune Effector Functions

Human monoclonal antibodies are being used in therapeutic applications for treatment of an increasing number of human diseases. Human antibodies may induce or block signaling through specific cell receptors. In some applications, human antibodies may activate any of a variety of accessory effector cells through an interaction between the Fc portion of the antibody molecule and a matching Fc receptor (FcR) on these effector cells. It is, therefore, of considerable interest to identify modifications of immunoglobulin heavy chain constant region sequences that enhance or inhibit binding and signaling through FcR or binding and activation of other mediators of immune effector functions such as components of the complement cascade. See. e.g., U.S. Pat. No. 5,624, 821; Xu, D., et al., *Cell Immunol* 200:16-26 (2000); and U.S. Pat. No. 6,194,551, the disclosures of which are incorporated herein by reference in their entireties.

One such specific effector function is antibody-dependent cell cytotoxicity (ADCC), a process in which antibody-coated target cells are destroyed by NK cells or other monocytes. ADCC is mediated by antibody molecules with variable region encoded specificity for a surface molecule of a target cell and constant region encoded specificity for FcγRIII on the NK cell. Through analysis of crystal structures and site-directed mutagenesis, it has been determined that the FcγRIII binding site on human IgG1 is localized mainly to the lower hinge, i.e., about amino acids 247-252 of IgG1, and the adjacent CH2 regions. See, e.g., Sarmay G., et al., *Mol Immunol* 29:633-639 (1992); and Michaelsen, T. E., et al., *Mol Immunol* 29:319-26 (1992). By constructing a library of genes encoding antibody molecules with randomly mutated lower hinge regions in a selectable mammalian expression vector, it would be feasible to select specific constant region variants with enhanced function for ADCC. To simplify execution of this strategy, a library is constructed with defined immunoglobulin variable region sequences that confer a desired specificity.

Figure 11:
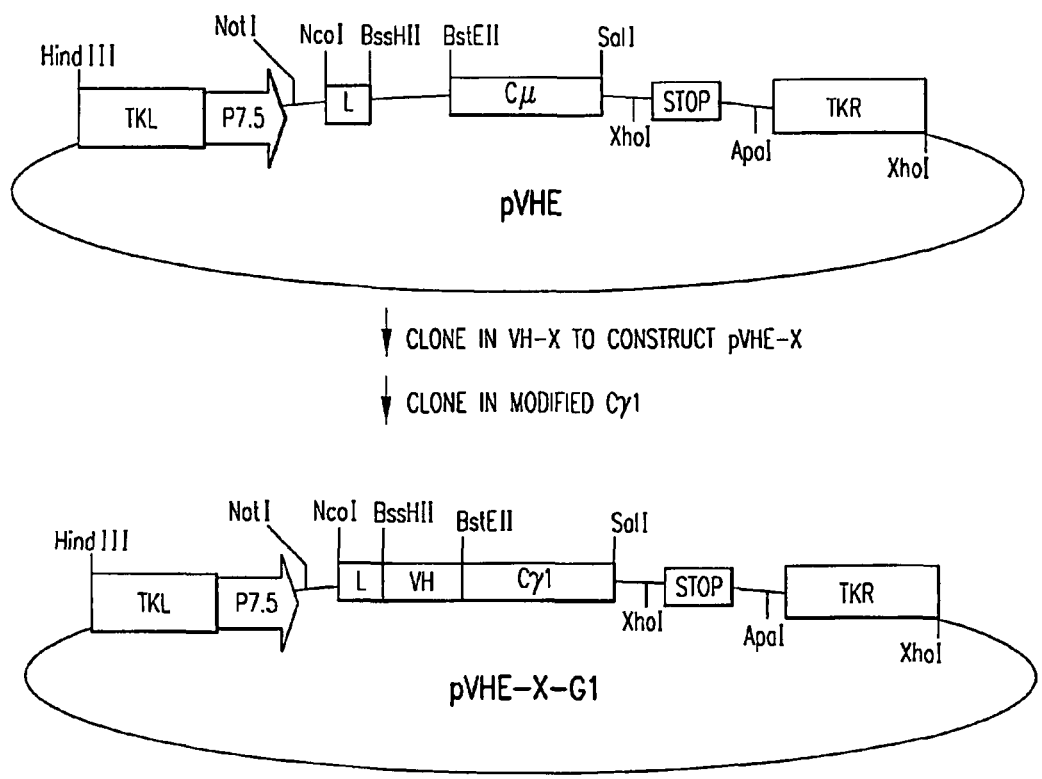
FIG. 11 Construction of pVHE-X-G1.

15.1. Construction of pVHE-X and pVKE-X or pVLE-X. Plasmid pVHE-X, a human VH expression vector with a defined variable region, designated herein as X, is constructed as follows. The construction is illustrated in FIG. 11. An antibody with a defined specificity X is isolated by conventional methods, or is produced and selected in eukaryotic cells using poxvirus vectors, by methods described herein. If necessary, the VH gene of the antibody is subcloned into pVHE, produced as described in Example 1.1, between the BssHII/BstEII sites, resulting in plasmid pVHE-X. Also if necessary, the VK or VL gene of the antibody is subcloned either into pVKE, produced as described in Example 1.3, at the ApaLI/XhoI sites to produce pVKE-X, or into pVLE, produced as described in Example 1.3, at ApaLI/HindIII sites, to produce pVLE-X, respectively.

15.2 Isolation of a human Cγ1 cassette. A cDNA coding for the human Cγ1 heavy chain is isolated from bone marrow RNA using SMART™ RACE cDNA Amplification Kit, using the following primers:

```
huCγ1-5B:                           (SEQ ID NO: 121)
5' ATTAGGATCC GGTCACCGTC TCCTCAGCC 3' huCγ1-3S:                           (SEQ ID NO: 122)
5' ATTAGTCGAC TCATTTACCC GGAGACAGGG AGAG 3'
```

The PCR product comprises the following elements: BamHI-BstEII-(nucleotides encoding amino acids 111-113 of VH)-(nucleotides encoding amino acids 114-478 of Cγ1)-TGA-SalI. This product is subcloned into pBluescriptII/KS at BamHI and SalI sites, and a second BstEII site corresponding to amino acids 191 and 192 within the CH1 domain of Cγ1 is removed by site-directed mutagenesis without change to the amino acid sequence.

15.3 Construction of Fcγ1 library. Cγ1 variants are generated by overlap PCR by the following method. The BstEII-mutagenized Cγ1 cassette, produced as described in section 15.2, is used as the template In the first round of PCR, amplifications are carried out in two separate reactions using Cγ1-sense/Cγ1-internal-R and Cγ1-internal-S/Cγ1-reverse primer sets.

```
Cγ1-sense:                          (SEQ ID NO: 123)
5' AATATGGTCACCGTCTCCTCAGCC 3'

Cγ1-internal-R:                     (SEQ ID NO: 124)
5' (MNN)₆TTCAGGTGCTGGGCACGG 3'

Cγ1-internal-S:                     (SEQ ID NO: 125)
5' (NNK)₆GTCTTCCTCTTCCCCCCA 3'

Cγ1-reverse:                        (SEQ ID NO: 126)
5' AATATGTCGACTCATTTACCCGG 3'
```

(M=A+C, K=G+T, N=A+T+G+C)

The Cγ1-Internal-R and Cγ1-Internal-S Primers have Degenerate Sequence tails that code for variants of the six amino acids comprising residues 247-252 in the lower hinge. In the second round of PCR, the purified products from the first round are fused by overlap PCR using the Cγ1-sense and Cγ1-reverse primers.

The resulting products are approximately 1000 bp in size, and randomly encode all 20 amino acids in each of the six amino acid positions 247-252. The PCR products are digested with BstEII and SalI, and are cloned into BstEII/SalI-digested pVHE-X, produced as described in section 15.1, to generate a library of pVHE-X-γ1 variants. These variants are then introduced into vaccinia virus using trimolecular recombination as described in Example 5. In conjunction with the recombinant vaccinia virus harboring the light chain, the Fcγ1 library will be used to select those Fc variants that confer enhanced ADCC activity on a VHE-X-γ1 expressing antibody.

15.4 Other applications. In addition the generation of variants at amino acids 247-252, other residues, such as amino acids 278-282 and amino acids 346-351 of IgG1, are also involved in binding to FcγRIII. Following the identification of Fcγ1 variant in amino acids 247-252 that exhibits an enhanced ADCC activity, the same strategy can be employed to identify additional mutations in the other two regions that exhibit synergistic enhancement of ADCC function.

The same principle/technique can be applied to identifying variants that confer enhanced effector function on other immunoglobulin heavy chain constant region isotypes that bind to different Fc receptors. In preferred embodiments the receptors to be targeted include FcγRI (CD64), FcγRII-A (CD32), FcγRII-B1, FcγRII-B2, FcγRIII (CD16), and FcϵRI. In other preferred embodiments, variants may be selected that enhance binding of complement components to the Fc region or Fc mediated binding to placental membrane for transplacental transport.

Example 16

Construction of Heavy Chain Fusion Proteins to Facilitate Selection of Cells Infected with Specific Immunoglobulin Gene Recombinant Vaccinia Virus 16.1 Construction of CH1-Fas. An expression vector which encodes a fusion protein comprising the human heavy chain CH1 domain of Cμ, fused to the transmembrane and death domains of Fas, designated herein as CH1-Fas, is constructed by the following method. The fusion protein is illustrated in FIG. 13(*a*).

Plasmid pVHE, produced as described in Example 1.1, is digested with BstEII and SalI and the smaller DNA fragment of about 1.4 Kb is gel purified. This smaller fragment is then used as a template in a PCR reaction using forward primer CH1(F)-5'ACACGGTCAC CGTCTCCTCA GGGAGTGC 3' (SEQ ID NO:127) and reverse primer CH1(R) 5'AGTTAGATCT GGATCCTGGA AGAGGCACGT T 3' (SEQ ID NO:128). The resulting PCR product of about 320 base pairs is gel purified.

A DNA fragment comprising the transmembrane and death domains of Fas is amplified from plasmid pBS-APO14.2 with forward primer FAS(F) 5'AACGTGCCTC TTCCAGGATC CAGATCTAAC 3' (SEQ ID NO:129) and reverse primer FAS(R) 5'ACGCGTCGAC CTAGACCAAG CTTTGGATTT CAT 3'(SEQ ID NO:130). The resulting PCR product of about 504 base pairs is gel purified.

The resulting 320 and 504-base pair fragments are then combined in a PCR using forward primer CH1(F) and reverse primer FAS (R), to produce a fusion fragment of about 824 base pairs. This fragment is digested with BstEII and SalI, and the resulting 810-base pair fragment is gel purified. Plasmid pVHE also digested with BstEII and SalI, and the larger resulting fragment of about 5.7 Kb is gel purified. These two BstEII/SalI fragments are then ligated to produce CH1-Fas.

16.2 Construction of CH4-Fas. An expression vector which encodes a fusion protein comprising the human heavy chain CH1-CH4 domains of Cμ, fused to the transmembrane and death domains of Fas, designated herein as CH4-Fas, is constructed by the following method. The fusion protein is illustrated in FIG. 13(b).

Plasmid pVHE, produced as described in Example 1.1, is digested with BstEII and SalI and the smaller DNA fragment of about 1.4 Kb is gel purified. This smaller fragment is then used as a template in a PCR reaction using forward primer CH4(F) 5'CTCTCCCGCG GACGTCTTCG T 3' (SEQ ID NO:131) and reverse primer CH4(R) 5'AGTTAGATCT GGATCCCTCA AAGCCCTCCT C 3' (SEQ ID NO:132). The resulting PCR product of about 268 base pairs is gel purified.

A DNA fragment comprising the transmembrane and death domains of Fas is amplified from plasmid pBS-APO14.2 with forward primer FAS(F2)—5' GAG-GAGGGCT TTGAGGGATC CAGATCTAAC 3' (SEQ ID NO:133) and reverse primer FAS(R), as shown in section 16.1. The resulting PCR product of about 504 base pairs is gel purified.

The resulting 268 and 504-base pair fragments are then combined in a PCR using forward primer CH4(F) and reverse primer FAS (R), to produce a fusion fragment of about 765 base pairs. This fragment is digested with SacII and SalI, and the resulting 750-base pair fragment is gel purified. Plasmid pVHE also digested with SacII and SalI, and the larger resulting fragment of about 6.8 Kb is gel purified. These two SacII/SalI fragments are then ligated to produce CH4-Fas.

16.3 Construction of CH4(TM)-Fas. An expression vector which encodes a fusion protein comprising the human heavy chain CH1-CH4 domains and the transmembrane domain of Cμ, fused to the death domain of Fas, designated herein as CH4(TM)-Fas, is constructed by the following method. The fusion protein is illustrated in FIG. 13(c).

Plasmid pVHE, produced as described in Example 1.1, is digested with BstEII and SalI and the smaller DNA fragment of about 1.4 Kb is gel purified. This smaller fragment is then used as a template in a PCR reaction using forward primer CH4(F) as shown in section 16.2, and reverse primer CH4 (R2) 5'AATAGTGGTG ATATATTTCA CCTTGAACAA 3' (SEQ ID NO:134). The resulting PCR product of about 356 base pairs is gel purified.

A DNA fragment comprising the death domains of Fas is amplified from plasmid pBS-API14.2 with forward primer FAS(F3)-5'TTGTTCAAGG TGAAAGTGAA GAGAAAG-GAA 3' (SEQ ID NO:135) and reverse primer FAS(R), as shown in section 16.1. The resulting PCR product of about 440 base pairs is gel purified.

The resulting 356 and 440-base pair fragments are then combined in a PCR using forward primer CH4(F) and reverse primer FAS (R), to produce a fusion fragment of about 795 base pairs. This fragment is digested with SacII and SalI, and the resulting 780-base pair fragment is gel purified. Plasmid pVHE also digested with SacII and SalI, and the larger resulting fragment of about 6.8 Kb is gel purified. These two SacII/SalI fragments are then ligated to produce CH4(TM)-Fas.

16.4 Cloning and insertion of diverse VH genes into the Ig-Fas fusion proteins. Heavy chain variable region (VH) PCR products (amino acids (−4) to (110)), produced as described in Example 1.4(a), using the primers listed in Tables 1 and 2, are cloned into BssHII and BstEII sites ov CH1-Fas, CH4-Fas and CH4(TM)-Fas. Because of the overlap between the CH1 domain sequence and the restriction enzyme sites selected, this results in construction of a contiguous heavy chain fragment which lacks a functional signal peptide but remains in the correct translational reading frame.

Example 17

Generation of Igα and Igβ-Expressing HeLaS3 and COS7 Cell Lines

In order to express specific human monoclonal antibodies on the cell surface, heavy and light chain immunoglobulins must physically associate with other proteins in the B cell receptor complex. Therefore, in order for host cells to be able to express the human antibody library they must be able to express the molecules and structures that are necessary for the efficient synthesis and assembly of antibodies into membrane-bound receptors. Mouse lymphoma cells express the molecules and structures that are necessary for the expression of specific human antibodies on the cell surface. However, one disadvantage of using lymphoma cells for human antibody library expression is that endogenously expressed immunoglobulin heavy and/or light chains can co-assemble with transgenic immunoglobulin chains, resulting in the formation of nonspecific heterogeneous molecules, which dilute antigen-specific receptors. Another disadvantage of using mouse lymphoma cells to express the human antibody library is that vaccinia virus replicates poorly in lymphocytic cell lines. Therefore, preferred cell types for the expression of specific human antibodies are those which permit the generation of high titers of vaccinia virus and those that are not derived from the B cell lineage. Preferred cell types include HeLa cells, COS7 cells and BSC-1 cells.

The immunoglobulin heavy and light chains of the B cell receptor physically associate with the heterodimer of the Igα and Igβ transmembrane proteins (Reth, M. 1992. Annu. Rev. Immunol. 10:97). This physical association is necessary for the efficient transport of membrane-bound immunoglobulin to the cell surface and for the transduction of signals through the B cell receptor (Venkitaraman, A. R. et al., 1991. Nature 352:777). However, it is unclear as to whether Igα/Igβ heterodimers are necessary and sufficient for the expression of membrane-bound immunoglobulin in heterologous cell lines. Therefore, the cell surface expression of human antibodies on HeLaS3 and COS7 cells was evaluated following their transfection with human Igα and Igβ cDNA.

17.1 Cloning the human Igα and Igβ cDNA by PCR.

cDNA generated from the EBV-transformed human B cells was used as the template in the PCR reactions to amplify human Igα and Igβ cDNA. Human Igα cDNA was amplified with the following primers:

igα5'-5'ATTAGAATTCATGCCTGGGGGTCCAGGA3', designated herein as (SEQ ID NO: 136);
and igα3'-5'ATTAGGATCCTCACGGCTTCTCCAGCTG3', designated herein as (SEQ ID NO: 137).

Human Igβ cDNA was amplified with the following primers:

igβ5'-5' ATTAGGATCCATGGCCAGGCTGGCGTTG3', designated herein as (SEQ ID NO: 138);
and igβ3'-5' ATTACCAGCACACTGGTCACTCCTGGCCTGGGTG3', designated herein as (SEQ ID NO: 139).

Products from Igα PCR reaction were cloned into pIRESneo expression vector (Clontech) at EcoRI and BamHI sites, while those from Igβ PCR reaction were cloned into pIREShyg vector (Clontech) at BamHI and BstXI sites. The identities of the cloned Igα and Igb were confirmed by DNA sequencing.

Figure 14:
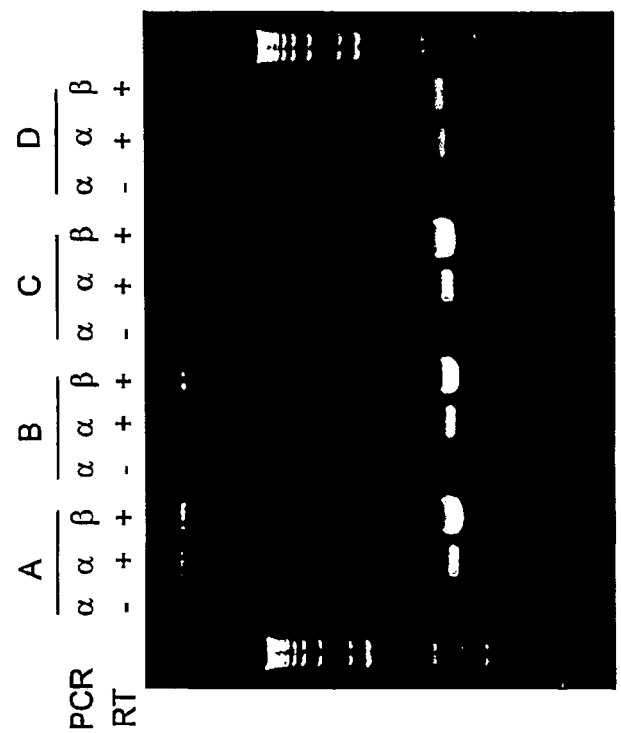
FIG. 14. Expression of Igα and Igβ in the transfected COS7 and HeLaS3 cell lines. Total RNA was isolated from (A) COS7-Igαβ-1, (B) COS7-Igαβ-2, (C) HeLaS3-Igαβ-1 and (D) EBV-transformed human B cells, reverse transcribed into cDNA in the presence or absence of reverse transcriptase, then PCR amplified with the igα5'/igα3' and igβ5'/igβ3' primer sets. PCR products were then analyzed on 0.8% agarose gels. It should be noted that human B cells exhibit alternative splicing for both Igα and Igβ See, e.g., Hashimoto, S., et al., *Mol. Immunol.* 32:651 (1995).

17.2 Establishing Igα and Igβ-expressing HeLaS3 and COS7 stable transfectants. HeLaS3 and COS7 cells ($1'10^6$ per well in a 6-well plate) were transfected with 0.5 to 1 μg each of the purified pIRESneo-Igα and pIREShyg-Igβ plasmid DNA using the LIPOFECTAMINE PLUS Reagent (Life technologies). Starting two days later, cells were selected with G418 (at 0.4 mg/ml) and hygromycin B (at 0.2 mg/ml) for about 2 weeks. Drug-resistant HeLaS3 colonies were directly isolated and COS7 transfectants were cloned by limiting dilution. The expression of Igα and Igβ in each of these clones was then analyzed by RT-PCR, and the results from the representative clones were as shown in FIG. 14.

Example 18

Construction of a Diverse Library of High Affinity Human Antibodies

The current invention is the only available method for the construction of a diverse library of immunoglobulin genes in vaccinia or other pox viruses. The vaccinia vector can be designed to give high levels of membrane receptor expression to allow efficient binding to an antigen coated matrix. Alternatively, the recombinant immunoglobulin heavy chain genes can be engineered to induce apoptosis upon crosslinking of receptors by antigen. Since vaccinia virus can be readily and efficiently recovered even from cells undergoing programmed cell death, the unique properties of this system make it possible to rapidly select specific human antibody genes.

Optimal immunoglobulin heavy and light chains are selected sequentially, which maximizes diversity by screening all available heavy and light chain combinations. The sequential screening strategy is to at first select an optimal heavy chain from a small library of $10^5$ H-chain recombinants in the presence of a small library of $10^4$ diverse light chains. This optimized H-chain is then used to select an optimized partner from a larger library of $10^6$ to $10^7$ recombinant L chains. Once an optimal L-chain is selected, it is possible to go back and select a further optimized H-chain from a larger library of $10^6$ to $10^7$ recombinant H-chains. This reiteration is a boot-strap strategy that allows selection of a specific high-affinity antibody from as many as $10^{14} H_2 L_2$ combinations. In contrast, selection of single chain Fv in a phage library or of Fab comprised of separate VH-CH1 and VL-CL genes encoded on a single plasmid is a one step process limited by the practical size limit of a single phage library—perhaps $10^{11}$ phage particles.

Since it is not feasible to screen $10^{14}$ combinations of $10^7$ H chains and $10^7$ L chains, the selection of optimal H chains begins from a library of $10^5$ H chain vaccinia recombinants in the presence of $10^4$ L chains in a non-infectious vector. These combinations will mostly give rise to low affinity antibodies against a variety of epitopes and result in selection of e.g., 1 to 100 different H chains. If 100 H chains are selected for a basic antibody, these can then be employed in a second cycle of selection with a larger library of $10^6$ or $10^7$ vaccinia recombinant L chains to pick 100 optimal L chain partners. The original H chains are then set aside and the 100 L chains are employed to select new, higher affinity H chains from a larger library of $10^6$ or $10^7$ H chains.

The strategy is a kind of in vitro affinity maturation. As is the case in normal immune responses, low affinity antibodies are initially selected and serve as the basis for selection of higher affinity progeny during repeated cycles of immunization. Whereas higher affinity clones may be derived through somatic mutation in vivo, this in vitro strategy achieves the same end by the re-association of immunoglobulin chains. In both cases, the partner of the improved immunoglobulin chain is the same as the partner in the original lower affinity antibody.

The basis of the strategy is leveraging the initial selection for a low affinity antibody. It is essential that a low affinity antibody be selected. The vaccinia-based method for sequential selection of H and L chains is well-suited to insure that an initial low affinity selection is successful because it has the avidity advantage that comes from expressing bivalent antibodies. In addition, the level of antibody expression can be regulated by employing different promoters in the vaccinia system. For example, the T7 polymerase system adapted to vaccinia gives high levels of expression relative to native vaccinia promoters. Initial rounds of selection can be based on a high level T7 expression system to insure selection of a low affinity "basic antibody" and later rounds of selection can be based on low level expression to drive selection of a higher affinity derivative.

An outline of a method of the current invention for the construction of a diverse library of immunoglobulin genes in vaccinia is as follows:

1. An immunoglobulin membrane associated heavy chain cDNA library is constructed from human lymphocytes in a vaccinia virus vector according to the methods described herein. Specially engineered cells, for example CH33 cells, mouse myeloma cells, and human EBV transformed cell lines or, preferably, HeLa cells and other non-lymphoid cells that do not produce a competing immunoglobulin chain and efficiently support vaccinia replication, are infected with the virus library at dilutions such than on average each cell is infected by one viral immunoglobulin heavy chain recombinant.

2. These same cells are also infected with psoralin inactivated immunoglobulin light chain recombinant vaccinia virus from an immunoglobulin light chain library constructed in the same vaccinia virus vector. Alternatively, the cells may be transfected with immunoglobulin light chain recombinants in a plasmid expression vector. In the population of cells as a whole, each heavy chain can be associated with any light chain.

3. The cells are incubated for a suitable period of time to allow optimal expression of fully assembled antibodies on the cell surface. When the host cell is not of lymphoid origin, the efficiency of membrane antibody expression is enhanced by employing host cells for example, Hela or Cos 7 cells, that have been stably transfected with genes or cDNA expressing Igα and Igβ proteins.

4a. The antigen of interest is bound to inert beads, which are then mixed with the library of antibody expressing cells. Cells that bind to antigen-coated beads are recovered and the associated immunoglobulin heavy chain recombinant virus is extracted.

4b. Alternatively, a fluorescence tag is linked, directly or indirectly, to the antigen of interest. Antibody expressing cells which bind the antigen are recovered by Fluorescence Activated Cell Sorting.

4c. Alternatively, host cells may be employed in which cross-linking of the antibody receptor with the antigen induces cell death. This may occur naturally in host cells that are immature cells of the B cell lineage or it may be a consequence of incorporation of a Fas encoded death domain at the carboxyl terminus of the immunoglobulin heavy chain constant region. The lysed cells are separated from the living cells and the recombinant viruses carrying the relevant immunoglobulin heavy chains are extracted.

5. The above cycle, steps 1-4, may be repeated multiple times, isolating recombinant virus each time and further enriching for heavy chains that contribute to optimal antigen binding.

6. Once specific antibody heavy chains have been selected, the entire procedure is repeated with an immunoglobulin light chain cDNA library constructed in the proprietary vaccinia vector in order to select the specific immunoglobulin light chains that contribute to optimal antigen binding. Sequential selection of heavy and light chains maximizes diversity by screening all available heavy and light chain combinations. The final MAb product is optimized by selection of a fully assembled bivalent antibody rather than a single chain Fv or monomeric Fab.

7. The MAb sequence is determined and specific binding verified through standard experimental techniques.

The final Mab product is optimized by selection of a fully assembled bivalent antibody rather than a single chain Fv. That is, selection is based on bivalent ($H_2L_2$) antibodies rather than scFv or Fab fragments. Synthesis and assembly of fully human, complete antibodies occurs in mammalian cells allowing immunoglobulin chains to undergo normal post-translational modification and assembly. Synthesis and assembly of complete antibodies would likely be very inefficient in bacterial cells and many specificities are lost due to failure of many antibodies to fold correctly in the abnormal physiological environment of a bacterial cell.

A relatively wide range of antibody epitope specificities can be selected, including the selection of specificities on the basis of functional activity. Specifically, antibodies can be selected on the basis of specific physiological effects on target cells (e.g., screening for inhibition of TNF-secretion by activated monocytes; induction of apoptosis; etc.) An outline of the method for screening for specific Mab on the basis of a functional assay is as follows:

1. An immunoglobulin heavy chain cDNA library in secretory form is constructed from naïve human lymphocytes in a vaccinia virus vector prepared according to the methods described herein. Multiple pools of, for example, about 100 to about 1000 recombinant viruses, are separately expanded and employed to infect producer cells at dilutions such that on average each cell is infected by one immunoglobulin heavy chain recombinant virus. These same cells are also infected with psoralin inactivated immunoglobulin light chain recombinant vaccinia virus from an immunoglobulin light chain library constructed in the same vaccinia virus vector. Alternatively, the infected cells may be transfected with immunoglobulin light chain recombinants in a plasmid expression vector. In the population of cells as a whole, each heavy chain can be associated with any light chain.

2. Infected cells are incubated for a time sufficient to allow secretion of fully assembled antibodies.

3. Assay wells are set up in which indicator cells of functional interest are incubated in the presence of aliquots of secreted antibody. These might, for example, include activated monocytes secreting TNFα. A simple ELISA assay for TNFα may then be employed to screen for any pool of antibodies that includes an activity that inhibits cytokine secretion.

4. Individual members of the selected pools are further analyzed to identify the relevant immunoglobulin heavy chain.

5. Once specific antibody heavy chains have been selected, the entire procedure is repeated with an immunoglobulin light chain cDNA library constructed in the proprietary vaccinia vector in order to select specific immunoglobulin light chains that contribute to optimal antigen binding.

6. The MAb sequences are identified and specific binding verified through standard experimental techniques. Because functional selection does not require a priori knowledge of the target membrane receptor, the selected Mab is both a potential therapeutic and a discovery tool to identify the relevant membrane receptor.

Selection occurs within human cell cultures following random association of immunoglobulin heavy and light chains. As noted above, this avoids repertoire restrictions due to limitations of synthesis in bacteria. It also avoids restrictions of the antibody repertoire due to tolerance to homologous gene products in mice. Mouse homologs of important human proteins are often 80% to 85% identical to the human sequence. It should be expected, therefore, that the mouse antibody response to a human protein would primarily focus on the 15% to 20% of epitopes that are different in man and mouse. This invention allows efficient selection of high affinity, fully human antibodies with a broad range of epitope specificities. The technology is applicable to a wide variety of projects and targets including functional selection of antibodies to previously unidentified membrane receptors with defined physiological significance.

* * *

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference. The disclosure and claims of U.S. application Ser. No. 08/935,377, filed Sep. 22, 1997 and U.S. Application No. 60/192,586, filed Mar. 28, 2000 are herein incorporated by reference.

What is claimed is:

1. A method of selecting polynucleotides which encode an antigen-specific immunoglobulin molecule, or antigen-specific fragment thereof, comprising:
   (a) introducing into a population of eukaryotic host cells capable of expressing said immunoglobulin molecule a first library of polynucleotides encoding, through operable association with a transcriptional control region, a plurality of first immunoglobulin subunit polypeptides, each first immunoglobulin subunit polypeptide comprising:
      (i) a first immunoglobulin constant region selected from the group consisting of a heavy chain constant region and a light chain constant region,
      (ii) an immunoglobulin variable region corresponding to said first constant region, and
      (iii) a signal peptide capable of directing cell surface expression or secretion of said first immunoglobulin subunit polypeptide;
   (b) introducing into said host cells a second library of polynucleotides encoding, through operable association with a transcriptional control region, a plurality of second immunoglobulin subunit polypeptides, each comprising:
      (i) a second immunoglobulin constant region selected from the group consisting of a heavy chain constant region and a light chain constant region, wherein said second immunoglobulin constant region is not the same as said first immunoglobulin constant region,
      (ii) an immunoglobulin variable region corresponding to said second constant region, and
      (iii) a signal peptide capable of directing cell surface expression or secretion of said second immunoglobulin subunit polypeptide,
   wherein said second immunoglobulin subunit polypeptide is capable of combining with said first immunoglobulin subunit polypeptide to form an immunoglobulin molecule, or antigen-specific fragment thereof;
   (c) permitting expression of immunoglobulin molecules, or antigen-specific fragments thereof, from said host cells;
   (d) contacting said immunoglobulin molecules with an antigen; and
   (e) recovering those polynucleotides of said first library which express immunoglobulin molecules, or antigen-specific fragments thereof, specific for said antigen,
   wherein said first library or said second library comprises at least 10 different polynucleotides.

2. The method of claim 1, further comprising:
   (f) introducing said recovered polynucleotides into a population of host cells capable of expressing said immunoglobulin molecule;
   (g) introducing into said host cells said second library polynucleotides;
   (h) permitting expression of immunoglobulin molecules, or antigen-specific fragments thereof, from said host cells;

(i) contacting said host cells with said antigen; and (j) recovering those polynucleotides of said first library which express immunoglobulin molecules, or antigen-specific fragments thereof, specific for said antigen.

3. The method of claim 2, further comprising repeating steps (f)-(j) one or more times, thereby enriching for polynucleotides of said first library which encode a first immunoglobulin subunit polypeptide which, as part of an immunoglobulin molecule, or antigen-specific fragment thereof, specifically binds said antigen.

4. The method of claim 1, further comprising isolating those polynucleotides recovered from said first library.

5. The method of claim 4, further comprising:

(k) introducing into a population of eukaryotic host cells capable of expressing said immunoglobulin molecule said second library of polynucleotides;

(l) introducing into said host cells those polynucleotides isolated from said first library;

(m) permitting expression of immunoglobulin molecules, or antigen-specific fragments thereof, from said host cells;

(n) contacting said host cells with said specific antigen; and (o) recovering those polynucleotides of said second library which express immunoglobulin molecules, or antigen-specific fragments thereof, specific for said antigen.

6. The method of claim 5, further comprising:

(p) introducing said recovered polynucleotides into a population of host cells capable of expressing said immunoglobulin molecule;

(q) introducing into said host cells those polynucleotides isolated from said first library;

(r) permitting expression of immunoglobulin molecules, or antigen-specific fragments thereof, from said host cells;

(s) contacting said host cells with said antigen; and (t) recovering those polynucleotides of said second library which express immunoglobulin molecules, or antigen-specific fragments thereof, specific for said antigen.

7. The method of claim 6, further comprising repeating steps (p)-(t) one or more times, thereby enriching for polynucleotides of said second library which encode a second immunoglobulin subunit polypeptide which, as part of an immunoglobulin molecule, or antigen-specific fragment thereof, specifically binds said antigen.

8. The method of claim 7, farther comprising isolating those poly-nucleotides recovered from said second library.

9. The method of claim 1, wherein said first library of polynucleotides is constructed in a eukaryotic virus vector.

10. The method of claim 1, wherein said second library of polynucleotides is constructed in a eukaryotic virus vector.

11. The method of claim 1, wherein said second library of polynucleotides is constructed in a plasmid vector.

12. The method of claim 1, wherein said polynucleotides encoding antigen-specific immunoglobulin molecules are identified through detection of an effect selected from the group consisting of:

(a) antigen-induced signaling; and (b) antigen-specific binding.

13. The method of claim 12, wherein said effect is antigen-specific binding.

14. The method of claim 13, comprising:

(a) contacting pools of said host cells with said antigen under conditions wherein antigen-specific immunoglobulin molecules expressed by said host cells will bind to said antigen; and (b) recovering polynucleotides of said first library from those host cell pools, or from replicate pools of polynucleotides set aside previously, expressing immunoglobulin molecules to which said antigen was bound.

15. The method of claim 14, further comprising:

(c) dividing said recovered polynucleotides into a plurality of sub-pools and introducing said sub-pools into populations of host cells capable of expressing said immunoglobulin molecule;

(d) permitting expression of immunoglobulin molecules, or antigen-specific fragments thereof, from said host cells;

(e) contacting said pools with said antigen under conditions wherein antigen-specific immunoglobulin molecules expressed by said host cells bind to said antigen; and (f) recovering polynucleotides of said first library from those host cell pools, or from replicate pools of polynucleotides set aside previously, expressing immunoglobulin molecules to which said antigen was bound.

* * * * *